United States Patent [19]
Crapo et al.

[11] Patent Number: 6,127,356
[45] Date of Patent: *Oct. 3, 2000

[54] OXIDANT SCAVENGERS

[75] Inventors: James D. Crapo; Irwin Fridovich; Tim Oury; Brian J. Day; Rodney J. Folz, all of Durham, N.C.; Bruce A. Freeman, Birmingham, Ala.; Michael P. Trova, Schenectady, N.Y.; Ines Batinic-Haberle, Durham, N.C.

[73] Assignee: Duke University, Durham, N.C.

[*] Notice: This patent issued on a continued prosecution application filed under 37 CFR 1.53(d), and is subject to the twenty year patent term provisions of 35 U.S.C. 154(a)(2).

[21] Appl. No.: 08/663,028

[22] Filed: Jun. 7, 1996

Related U.S. Application Data

[63] Continuation-in-part of application No. 08/613,418, Mar. 11, 1996, abandoned, which is a continuation-in-part of application No. 08/476,866, Jun. 7, 1995, which is a continuation-in-part of application No. 08/322,766, Oct. 13, 1994, which is a continuation-in-part of application No. 08/136,207, Oct. 15, 1993, abandoned.

[51] Int. Cl.$^7$ .......................... A01N 55/02; C07B 47/00; C09K 15/04; C09K 15/32
[52] U.S. Cl. .......................... 514/185; 540/145; 252/399; 252/400.23; 435/189; 435/252.3; 435/320.1
[58] Field of Search .......................... 514/185; 435/189, 435/252.3, 254, 320.1; 536/27; 540/145; 252/399, 400.23

[56] References Cited

U.S. PATENT DOCUMENTS 4,614,723  9/1986  Schmidt .................................. 436/536
4,746,735  5/1988  Kruper, Jr. et al. ..................... 540/145

(List continued on next page.)

FOREIGN PATENT DOCUMENTS 0 127 797  12/1984  European Pat. Off. .
0 186 962   7/1986  European Pat. Off. .

(List continued on next page.)

OTHER PUBLICATIONS

Sharma et al, "Synthesis of amphiphilic 5–(4–N–alkylpyridiniumyl)–10, 15,20–triphenylporphyrins and their aggregational properties in different solvent systems", Chemical Abstracts, vol. 123, No. 1, Jul. 3, 1995 –Abstract No. 9222.

Schneider et al, "Ligand–Porphyrin Complexes: Quantitative Evaluation of Stacking and Ionic Contributions", J. Org. Chem. 7464–7472 (1994).

Giraudeau et al, "Substituent Effects in the Electroreduction of Porphyrins and Metalloporphyrins", J. Am. Chem. Soc. 101(14):3857–3862 (1979).

Stralin et al, "Effects of Oxidative Stress on Expression of Extracellular Superoxide Dismutase, CuZn–Superoxide Fibroblast", Biochem. J. 298:347–352 (1994).

(List continued on next page.)

Primary Examiner—Robert A. Wax
Assistant Examiner—Tekchand Saidha
Attorney, Agent, or Firm—Nixon & Vanderhye P.C.

[57] ABSTRACT

The present invention relates, in general, to a method of modulating physiological and pathological processes and, in particular, to a method of modulating intra- and extracellular levels of oxidants and thereby processes in which such oxidants are a participant. The invention also relates to compounds and compositions suitable for use in such methods.

53 Claims, 50 Drawing Sheets

U.S. PATENT DOCUMENTS

| | | | |
|---|---|---|---|
| 4,758,422 | 7/1988 | Quay | 540/145 |
| 4,837,221 | 6/1989 | Bonnett | 514/410 |
| 4,851,403 | 7/1989 | Picker et al. | 424/485 |
| 4,892,941 | 1/1990 | Dolphin et al. | 540/145 |
| 4,895,719 | 1/1990 | Radhakrishnam | 424/45 |
| 4,963,367 | 10/1990 | Ecanow | 424/485 |
| 5,051,337 | 9/1991 | Sakoda et al. | 430/270 |
| 5,130,245 | 7/1992 | Marklund et al. | 435/189 |
| 5,162,519 | 11/1992 | Bonnett | 540/145 |
| 5,169,630 | 12/1992 | Okaya et al. | 424/401 |
| 5,202,317 | 4/1993 | Bruice | 514/185 |
| 5,217,966 | 6/1993 | Bruice | 514/185 |
| 5,223,538 | 6/1993 | Fridovich | 514/616 |
| 5,227,405 | 7/1993 | Fridovich | 514/612 |
| 5,236,914 | 8/1993 | Meunien | 514/185 |
| 5,236,915 | 8/1993 | Fiel | 540/145 |
| 5,248,603 | 9/1993 | Marklund et al. | 635/189 |
| 5,262,532 | 11/1993 | Tweedle et al. | 540/145 |
| 5,284,647 | 2/1994 | Niedballa | 424/81 |
| 5,366,729 | 11/1994 | Marklund et al. | 424/96.4 |
| 5,472,691 | 12/1995 | Marlund et al. | 424/94.4 |
| 5,493,017 | 2/1996 | Therien et al. | 424/94.4 |

FOREIGN PATENT DOCUMENTS

| | | |
|---|---|---|
| 0 282 899 | 9/1988 | European Pat. Off. . |
| 0 336 879 | 10/1989 | European Pat. Off. . |
| 0 337 601 | 10/1989 | European Pat. Off. . |
| 0 345 171 | 12/1989 | European Pat. Off. . |
| 0 462 836 | 12/1991 | European Pat. Off. . |
| 0 532 327 | 3/1993 | European Pat. Off. . |
| 2 676 738 | 11/1992 | France . |
| WO 93/02090 | 2/1993 | WIPO . |
| WO 94/04614 | 3/1994 | WIPO . |
| WO 95/10185 | 4/1995 | WIPO . |
| WO 95/31197 | 11/1995 | WIPO . |
| WO 96/09053 | 3/1996 | WIPO . |

OTHER PUBLICATIONS

Folz et al, "Extracellular Superoxide Dismutase (SOD3): Tissue–Specific Expression, Genomic Characterization, and Computer–Assisted Sequence Analysis of the Human EC SOD Gene", Genomics 22:162–171 (1994).

Clyde et al, "Distribution of Manganese Superoxide Distumase mRNA in Normal and Hyperoxic Rat Lung", American Journal of Respiratory Cell and Molecular Biology 8:530–537 (1993).

Wolberg et al, Electrocical and Electron Paramagnetic Resonance Studies of Metalloporphyrins and Thier Electrochemical Oxidation Products:, Journal of the American Chemical Society 92(10):2982–2990 (1970).

Pastemack et al, "Superoxide Distumase Activities of an Iron Porphyrin and Other Iron Complexes", Journal of the American Chemical Society 101(4):1026–1031 (1979).

Winkelman, James, "The Distribution of Tetraphenylporphinesulfonate in the Tumor–bearing Rat", Cancer Research 22:589–596 (1962).

Moisy et al, "Catalytic Oxidation of 2,6–Di–Terbutylphenol by Molecular Oxygen Electroassisted by Poly(Pyrrole––Manganese–Porphyrin)", New J. Chem. 13:511–514 (1989).

Malinski et al, "Characterization of Conductive Polymeric Nickel(II) Tetrakis(3–methoxy–4–hydroxy–phenyl)Porphyrin as an Anodic Material for Electrocatalysis", J. Electrochem. Soc. 138(7):2008–2015 (1991).

Weinraub et al, "Chemical properties of water–soluble porphyrins. 5. Reactions of some manganese (III) porphyrins with the superoxide and other reducing radicals", Int. J. Radiat. Biol. 50(4):649–658 (1986) (Abs).

Fajer et al, "π–Cation Radicals and Dications of Metalloporphyrins", Journal of the American Chemical Society 92(11):3451–3459 (1970).

Pasternack et al, "Aggregation of Nickel(II), Coppwer (II), and Zinc(II) Derivatives of Water–Soluble Porphyrins", Inorganic Chemistry 12(11):2606–2610 (1973).

Datta–Gupta et al, "Synthetic Porphyrins. I. Synthesis and Spectra of Some para–Substituted meso–Tetraphenylporphines (1)", J. Heterocycl. Chem. 3:495–502 (1966).

Harriman et al, "Photochemistry of Manganese Porphyrins Part 2.–Photoreduction", pp. 1543–1552.

Longo et al, "The Synthesis and Some Physical Properties of ms–Tetra(pentafluorophenyl)–porphin and ms–Tetraphenylporphines (1)", Notes 6:927–931 (1969).

Barnitz et al, "Reactions of Fe "(meso–$\alpha,\alpha,\alpha,\alpha$–tetrakis O–[N–methylisonicotinamido)phenyl]porphyrin)$^{5-}$ and Fe"(meso–tetrakis[N–methylpyridinium–4–yl]porphyrin)$^{5-}$ with $NC_1CO_2$, and $O_2$", Inorg. Chem. 32:941–947 (1993).

Pasternack et al, "On the Aggregation of Meso–Substituted Water–Soluble Porphyrins", Journal of American Chemical Society 94(13):4511–4517 (1972).

Datta–Gupta et al, "Synthetic Porphyrins II Preparation and Spectra of Some Metal Chelates of para", Journal of Substituted–mesa–Tetraphenylporphines, Journal of Pharmaceutical Science 57(2):300–304 (1968).

Boissinot et al, "Rational Design and Expression of a Heparin–Targeted Human Superoxide Dismutase", Biochemical and Biophysical Research Communication 190(1):250–256 (1993).

Oury et al, "Cold–induced Brain Edema in Mice", The Jouranl of Biological Chemistry 268(21):15394–15398 (1993).

Oury et al, "Extracellular superoxide dismutase, nitric oxide, and central nervous system $O_2$ toxicity",Proc. Natl. Acad. Sci. USA 89:9715–9719 (1992).

Pasternack et al, "Catalyst of the Disproportionation of Superoxide by Metalloporphyrins III", Journal of Inorganic Biochemistry 15:261–267 (1981).

Oury et al, "Establishment of Transgenic Mice Expressing Human Extracellular Superoxide Dismutase", American Review of Respiratory Disease 143(4):A515 (1991), International Conference Supplement Abstracts –No. 236.

Oury et al, "Transgenic Mice Superexpressing Human Extracellular Superoxide Dismutase Show Increased Resistance to Cold–induced Brain Edema, But are More Susceptible to Hyperbaric Oxygen", American Review of Respiratory Disease 145(4):A713 (1992), International Conference Supplement Abstracts –No. 211.

Oury et al, "Immunocytochemical Localization of Extracellular Superoxide Dismutase in Human Lung", American Review of Respiratory Disease 147(4):A713 (1993), International Conference Supplement Abstracts –No. 246.

Oury, Tim D., "Extracellular Superoxide Dismutase and Nitric Oxide: Transgenic and Immunocytochemical Studies", Dissertation submitted in partial fulfillment of the requirements for the degree of Doctor of Philosophy in the Department of Pathology in the Graduate School of Duke University (Jun. 17, 1993).

Gosh, "Substituent Effects on Valence Ionization Potentials of Free Base Porphyrins: Local Density Functional Calculations and Their Relevance to Electrochemical and Photoelectron Spectroscopic Studies", J. Am. Chem. Soc. 117:4691–4699 (1995).

De Peretti et al, "Imidazol[2, 1–b]benzoxazole–3–acetamide derivatives, their preparation, and their therapeutic use", Chemical Abstracts 121:1016, Abstract No. 121:200896u.

Oberley et al, "Anticancer activity of metal compounds with superoxide dismutase activity", Agents and Actions 15(5/6):535–538 (1984).

Collman et al, "Synthesis of "Face to Face" Porphyrin Dimers Linked by 5, 15–Substituents: Potential Binuclear Multielectron Redox Catalysts", J. Am. Chem. Soc. 103:516–533 (1981).

Gassman et al, "Electronic Effects of Peripheral Substituents in Porphyrins: X–ray Photoelectron Spectroscopy and ab Initio Self–Consistent Field Calculations", J. Am. Chem. Soc. 114:9990–10000 (1992).

Bishop et al, "The Reaction of Thiomides with Phosphorus Ylides", J. Org. Chem. 56:5079–5091 (1991).

Picker et al, "Cobalt (III) complexes of water soluble synthetic meso–substituted porphyrins as radiation sensitizers for oxic and hypoxic tumor cells", 8–Radiation 112:405 (1990) Abstract No. 112:73026d.

McCord et al, "Superoxide Dismutase–An Enzymic Function for Erythrocuprein", Biochemistry 492, p. 346.

McCord et al, Superoxide Dismutase An Enzymic Function for Erythrocuprein (Hemocuprein), The Journal of Biological Chemistry 244(22):6049–6055 (1969).

Crapo et al, "Superoxide Dismutase and Oxygen Toxicity", Clinical Research, p. 222.

Crapo et al, "The Failure of Aerosolized Superoxide Dismutase to Modify Pulmonary Oxygen Toxicity", American Review of Respiratory Disease 115:1027–1033 (1977).

Joester et al, "Superoxide Dismutase Activity of $Cu^{2+}$–Amino Acid Chelates", FEBS Letters 25(1), 25–28 (1972).

Brigelius et al, "Superoxide Dismutase Activity of Low Molecular Weight Cu2+–Chelates Studied by Pulse Radiolysis", FEBS Letters 47(1):72–75 (1974).

Sorenson, John R.J., "Copper Chelates as Possible Active Forms of the Antiarthritic Agents", Journal of Medicinal Chemistry 19(1):135–148 (1976).

deAlvare et al, "Mechanism of Superoxide Anion Scavenging Reaction by Bis–(Salicylato)–Copper(II) Complex", Biochemical and Biophysical Research Communications 69(3):687–694 (1976).

Halliwell, Barry, "The Superoxide Dismutase Activity of Iron Complexes", FEBS Letters 56(1):34–38 (1975).

McClune et al, "Catalysis of Superoxide Dismutation by Iron–Ethylenediaminetetraacetic Acid Complexes. Mechanism of the Reaction and Evidence for the Direct Formation of an Iron(III)–Ethylenediaminetetraacetic Acid Peroxo Complex from the Reaction of Superoxide with Iron(II)–Ethylenediaminetetraacetic Acid", Communications to the Editor, pp. 5220–5222 (1977).

Diguiseppi et al, "Putative Superoxide Dismutase Activity of Iron–EDTA: A Reexamination", Archives of Biochemistry and Biophysics 203(1):145–150 (1980).

Robertson, Jr. et al, "Does Copper–D–Penicillamine Catalyze the Dismutation of $O_2$?", Archives of Biochemistry and Biophysics 203(2):830–831 (1980).

Werringloer et al, "The Integration of Divalent Copper and the Microsomal Electron Transport System", The Journal of Biological Chemistry, 254(23):11839–11846 (1979).

Pasternack et al, "Catalyst of the Disproportionation of Superoxide by Metalloporphyrins", Journal of Inorganic Biochemistry 11:261–267 (1979).

Archibald et al, Manganese and Defenses against Oxygen Toxicity in *Lactobacillus plantarum*, Journal of Bacteriology 145(1):442–451 (1981).

Archibald et al, Manganese, Superoxide Dismutase, Oxygen Tolerance in Some Lactic Acid Bacteria, Journal of Bacteriology 146(3):928–936 (1981).

Archibald et al, The Scavenging of Superoxide Radical by Manganous Complex: In Vitro, Archives of Biochemistry and Boiphysics 214(2):452–463 (1982).

Archibald et al, Investigations of the State of the Manganese in *Lactobacillus plantarum*, Archives of Biochemistry and Biophysics 215(2):589–596 (1982).

Darr et al, "A Mimic of Superoxide Dismutase Activity Based Upon Desferrioxamine B and ManganEse(IV)", Archives of Biochemistry and Biophysics 258(2):351–355 (1987).

Beyer, Jr., Characterization of Superoxide Dismutase Mimic Prepared from Desferrioxamine and $MnO_2$, Archives of Biochemistry and Biophysics 27(1):149–156 (1989).

Faulkner et al, "Characterization of Mn(III) Complexes of Linear and Cyclic Desferrioxamines as Mimics of Superoxide Dismutase Activity", Archives of Biochemistry and Biophysics 310(2):341–346 (1994).

Faulkner et al, Stable Mn)III) Porphyrins Mimic Superoxide Dismutase in Vitro and Substitute for It in Vivo, The Journal of Biological Chemistry 269(38):23471–23476 (1994).

Liochev et al, "A Cationic Manganic Porphyrin Inhibits Uptake of Paraquat by *Escherichia coli*", Archives of Biochemistry and Biophysics 321(1):271–275 (1995).

Peretz et al, "Chemical properties of water–soluble porphyrins 3. The reaction of superoxide radials with some metalloporphyrins", Int. J. Radiat. Biol. 42(4):449–456 (1982).

Baudry et al, "Salen–Manganese Complexes are Superoxide Dismutase–Mimics", Biochemical and Biophysical Research Communication 192(2):964–968 (1993).

Gonzalez et al, "EUK–8, a Synthetic Superoxide Dismutase and Catalase Mimetic, Ameliorates Acute Lung Injury In Endotexemic Swine", The Journal of Pharmacology and Experimental Therapeutics 275(2):798–806 (1995).

Deune et al, "Prevention of Ischemia–Reperfusion Injury with a Synthetic Metalloprotein Superoxide Dismutase Mimic, SC52608", Plastic and Reconstructive Surgery 98(4):711–718 (1996).

Lowe et al, "Comparison of the cardiovascular effects of two novel superoxide dismutase mimetics, SC–55858 and SC–54417, in conscious dogs", European Journal of Pharmacoloty 304:81–86 (1996).

Weiss et al, "Manganese–based Superoxide Dismutase Mimetics Inhjibit Neutral Infiltration in Vivo", The Journal of Biological Chemistry 271(42):26149–26156 (1996).

Jin et al, "A New route to water soluble porphyrins: Phosphonium and ammonium type cationic porphyrins and self–assembly", Chem. Commun., pp. 1939–1940 (1996).

Pitié et al, "Oxidation at Carbon–1' of DNA Deoxyriboses by the Mn–TMPyP/KHSO5 System Results from a Cytochrome P–450–Type Hydroxylation Reaction", J. Am. Chem. Soc. 117:2935–2936 (1995).

Libby et al, "Cationic Porphyrin Derivatives As Inhibitors of Polyamine Catabolism", Biochemical Pharmacology 50(9):1527–1530 (1995).

Ilan et al, "Superoxide Dismuting Activity of an Iron Porphyrin", Inorg. Nucl. Chem. Letters 17((3/4):93–96 (1981).

Solomon et al, "Chemical properties of Water–Soluble Porphyrins. 2. The Reaction of Iron(III) Tetrakis4–N–methylpyridyl)porphyrin with th Superoxide Radical Dioxygen Couple", J. Phys. Chem. 86:1842–1849 (1982).

Weinraub et al, "Chemical Properties of Water–Soluble Porphyrins. 1. Equilibria between Some Ligands and Iron(III) Tetrakis (4–N–methylpyridyl)porphyrin", J. Phys. Chem. 86:1839–1842 (1982).

Day et al, "A Metalloporphyrin Superoxide Dismutase Mimetic Protects Against Paraquat–Induced Endothelial Cell Injury, in Vitro", The Journal of Pharmacology and Experimental Therapeutics 275(3):1227–1232 (1995).

Kariya et al, "Superoxide Dismutase (SOD) Activity with Fe–chlorin e6–Na and Suppression of Malignant Tumor Growth in Rats", Cancer Biotheraphy 10(2):139–145 (1995).

Liochev et al, A Cationic Manganic Porphyrin Inhibits Uptake of Paraquat by *Escherichia Coli*, Archives of Biochemistry and Biophysics 321(1):271–275 (1995).

Ohkawa et al, "Assay for Lipid Peroxides in Animal Tisues by Thiobarbituric Acid Reaction", Analytical Biochemistry 95:351 (1979).

Yue et al, "Carvedilol, a New Vasodilator and Beta Adrenoceptor Antagonist, is an Antioxidant and Free Radical Scavenger", The Journal of Pharmacology and Experimental Therapeutics 263:(1992).

Song et al, "Anti–HIV activities of anionic metalloporphyrins and related compounds", Antiviral Chemistry and Chemotherapy 8(2):85 (1996).

Harriman and Porter, "Photochemistry of Manganese Porphyrins", J. Chem. Soc. 275:1532–1542 (1979).

Bedioui et al, "Metalloporphyrin–Polypyrrole Film Electrode: Characterization and Catalytic Application", J. Electroanal. Chem. 207:87–99 (1986).

Ruoslahti et al, "Arg–Gly–Asp: A Versatile Cell Recognition Signal", Cell 44:517–518 (1986).

Kumar et al, "Radioprotection by Antioxidant Enzymes and Enzyme Mimetics", Pharmac. Ther. 39:301–309 (1988).

Weiss et al, "Evaluation of Activity of Putative Superoxide Dismutase Mimics", The Journal of Biological Chemistry 2638(31):23049–23054 (1993).

Parge et al, "Atomic structures of wild–type and thermostable mutant recombinant human Cu,Zn superoxide dismutase", Proc. Natl. Acad. Sci. USA 89:6109–6113 (1992).

Lappin, "part III Bioinorganic Studies", Inorganic Reaction Mechanisms 7:343–434 (1981).

Schloger et al, Reactivity of Unsubstituted Porphyrin, German version Angew Chem. 87:388 (1975).

Foran et al, "Effect of Electrolyte Concentration on Axial Anion Ligation in Manganese(III) meso–Tetraphenylporphyrin Chlorides", Inorg. Chem. 31:1463–1470 (1992).

Milgrom, Facile Aerial Oxidation of a Porphyrin. Part 3. Some Metal Complexes of meso–Terakis–(3, 5–di–t–butyl–4–hydroxyphenyl)porphyrin, J. Chem. Soc. Perkin Trans. 11:71–79 (1988).

Bockhorst and Hoehn–Berlage, "An Optimized Synthesis of Manganese meso–Tetra(4–sulfunato–phenyl)porphine:A Tumor–Selective MRI Contrast Agent", Tetrahedron 50(29):8657–8660 (1994).

Keinan et al, "Catalytic Antibodies. Circular Dichroism and UV–Vis Studies of Antibody–Metalloporphyrin Interactions", Inorg. Chem. 31:5433–5438 (1992).

Marx, "Role of Gene Defect in Heredity ALS Clarified", Science 261:986 (1993).

Epp et al, "Superoxide Dismutase Activity of Manganese Chelates", 76–78 (1986).

Bors et al, "An expanded function for superoxide dismutase", Chemical Abstracts 115:388 (1991), Abstract No. 109185h.

Milgrom et al, "Redox Behaviour of Phenolic Porphyrins in Basic Solutions: A Reappraisal", Free Rad. Res. 24(1):19–29 (1996).

Szabo et al, "Evaluation of the relative contribution of nitric oxide and peroxynitrite to the suppression of mitochondrial respiration in immunostimulated macrophages using a manganese mesoporphyrin superoxide dismutase mimetic and peroxynitrite scavenger", FEBS Letters 381:82–86 (1996).

Patel et al, "Requirement for Superoxide in Excitotoxic Cell Death", Neuron 16:345–355 (1996).

Bamford et al, "The Squalestatins: Synthesis and Biological Activity of Some C3–Modified Analogues; Replacement of a carboxylic Acid or Methyl Ester with an Isoelectric Heterocyclic Functionality", J. Med. Chem. 38:3502–3513 (1995).

Szabo et al, "Peroxynitrite is Involved in the Pathogenesis of the Vascular Contractile and Energetic Failure in Endotoxic Shock", Shock Society Meeting (1996).

FIG. 20A
RESTRICTION MAP
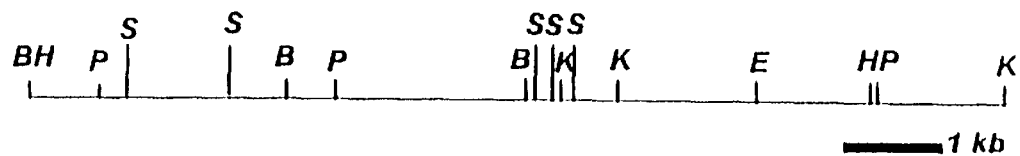
FIG. 20B
SEQUENCING STRATEGY
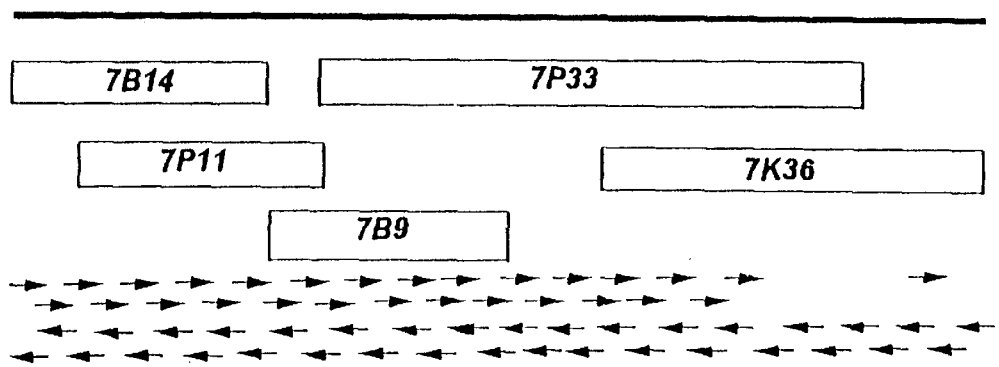
FIG. 20C GENE STRUCTURE
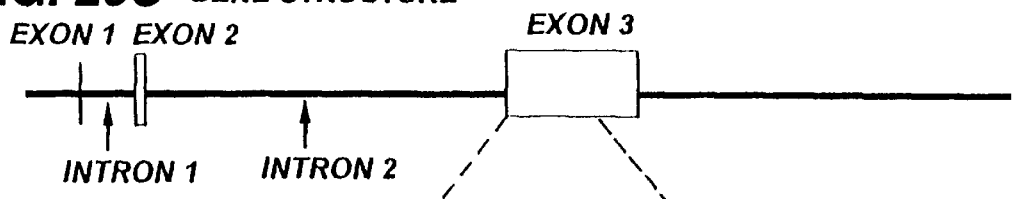
FIG. 20D
PROTEIN STRUCTURE
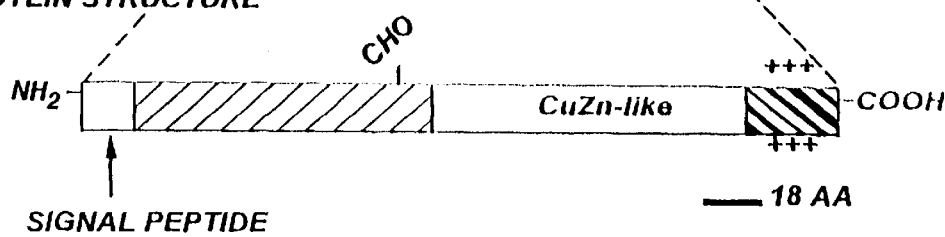

FIG. 24

```
GGATCCAGAG ATTTAGATTT TTTATAAGCT TTCCTGCCAC CGAAACGGGT GTTTGGGACC    60
TCACGAGGCC CTGTTCATTC TTCGTCGCTG CGCTCCCCAC TCTGTACTGG ATGCATTTAC   120
TGACGTTGTT GTCTCCGTCC CCAGAGTATG AACCCCCAAG GTGACTCATG CAGCTGTGGG   180
TGCCCGGCAT ACAGCATGGT GACTGGAATG GATGAGCACC CAATAAACAT TTGTTGCAGG   240
AATGCAGGAG GACGGGCAGG CCAGCAAGCA GGCTGCCTGG TTTTTCCCAC ATGGGCTTTT   300
CTGGGAAAGA AGAGCTTCTA TTTTTGGAAA GGGCTGCTAT GATTGAGAAA AGTTCATGGC   360
AGCAAAAAAA GGACAGACGT CGGGAGGGAA ACACTCCTAG TTCTCCCAGA CAACACATTT   420
TTTAAAAAGA CTCCTTCATC TCTTTAATAA TAACGGTAAC GACAATGACA ATGATGATTA   480
CTTATGAGTG CGGCTAGTGC CAGCCACTGT GTTGTCACTG GGCGAGTAAT GATCTCATTG   540
GATCTTCACG GTGGGCGTGC GGGGTGGACA GCCTCACACC CCCATTTTAC AGATGATGAA   600
AAGGAGGTGC AGGGAGTGGT GCAGCTGCTT CAGGCGTACA CAGATAGGAA GTGACAAGGC   660
TGGGACTCTG CAGCCTGAGT GTGTCATCAC GACCCACCCG CTGCTCTGCT CTCATAGGTA   720
TGACAGCACA GCTCTGGAGC AAATGCCATG CACATTTGCA AGGTGCCCAT TTCCATGCAG   780
CAAAAATAAG TCAATAAGTT ATTGACTTAG AGAAAGCAA AGGGCCTCTC AATAAAGAGG   840
TCATTGTACA CCTCTCCAAA CAGGCGATTT TCTTTCTCAT TTTTATTCCC CTGCTGTGTG   900
CTGAAGGTCA CTGGCTACAA GCCGGTGAAG TCGCGGAATG GAATCCTTGG CCCGAAAACC   960
CAAAAATGGG AGGGGCAGAG GAGGTGGGGA CAGAGCGGGA GGAGGTGGAG GCGAAGCAAT  1020
TCTACAACCC GGGGAGGTCT GGCCTGCTTT TCCTCCCTGA ACTGGCCCAA TGACTGGCTC  1080
CCTCACGCTG ACCACTCCTC TGGGCTGGCC TCCTGCACTC GCGCTAACAG CCCAGGCTCC  1140
AGGGACAGCC TGCGTTCCTG GCTGGCTGG GTGCAGCTCT CTTTTCAGGA GAGAAAGCTC  1200
TCTTGGAGGA GCTGGAAAGG TGGGTGCTAA GTTGAGGTTC ATTTGTTCT TCTCGGAGTG  1260
TGCTTATTGA GTCTGAAGCT GGGTTGGGGC AACGGGCCTC TTCTTGGGAA CAAATTGGAT  1320
CATCTTCTTG GGAAGGAAAT GTACTTTCCC TGGCTGCTCT GAGGGGTTAG TGGGGAGGTG  1380
GAGTGAGCGG GGAGGAAGGC AAGGAGGGGA GGAAGAAACC GTTCCTCCTG TGGATCTGCA  1440
AAGACCAGTC CAAGAGGATT TTAGTGTTAG GAAAAGGAAT CTGGAGTGAC GAGAAAGGGG  1500
GCCTTTCTAG ATGTTGCATG GCTTTGGTGT CGGGAGCCAC TTATGGGACA GCAGGTACTC  1560
TAAAAAGCCA CCTCCTTAGG AAAGCAGAGA GGCCCTGGCC AGCTCAGGCT CCCAGCAAGA  1620
GCTCCTTCTA GGAGACAGCT GAGGGATGAA ACACACCCAA GGCTCAAGAG GGGCAGGTTC  1680
TTCCCAGATA CAGACCCAGG AAGGAGATAA AGGCTTGGTG CCTCTATTTG GTTCAGGATA  1740
AGGGCCCCTG TCCTCTTTCT CTGATAACAC TGTCCTCTTT CTCTGATAAC ACCGTCCTCC  1800
CTTCCAGATC CACGTACAAA GGAGGCCCTT AAAAAGGCAC TTGGTCATTC ACAGCTCAAA  1860
CTGAGCAAGA GGCTGTGGGA GAAGAATCAA GTTGGTCCCG AGGGGAAGAG GTGTCAAAGG  1920
CTTAAGAAAC AAGAAGTCAG AGTTACCTG GGTTTGAGGG AGAATTTTCT TTCCCCCTTT  1980
```

FIG. 24-1

```
TCCTCCTCCT CCTCCTTCTT CTCTTTTTTT TTTTTTTTTT TTTTTTTTTT TTGAGACATG    2040
GTCTCATTCT GTCACCCAGC ACCCAGGCTG GAATGTAGTG GCACGATCAC TATCACGGCT    2100
CACTACAGCC TCTACCTCCC GGGCTCAAGT GATCCTCCTA CCTCAGCCTC CTGAGTAACT    2160
GGGACTACAG GCACATGCCA CCACACCCAG CTATTTTTTT TTTTGCTAGA GATGGGGGTC    2220
TCTACCAGGT TGGTCTCATA CTCTTGTACT CAAATGATTC TCCTGTCTCA TCCTCCCAAA    2280
GGGTGGGATT ACAGGCATAA GCCACCATGC CTGGCTCTTC TTTTGGTTTC AGAGAAAAAC    2340
ATCTCCTTAA AATGTTTATT TCCCAAGGAT TCTTGAAAAA GAAAGCTCAC TGACACACCC    2400
AAAACAATCT GGTTTTGCTC TGTGCTTTTA GGGAGAACTT TCTAAGCAGC AGAGCCCTTC    2460
TGAGTGGCAG GGCTGTCTTA GGAGGAAGGT GTCTTTTGAT GATGGGGAAC TTCATGTCCA    2520
GGTCTGGCAG GAGAGTTACC CCACTTTCCT GCCTACTCCC TGGGGCTTTG GGTAGTAGT    2580
ACCACATTGG GCCATGTCAT TTAGGTGAGT CCTTCAACAT CACTTTCTCT GCTTCTCCCT    2640
CTTTCTGGAT CCTCCTTCTT GGAGCCTTTC AAGGGGACCT CCTCTCACAG TGTCCATAGC    2700
ATCTCTTAGC TAATGGTCCT TAAAATCTCT ACCAGCAGCT TCTCTCTGAT AGCTAAGAGC    2760
TGCCATTTAC TGGGAACTTT CTATGTACTG GGCTCTGTGC TAAGTGCCCT AGATGAGAGA    2820
TGTGCAGTGT GGTGCCTAAA CCTTGGGCTT GGAGCAGACA CACACTTTCA AATCCTGCCT    2880
TCAGCTCCTT AGTGAACATG TCACCTTGGG CGGGACACAC GCCTCTCTGT GCCTCAGTTT    2940
CCTACACTTT AGAATGGGGA TAACACTGAA TAATGTTCTT GTGAGGATGC AGGGAATTAA    3000
CCCACGCACA GTACTTATAA TAGTGTCTGG CGCCTGTGTT CGATAAGTTT TAGCAATTCT    3060
AATCATCTCT TTTAAGCCTC GCAGCAAGCC TCTAAGGTAA GTCTGTATTA GTATCCCTAT    3120
TTACAGATGA GAAAACTGAG GTTCACAGGG GATGAGACAG TGTACAGTCT GCAGTCCAGC    3180
AATTACTCTG CTACTCAGCA ATAAAAATAG TAACAGCTAA CCCTTAGACT AAGTGGCAGA    3240
GTCAGGCTTT AGATTCATGA GGTGAGTTCT GGAATCCATC CCTTTAATAA CCACACTAAA    3300
TTGCCTTTCT GAAATGGTTA TATAAAGCAT ATCTACCCAA TCTTGGAGTT TTTTAAATGG    3360
CACCTAGTTT GGTGCTGGAA ATGCAGTTGA CCTTCAAAGC AATTCTTTGG AGGCAGCATC    3420
AATCCCTCTG GAAATACCTC GGTGGCATGG CTGGCCTTAT TCTACAGGTA AGGAACTTGA    3480
AGCTAAGCAT CAGTAACCCC GTGAAGTCAC AGTTAGTATA GGTTGGAATT GGGATTCAAA    3540
TCTGTACCTG ACTTTATAAT TCCTAGCTGG GCCCAGAAT CTTTGATAGA GGTGTCTTCT     3600
TTCTTTTCTT TTCTTTCTTT CCTCTTTCTT TCCCTTCCTT CCTCTCTCTC TGTCTTTCTT    3660
CTCTCCTTTC TTTCTCACAG AATCAAAATC TCTTGGGGTG GGGCCTGGGC ATCTGATTTT    3720
TAAAAACCAG ACATCTGATG TGCAGTCAAC ACTGAGAACC CCTGCCAGCT TCATCTCCTC    3780
TTCTAAGTGC CAGACCCAAG TTTCCAACTG TCTGCCCACC TGTCTCCCCA CCTGGGCACC    3840
CGCCAGCGTC TCACCCTCAG GAGACTCCAG CTGAACTAAT CCTCTCTCCC TGCTTTTCCA    3900
GAACAGGTCC CACCCTCCCT CCACTCAGTC TCTCCTGCTG GGAACCCTGG TCATCTGCAC    3960
```

FIG. 24-2

```
TGTGCCTTCA TCTTCCATCC TGCCAGTGCT GCCCGGTGTG TCTCTTAAAC CCATGCCTCC    4020
TCTGTGTGCA CCACCTGCAC TTTGGTAAAA GCCTTCATTT CCTGCTTGGG TTACTACAAC    4080
GCCCCCTAAC TCATCTCACT GTCTCTATTT CTGCTTCTCT GTCTCTCCCT AGGCTACTCC    4140
CATTCTTCCT CCCCTTTCCT CTTCATCCCA AAGTCCAACC CATATCCTTT TACCAGTAGG    4200
ACTTAAGGAA CTAAAGACTA TCTCATCACC CACTTTTCTT CTTAAAAACT TCCACTGCAC    4260
TGCCTGCTGA GATGGCCTTC CTACCCAACT TGGCTGGAAA ACTCCTACCC ATCTTGTGGA    4320
ACCCAGTTCA AAAGTCACCA CCTCTGAGAA GCCTTCCCTG AGGCTCCTAG GGAGATGGGT    4380
ACTGCCTCCT CTGTCCTTCT CCAGCACAGG CCCCATCTTC AATCACAGGA TTGTGCTGGA    4440
ATGATTGGAT GCCAAGTCTG TCCCTCACTG AACTCCTTAT GCAAAATCCA TATTATATGT    4500
TTCCTTTTGC CAGGTGTGGG CCCAGGTGCT GGGGATACCG ATGAATAAAA CTGAGTTTCT    4560
GTCTTCAAGA AGCTCCAAGT CTACTGAGTG TAGCAGAGAA CAGGGAGAAG GCACTTCAGG    4620
GAGAAGGGGT AGCACATGCA AAGCCCAGA AGGCAGGGAC AGAAGCCTTA GGGATGTCTG     4680
TGGGGGAGGA TGGAGGAAGA GGGTAACAGG AGACCAGGTG GGGAGATGAG GGAGGTGGTC    4740
TGGAAGGGCC ATGAGACACC CCTCACGCTC CCTGAGACCC CCTCCACGCT ATAGAGATGG    4800
GACTGGAGAG GACGATGATC ATTTGTGACT CAGATCCCTG TGGGTTTCTT CAGATTGGGT    4860
CTCACCCATC TTTACAGCCA CAGCACCTAA CACAGTGCCC GGCACACAGC AGGCCCTAGA    4920
CAAACGTTTG CCACATGAAG TCATGCCACT GGCCAGGAAG CCCACTGGGG ACTGGGGGT     4980
TGGTTCTGCG ATAATGGGGT CCCTGAGATT CTATGTTTCA CGTGACTAAG CCTCACTCTG    5040
CCCCCACCTC CGCGGGGGCG TCCCGCAC GT GCCCGACTCC AGCC A TG CTG GCG CTA   5096
                                               Met Leu Ala Leu
                                                1
CTG TGT TCC TGC CTG CTC CTG GCA GCC GGT GCC TCG GAC GCC TGG ACG     5144
Leu Cys Ser Cys Leu Leu Leu Ala Ala Gly Ala Ser Asp Ala Trp Thr
 5              10                  15                  20
GGC GAG GAC TCG GCG GAG CCC AAC TCT GAC TCG GCG GAG TGG ATC CGA     5192
Gly Glu Asp Ser Ala Glu Pro Asn Ser Asp Ser Ala Glu Trp Ile Arg
         25                  30                  35
GAC ATG TAC GCC AAG GTC ACG GAG ATC TGG CAG GAG GTC ATG CAG CGG     5240
Asp Met Tyr Ala Lys Val Thr Glu Ile Trp Gln Glu Val Met Gln Arg
         40                  45                  50
CGG GAC GAC GAC GGC ACG CTC CAC GCC GCC TGC CAG GTG CAG CCG TCG     5288
Arg Asp Asp Asp Gly Thr Leu His Ala Ala Cys Gln Val Gln Pro Ser
         55                  60                  65
GCC ACG CTG GAC GCC GCG CAG CCC CGG GTG ACC GGC GTC GTC CTC TTC     5336
Ala Thr Leu Asp Ala Ala Gln Pro Arg Val Thr Gly Val Val Leu Phe
     70                  75                  80
CGG CAG CTT GCG CCC CGC GCC AAG CTC GAC GCC TTC TTC GCC CTG GAG     5384
Arg Gln Leu Ala Pro Arg Ala Lys Leu Asp Ala Phe Phe Ala Leu Glu
 85              90                  95                  100
GGC TTC CCG ACC GAG CCG AAC AGC TCC AGC CGC GCC ATC CAC GTG CAC     5432
```

FIG. 24-3

| | |
|---|---|
| Gly Phe Pro Thr Glu Pro Asn Ser Ser Ser Arg Ala Ile His Val His<br>105                       110                   115 | |
| CAG TTC GGG GAC CTG AGC CAG GGC TGC GAG TCC ACC GGG CCC CAC TAC<br>Gln Phe Gly Asp Leu Ser Gln Gly Cys Glu Ser Thr Gly Pro His Tyr<br>120                       125                   130 | 5480 |
| AAC CCG CTG GCC GTG CCG CAC CCG CAG CAC CCG GGC GAC TTC GGC AAC<br>Asn Pro Leu Ala Val Pro His Pro Gln His Pro Gly Asp Phe Gly Asn<br>135                       140                   145 | 5528 |
| TTC GCG GTC CGC GAC GGC AGC CTC TGG AGG TAC CGC GCC GGC CTG GCC<br>Phe Ala Val Arg Asp Gly Ser Leu Trp Arg Tyr Arg Ala Gly Leu Ala<br>150                       155                   160 | 5576 |
| GCC TCG CTC GCG GGC CCG CAC TCC ATC GTG GGC CGG GCC GTG GTC GTC<br>Ala Ser Leu Ala Gly Pro His Ser Ile Val Gly Arg Ala Val Val Val<br>165                       170                   175                   180 | 5624 |
| CAC GCT GGC GAG GAC GAC CTG GGC CGC GGC GGC AAC CAG GCC AGC GTG<br>His Ala Gly Glu Asp Asp Leu Gly Arg Gly Gly Asn Gln Ala Ser Val<br>185                       190                   195 | 5672 |
| GAG AAC GGG AAC GCG GGC CGG CGG CTG GCC TGC TGC GTG GTG GGC GTG<br>Glu Asn Gly Asn Ala Gly Arg Arg Leu Ala Cys Cys Val Val Gly Val<br>200                       205                   210 | 5720 |
| TGC GGG CCC GGG CTC TGG GAG CGC CAG GCG CGG GAG CAC TCA GAG CGC<br>Cys Gly Pro Gly Leu Trp Glu Arg Gln Ala Arg Glu His Ser Glu Arg<br>215                       220                   225 | 5768 |
| AAG AAG CGG CGG CGC GAG AGC GAG TGC AAG GCC GCC T GAGCGCGGCC<br>Lys Lys Arg Arg Arg Glu Ser Glu Cys Lys Ala Ala<br>230                       235                   240 | 5815 |
| CCCACCCGGC GGCGGCCAGG GACCCCGAG GCCCCCTCT GCCTTTGAGC TTCTCCTCTG | 5875 |
| CTCCAACAGA CACCTTCCAC TCTGAGGTCT CACCTTCGCC TCTGCTGAAG TCTCCCCGCA | 5935 |
| GCCCTCTCCA CCCAGAGGTC TCCCTATACC GAGACCCACC ATCCTTCCAT CCTGAGGACC | 5995 |
| GCCCCAACCC TCGGAGCCCC CCACTCAGTA GGTCTGAAGG CCTCCATTTG TACCGAAACA | 6055 |
| CCCCGCTCAC GCTGACAGCC TCCTAGGCTC CCTGAGGTAC CTTTCCACCC AGACCCTCCT | 6115 |
| TCCCCACCCC ATAAGCCCTG AGACTCCCGC CTTTGACCTG ACGATCTTCC CCCTTCCCGC | 6175 |
| CTTCAGGTTC CTCCTAGGCG CTCAGAGGCC GCTCTGGGGG GTTGCCTCGA GTCCCCCCAC | 6235 |
| CCCTCCCCAC CCACCACCGC TCCCGCGGCA AGCCAGCCCG TGCAACGGAA GCCAGGCCAA | 6295 |
| CTGCCCCGCG TCTTCAGCTG TTTCGCATCC ACCGCCACCC CACTGAGAGC TGCTCCTTTG | 6355 |
| GGGGAATGTT TGGCAACCTT TGTGTTACAG ATTAAAAATT CAGCAATTCA GTACTGCGTC | 6415 |
| GAGGTCTTGG TTACTTTTTT GTTTGTTTGT TTTAGGCTTC TCTCCCAAGC TGAGCTTTTT | 6475 |
| TTTGTTTTGT TTTCGTTTTC CTTTTTTTTC TTTTTTTTGG GAGTGGCAAA CATGCTTCCC | 6535 |
| AAATCCCTAC AGGACTTCTC CTTATCCTCT GCCCCCACCT CCCTAACCCT GCTGGCAACA | 6595 |
| ACGTTCAGCC ACTGCTTGTC TTGCCCTTCA GTGTGGCTCC AAGAGGAAGA TCACCAGAAT | 6655 |
| CACTCAGGGA AGTTAAAAAA AAAAATACAG CTTCCTGGGC TACATCCCAG AGCTGTGGAA | 6715 |

FIG. 24-4

```
TCCAAAGGGA GAAGAGAAAG TGAATTTGCG ACAAGCGTCG GGATGATTCT GGCACTGGAC    6775
CCTCTGGCCT GAGAGGGGAA GAGGCCTTCC ATCTCACCTG GGCTGGTAGC TTGTCACATC    6835
TGCCTCCGAG TACAGCCTTA GGTCCATTTC CCAGATATCA GAGACAGTGC CAGGGAAGCC    6895
AGGTGACTGC ATCTTGCCTA GGCACAGAAG AGTAGGGTTG GAATGTGACG TTGTTAGCAT    6955
TTGGCAGGAC CAAAACCAGA GGCAAACGGA GGCAGTGGGA TGGAAAGGCA GTTGATTTTG    7015
ATGAAGGCTT GTTGGGAGTT CAGCTTTCTT TTGAAACTTA TAATCTATAC CCAGGCTAGA    7075
ACAGTCTTGT GTATACACCT TCATTCATGG AATAAACGTA CTTGCAATAA CTTTTTAGCC    7135
TCCCAGGGTA GCCTCACTTC CTAGCTGTGA CTTTTCCACC CTGGTTACTG GGAGGCAGCT    7195
TCCATTTCTC CCAGACTAGC TAGGCAGTGC GTCCAACTGA ACCGCAGCCA GAAACCTGTC    7255
TCCAGGGGTT ATTTTTACCT CTAACTAGGA CTAACTTATT TTAAAATCTT CCTTGAGCC    7315
CAAGTGACAA CTGAAGAGAA AGGCTATTGC CTGGTGATTT TGCTCCACCA GTTGGTTCTC    7375
ACTGGTTTGA ATACTAACTT GAACTGTACT CATCGACACT GAAAGGGGAT GAGCAAACAG    7435
TGTCTCTAAA TCTCCTGATC CTGATCTCAA ATATCCCCCT AATTACAAGT TGCAACAAGG    7495
CAGCTATTAC ACGGGACAC AGGATGGAGA GGATGGGTGC CAAACACCCA TCGTCTACTC     7555
TGCTGCCTCG GTTATGGTGA ATTCAGGACC ATCAAGGGAG GTGTGGACCT TTTTTTTCAG    7615
AAGGAGGCTG ACACTTCTTG TCAATTGCAT TGTGTTCTTA GTTTTGCTCT TCACAACCCT    7675
TGACCCCGTA GATGGGGCT GAAGAGGCAC CCTGGCCGAC TCACTCTATT TCTGTTTTGG     7735
GAATGGGATG GATAAACTAT CCCATGGCCT CCAGAGCCAA AAAACCAAAA CGAAACAAAA    7795
CAAAAACCC CAAAACAAAA AAGCAAAAAG CAAACAAGAA AAAAAAAAA AGAGGAAATA      7855
ATAGGCAGAC AATTTACAGT TCATTGTAAG GGCAAAGATA TGCATATAGC ATGATGGTTA    7915
ACAGGTCAGG CTCAGGTAGA AAGGCCCATT TGAACCCCAG CTCTGCCACA CTCAGAAACT    7975
GTGTGACCCG AACAAGTCAC TTAACCTCTC TGAGCATAGG TAAAATAAGA TCATCATACC    8035
AGATTGTTTT GAAGATTAAA TCAAGTGTTA TTCACGAGAG GTGCACAGCA TAGCATGCAC    8095
AACAAATAAG GACCTGGTAA GTATCTAATT AATAACAATG GCTAAGATCC AAAAAACAGC    8155
TACCTACTAA TAAATAGATG GGGCTGCCTT GTAAGGCAGT GAGCATCATG CAACCAGGAT    8215
TCAAATGAAG GACAGTTGCT ACCTCTGAGG TTCCCGAGAA GGATTTCTCG ATCCATTGAG    8275
AGACTGAATG ACATGAACTC TGCGATCCCA TCTCTTGTGG GGAGGGAACC TAGAATGAAG    8335
GGAAGATTGT GGGCCATAAA GGCAGACATC TGGTTCCTGG GCACAGAACC ATATGTGTGC    8395
CACCAAAGCC ACCCACCGGA CCCCACTTGG CCCCTGGAGT CTATTTTTAC TCCTCTCATC    8455
TTACAAGATC TATTTTGTTA ATCTCCTTAT ATTTGCTGTT TTGACTTCCC AGCCAGCTTG    8515
CTAATCAGTT TGCCTATTTG ACTCACAGGG TTTGCATTTG TCACGGGAC TGAAACACAC     8575
GCTTGTTTTG ATTTCTTTTT GTAAATTAGA AGCGTTGATG TAATGACTCT ACCTAGACAC    8635
AGCTGGTAAA GTGAGAATAA TGCTCAAGTT TGCACAGTTT AAACACAATG TAGACAATAA    8695
```

FIG. 24-5

| | | | | | |
|---|---|---|---|---|---|
| TTAGAAATGC | TATCTTTAGA | TGTTTAGGAT | AAGCTTTTCT | CAGAATTGCA | CTGATTTTTT | 8755 |
| TTTTCTGAGT | GGGGCTTTTT | AGTGCATATA | TACAGAAATA | CTAAAAACGT | AAGAAAATAG | 8815 |
| AGCAAATCAG | TGAGTGCTTT | GGTCAACTTG | AAAGACTGCA | GGAAATAAAC | CAACTGATTT | 8875 |
| TAGATCTGCC | TTTTTTTGAC | TGAATGCATA | AAATCTTTAC | ATTCTCCATA | TTTTTCATGA | 8935 |
| CTACCATATG | ATCAAATAGT | TTTAGGTGAC | AGATTGCAAC | TGATAAGTTG | CTGCAATATG | 8995 |
| GCAGAAGTCA | TGCTCAGCCT | CCGCTTGCCC | GGTGGTGAGG | GTGGAATATG | AAGCAAACAA | 9055 |
| TAAAGATAAT | TCATCATCTC | TATCAGGAAA | ATTGCCACAT | GTTTATTTCA | GGTAACAAAA | 9115 |
| AAGATATAGT | TATGATATAC | AATGACCATA | GAATCCAATA | AAGCAACTTC | TGCAAATGAA | 9175 |
| TAGAAGGTAC | TTTTTCTTTA | AATGAAACTA | CAAAATAGCA | GCTGGTTTTA | AAAACAAAGC | 9235 |
| CAATTGTTTT | AGATTTAATA | GGCTACCACT | GGCCTCTGCT | AAGATCCCCA | AATATATTCC | 9295 |
| TGAGCTCACA | TAGATTCCAG | AAAGTCAAAC | TTTTCAATAT | TATGCAAACT | TCCCTATGC | 9355 |
| ATCCAAAAAA | TTCTCATTTA | GTAAAGAGGT | GATATGAAAT | GTAAGGCAGC | ATGTCCATAT | 9415 |
| CTATCATTTT | AAATTGCCTT | CATGCTGTAT | CAACTGGTTT | TGTTTTGGGA | AGCAACCATA | 9475 |
| ATATTGAGAG | ACGGGTCTTT | CCTATTTTTT | CTGCTACTCA | TTTCTAACTA | GATTCACTAC | 9535 |
| GGAGCTCCCA | ATTGCATCTC | TCTGATCTAC | AAATTTTTCT | CTCTTCAGGA | AGACACCTGG | 9595 |
| AAAGAAGGGA | CTACATTAAA | GGAGTGTGTT | GGGGGCAATG | CTTTGGCCTT | TTGACATCCT | 9655 |
| ATCTAGTCTG | AAGGGACCCT | CACTATTGCT | AAGGAGGAGG | AGTGTTTTAA | ATGGAGGCTT | 9715 |
| CAGAATGAAA | GCAGAGGAAG | AAGGTACTCT | CTTTTTCAAA | AAGAAGGAGG | GTACAGGCCG | 9775 |
| GGCGCAGCTG | TCACGCCTGC | AATCCCAGCA | CTTTGGGAGG | CCGAGGAAGG | CAGATCACGA | 9835 |
| GGTTGGGAGT | TTGAGCCAGC | CTGGTCAACA | TAGTGAAACC | CCGTCTCTAC | TAAAAATACA | 9895 |
| AAAATTAGCC | AGCATGGTGG | TGCATGCCTG | TAGTCCCAGT | TACTCGGGAG | GCTGAGGCAG | 9955 |
| GAGAATCGCT | TGAACTCGGG | AAGTGGAGGT | TGCAGTGAGC | CGAGATCATG | CCACTGCACT | 10015 |
| CCACCCTGGG | TGACAGAGTG | AGACTCTCAA | AAAAAAAAA | AAAAAAAAA | AGAAGTAGGG | 10075 |
| TACC | | | | | | 10079 |

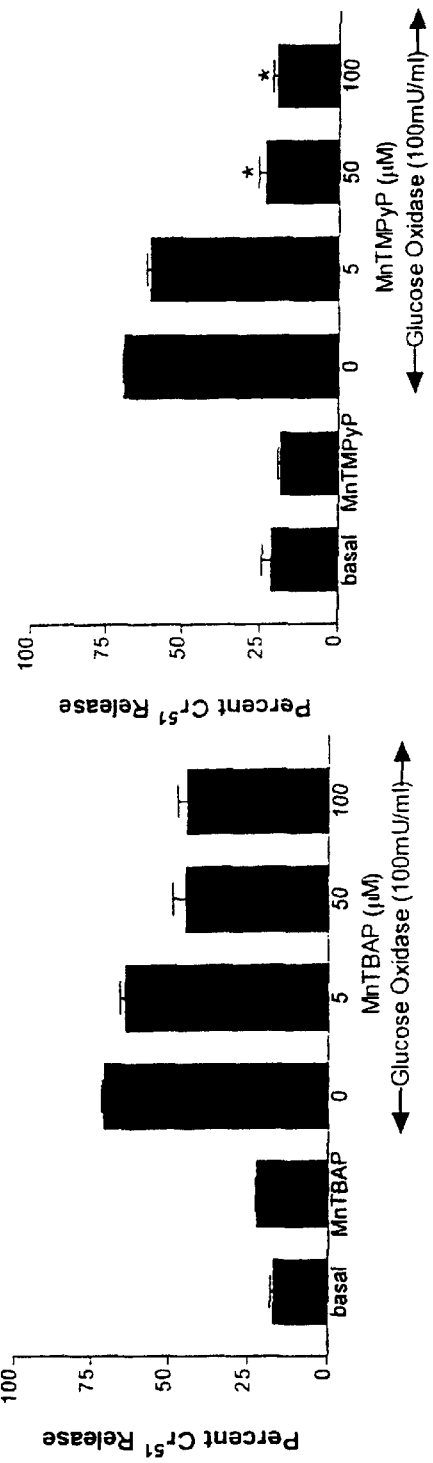
FIG. 33A
FIG. 33B
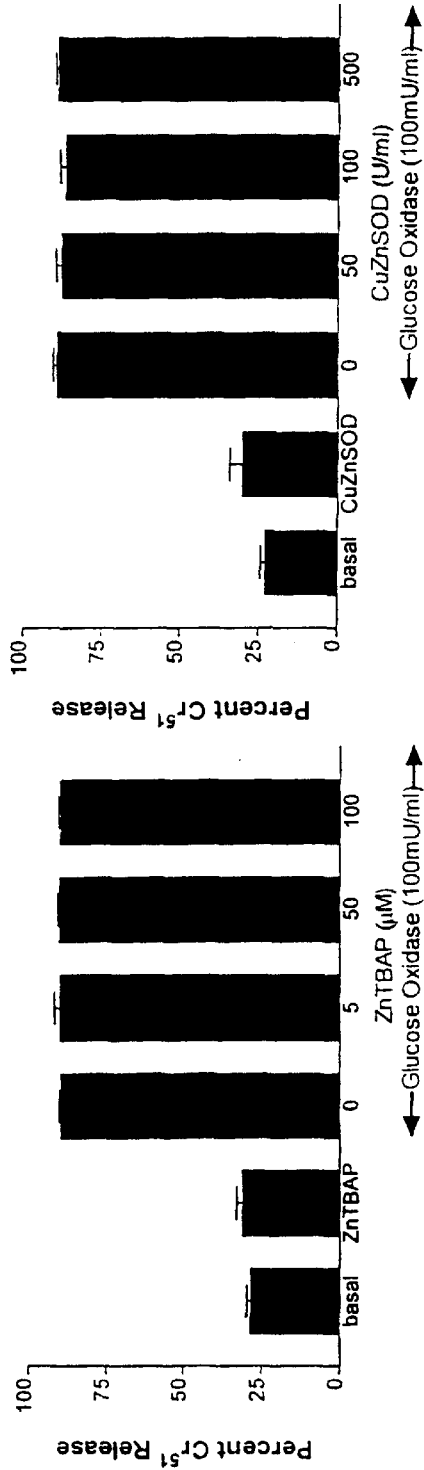
FIG. 33C
FIG. 33D

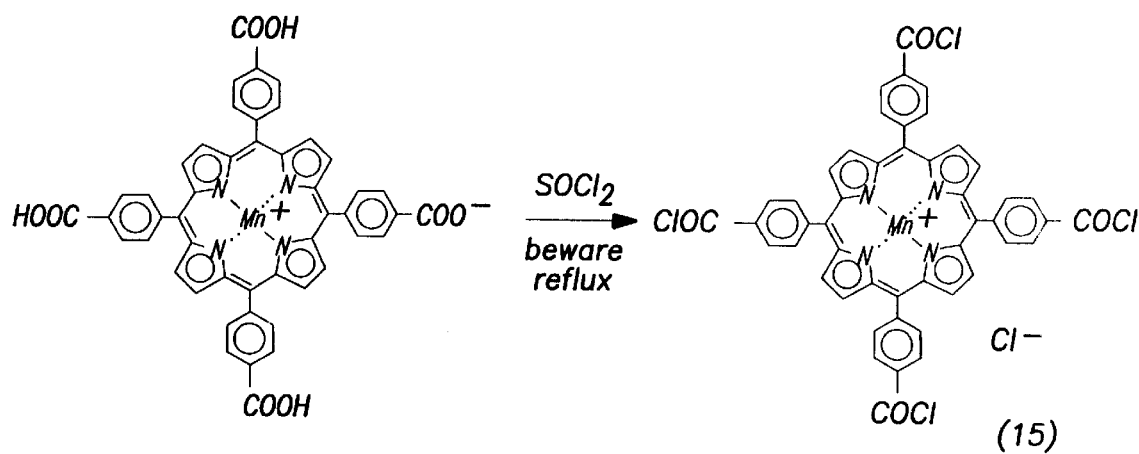
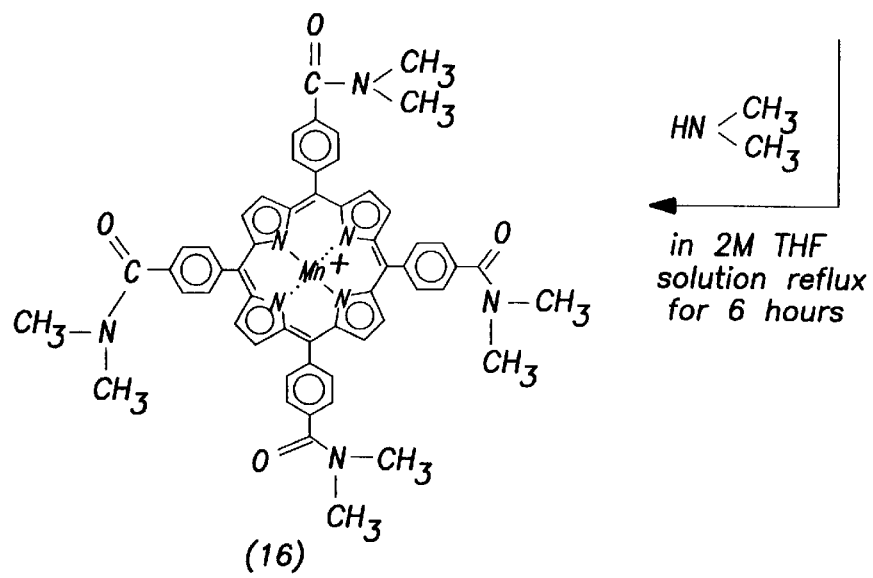
FIG. 42D

OXIDANT SCAVENGERS

This is a continuation-in-part application Ser. No. 08/613,418, filed Mar. 11, 1996, now abandoned, which is a continuation-in-part of application Ser. No. 08/476,866 filed Jun. 7, 1995, which is a continuation-in-part of application Ser. No. 08/322,766 filed Oct. 13, 1994, which is a continuation-in-part of application Ser. No. 08/136,207, filed Oct. 15, 1993, now abandoned, the contents of these applications being incorporated herein by reference.

TECHNICAL FIELD

The present invention relates, in general, to a method of modulating physiological and pathological processes and, in particular, to a method of modulating intra- and extracellular levels of oxidants such as superoxide radicals and hydrogen peroxide and thereby processes in which such radicals are a participant. The invention also relates to compounds and compositions suitable for use in such methods.

BACKGROUND

Oxidants are produced as part of the normal metabolism of all cells but also are an important component of the pathogenesis of many disease processes. Reactive oxygen species, for example, are critical elements of the pathogenesis of diseases of the lung, the central nervous system and skeletal muscle. Oxygen free radicals also play a role in modulating the effects of nitric oxide (NO·). In this context, they contribute to the pathogenesis of vascular disorders, inflammatory diseases and the aging process.

A critical balance of defensive enzymes against oxidants is required to maintain normal cell and organ function. Superoxide dismutases (SODs), a family of metalloenzymes which catalyze the intra- and extracellular conversion of $O_2^-$ into $H_2O_2$ plus $O_2$, and represent the first line of defense against the detrimental effects of superoxide radicals. Mammals produce three distinct SODs. One is a dimeric copper- and zinc-containing enzyme (CuZn SOD) found in the cytosol of all cells. A second is a tetrameric manganese-containing SOD (Mn SOD) found within mitochondria, and the third is a tetrameric, glycosylated, copper- and zinc-containing enzyme (EC-SOD) found in the extracellular fluids and bound to the extracellular matrix. Several other important antioxidant enzymes are known to exist within cells, including catalase and glutathione peroxidase. While extracellular fluids and the extracellular matrix contain only small amounts of these enzymes, other extracellular anti-oxidants are known to exist, including radical scavengers and inhibitors of lipid peroxidation, such as ascorbic acid, uric acid, and α-tocopherol (Halliwell et al, Arch. Biochem. Biophys. 280:1 (1990)). The relative lack of extracellular antioxidant enzymes may reflect the possible function of extracellular reactive oxygen species as bioeffector molecules (Halliwell et al, Arch. Biochem. Biophys. 280:1 (1990)). The relative deficiency of such enzymes may also result in greater susceptibility to extracellular oxidant stresses.

The enzyme EC-SOD, in many extracellular locations, exists only at low concentrations. While its physiologic role in vivo is yet to be defined, in many extracellular locations, EC-SOD is not thought to function as a bulk scavenger of $O_2^-$. As indicated above, EC-SOD is a tetrameric Cu/Zn-containing glycoprotein with a subunit molecular weight of 30,000 (Marklund, Proc. Natl. Acad. Sci. USA 79:7634 (1982); Tibell et al, Proc. Natl. Acad. Sci. USA 84:6634 (1987); see also U.S. Pat. No. 5,130,245 and WO 91/04315). Biochemical data suggest that EC-SOD binds to heparan sulfate proteoglycans on endothelial cells, where it has been speculated to serve as a "protective coat" (Marklund, J. Clin. Invest. 74:1398 (1984); Karlsson et al, Biochem. J. 255:223 (1988)). Endothelial cells secrete both $O_2^-$ (Halliwell, Free Radical Res. Commun. 5:315 (1989)) and endothelium-derived relaxing factor, putatively identified as nitric oxide (NO·) (Noak and Murphy, in Oxidative Stress Oxidants and Antioxidants, eds Sies, H. (Academic, San Diego), pp. 445–489 (1991)). NO· functions as a vasoregulator and as a regulator of neurotransmission (Schuman and Madison, Science 254:1503 (1991)). NO· can, however, be toxic to neurons in some situations (Dawson et al, Proc. Natl. Acad. Sci. USA 88:6368 (1991)). $O_2^-$ is known to inactivate NO·-induced vasorelaxation (Gryglewski et al, Nature 320:454 (1986); Rubanyi and Vanhoutte, Am. J. Physiol. 250:H822 (1986); Rubanyi and Vanhoutte, Am. J. Physiol. 250:H815 (1986); Bult et al, Br. J. Pharmacol. 95:1308 (1988); Nucci et al, Proc. Natl. Acad. Sci. USA 85:2334 (1988)). Thus, a possible function for EC-SOD is to protect NO· released from cells from $O_2^-$-mediated inactivation.

The reaction of $O_2^-$ with NO· is also known to produce a potentially toxic intermediate in the form of the peroxynitrite anion ($ONOO^-$) (Beckman et al, Proc. Natl. Acad. Sci. USA 87:1620 (1990); Mulligan et al, Proc. Natl. Acad. Sci. USA 88:6338 (1991); Hogg et al, Biochem. J. 281:419 (1992); Matheis et al, Am. J. Physiol. 262:H616 (1992)). Thus EC-SOD may also function to prevent the formation of $ONOO^-$.

Surprisingly, it has been found that EC-SOD increases, rather than decreases, central nervous system $O_2$ toxicity and that this effect of EC-SOD occurs through modulation of NO· This result implicates NO· as an important mediator in $O_2$ toxicity. The invention thus relates to methods of manipulating nitric oxide function that involve the use of extracellular antioxidants.

In addition to superoxide radicals, hydrogen peroxide is an oxidant species that is produced under a wide variety of conditions of oxidant stress. The invention thus also provides a method of manipulating hydrogen peroxide levels.

The methods of the invention find application in various disease and non-disease states in which oxidative stress plays a role, including inflammation. In a broader sense, the invention relates generally to methods of modulating intra- and extracellular processes in which an oxidant such as $O_2^-$ or hydrogen peroxide is a participant.

SUMMARY OF THE INVENTION

The present invention relates to a method of modulating intra- or extracellular levels of oxidants such as superoxide radicals, hydrogen peroxide and peroxynitrite. More particularly, the invention relates to a method of modulating normal or pathological processes involving superoxide radicals, hydrogen peroxide, nitric oxide or peroxynitrite using low molecular weight antioxidants, for example, mimetics of SOD, catalase or peroxidase.

In one embodiment, the present invention relates to an oxidant scavenger, for example, a mimetic of superoxide dismutase, catalase or peroxidase, comprising a nitrogen-containing macrocyclic moiety and a cell surface or extracellular matrix targeting moiety, or a pharmaceutically acceptable salt thereof.

In another embodiment, the present invention relates to oxidant scavenger of the formula:

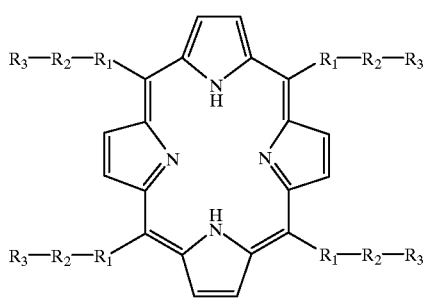

or a pharmaceutically acceptable salt thereof, wherein:

$R_1$ is a bond,

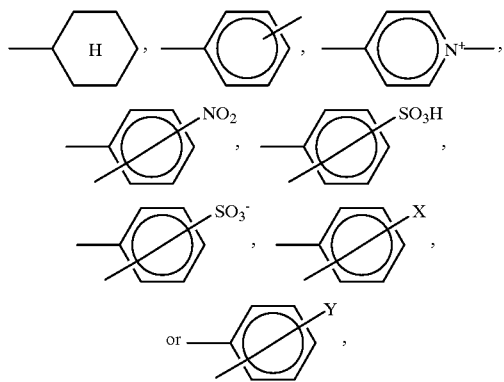

wherein X is a halogen and Y is an alkyl group and wherein

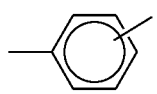

indicates bonding to $R_2$ at any position and

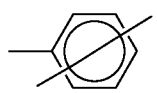

indicates bonding to $R_2$ and the substituent at any position; and $R_2$ is a bond, $-(CY'_2)_n-$, $-(CY'_2-CY'=CY')_n-$, $-(CY'_2-CY'_2-CH=CH)_n-$, $-(CY'=CY')_n-$, or

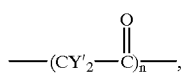

wherein Y' is hydrogen or an alkyl group and wherein n is 1 to 8; and $R_3$ is $-Y''$, $-OH$, $-NH_2$, $-N^+(Y'')_3$, $-COOH$, $-COO^-$, $-SO_3H$, $-SO_3^-$, $-C-PO_3H_2$ or $-C-PO_3H^-$, wherein Y'' is an alkyl group, wherein, when $R_1$ is

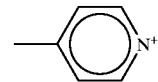

and $R_2$ is a bond, $R_3$ is not Y'' (eg $-CH_3$), and wherein, when $R_1$ is

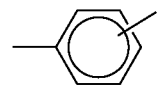

and $R_2$ is a bond, $R_3$ is not $-Y''$ (eg $-CH_3$), $-N^+(Y'')_3$ (eg $-N^-(CH_3)_3$), or COOH.

In a further embodiment, the present invention relates to an oxidant scavenger of the formula:

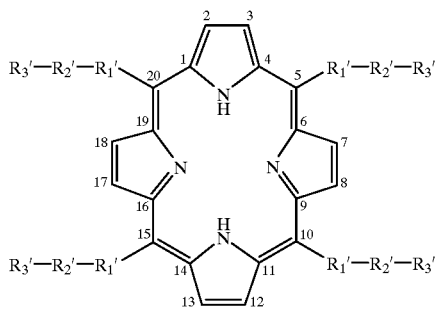

or a pharmaceutically acceptable salt thereof, or metal complex thereof wherein said metal is selected from the group consisting of manganese, copper and iron, wherein:

each $R_1'$ is independently a bond,

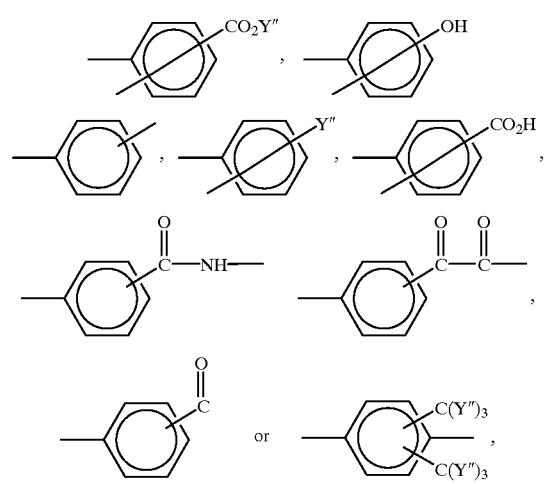

wherein Y" is an alkyl group, and wherein

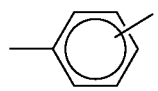

indicates bonding to $R_2'$ at any position and

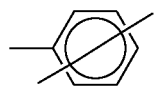

indicates bonding to $R_2'$ and the $R_1'$ phenyl substituent at any position;

each $R_2'$ is independently a bond, or $-(CH_2)_n-$ wherein n is 1–4, each $R_3'$ is independently $-Y''$, $-Y'''$, $-H$, $-OH$, $-OY''$, $-NO_2$, $-CN$, $-NH_2$, $-COOH$, $-COY''$, $-COO^-$, or a heterocyclic group, wherein Y" is as defined above and Y''' is a primary, secondary, tertiary or quaternary amine, wherein when $R_1'$ is

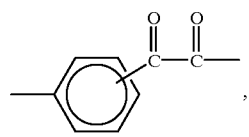

$R_3'$ is not COOH, COY" or COO$^-$, wherein when $R_1'$ is

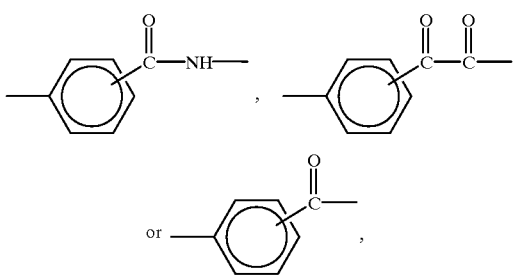

$R_3'$ is not $-NO_3$, and wherein $-R_1'-R_2'R_3'$, collectively, are not $-H$,

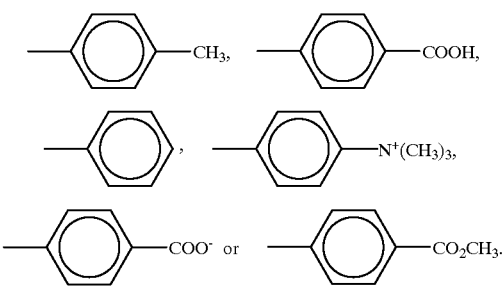

In yet a further embodiment, the present invention relates to a method of protecting cells from superoxide radical-, hydrogen peroxide- or peroxynitrite-induced toxicity comprising contacting the cells with an oxidant scavenger, eg a SOD, catalase or peroxidase mimetic, sufficient to effect the protection.

In another embodiment, the present invention relates to a method of inhibiting damage due to oxidation of a substance, for example, with the subsequent formation of $O_2^-$, hydrogen peroxide, or peroxynitrite comprising contacting the substance with an amount of a SOD mimetic sufficient to effect the inhibition.

In a further embodiment, the present invention relates to a method of inhibiting xanthine oxidase activity of a cell or tissue comprising contacting the cell or tissue with an amount of an oxidant scavenger sufficient to effect the inhibition.

In another embodiment, the present invention relates to a method of treating a pathological condition of a patient (eg, of the lungs of a patient) resulting from superoxide radical-induced degradation of NO· The method comprises administering to the patient (eg, to the airways of the patient) an effective amount of a compound having the activity and tissue specificity of SOD (eg EC-SOD) under conditions such that the treatment is effected.

In a further embodiment, the present invention relates to a method of treating an inflammatory condition in a patient in need of such treatment comprising administering to the patient an effective amount of an oxidant scavenger, eg a mimetic of SOD, (eg EC-SOD), catalase or peroxidase, under conditions such that the treatment is effected.

In another embodiment, the present invention relates to a method of treating a disorder resulting from aberrant smooth muscle function in a patient in need of such treatment comprising administering to the patient an effective amount of a mimetic of SOD (eg EC-SOD) under conditions such that the treatment is effected.

In a further embodiment, the present invention relates to a method of modulating physiologic functions of NO· in a mammal comprising administering to the mammal an oxidant scavenger in an amount sufficient to effect the modulation. Physiologic functions of NO· include its function as a smooth muscle relaxant, neurotransmitter and immune modulator.

In yet a further embodiment, the present invention relates to soluble oxidant scavengers, for example, mimetics of SOD, catalase or peroxidase, and to targeted forms thereof, in particular, mimetics of EC-SOD having a GAG binding moiety attached thereto.

In another embodiment, the present invention relates to an isolated EC-SOD gene sequence, or portion thereof.

Objects and advantages of the present invention will be clear from the description that follows.

Note the intense labeling of EC-SOD in association with type I collagen and the lack of labeling in association with elastin (E). In addition, absorption of anti-EC-SOD antibody abolished all labeling for EC-SOD in association with type I collagen. (Bars=200 nm).

Figure 17:
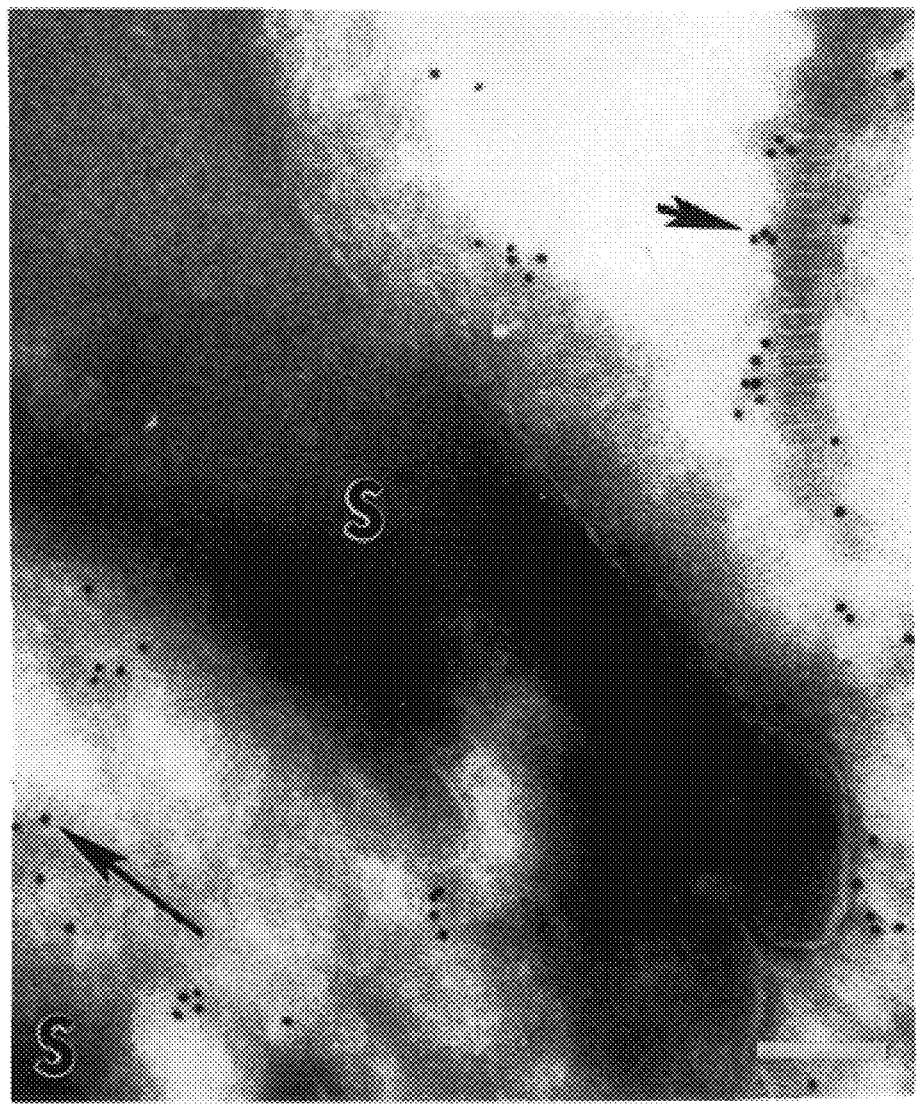

FIG. 17 shows the electron microscopic immunolocalization of EC-SOD around vascular smooth muscle. Tissues were labeled using the antibody to recombinant human EC-SOD (40 µg/ml). Antibody was detected using 10 nm protein-A gold. There is a high degree of labeling in the connective tissue matrix around the vascular smooth muscle cell (S) in association with type I collagen (short arrow), and other unidentified matrix elements (long arrow). (Bars=200 nm).

Figure 18A:
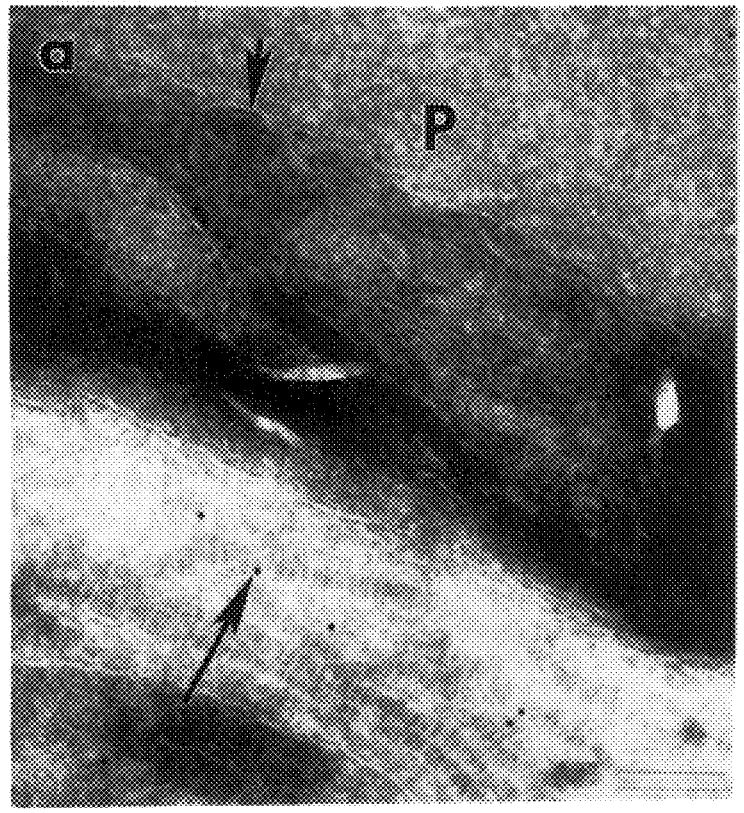
Figure 18B:
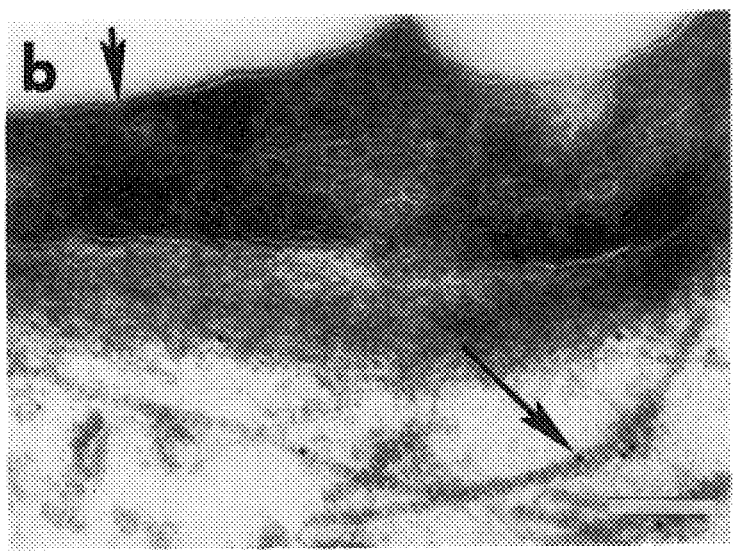

FIGS. 18A-18B show the electron miscropic immunolocalization of EC-SOD on the surface of pulmonary endothelial cells. Tissues were labeled using the antibody to recombinant human EC-SOD (40 µg/ml). Antibody was detected using 10 nm protein-A gold. A, Endothelial cell from a small muscular pulmonary artery, B, Endothelial cell from a pulmonary capillary. No labeling for EC-SOD was on the surface of the endothelial cells (short arrows). EC-SOD is seen in the plasma (P) and is associated with extracellular matrix proteins beneath the endothelium (long arrows). (Bars=200 nm).

Figure 19:

FIG. 19 shows the electron microscopic immunolocalization of EC-SOD around bronchial epithelial cells. Tissues were labeled using the antibody to recombinant human EC-SOD (40 µg/ml). Antibody was detected using 10 nm protein-A gold. EC-SOD was found in the junction between the epithelial cells (arrow) and was also seen to some extent inside the cells. (Bars=200 nm).

FIGS. 20A–20D show a partial restriction map, sequencing strategy, genomic structure, and protein structure of human EC-SOD Clone #7. FIG. 20A, a partial restriction map of human EC-SOD genomic clone #7 is shown in the 5' to 3' orientation. A 1 kb size marker is indicated. B, BamH I; H, Hind III; P, Pst I; S, Sal I; K, Kpn I; E, EcoR I. In FIG. 20B, the subcloning and sequencing strategy is shown. Various size overlapping restriction fragments were subcloned into the plasmid vector pGEM3Zf(+) for subsequent DNA sequence analysis. All DNA was sequenced on both strands using Sequenase (USB) and double-stranded DNA template, except for ~2 kb of the 3' 7K36 fragment in which only one orientation was sequenced. In FIG. 20C, the exon/intron structure of the human EC-SOD gene is shown. The position of the coding region for preEC-SOD in exon 3 is shown by the dashed lines. In FIG. 20D, the four structural domains of human EC-SOD protein are diagrammed. The signal peptide is indicated by an arrow. This is followed by the mature glycosylated (CHO) amino terminal peptide domain. A third region has very high amino acid sequence homology to human CuZn-SOD. The carboxy terminal domain has multiple charged basic residues (+) which are critical for binding heparin glycosaminoglycan.

Figure 21A:
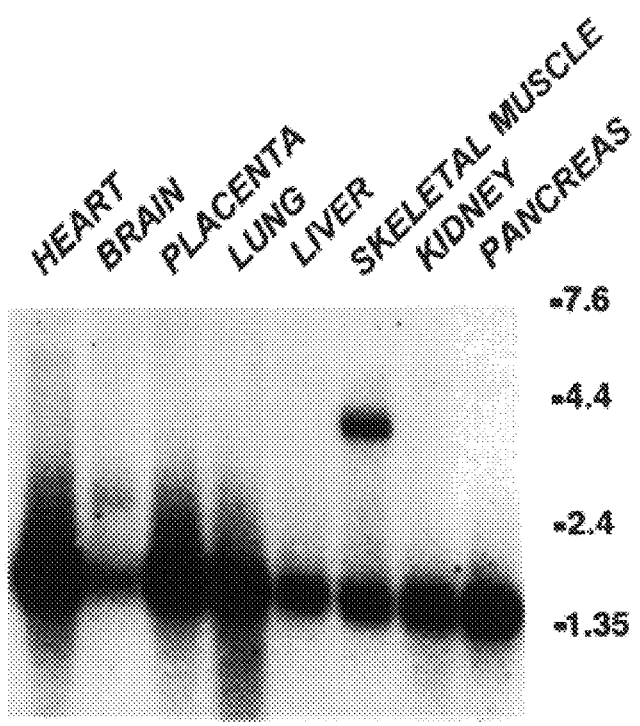
Figure 21B:
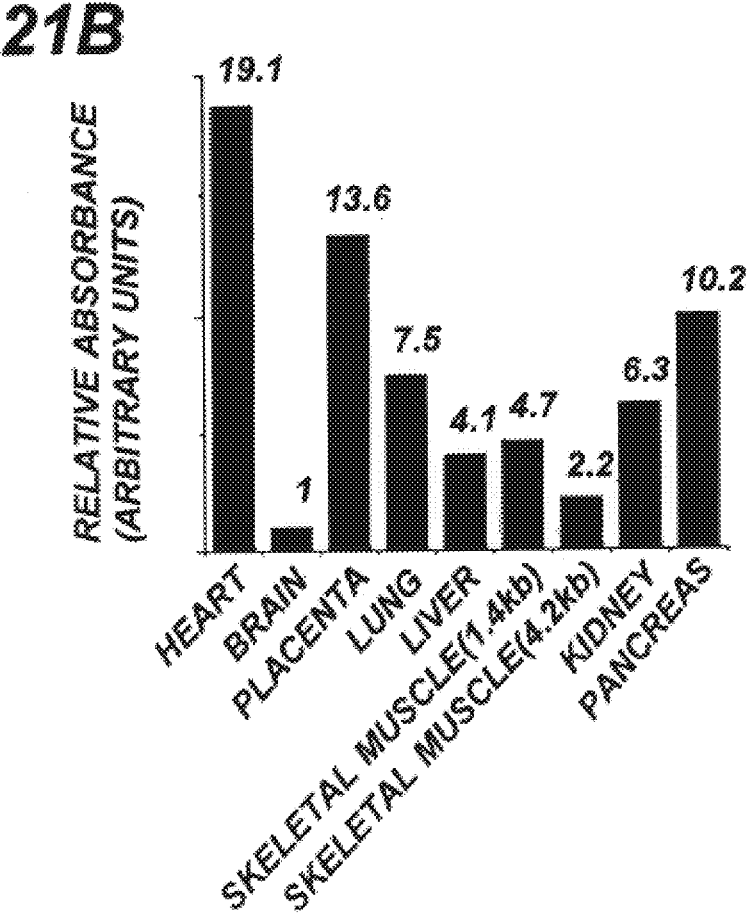

FIGS. 21A-21B show human multiple tissue Northern blots of EC-SOD. FIG. 21A, two µg of poly A(+) mRNA from eight different human tissues were electrophoresed on a denaturing agarose gel, transferred to a charged nylon membrane, and probed with [$^{32}$P]-labeled antisense human EC-SOD cRNA. RNA molecular size markers (kilobases) are shown on the right. Quantitative transfer was monitored by ethidium bromide staining. The results demonstrate a unique 1.4 kb mRNA present in all eight tissues examined. Interestingly skeletal muscle demonstrates a second, larger mRNA of ~4.2 kb, while brain shows a faint approximately 2.2 kb band. In FIG. 21B, bands corresponding to EC-SOD mRNA were quantitated by laser densitometric scanning, normalized to the 1.4 kb brain band, and expressed as relative absorbance units.

Figure 22A:
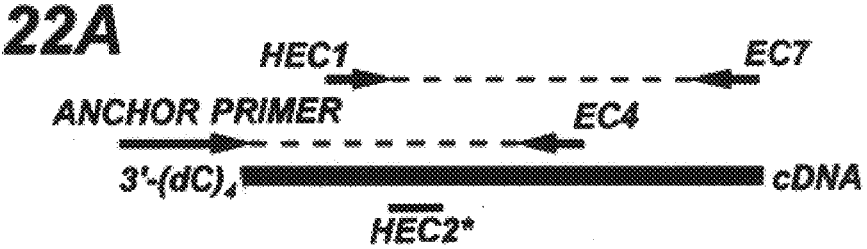
Figure 22B:
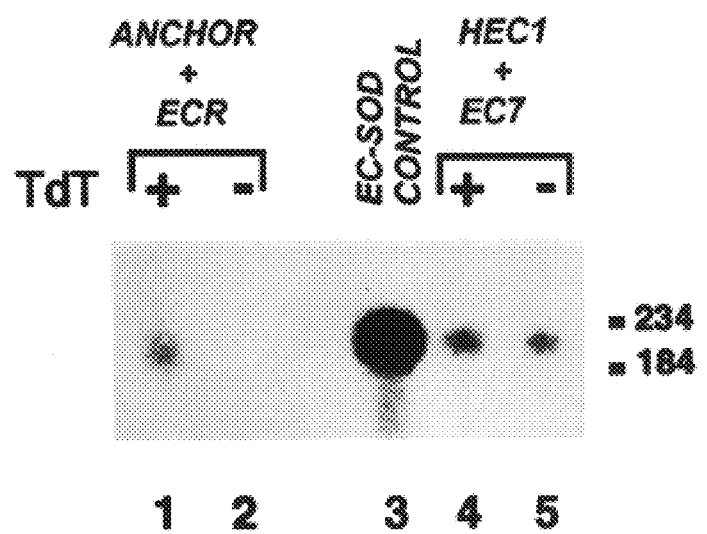

FIGS. 22A-22B show analysis of the transcription initiation site. The 5' rapid amplification of cDNA ends (5' RACE) technique was used to identify the site of transcription initiation for the human EC-SOD gene. In FIG. 22A, a schematic diagram illustrates the annealing sites for the various oligonucleotides. The dark line represents first-strand reverse transcribed cDNA of human heart poly A(+) mRNA which has been primed with EC7 (an EC-SOD gene specific primer) and poly C tailed using terminal deoxynucleotidyl transferase (TdT). HEC1, HEC2, EC4, and EC7 are 5' human EC-SOD gene specific primers. The anchor primer is supplied with the 5' RACE kit (GIBCO BRL) and hybridized to the poly C tail. In FIG. 22B, PCR was used to amplify segments of DNA using [anchor+EC4] or [HEC1+EC7] as primers and either poly C tailed (+TdT, lanes 1 & 4) or non-poly C tailed (-TdT, lanes 2 & 5) cDNA as template. Lane 3 includes PCR amplified DNA using [HEC1+EC7] as primers and a full-length human EC-SOD cDNA as template. The resulting amplified DNAs were electrophoresed on a 2% agarose gel, transferred to charged nylon membranes, and probed with [$^{32}$P]-labeled HEC2, a 5' nested gene specific EC-SOD primer. DNA molecular weight markers were run between lanes 2 and 3. The expected size of the PCR amplified region in lanes 3, 4 and 5 is 217 bp. Only a single band is seen in lane 1, with a molecular size of approximately 185 to 200 bp.

Figure 23:
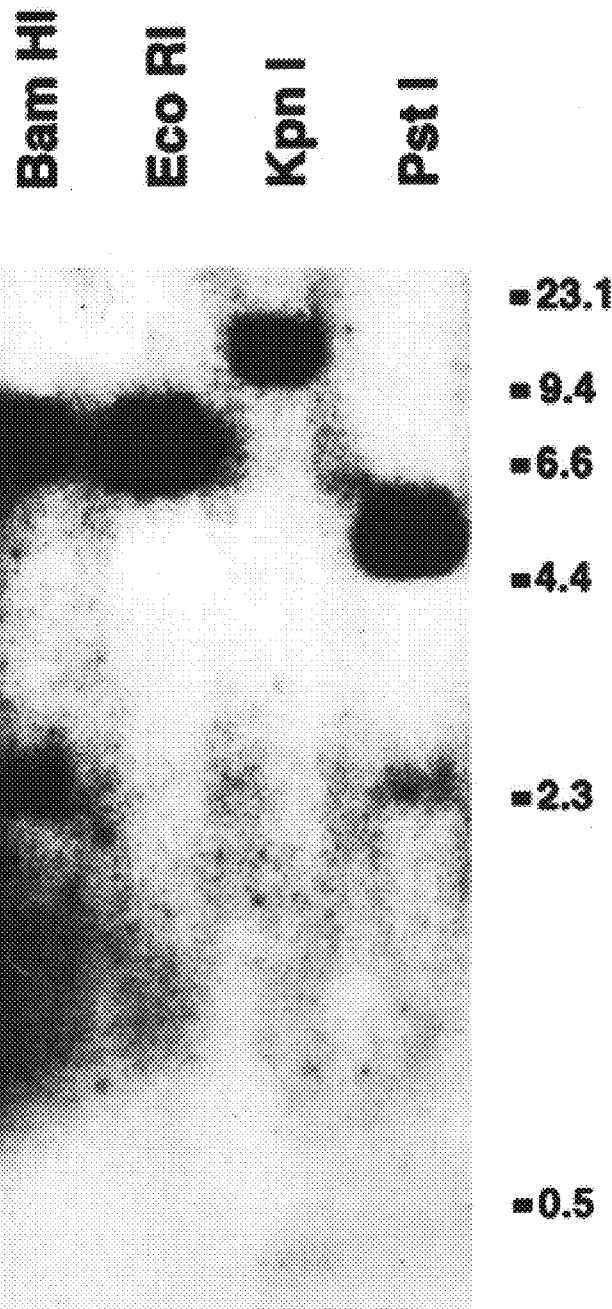

FIG. 23 shows genomic Southern blot analysis of the human EC-SOD gene. Ten micrograms of human genomic DNA were completely digested with each of the restriction enzymes shown, electrophoresed on a 1% agarose gel and transferred to charged nylon membranes. The blots were proved with a [$^{32}$P]-labeled EC-SOD partial length cRNA which corresponds to the first approximate 1050 nucleotides and autoradiographed. The specific restriction endonuclease is shown at the top of each lane. DNA molecular size markers (in kilobases) are shown on the right.

FIGS. 24 through 24.5 shows the nucleotide sequence and deduced amino acid sequence of the human EC-SOD gene. The complete nucleotide sequence of the human gene is shown. The deduced amino acid sequence of the signal peptide and mature protein is indicated using the single letter amino acid code.

Figure 25:
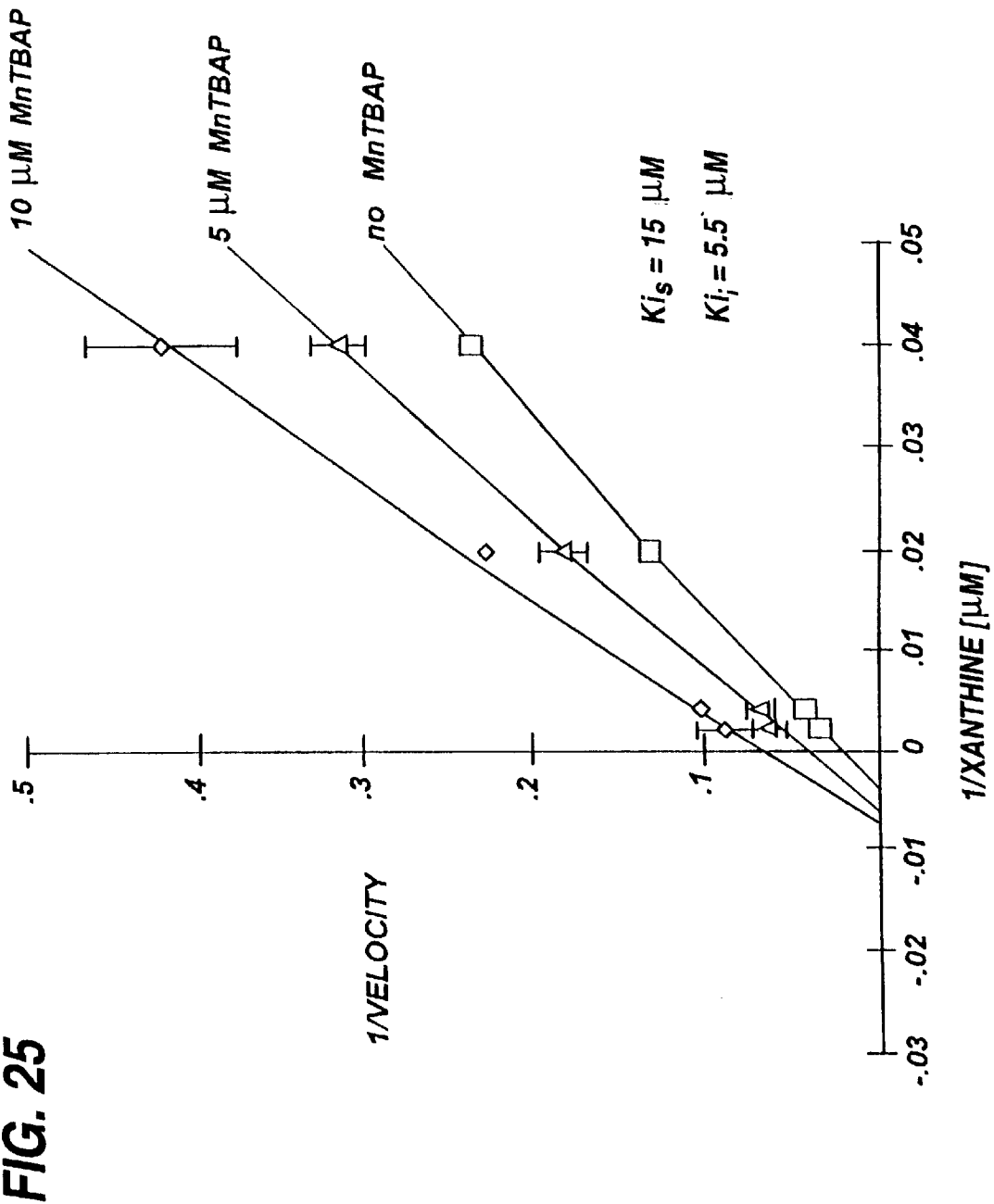

FIG. 25 shows a Lineweaver-Burk plot demonstrating non-competitive inhibition of xanthine oxidase by MnTBAP.

Figure 26:
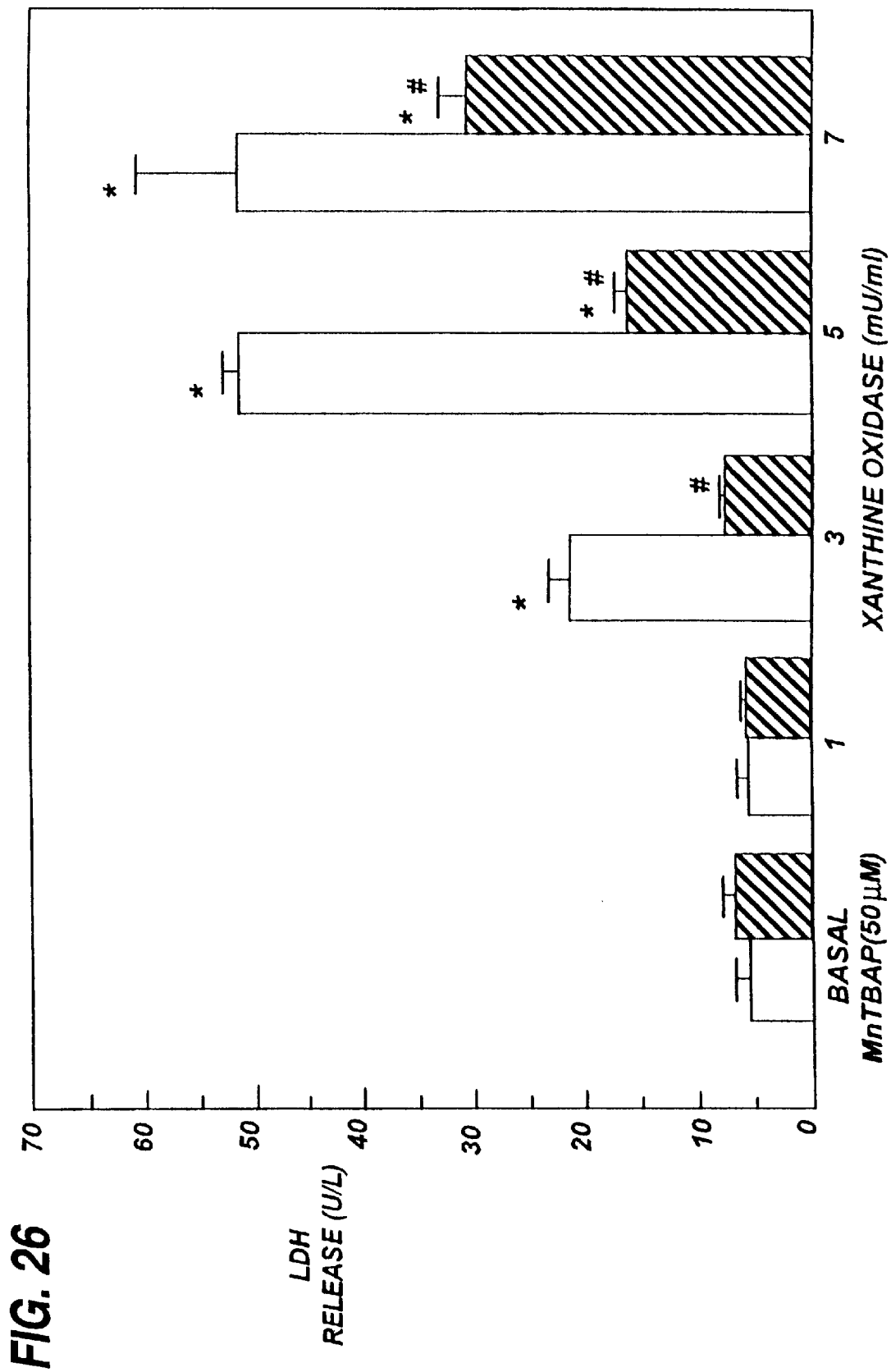

FIG. 26 shows the protection of pulmonary artery endothelial cells from xanthine oxidase-induced injury by MnTBAP. Control ▢; MnTBAP ▨.

Figure 27:
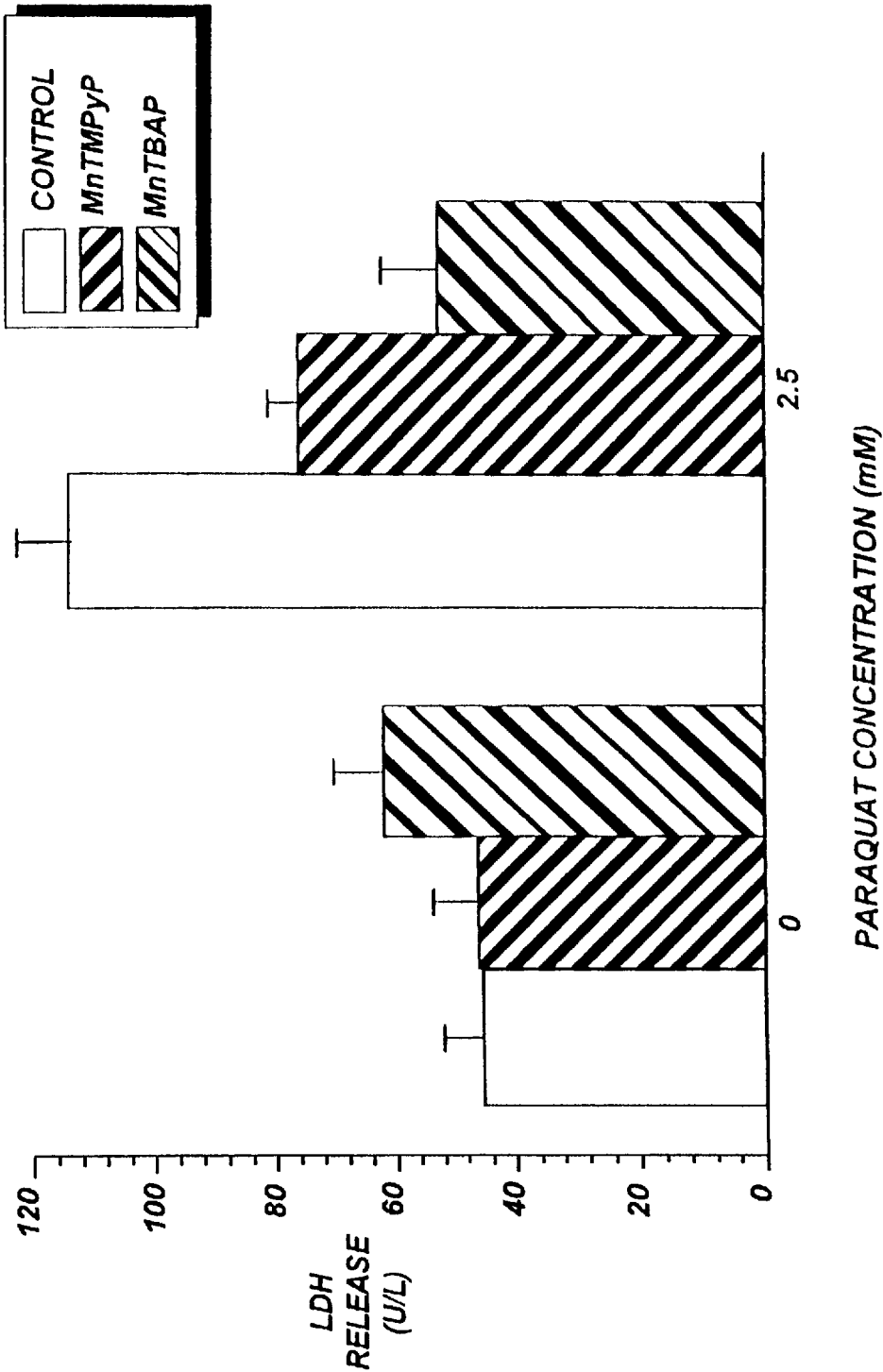

FIG. 27 shows the protection of lung epithelial cells from paraquat-induced injury of SOD mimetics.

Figure 28:
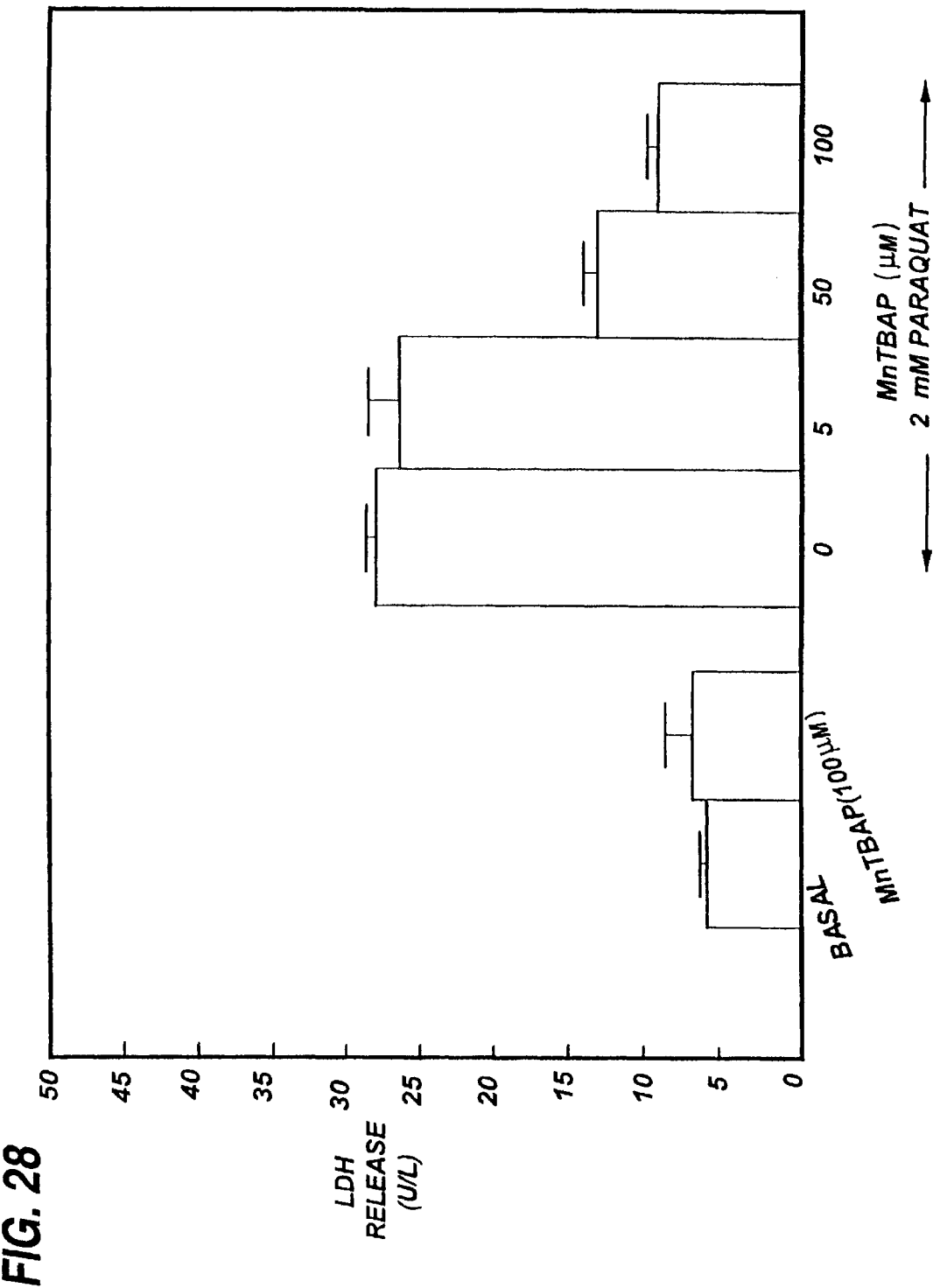

FIG. 28 shows the protection of pulmonary artery endothelial cells from paraquat-induced injury by MnTBAP.

Figure 29:
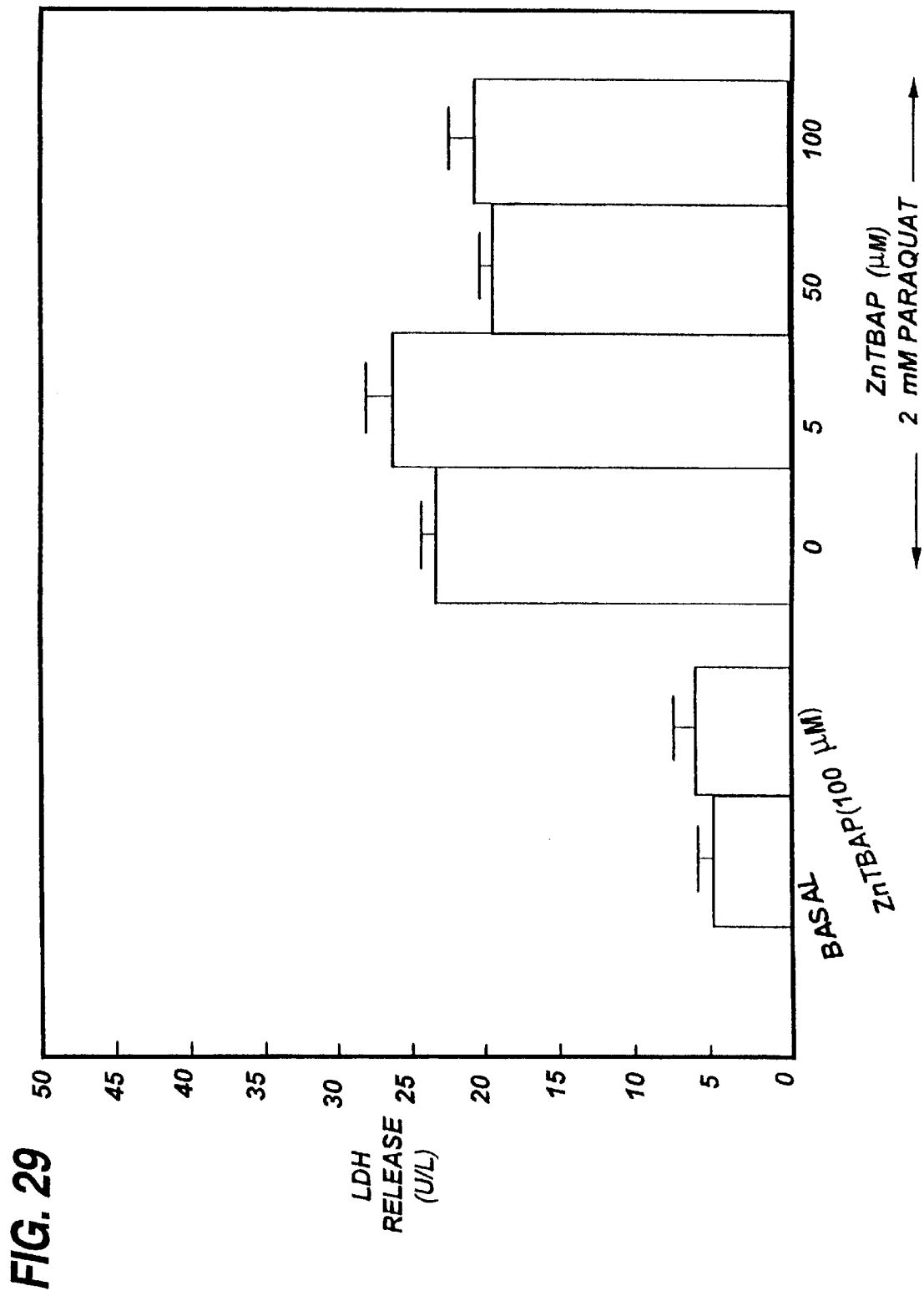

FIG. 29 shows the lack of protection of pulmonary artery endothelial cells from paraquat-induced injury by ZnTBAP.

Figure 30:
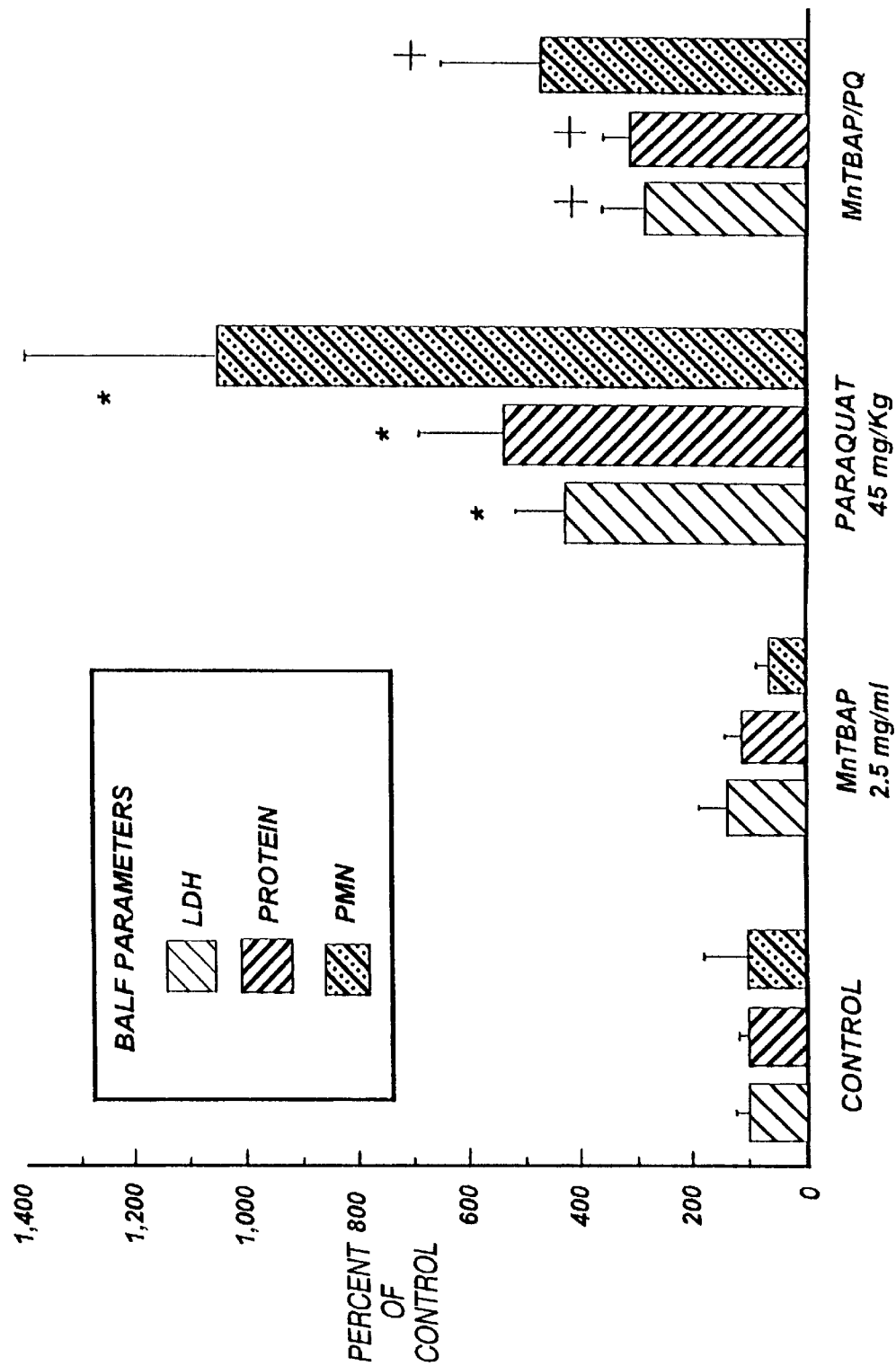

FIG. 30 shows the protection of MnTBAP against paraquat-induced lung injury.

Figure 31:
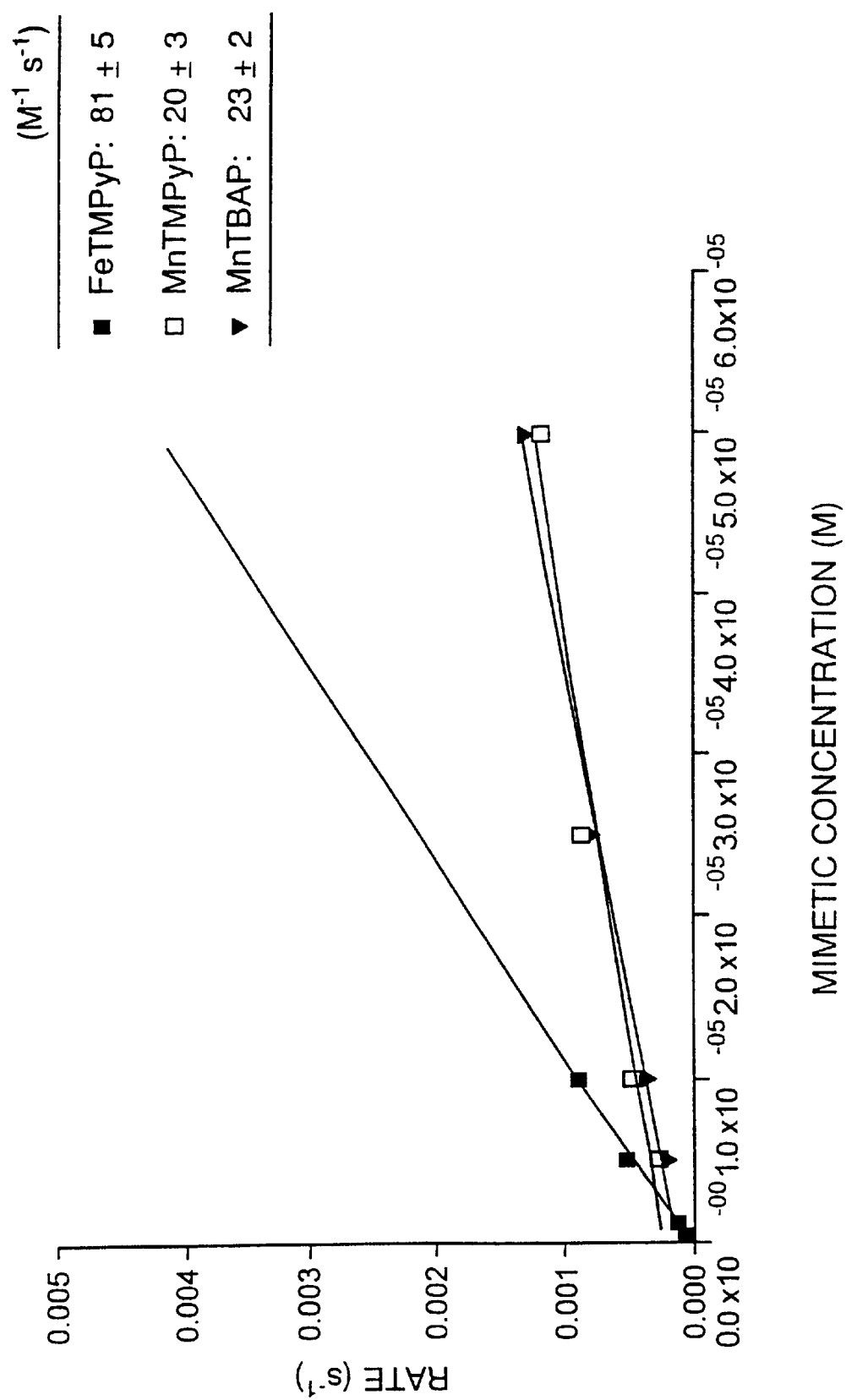

FIG. 31 shows a second order rate constant plot for catalase mimetics.

Figure 32:
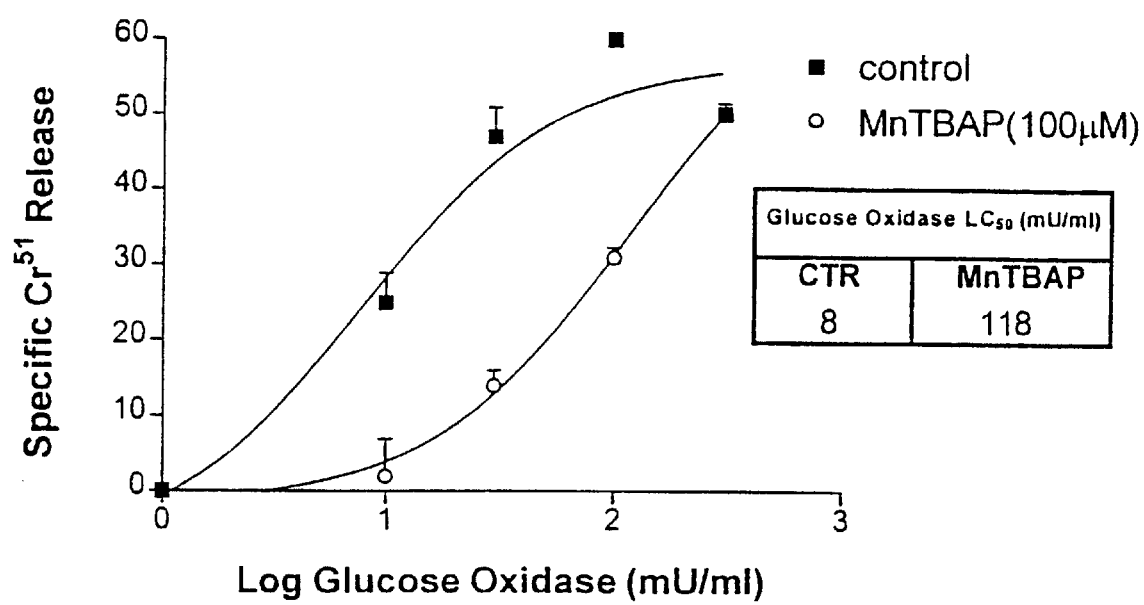

FIG. 32 shows the effect of MnTBAP on $H_2O_2$-induced endothelial injury.

FIGS. 33A and 33B show the reduction by MnTBAP and MnTmPyP of endothelial cell injuries caused by exposure to glucose oxidase-produced hydrogen peroxide. FIG. 33C shows that ZnTBAP does not reduce hydrogen peroxide-induced endothelial cell injury. FIG. 33D shows that endothelial cells are not protected from hydrogen peroxide-induced injury by CuZnSOD.

Figure 34A:
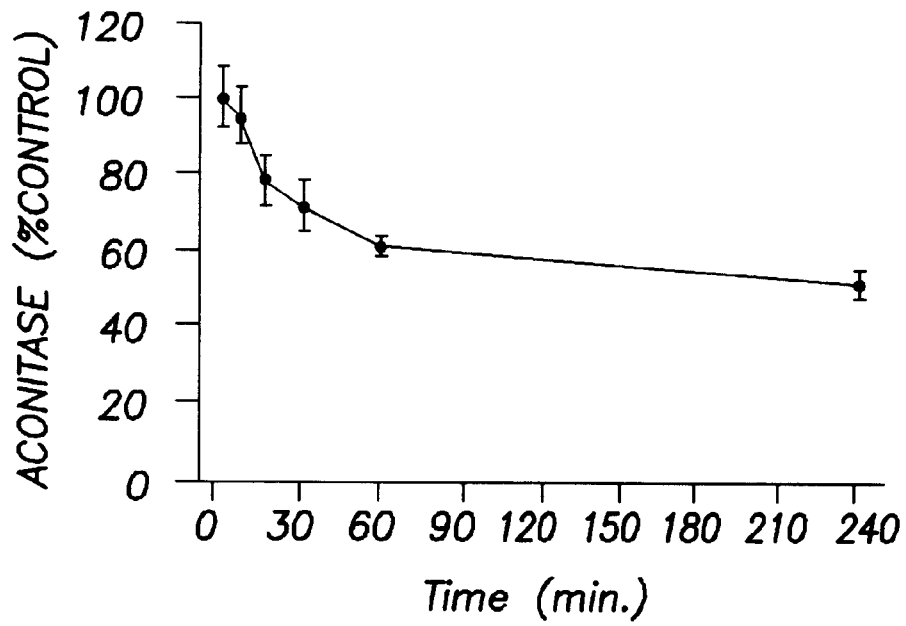
Figure 34B:
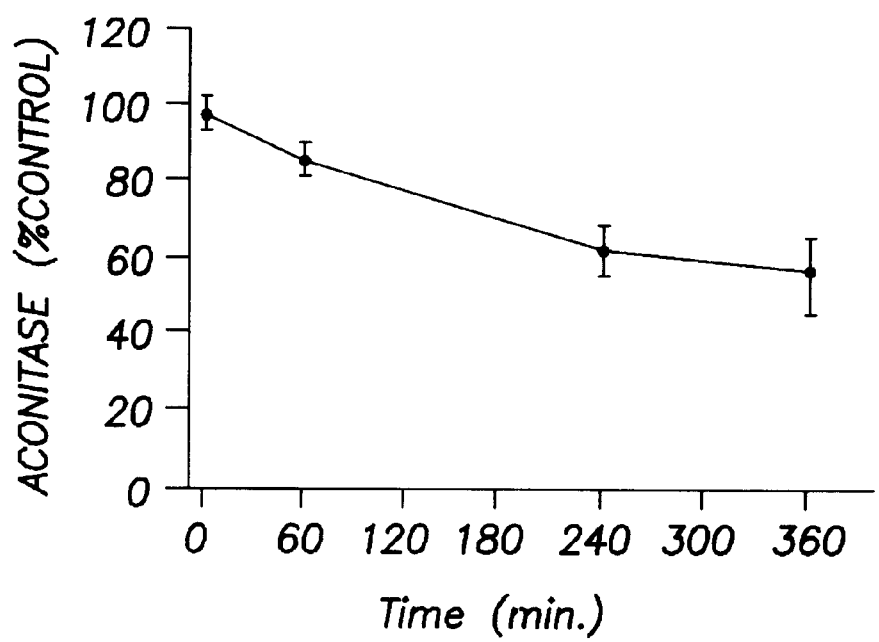

FIGS. 34A and 34B show the time course of NMDA-and KA-induced inactivation of aconitase. FIG. 34A. Cortical cells treated with vehicle or 50 $\mu$M NMDA for 0, 5, 15, 30, 60 and 240 min. and aconitase activity measured in cell lysates. Each point represents the mean±S.E.M. (n=6–8). FIG. 34B. Cortical cells treated with vehicle or 300 $\mu$M kainate for 0, 60, 240, and 360 min. and aconitase activity measured in cell lysates. Each point represents the mean±S.E.M. (n=4–8).

Figure 35A:
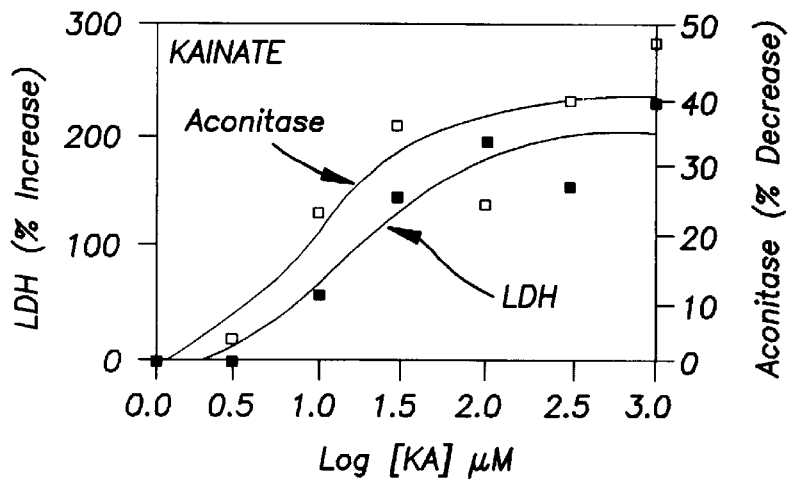
Figure 35B:
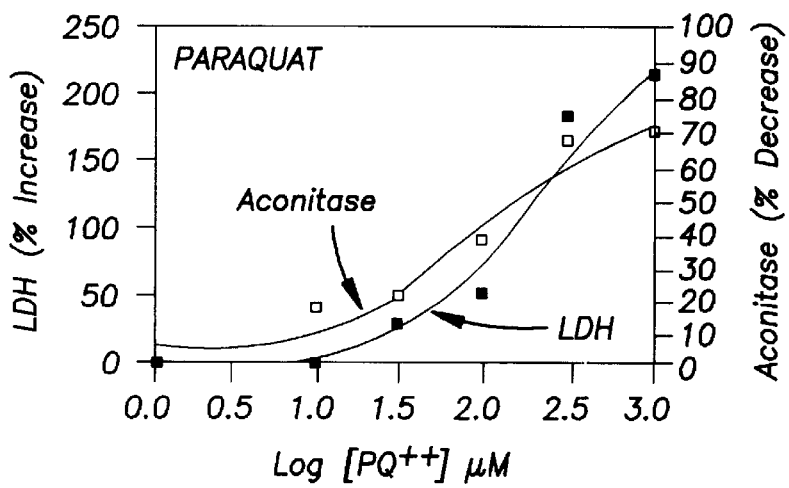
Figure 35C:
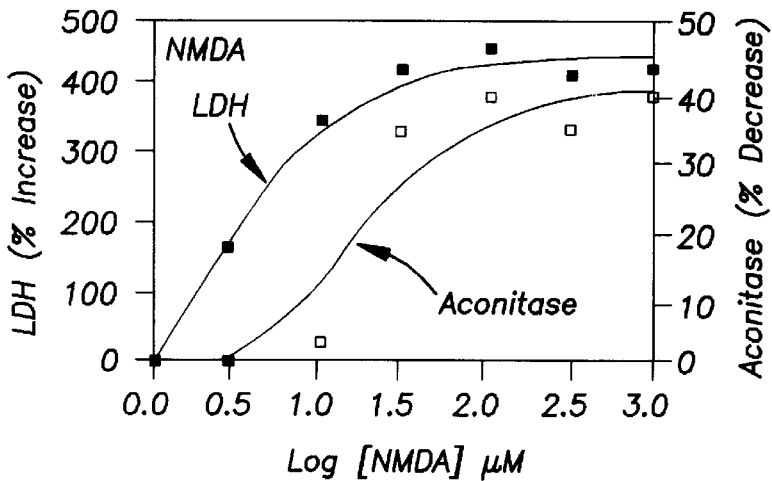

FIGS. 35A–35C show the correlation of toxicity with aconitase inactivation. Concentration-dependence of KA (FIG. 35A), PQ$^{++}$ (FIG. 35B) and NMDA (FIG. 35C) to induce toxicity (left axis) and aconitase inactivation (right axis) were determined. Values normalized as a percent LDH release or aconitase inhibition and plotted to assess the correlation between LDH release and aconitase inactivation. Closed squares represent LDH and open squares represent aconitase. Curves were computer-generated using non-linear regression analysis using the equation Y=Bottom+(Top-Bottom)/1+10$^{LogEC50-X}$ (GraphPad Prism). Each point represents the mean value (n=4–6).

Figure 36A:
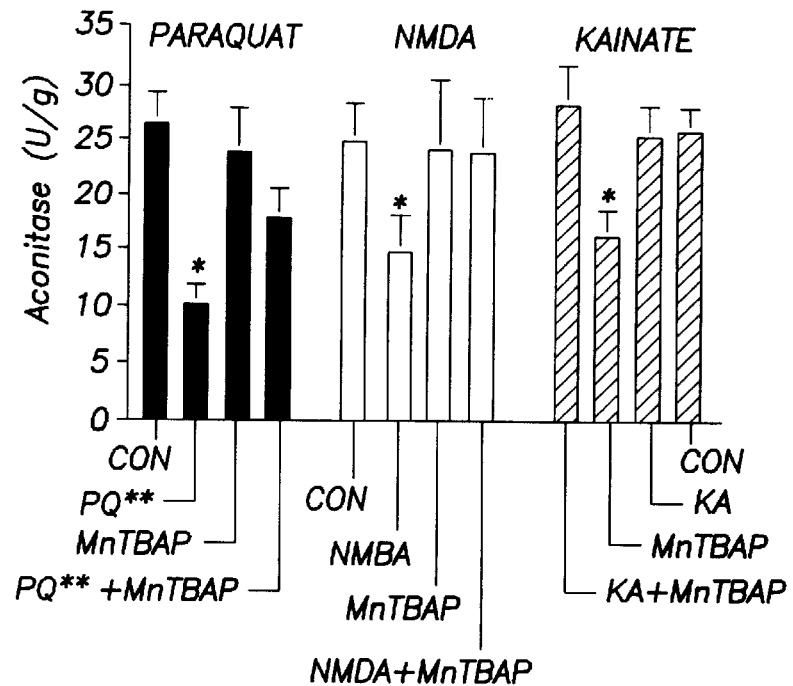
Figure 36B:
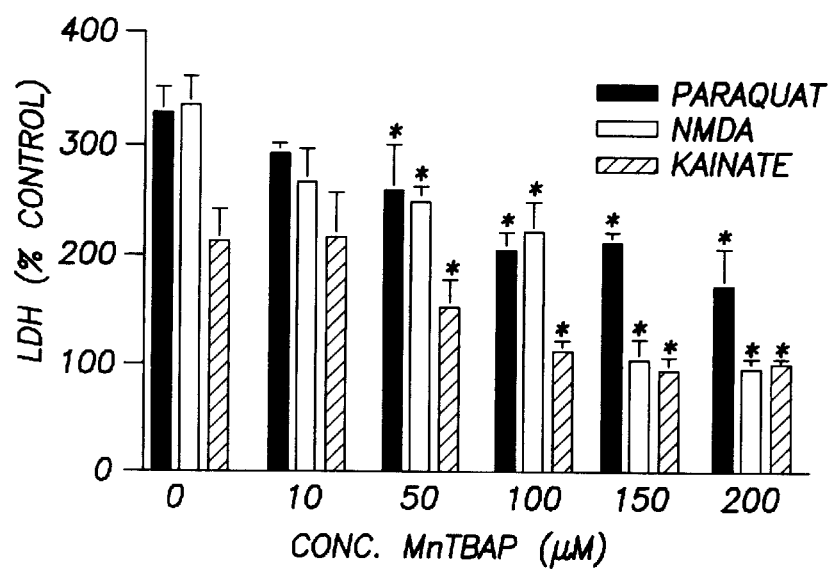

FIGS. 36A and 36B show the blockade of aconitase inactivation and neurotoxicity by MnTBAP. FIG. 36A. Cortical cells were treated with 150 $\mu$M PQ$^{++}$ for 3 hr. (solid bars), 50 $\mu$M NMDA for 1 hr. (open bars) or 300 $\mu$M KA for 6 hr. (hatched bars) in the presence or absence of 200 $\mu$M MnTBAP (present 15 min. prior to and throughout the duration of treatment) and aconitase activity measured in cell lysates. Bars represent mean±S.E.M. (n=8–12). Asterisk indicates a difference from all other treatments (p<0.05, one-way ANOVA). FIG. 36B. Cortical cells were treated with 150 $\mu$M PQ$^{++}$ (solid bars), 50 $\mu$M NMDA (open bars) or 300 $\mu$M KA (hatched bars) in the presence of varying concentrations of MnTBAP (present 15 min. prior to and throughout the duration of treatment) for 18 hr. and LDH release measured in the medium. Asterisk represents a difference from controls (agonist in the absence of MnTBAP; p<0.05 Dunnet's test). Bars represent mean±S.E.M. (n=3–6).

Figure 37:
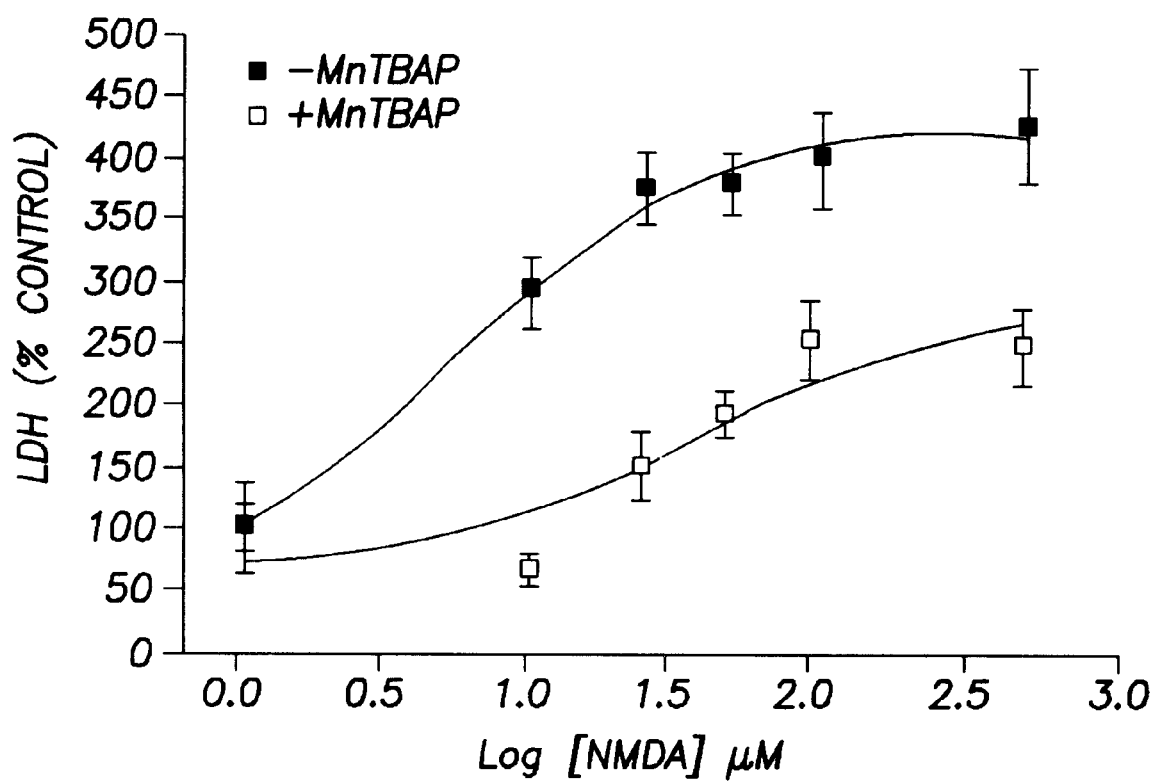

FIG. 37 shows the inhibition of NMDA toxicity by MnTBAP. Cortical cells were treated with varying concentrations of NMDA in the presence and absence of 200 $\mu$M MnTBAP for 18 hr. and LDH measured in media. Each points represents mean±S.E.M., n=3–4.

Figure 38A:
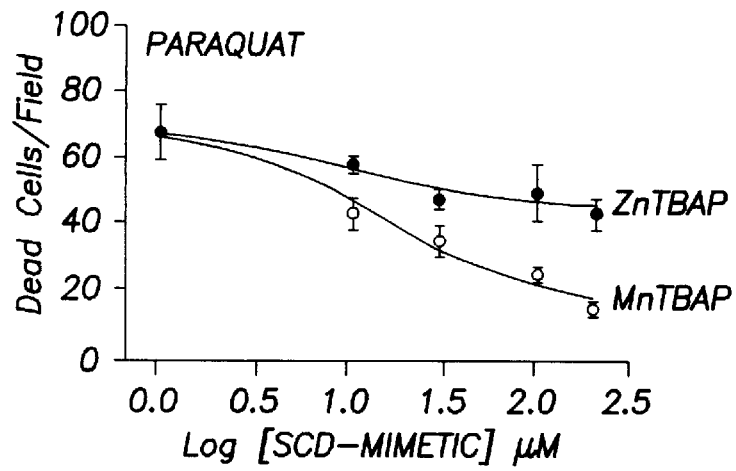
Figure 38B:
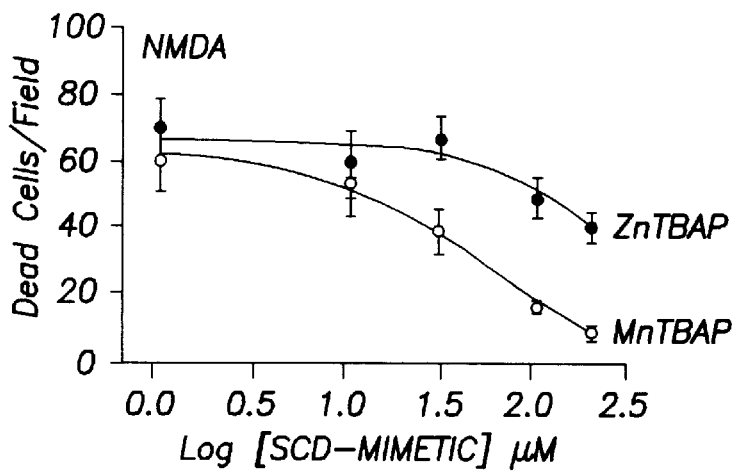
Figure 38C:
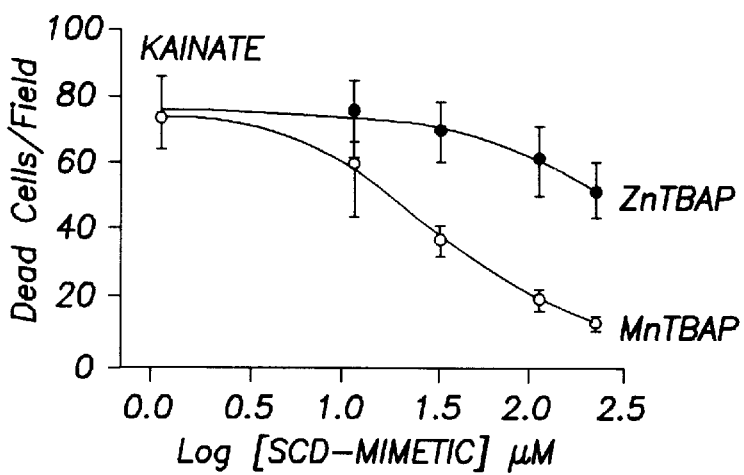

FIGS. 38A–38C show the differential effect of MnTBAP and ZnTBAP on cell death. Cortical cells were treated with 150 $\mu$M PQ$^{++}$ (FIG. 38A), 50 $\mu$M NMDA (FIG. 38B) or 300 $\mu$M KA (FIG. 38C) in the presence or absence of varying concentrations of MnTBAP (open squares) or ZnTBAP (closed squares) and dead cells stained with EthD-1. Images of EthD-1-positive cells were stored and counted in randomly selected fields using a digital image analyzer. Data are expressed as the number of dead cells per field. Each point represents measurements made from 1200–1500 cells.

Figure 39:
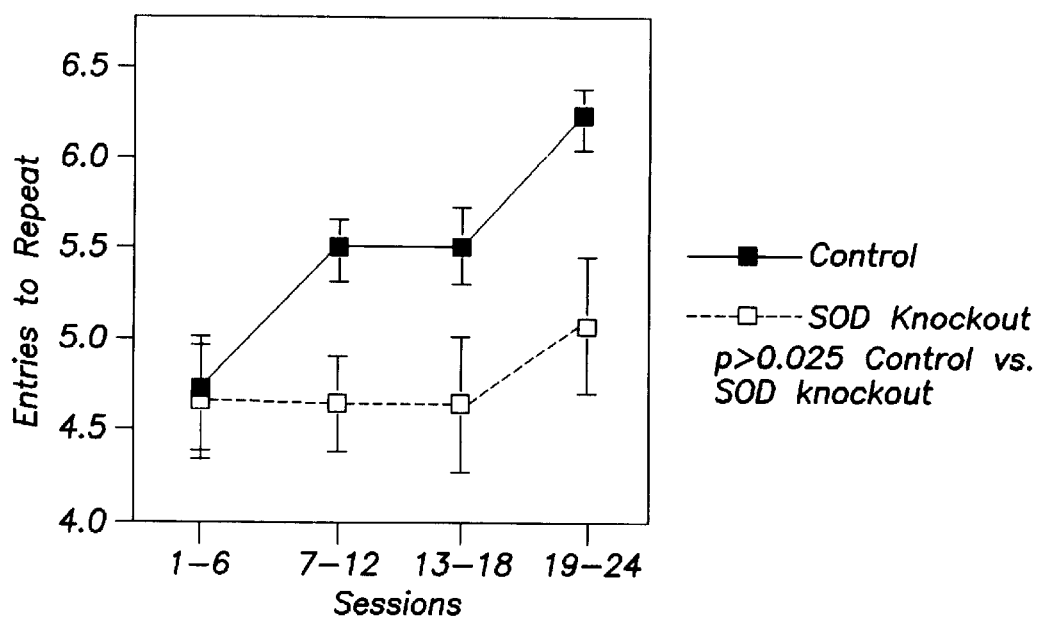

FIG. 39 shows the effect on learning of removal of the EC SOD gene in a mouse model.

Figure 40:
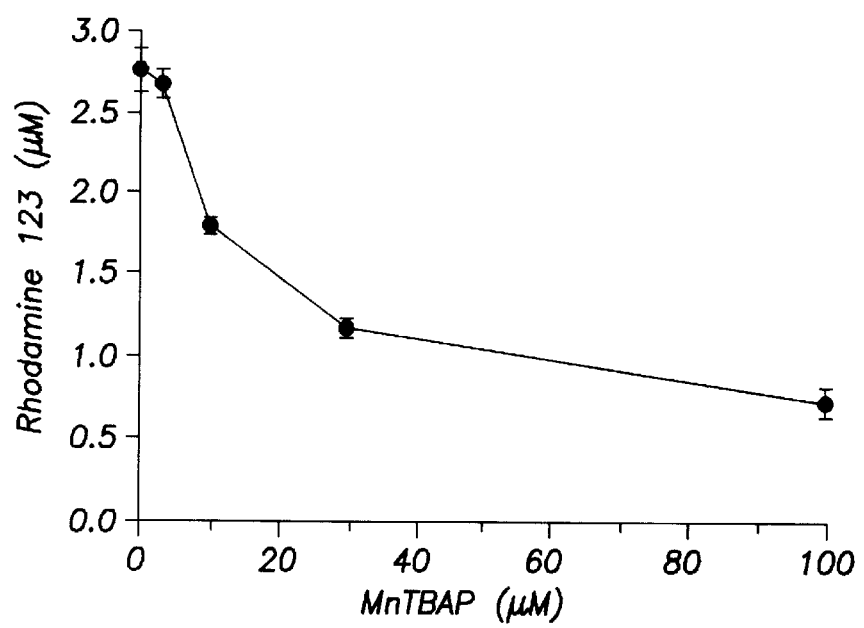

FIG. 40. Effect of Mn(III)tetrakis (4-benzoic acid) porphyrin (MnTBAP) (3–100 $\mu$M) on the oxidation of dihydrorhodamine 123 to rhodamine 123 in response to peroxynitrite (5 $\mu$M). Data are expressed as means±s.e.m. of triplicate determinations.

Figure 41A:
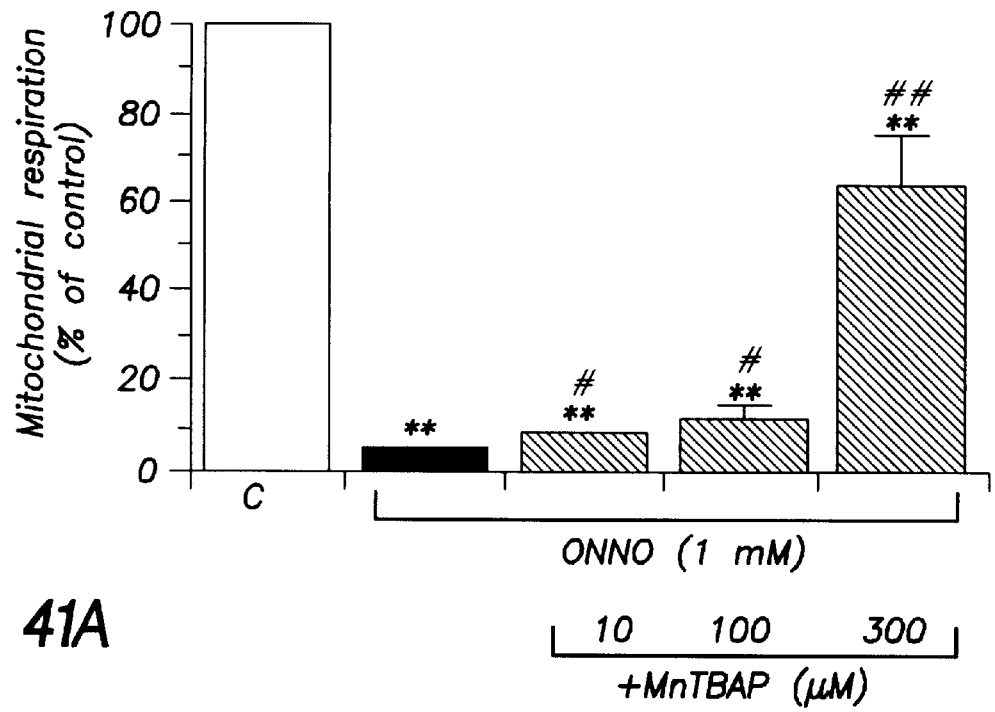
Figure 41B:
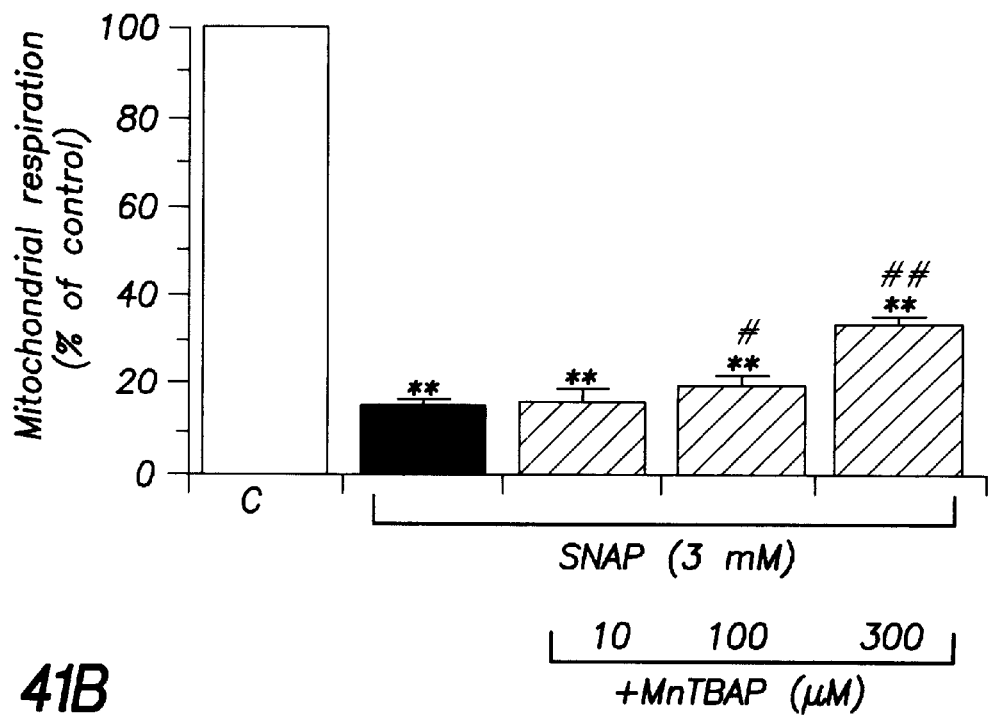
Figure 41C:
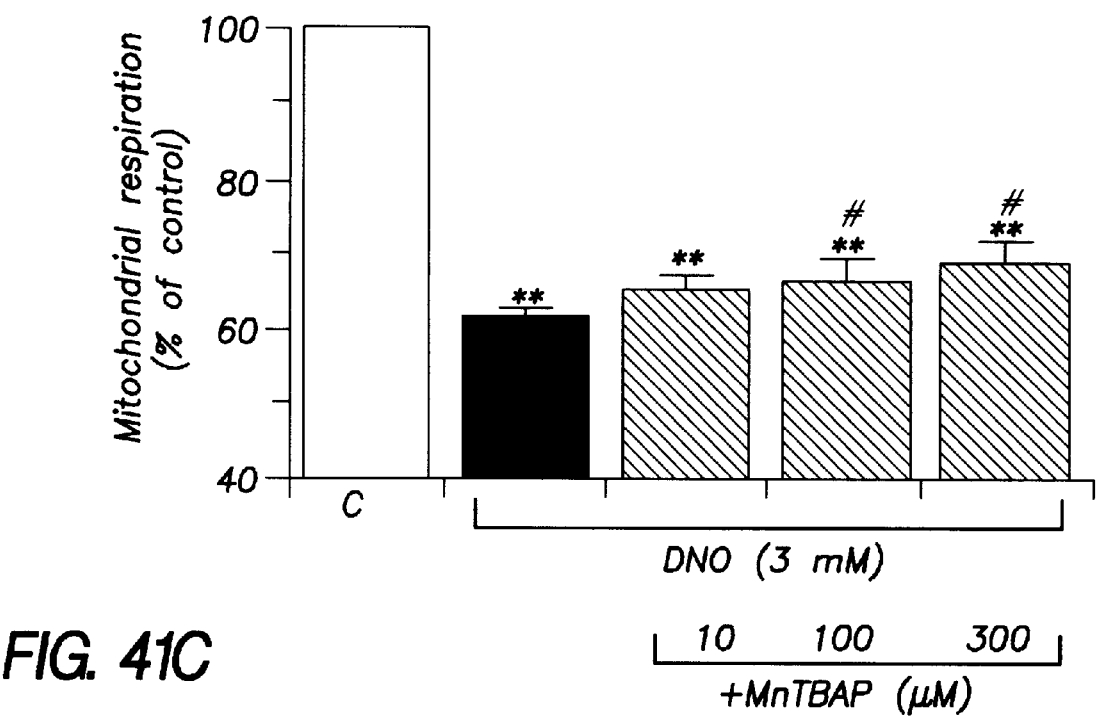

FIG. 41. Suppression by the peroxynitrite (FIG. 41A) and the NO donor compounds S-nitroso-N-acetyl-DL-penicillamine (SNAP, 3 mM) (FIG. 41B) and diethylamine:NO NONOate (DNO) (FIG. 41C) on mitochondrial respiration (expressed as percent of respiration of unstimulated cells) in J774 macrophages, and the protective effect of Mn(III)tetrakis (4-benzoic acid) porphyrin (MnTBAP) (10–300 $\mu$M) against this suppression. Data are expressed as means±s.e.m. of n=12 wells. **p<0.01 represents significant effect of SNAP when compared to control (C) values; #,##represent significant protective effects of MnTBAP (p<0.05 and p<0.01, respectively).

FIGS. 42A–D show synthetic reaction schemes.

DETAILED DESCRIPTION OF THE INVENTION

The present invention relates to methods of protecting against the deleterious effects of oxidants, particularly, superoxide radicals, hydrogen peroxide and peroxynitrite, and to methods of preventing and treating disease states that involve or result from oxidant stress. The invention also relates methods of modulating biological processes involving oxidants, including superoxide radicals, hydrogen peroxide, nitric oxide and peroxynitrite. The invention further relates to compounds and compositions, including low molecular weight antioxidants (eg mimetics of scavengers of reactive oxygen species, including mimetics of SODs, catalases and peroxidases) and formulations thereof, suitable for use in such methods.

Mimetics of scavengers of reactive oxygen species appropriate for use in the present methods include manganic derivatives of methine substituted porphines, or pharmaceutically acceptable salts thereof. The methine substituents can be selected so as to facilitate electron exchange between the mimetic metal (eg Mn) and the oxygen radical. Substituents that withdraw electrons from the ring assist in delocalizing the charge of the metal and thereby enhance catalytic activity. Accordingly, the substituents can be selected so as to modulate the redox potential of the porphine. Substituents can also be selected so as to render the porphyrin resistant to degradation by hemeoxygenase. Hemeoxygenase, a key enzyme in normal porphyrin degradation and an enzyme that plays a role in the regulation of inflammation, attacks at the methine bridge carbons. By designing compounds not susceptible to attack (eg by introducing substituents at the methine bridge carbons), the half life of the porphyrin can be increased. Such compounds have the further advantage that they do not interfere with normal porphyrin metabolism. Selection of substituents can also be made based on a result sought to be achieved. For example, when passage through cell membranes is advantageous in a given treatment regimen, non-polar substituents can be selected so as to render the mimetic lipid soluble. Substituents can also be selected so as to render the mimetic capable of binding to cell surface or extracellular matrix elements. Such substituents can be selected so as to target the mimetic on the basis of charge, shape, structure, etc. Targeting substituents can be specific, for example, for certain cell surface receptors (eg mannose receptors found on epithelial cells) or for certain sugars or lectins present on the cell surface.

In one embodiment, the mimetics are of the formula:

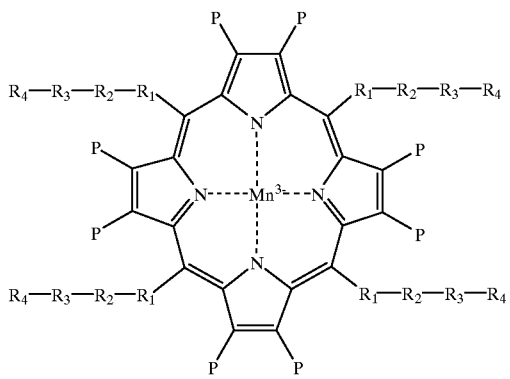

wherein:
$R_1$ is a bond,

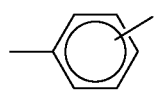

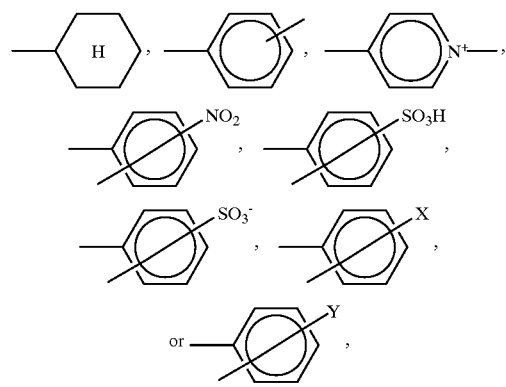

wherein X is a halogen and Y is an alkyl group and wherein

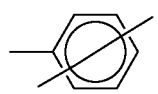

indicates bonding to $R_2$ at any position and

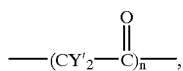

indicates bonding to $R_2$ and the substituent at any position; and
$R_2$ is a bond, $-(CY'_2)_n^-$, $-(CY'_2-CY'=CY')_n^-$, $-(CY'_2-CY'_2-CH=CH)_n^-$, $-(CY'=CY')_n^-$, or $$-(CY'_2-\overset{\overset{O}{\|}}{C})_n^-,$$

wherein Y' is hydrogen or an alkyl group and wherein n is 1 to 8;
$R_3$ is a bond, hydrogen, $-Y''$, $-OH$, $-NH-$, $-N^+(Y'')_3$, $-COO-$, $-COO^-$, $-SO_3-$, $-SO_3^-$, $-C-PO_3H-$ or $-C-PO_3H^-$, wherein Y'' is an alkyl group, and $R_4$ is nothing, hydrogen, a cell surface or extracellular matrix targeting moiety or a linker-cell surface or extracellular matrix targeting moiety (wherein a "linker" is a moiety that links the mimetic core (porphyrin ring and $R_1$, $R_2$, $R_3$) to the targeting moiety).
In a more specific embodiment,
$R_1$ is a bond,

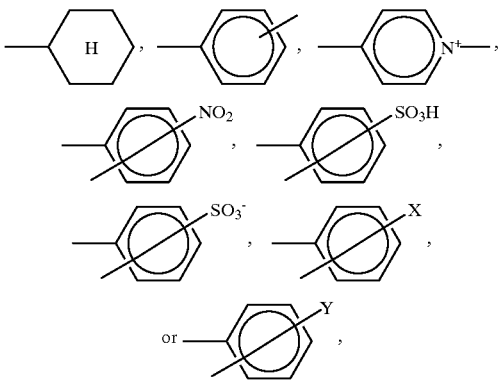

wherein X is Cl or Br and Y is a $C_{1-4}$ alkyl group;
$R_2$ is a bond, $-(CY'_2)_n^-$, $-(CY'_2-CY'=CY')_n^-$, $-(CY'_2-CY'_2-CH=CH)_n^-$, $-(CY'=CY')_n^-$, or

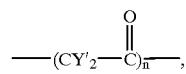

wherein Y' is hydrogen or a $C_{1-4}$ alkyl group and wherein n is 1 to 4;
$R_3$ is a bond, hydrogen, Y'', $-OH$, $-NH-$, $-N^+(Y'')_3$, $-COO-$, $-COO^-$, $-SO_3-$, $-SO_3^-$, $-C-PO_3H-$ or $-C-PO_3H^-$, wherein Y'' is a $C_{1-4}$ alkyl group, and
$R_4$ is nothing, hydrogen, a cell surface or extracellular matrix targeting moiety or a linker-cell surface or extracellular matrix targeting moiety.
In a further specific embodiments,
$R_1$ is a bond,

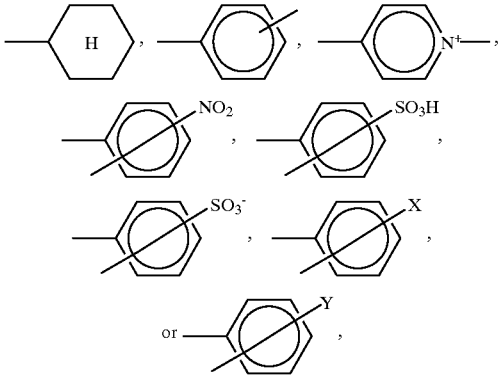

wherein X is Cl or Br and Y is methyl or ethyl, and
$R_2$ is a bond, $-(CY'_2)_n^-$, $-(CY'_2-CY'=CY')_n^-$, $-(CY'_2-CY'_2-CH=CH)_n^-$, $-(CY'=CY')_n^-$, or

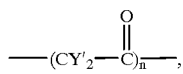

wherein Y' is hydrogen or methyl or ethyl and wherein n is 1 or 2; and $R_3$ is a bond, hydrogen, methyl, ethyl, —OH, —NH—, —N$^+$(CH$_3$)$_3$, —N$^+$(CH$_2$CH$_3$)$_3$, —COO—, —COO$^-$, —SO$_3$—, —SO$_3^-$, —C—PO$_3$H— or —C—PO$_3$H$^-$, and $R_4$ is nothing, hydrogen, a cell surface or extracellular matrix targeting moiety, or a linker-cell surface or extracellular matrix targeting moiety.

In another specific embodiment, $R_1$ is a bond,

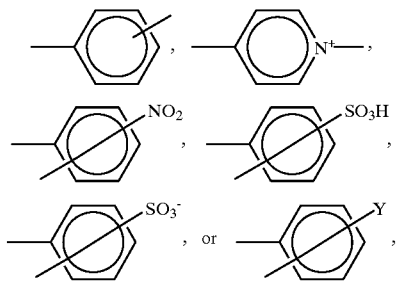

wherein Y is alkyl, preferably, $C_{1-4}$ alkyl, more preferably methyl or ethyl, $R_2$ is a bond, —(CY'$_2$)$_n^-$, —(CY'=CY')$_n^-$, or

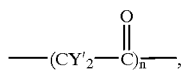

wherein Y' is hydrogen or alkyl (preferably $C_{1-4}$ alkyl, more preferably methyl or ethyl) and wherein n is 1 to 4 (preferably 1 or 2); and $R_3$ is a bond, hydrogen, $C_{1-4}$ alkyl (preferably methyl or ethyl), —OH, —NH—, —N$^+$(CH$_3$)$_3$, —N$^+$(CH$_2$CH$_3$)$_3$, —COO—, —COO$^-$, —SO$_3$—, —SO$_3^-$, —C—PO$_3$H— or —C—PO$_3$H$^-$; and $R_4$ is nothing, hydrogen, a cell surface or extracellular matrix targeting moiety or a linker-cell surface or extracellular matrix targeting moiety.

In yet another specific embodiment, $R_1$ is a bond,

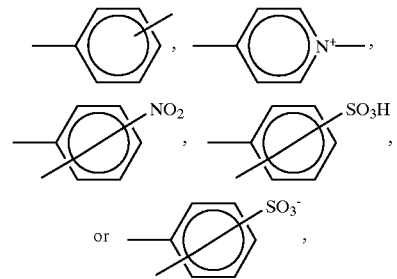

$R_2$ is a bond, —(CY'$_2$)$_n^-$ or —(CY'=CY')$_n^-$, wherein Y' is hydrogen or alkyl (preferably $C_{1-4}$ alkyl, more preferably methyl or ethyl) and wherein n is 1 to 4 (preferably 1 or 2);

$R_3$ is a bond, hydrogen, $C_{1-4}$ alkyl (preferably methyl or ethyl), —OH, —NH—, —N$^+$(CH$_3$)$_3$, —N$^+$(CH$_2$CH$_3$)$_3$, —COO—, —COO$^-$, —SO$_3$—, —SO$_3^-$, —C—PO$_3$H— or —C—PO$_3$H$^-$; and $R_4$ is nothing, hydrogen, a cell surface or extracellular matrix targeting moiety or a linker-cell surface or extracellular matrix targeting moiety.

In addition to the substituents described above, one or more of the pyrrole rings of the porphyrin can be substituted (at any or all of carbons 2, 4, 7, 8, 12, 13, 17 or 18) with an electron withdrawing group (designated P), for example, each P being, independently, a NO$_2$ group, a halogen (eg Cl, Br or F), a nitrile, a vinyl group, or a formyl group. Such substituents alter the redox potential of the porphyrin and thus enhance its ability to scavenge oxygen radicals. Each P can, independently, also be hydrogen. Specific mimetics suitable for use in the present methods include Mn(III) tetrakis (1-methy-4-pyridyl)porphyrin (MnTMPyP), Mn(III) tetrakis (4-trimethyl-aminophenyl)porphyrin (MnTMAP) and Mn(III) tetrakis (4-benzoic acid)porphyrin (MnTBAP), with or without a cell surface or extracellular matrix targeting moiety or a linker-cell surface or extracellular matrix targeting moiety at the $R_4$ position.

Although the foregoing mimetics are described as manganese chelates, metals other than manganese, such as iron (III) and copper (II), can also be used. The present invention also relates to the metal-free nitrogen-containing macro cyclic ligand. It will be appreciated that the metal selected may have various valence states, for example, manganese II, III or V can be used. The change in charge will be dependent upon the acceptance or release of electrons.

In addition to the foregoing mimetics, the invention also includes compounds (and targeted forms thereof as described above, including linker-cell surface or extracellular matrix targeted forms) of the formula:

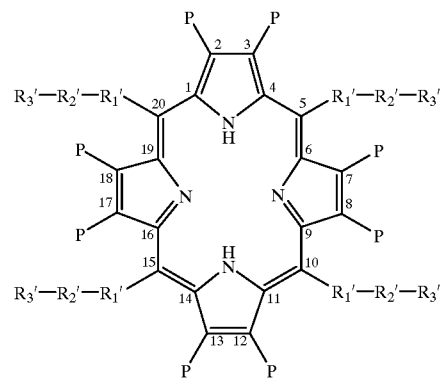

or a pharmaceutically acceptable salt thereof, or metal complex thereof wherein the metal is, for example, manganese, copper or iron, wherein:

each $R_1'$ is independently a bond,

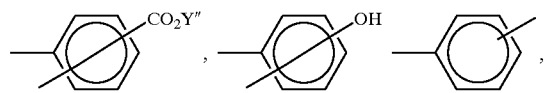

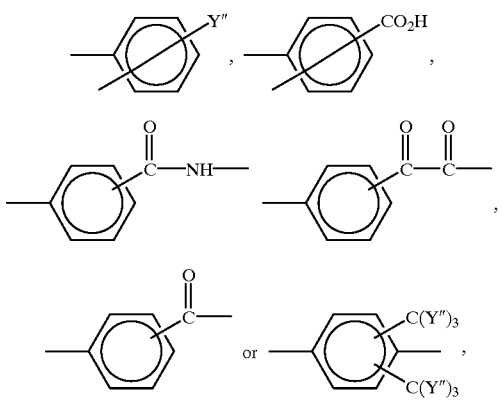

wherein Y" is an alkyl group (eg $C_1$–$C_4$) and wherein

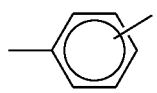

indicates bonding to $R_2'$ at any position and

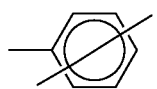

indicates bonding to $R_2'$ and the $R_1'$ phenyl substituent at any position;

each $R_2'$ is independently a bond, or —$(CH_2)_n$— wherein n is 1–4, each $R_3'$ is independently —Y", —Y'", —H, —OH, —OY", —$NO_2$, —CN, —$NH_2$, —COOH, —COY", —COO⁻, or a heterocyclic group, wherein Y" is as defined above and Y'" is a primary, secondary, tertiary or quaternary amine (preferably, an alkyl amine wherein the alkyl groups are, for example, $C_1$–$C_5$ alkyls)

wherein when $R_1'$ is

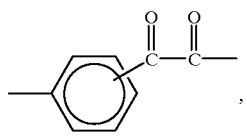

$R_3'$ is not COOH, COY" or COO⁻, wherein when $R_1'$ is

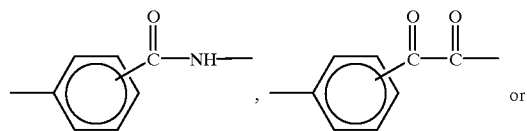

or

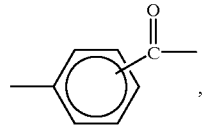

$R_3'$ is not —$NO_2$.

In certain embodiments of the invention, —$R_1'$—$R_2'$—$R_3'$, collectively, are not —H,

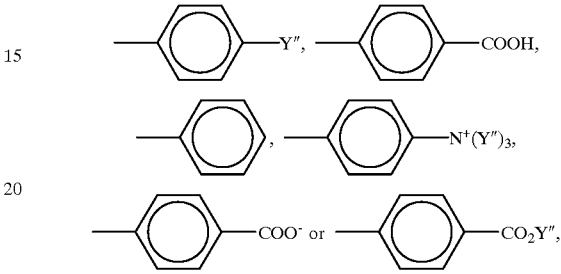

for example, when Y" is a methyl.

As indicated above, $R_3'$ can represent a heterocyclic moiety. Possible heterocyclics include substituted or unsubstituted tetrazoles, furans, thiophenes, indoles, imadazoles, pyridines, oxadiazoles and quinolines. Possible substituents on such moieties include halogen (eg Br or Cl), —$NO_2$, $C_{1-4}$ alkyl, and $C_{1-4}$ alkyl alcohol groups.

As above, one or more of the pyrrole rings of the porphyrin can be substituted (at any or all of carbons 2, 4, 7, 8, 12, 13, 17 or 18) with an electron withdrawing group (designated P), for example, each P being, independently, a $NO_2$ group, a halogen (eg Cl, Br or F), a nitrile, a vinyl group, or a formyl group. P can also be hydrogen.

Where rotational isomers are possible, all such isomers of the herein described mimetics (oxidant scavengers) are within the scope of the invention.

In addition to the compounds described above, the present invention includes within its scope porphine mimetics (and targeted forms thereof) bearing any of the above substituents in any of the possible combinations. For example $R_1$ can be selected from the group described above with respect to $R_1$ or $R_1'$, $R_2$ can be selected from the group described above with respect to $R_2$ and $R_2'$, and $R_3$ can be selected from the group described above with respect to $R_3$ or $R_3'$.

Targeted forms of the mimetics can be produced by coupling the porphine directly or via a linker to a cell surface or extracellular matrix targeting moiety, for example, as indicated above in the definition of $R_4$. The targeted mimetics can be used, for example, to mimic EC-SOD. Since the sequence of human EC-SOD is known (Hjalmarsson et al, Proc. Natl. Acad. Sci. USA 84:6340 (1987)), the C-terminal oligopeptide can be prepared and attached to the "mimetic core" (eg, a Mn(III)-porphyrin) via, for example, a free amine or carboxy group with a 1-ethyl-3-(3-dimethylaminopropyl)carbodiimide (EDC) coupling reaction (Yamada et al, Biochemistry 20:4836 (1981); Davis and Preston, Anal. Biochem. 116:402 (1981)). This simple cou pling procedure makes it possible to attach a wide variety of different binding domains in order to target the mimetics of the invention. Heparin binding affinity of a mimetic can be assessed by passing the mimetic over a heparin-sepharose CL-6B column (Karlsson et al, Biochem. J. 256:29 (1988)).

Candidate targeting moieties suitable for attaching to the mimetics of the invention to confer GAG binding properties include the following:

i) the A+ helix of protein C inhibitor (Boissinot et al, Biochem. Biophys. Res. Commun. 190:250 (1993))—NH$_2$—His Arg His His Pro Arg Glu Met Lys Lys Arg Val Glu Asp Leu—COOH;

ii) the C-terminal end of human EC-SOD (heparin binding domain) (Karlsson et al, Biochem. J. 255:223 (1988))—NH$_2$—Arg Glu His Ser Glu Arg Lys Lys Arg Arg Arg Glu Ser Glu Cys Lys Ala Ala—COOH;

iii) variants of the C-terminal end of human EC-SOD having heparin binding affinity (Sandström et al, J. Biol. Chem. 267:18205 (1992))
   a. NH$_2$—Arg Glu His Ser Glu Arg Lys Lys Arg Arg Arg Glu—COOH;
   b. NH$_2$—Arg Glu His Ser Glu Arg Lys Lys Arg Arg Arg Ala—COOH;
   c. NH$_2$—Arg Glu His Ser Glu Arg Lys Lys Arg Arg Arg Ala Ser Glu Cys Lys Ala Ala—COOH;
   d. NH$_2$—Arg Glu His Ser Glu Arg Lys Lys Arg Arg Arg Glu Ser Glu Ala Lys Ala Ala—COOH;
   e. NH$_2$—Arg Glu His Ser Glu Arg Lys Lys Arg Arg Arg Glu Ser Glu Cys Ala Ala Ala—COOH;
   f. NH$_2$—Arg Glu His Ser Glu Arg Lys Lys Arg Arg Arg Ala Ser Ala Cys Lys Ala Ala—COOH;
   g. NH$_2$—Arg Glu His Ser Glu Arg Lys Lys Arg Arg Arg Ala Ser Glu Cys Ala Ala Ala—COOH;
   h. NH$_2$—Arg Glu His Ser Glu Arg Lys Lys Gly Arg Arg Ala Ser Glu Cys Ala Ala Ala—COOH;

iv) any combination of repeating positively changed amino acids (ie poly (Arg)$_n$, poly (Lys)$_n$, poly (Arg)$_n$ (Lys)$_n$ or poly (Arg Lys)$_n$ or poly (Lys Arg)$_n$, poly (Lys Lys Arg Arg)$_n$, wherein n is, preferably, in the range of 1 to 12, more preferably, 1 to 8, and, most preferably, 1 to 6, with or without a C-terminal Glu or Ala (Sandström et al, J. Biol. Chem. 267:18205 (1992)); and v) polyethyleneimine, e.g. (NH—CH$_2$—CH$_2$—NH)nH, wherein n is 1 to 6.

In addition to the foregoing, targeting moieties also include heparin binding proteins generally and sugars, including mannose and oligosaccharides.

Appropriate linkers include

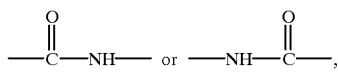

—SO$_2$—NH—, —PO$_3$—NH—, or

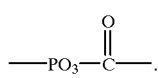

Specific examples of suitable mimetics of the invention are set forth below:

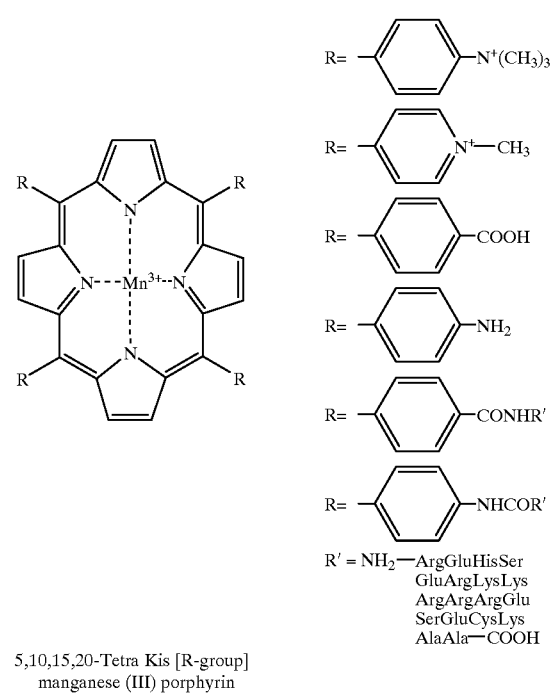

5,10,15,20-Tetra Kis [R-group] manganese (III) porphyrin

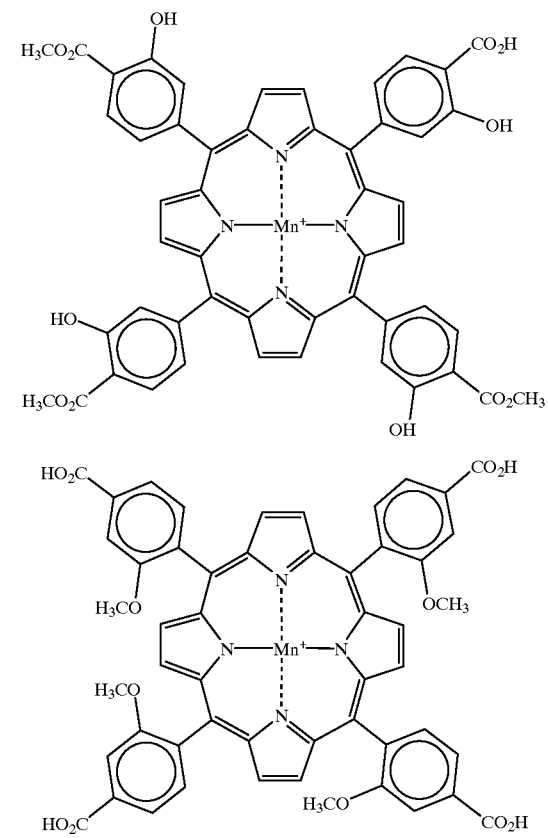

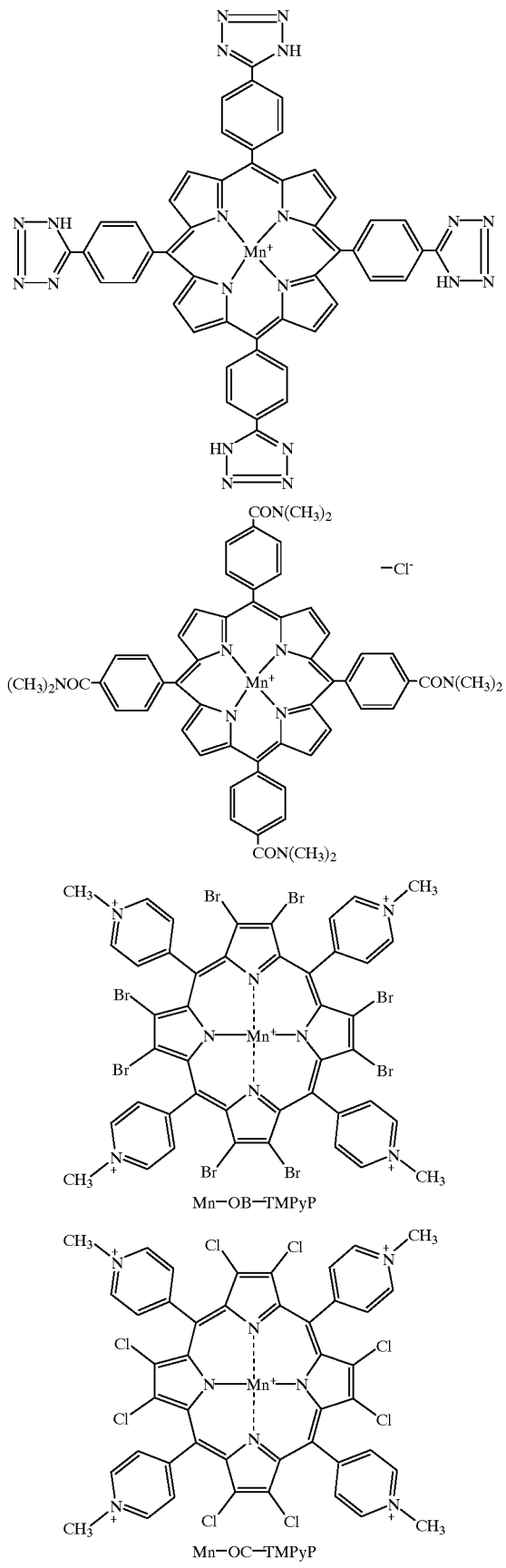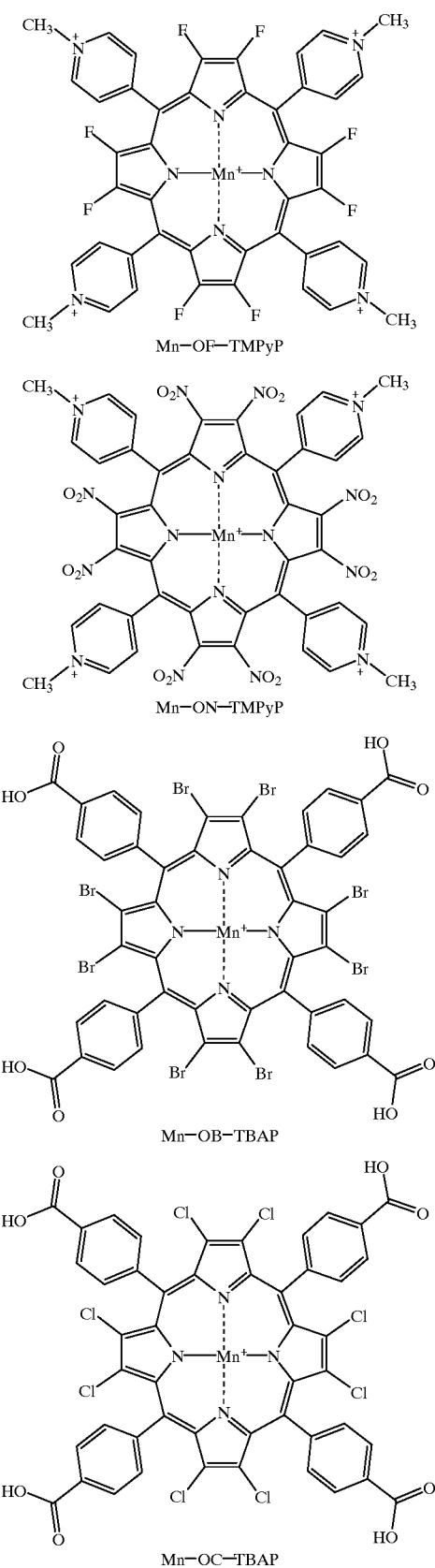

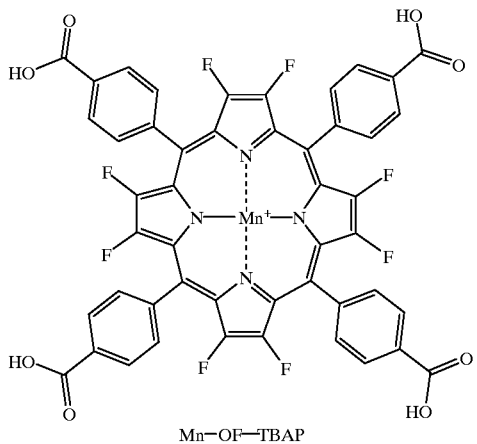

Mn—OF—TBAP

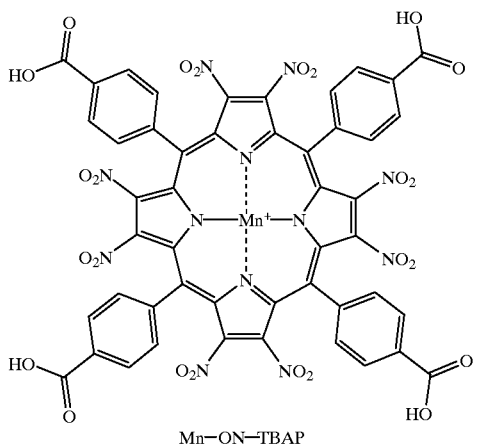

Mn—ON—TBAP

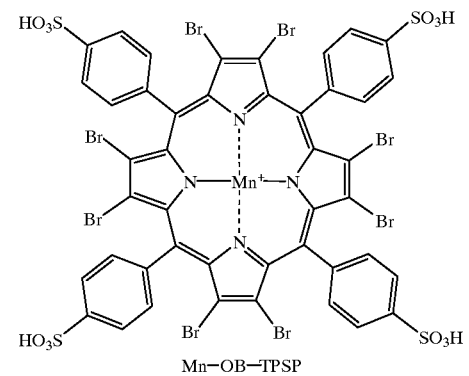

Mn—OB—TPSP

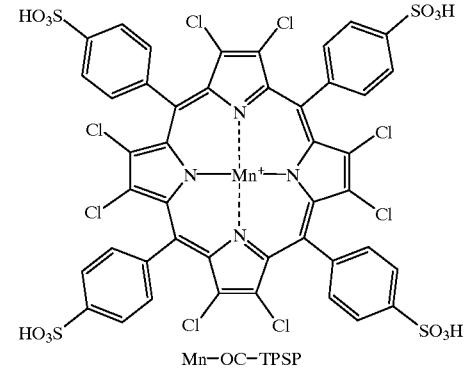

Mn—OC—TPSP

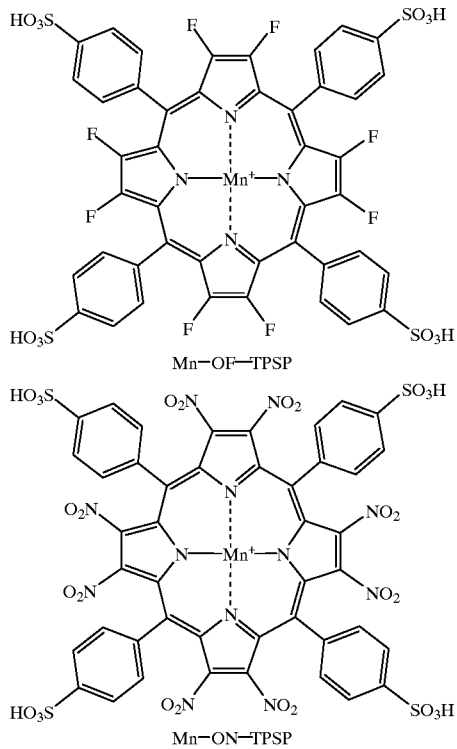

Mn—OF—TPSP

Mn—ON—TPSP

Mimetics suitable for use in the present methods can be selected by assaying for SOD, catalase and/or peroxidase activity and stability. The selective, reversible and SOD-sensitive inactivation of aconitase by known $O^-_2$ generators can be used as a marker of $O^-_2$ generation. Thus, suitable mimetics can be selected by assaying for the ability to protect aconitase activity.

SOD activity can be monitored in the presence and absence of EDTA using the method of McCord and Fridovich (J. Biol. Chem. 244:6049 (1969)). The efficacy of a mimetic can be determined by measuring the effect of the mimetic on the growth of a SOD null E. coli strain versus a wild type strain. Specifically, wild type E. coli (AB1157) and SOD null E. coli. (JI132) can be grown in M9 medium containing 0.2% casamino acids and 0.2% glucose at pH 7.0 and 37° C.; growth can be monitored in terms of turbidity followed at 700 nm spectrophotometrically. Active mimetics can be tested for toxicity in mammalian cell culture by measuring lactate dehydrogenase (LDH) release. Specifically, rat L2 cells (a lung Type II like cell; (Kaighn and Douglas, J. Cell Biol. 59:160a (1973))can be grown in Ham's F-12 medium with 10% fetal calf serum supplement at pH 7.4 and 37° C.; cells can be seeded at equal densities in 24 well culture dishes and grown to approximately 90% confluence; SOD mimetics can be added to the cells at log doses (eg micromolar doses in minimal essential medium (MEM)) and incubated for 24 hours. Toxicity can be assessed by morphology and by measuring the release of the cytosolic injury marker, LDH (eg on a thermokinetic plate reader), as described by Vassault (In: Methods of Enzymatic Analysis, Bergmeyer (ed) pp. 118–26 (1983); oxidation of NADH is measured at 340 nm). Efficacy of active mimetics can be assessed by determining their ability to protect mammalian cells against methylviologen (paraquat)-induced toxicity. Specifically, rat L2 cells grown as described above and seeded into 24 well dishes can be pre-incubated with various concentrations of the SOD mimetic and then incubated with a concentration of methylviologen previously shown to produce an $LC_{75}$ in control L2 cells. Efficacy of the mimetic can be correlated with a decrease in the methylviologen-induced LDH release (St. Clair et al, FEBS Lett. 293:199 (1991)). The efficacy of SOD mimetics can be tested in vivo with mouse and/or rat models using both aerosol administration and parenteral injection. For example, male Balb/c mice can be randomized into 4 groups of 8 mice each to form a standard 2×2 contingency statistical model. Animals can be treated with either paraquat (40 mg/kg, ip) or saline and treated with SOD mimetic or vehicle control. Lung injury can be assessed 48 hours after paraquat treatment by analysis of bronchoalveolar lavage fluid (BALF) damage parameters (LDH, protein and % PMN) as previously described (Hampson et al, Tox. Appl. Pharm. 98:206 (1989); Day et al, J. Pharm. Methods 24:1 (1990)). Lungs from 2 mice of each group can be instillation-fixed with 4% paraformaldehyde and processed for histopathology at the light microscopic level.

Catalase activity can be monitored by measuring absorbance at 240 nm in the presence of hydrogen peroxide (see Beers and Sizer, J. Biol. Chem. 195:133 (1952)) or by measuring oxygen evolution with a Clark oxygen electrode (Del Rio et al, Anal. Biochem. 80:409 (1977)). Peroxidase activity can be measured spectrophotometrically as previously described by Putter and Becker: Peroxidases. In: Methods of Enzymatic Analysis, H. U. Bergmeyer (ed.), Verlag Chemie, Weinheim, pp. 286–292 (1983. Aconitase activity can be measured as described in Example XI below.

Table IX below provides a summary of the activities of various oxidant scavengers of the invention. The footnote to that Table provides details of the assays used.

Synthesis of mimetics suitable for use in the present method can be effected using art-recognized protocols. Example XIV includes a detailed description of the synthesis of four specific mimetics. In the case of Mn(III)-porphyrin mimetics, porphyrin rings with various methine bridge carbon side groups can be purchased commercially and the Mn(III) metal ion inserted into the porphyrin ring by methods including the following: (1) admixture of Mn(II) acetate with porphyrin in the presence of oxygen, under which condition selective stabilization of Mn(III) by the porphyrin causes autooxidation of Mn(II); (2) preparation of $Mn(III)(OH)_3$ by a modification of the Winkler method (Sastry et al, Anal. Chem. 41:857 (1969)) followed by reaction with the porphyrin; (3) stirring $MnO_2$ with the porphyrin in the presence of $NH_2OH$, which serves to reduce the Mn(IV) to Mn(III), which is then trapped by the porphyrin; or (4) a method modified from Pasternack et al (Biochemistry 22:2406 (1983)) which refluxes excess $MnCl_3$ with the porphyrin. Mn(III)-porphyrin complexes can be precipitated from solution with sodium perchlorate, washed and residue perchlorate removed by strong anionic exchange resin. Formation of the Mn(III)-porphyrin can be followed spectrophotometrically by monitoring a characteristic Sorét band at 468 nm. Synthesis of compounds of the invention bearing electron-withdrawing groups at one or more pyrrole carbons can be carried out as described by Richards et al, Inorg. Chem. 35:1940 (1996). Purification of the mimetics can be effected using art-recognized techniques such as recrystallization, chromatography, etc. Coupling of a binding domain to the "mimetic core" can be carried out as described above.

One embodiment of the present invention results, at least in part, from the realization that EC-SOD specifically regulates NO· function. In addition, the invention is based on the realization that EC-SOD is synthesized by epithelial cells and is primarily localized in the interstitium, on matrix elements and collagen and around smooth muscle cells (particularly lung airways and vasculature). NO· is an intercellular signal and, as such, NO· must traverse the extracellular matrix to exert its effects. NO·, however, is highly sensitive to inactivation mediated by $O_2^-$ present in the extracellular spaces. EC-SOD is thus an enzyme ideally suited to increase the bioavailability of NO· by preventing its degradation by $O_2^-$.

One embodiment of the present invention relates to a method of regulating extracellular NO· levels using polypeptides having EC-SOD activity. As indicated above, the invention also relates to mimetics of EC-SOD that can be targeted to strategic locations and to the use of such mimetics in manipulating extracellular levels of NO· The invention, however, is not limited to NO· manipulation as the sole mechanism of action of the compounds, mimetics, etc, of the invention. Rather, the invention relates to oxygen radical, hydrogen peroxide and peroxynitrite scavenging generally.

The present invention relates, in a further specific embodiment, to a method of inhibiting production of superoxide radicals. In this embodiment, the mimetics of the invention are used to inhibit oxidases, such as xanthine oxidase, that are responsible for production of superoxide radicals (see Example VII). The ability of a mimetic to protect mammalian cells from xanthine/xanthine oxidase-induced injury can be assessed, for example, by growing rat L2 cells in 24-well dishes. Cells can be pre-incubated with various concentrations of a mimetic and then xanthine oxidase (XO) can be added to the culture along with xanthine (X). The appropriate amount of XO/X used in the study can be pre-determined for each cell line by performing a dose-response curve for injury. X/XO can be used in an amount that produces approximately an $LC_{75}$ in the culture. Efficacy of the mimetic can be correlated with a decrease in XO/X-induced LDH release. The ability of the mimetics to inhibit the production of such radicals makes possible the use the mimetics as therapeutics for the treatment of gout and reperfusion injuries.

The mimetics of the invention can be used as catalytic scavengers of reactive oxygen species to protect against ischemia reperfusion injuries associated with myocardial infarction, stroke, acute head trauma, organ reperfusion following transplantation, bowel ischemia, pulmonary infarction, surgical occlusion of blood flow, and soft tissue injury. The mimetics can further be used to protect against skeletal muscle reperfusion injuries. The mimetics can also be used to protect against damage to the eye due to sunlight (and to the skin) as well as glaucoma, and macular degeneration of the eye. Diseases of the bone are also amenable to treatment with the mimetics. Further, connective tissue disorders associated with defects in collagen synthesis or degradation can be expected to be susceptible to treatment with the present mimetics.

In addition to scavenging superoxide, the ability of the mimetics of the invention to scavenge hydrogen peroxide would protect from the possible formation of the highly reactive hydroxyl radical by interfering with Fenton chemistry (Aruoma and Halliwell, Biochem. J. 241:273 (1987); Mello Filho et al, Biochem. J. 218:273 (1984); Rush and Bielski, J. Phys. Chem. 89:5062 (1985). These metalloporphyrins have been shown to scavenge peroxynitrite as demonstrated indirectly by inhibition of the oxidation of dihydrorhodamine 123 to rhodamine 123 (see Example XIII) and directly by accelerating peroxynitrite degradation by stop flow analysis.

In addition to the above, the mimetics of the invention can be used as catalytic scavengers of reactive oxygen species to increase the very limited storage viability of transplanted hearts, kidneys, skin and other organs and tissues. The invention also provides methods of inhibiting damage due to autoxidation of substances resulting in the formation of $O_2^-$ including food products, pharmaceuticals, stored blood, etc. To effect this end, the mimetics of the invention are added to food products, pharmaceuticals, stored blood and the like, in an amount sufficient to inhibit or prevent oxidation damage and thereby to inhibit or prevent the degradation associated with the autoxidation reactions. (For other uses of the mimetics of the invention, see U.S. Pat. No. 5,227,405). The amount of mimetic to be used in a particular treatment or to be associated with a particular substance can be determined by one skilled in the art.

The availability of the mimetics of the invention also makes possible studies of processes mediated by $O_2^-$, hydrogen peroxide, nitric oxide and peroxynitrite.

In addition to the above, the present invention relates to diagnostic protocols made possible by the availability of the EC-SOD gene sequence (see Example V and FIG. 24). A defect in the EC-SOD gene is more likely to occur than a defect in nitric oxide synthase due to the nature and number of physiological functions served by NO· Detection of an EC-SOD gene defect would signal the need for measures to be undertaken to elevate levels of functional EC-SOD, or related superoxide scavenging compounds, at strategic locations to correct NO· imbalances and thus disorders involving oxidative stress.

To effect modulation of the efficacy of extracellular NO·, eg, in relaxing smooth muscle, molecules (agents) having EC-SOD activity are administered under conditions such that levels of extracellular $O_2^-$ are altered. Molecules suitable for use in this method include forms of SOD that bind heparin sulfate or other glycosaminoglycans (GAG), for example, by virtue of the fact that they contain positively charged amino acids near their carboxy terminal end. Proteinaceous agents suitable for use in the present method include forms of EC-SOD C described in WO 91/04315, as well as additional polypeptides defined and described therein as having comparable or enhanced binding to heparin as compared to recombinant EC-SOD C (eg, polypeptides G1 and SA216; note also polypeptide SA219 which has the same heparin binding as recombinant EC-SOD C. Further proteinaceous agents suitable for use in the present method include chimeric proteins with targeted binding and SOD activity, for example, Cu/Zn SOD linked to an EC-SOD binding sequence (see also Boissinot et al, Biochem. Biophys. Res. Commun. 190:250 (1993)).

Proteinaceous molecules suitable for use in the present method can be synthesized chemically or recombinantly using art-recognized protocols (see WO 91/04315). Nonglycosylated recombinant peptides can be produced, for example, using host cells (ie, E. coli cells) that are incapable of effecting glycosylation, or using DNA sequences encoding functional proteins lacking glycosylation sites.

In addition to polypeptides, molecules suitable for use in the present method include mimetics of EC-SOD (eg targeted mimetics), including those described above. The general requirements of such mimetics are that they: (a) be stable enough to retain the ligated metal (eg Cu or Mn) in the presence of the multiple chelating agents present in living systems, (b) be active enough that reasonable doses can serve to significantly augment the total SOD activity in the extracellular spaces, (c) be able to adhere to the surfaces of cells or extracellular matrix elements (eg collagen) when protection against extracellular sources Of $O_2^-$ is needed, and d) be of low toxicity. Examples of suitable mimetics include nitrogen-containing macrocyclic ligands effective as catalysts for dismutating superoxide, including Mn(III) complexes of porphyrins with bulky cationic substituents on the methine bridge carbons, such as those described above (eg MnTMAP and MnTMPyP). Such complexes are very active and are stable enough to retain full activity in the presence of excess EDTA or in the presence of tissue extracts.

The polypeptides and mimetics described above can be formulated into pharmaceutical compositions suitable for use in the present methods. Such compositions include the active agent (polypeptide or mimetic) together with a pharmaceutically acceptable carrier, excipient or diluent. The composition can be present in dosage unit form for example, tablets, capsules or suppositories. The composition can also be in the form of a sterile solution suitable for injection or nebulization. Compositions can also be in a form suitable for opthalmic use. The invention also includes compositions formulated for topical administration, such compositions taking the form, for example, of a lotion, cream, gel or ointment. The concentration of active agent to be included in the composition can be selected based on the nature of the agent, the dosage regimen and the result sought.

The dosage of the composition of the invention to be administered can be determined without undue experimentation and will be dependent upon various factors including the nature of the active agent, the route of administration, the patient, and the result sought to be achieved. A suitable dosage of protein administered IV can be expected to be in the range of about 10–1000 mg/day. For topical treatment, it is expected that lower doses will be required (see WO 91/04315); for aerosol administration, it is expected that doses will be in the range of 1 to 10 mg/kg. Suitable doses of mimetics will vary, for example, with the mimetic and with the result sought. The results of Faulkner et al (J. Biol. Chem. 269:23471 (1994)) indicate that the in vivo oxidoreductase activity of the mimetics is such that a pharmaceutically effective dose will be low enough to avoid problems of toxicity. Doses that can be used include those in the range of 1 to 50 mg/kg.

In addition to compositions of the types described above, the present invention also includes compositions suitable for use in gene therapy types of protocols. For example, the invention includes DNA sequences encoding proteins having EC-SOD activity and formulated so as to be incorporated into cells (eg, lung cells) upon contact therewith (eg, via inhalation). The sequence can be present in a vector, eg, a viral vector, and/or the sequence can be present in a delivery vehicle, such as a liposome. The amounts of such compositions to be administered can be readily determined by one skilled in the art.

Further examples of diseases or disorders appropriate for treatment using the compounds and compositions of-the present invention include diseases of the central nervous system (including AIDS dementia, stroke, amyotrophic lateral sclerosis (ALS), Parkinson's disease and Huntington's disease) and diseases of the musculature (including diaphramic diseases (eg respiratory fatigue in emphysema, bronchitis and cystic fibrosis), cardiac fatigue of congestive heart failure, muscle weakness syndromes associated with myopathies, ALS and multiple sclerosis). Many neurologic disorders (including stroke, Huntington's disease, Parkinson's disease, ALS, Alzheimer's and AIDS dementia) are associated with an over stimulation of the major subtype of glutamate receptor, the NMDA (or N-methyl-D-aspartate) subtype. On stimulation of the NMDA receptor, excessive neuronal calcium concentrations contribute to a series of membrane and cytoplasmic events leading to production of oxygen free radicals and nitric oxide (NO·). Interactions between oxygen free radicals and NO· have been shown to contribute to neuronal cell death. Well-established neuronal cortical culture models of NMDA-toxicity have been developed and used as the basis for drug development. In these same systems, the mimetics of the invention inhibit NMDA induced injury. The results presented in Example XI demonstrate that the formation of $O^-_2$ radicals is an obligate step in the intracellular events culminating in excitotoxic death of cortical neurons and further demonstrate that the mimetics of the invention can be used to scavenge $O^-_2$ radicals and thereby serve as protectants against excitotoxic injury. Compound 10303 (see Table IX) decreases NMDA- and kainate-induced excitotoxicity in rat cortical cells in a dose dependent manner with 100% protection against NMDA-induced excitotoxicity (50 μM) being achieved at 25 μM compound 10303, 100 μM compound 10303 in the case of kainate-induced excitotoxicity (300 μM).

The present invention also relates to methods of treating arthritis, systemic hypertension, atherosclerosis, edema, septic shock, pulmonary hypertension, including primary pulmonary hypertension, impotence, infertility, endometriosis, premature uterine contractions, microbial infections, gout and in the treatment of Type II diabetes mellitus. The scavengers of the invention can be used to ameliorate the toxic effects associated with endotoxin, for example, by preserving vascular tone and preventing multi-organ system damage.

The invention further relates to methods of treating memory disorders. While not wishing to be bound by theory, it is believed that nitric oxide is a neurotransmitter involved in long-term memory potentiation. Using an EC-SOD knocked-out mouse model, it can be shown that learning impairment correlates with reduced superoxide scavenging in extracellular spaces of the brain (see Example XII). Reduced scavenging results in higher extracellular $O^-_2$ levels. $O^-_2$ is believed to react with nitric oxide thereby preventing or inhibiting nitric oxide-medicated neurotransmission and thus long-term memory potentiation. The mimetics of the invention can be used to treat dementias and memory/learning disorders.

Therapeutic regimens, including mode of administration, appropriate for effecting treatment of the conditions described above can be readily determined by one skilled in the art.

Inflammations, particularly inflammations of the lung, are amenable to treatment using the present invention (note particularly the inflammatory based disorders of asthma, ARDS including oxygen toxicity, pneumonia (especially AIDS-related pneumonia), cystic fibrosis, chronic sinusitis and autoimmune diseases (such as rheumatoid arthritis)). EC-SOD is localized in the interstitial spaces surrounding airways and vasculature smooth muscle cells. EC-SOD and $O_2^-$ mediate the antiinflammatory-proinflammatory balance in the alveolar septum. NO· released by alveolar septal cells acts to suppress inflammation unless it reacts with $O_2^-$ to form $ONOO^-$. By scavenging $O_2^-$, EC-SOD tips the balance in the alveolar septum against inflammation. Significant amounts of $ONOO^-$ will form only when EC-SOD is deficient or when there is greatly increased $O_2^-$ release. EC-SOD mimetics, such as those described herein, can be used to protect against destruction caused by hyperoxia. Appropriate therapeutic regimens can be readily established by one skilled in the art.

As indicated above, it is expected that defects in the EC-SOD gene, that are manifest in the protein itself, may in fact be the cause of pathologic problems related to NO· function, rather than defects in nitric oxide synthase. Thus, in a further embodiment, the present invention relates to diagnostic protocols suitable for use in identifying EC-SOD gene defects. This aspect of the invention is based on the availability of the EC-SOD gene sequence. The present invention includes within its scope the gene sequence presented in FIG. 24 as well as portions of non-coding regions of that sequence of at least 15 bases, preferably, at least 50 bases, more preferably, at least 100 bases and most preferably, at least 500 bases. Such portions, and the complements thereof, which are also within the scope of the invention, can be used as probes or primers in protocols including those described in Example VI.

Screening of subjects for defects in the EC-SOD gene can be done using the approach used to identify mutations on the β-adrenergic receptor gene (Reihaus et al, Am. J. Respir. Cell. Mol. Biol. 8:334 (1993)). That approach is similar to the one used by Rosen et al (Nature 262:59 (1993)) (see Example VI).

The following are predicted sites of important gene mutations:

Positions 1–558: This represents a 5' flanking region which contains transcriptional regulatory elements. Mutations here can be expected to lead to deficient levels of EC-SOD or defective enhancement or reduction in EC-SOD levels under conditions which require manipulating the EC-SOD concentration. The following regions have been identified as putative regulatory regions. Mutations in these regions can be expected to result in deficient levels of EC-SOD:

| | |
|---|---|
| 89–95 | metal regulatory response element |
| 121–126 | cyclic AMP responsive element |
| 370–375 | glucocorticoid response element |
| 238–244 | skeletal muscle trans-activating factor response element |
| 251–256 | is responsive element in the induction of the c-fos proto-oncogene |
| 162–168 | TPA reponsive element |
| 171–179 | SV40 enhancer region |

Positions 560–570: Mutations here can be expected to lead to an inability to splice out intron 1. This would result in no EC-SOD production (or much reduced) due to initiation of translation at multiple cryptic ATG sites located in intron 1 which are upstream of the EC-SOD ATG start codon. For example, base pair 653, 656, 720, 743, 748, etc, would potentially initiate translation.

Positions 564–1135: Intron 1 contains DNA sequence unique to EC-SOD. In addition, there are potential transcription regulatory regions within this DNA stretch which are listed below; mutations in intron 1 would lead to deficient levels of EC-SOD or defective enhancement or reduction in EC-SOD levels under conditions that require manipulating the EC-SOD concentration:

| | |
|---|---|
| 1085–1095 | Xenobiotic responsive region |
| 650–661 | Antioxidant responsive element |

Positions 71–95: Mutations here can be expected to lead to an inability to splice out intron 1. This would result in no EC-SOD production (or much reduced) due to initiation of translation at multiple cryptic ATG sites located in intron 1 that are upstream of the EC-SOD ATG start codon. For example, base pair 653, 656, 720, 743, 748, etc, would potentially initiate translation.

Positions 1211–1230: Mutations here can be expected to lead to an inability to splice out intron 2. This would result in no EC-SOD production (or much reduced) due to initiation of translation at multiple cryptic ATG sites located in intron 2 that are upstream of the EC-SOD ATG start codon. Examples of upstream ATG translation start sites can be found at 1339 and 1518.

Positions 5055–5080: Mutations here would lead to an inability to splice out intron 2. This would result in no EC-SOD production (or much reduced) due to initiation of translation at multiple cryptic ATG sites located in intron 2 which are upstream of the EC-SOD ATG start codon. Examples of upstream ATG translation start sites can be found at 1339 and 1518.

Positions 5085–5138: Mutations here would (1) interfere with efficiency of translation of EC-SOD resulting in deficient levels of the enzyme (2) interfere with targeting of EC-SOD to the endoplasmic reticulum which is required for secretion of EC-SOD, (3) interfere with co-translational signal peptide processing (ie, removal of the signal peptide) that may lead to deficient levels due to inability to proteolytically cleave the signal peptide from the mature protein which in turn would result in the protein being trapped in the endoplasmic reticulum, (4) interfere with post-translational processing (specifically glycosylation) which may result in defective levels due to the synthesis of poorly soluble protein.

Positions 5139–5150: Mutations here may interfere with the signal peptidase cleavage site resulting in a mutant EC-SOD which would contain an altered amino terminus leading to defective EC-SOD function of deficient levels.

Positions 5403–5405: Mutations here can be expected to result in loss of glycosylation which may result in defective levels due to the synthesis of poorly soluble protein.

Positions 5424–5720: Mutations here can be expected to result in defective EC-SOD activity. This region is critical for binding to the substrate and catalyzing the dismutation of superoxide anion radical. In addition, this region would also affect any other activities of this enzyme including the reduction of other species such as nitric oxide, etc.

Positions 5721–5804: Mutations in this region would cause defects in binding of EC-SOD to target tissues such as type I collagen in the extracellular matrix, and around smooth muscle cells in both vessels and bronchi. Such mutations here are highly likely to cause disease.

Positions 6385–6395: Mutations here can be expected to result in defective polyadenylation that can lead to deficient levels of EC-SOD due to a decreased half-life of EC-SOD mRNA species.

The present invention relates not only to the entire EC-SOD gene sequence, but to portions thereof for use, for example, as probes or primers in detecting mutations in regions of the gene including those noted above. Such portions can be expected to be, for example, 18–1500 bases in length, preferably 18–22 bases in length, 50–75 bases in length, 100–400 bases in length or 500 to 1500 bases in length.

Certain details of the present invention are described in greater detail in the non-limiting Examples that follow.

EXAMPLE I

Preparation and Characterization of Transgenic Mice

Protocols:

i) Construction of Transgenic Mice

Construction of the human EC-SOD expression vector: The EC-SOD expression vector (FIG. 1) was constructed as follows: The entire human EC-SOD cDNA fragment (Hjalmarrson et al, Proc. Natl. Acad. Sci. USA 84:6340 (1987); Hendrickson et al, Genomics 8:736 (1990)) flanked by EcoRI restriction sites was converted with mung bean nuclease to form blunt-ends, ligated to SalI linkers, digested with SalI, and then inserted into the SalI site of the human β-actin expression vector pHβAPr-1. The EcoRI-HindIII fragment of the resultant plasmid containing the human β-actin promoter (provided by Dr. Larry Kedes of the University of Southern California, Los Angeles, Calif.), intron, and EC-SOD cDNA was isolated. In addition, the HpaI site of SV40 at position 2666 in plasmid PMSG (Pharmacia LKB Biotechnology, Piscataway, N.J.) was converted to a HindIII site by linker ligation and the HindIII-PstI fragment containing the polyadenylation site of the SV40 early region was isolated. These two DNA fragments were then ligated to an EcoRI plus PstI digested pKS vector (Stratogene, La Jolla, Calif.). The EcoRI-XbaI fragment containing the entire expression construct free of plasmid sequences was isolated and used to establish transgenic mice. All of the recombinant DNA procedures were done according to established methods (Sambrook et al, Molecular Cloning: A Laboratory Manual 3, Cold Spring Harbor; Cold Spring Harbor Laboratory, 1989).

Development of transgenic mice: Purified DNA at 2.5 μg/ml in 5 mM Tris-HCl, pH 7.4, 0.1 mM EDTA was injected into the pronuclei of fertilized eggs isolated from mice ((C57BL/6 X C3H)F1 X (C57BL/6 X C3H)F1) ((C57BL/6 X C3H)F1 mice were purchased from Charles River). Mouse eggs surviving microinjection were then implanted into the oviducts of pseudopregnant foster mothers (CD1) (CD1 mice were purchased from Charles River) following procedures described by Hogan et al (Hogan et al, Manipulating the Mouse Embryo, Cold Spring Harbor; Cold Spring Harbor Laboratory 1986, 32). Mice carrying the transgene were identified by Southern blot analysis of tail DNA probed with the entire human EC-SOD cDNA. Transgenic founders were found the first litter screened. These mice were bred with (C57BL/6 X C3H)FI to produce offspring for further studies. (In all of the following experiments with the EC-SOD transgenic mice, the nontransgenic mice refer to littermates of the transgenic mice that did not contain the transgene for the human EC-SOD. In experiments in which EC-SOD transgenic mice were not used, wild type (C57BL/6 X C3H)FI were used.)

Production of homozygous EC-SOD transgenic mice: Homozygous transgenic mice were produced by an $F_1$ cross of heterozygous transgenic mice. Tail DNA from $F_2$ mice were isolated and treated with RNAase. 10 μg of DNA from each mouse was cut with PstI and then electrophoresed through a 1.2% agarose gel. Southern blot analysis of tail DNA probed with the entire human EC-SOD cDNA was then done. The human EC-SOD cDNA did not cross-react with the mouse EC-SOD gene. Band intensity was compared visually to determine which mice were homozygous, heterozygous, or negative for the human EC-SOD transgene.

ii) Characterization of Transgenic Mice

Northern analysis: Transgenic mice and nontransgenic littermates were killed with an overdose of pentobarbital. Tissues were quickly excised and frozen in liquid nitrogen until ready for further processing. Total RNA was then isolated by the CsCl procedure was described (Sambrook et al, Molecular Cloning: A Laboratory Manual. 3. Cold Spring Harbor, Cold Spring Harbor Laboratory, 1989). Twenty μg of total RNA from the tissues of transgenic mice and nontransgenic littermates and an RNA ladder were then denatured with glyoxal, electrophoresed through a 1.2% agarose gel and blotted to nitrocellulose as described (Sambrook et al, Molecular Cloning: A Laboratory Manual. 3. Cold Spring Harbor, Cold Spring Harbor Laboratory, 1989). The blots were then probed with the entire human EC-SOD cDNA.

Separation of SOD isoenzymes by concanavalin A sepharose chromatography: Tissues taken from 3 mice were weighed, then combined and homogenized in 10 volumes of ice-cold 50 mM potassium phosphate, pH 7.4, with 0.3 M KBr, 3 mM diethylenetriaminepentaacetic acid, and 0.5 mM phenylmethylsulfonyl fluoride. Separation of EC-SOD from CuZn SOD and Mn SOD was accomplished by passing tissue homogenates over a concanavalin A sepharose column as described (Marklund et al, Clin. Chim. Acta 126:4 (1982)).

SOD activity: EC-SOD activity and total SOD activity (CuZn SOD and Mn SOD) remaining after EC-SOD extraction were measured by inhibition of cytochrome C reduction at pH 10, as previously described (Crapo et al, Methods Enzymol. 53:382 (1978)). Total protein was determined by the BCA protein assay (Pierce, Rockford, Ill.). The SOD activities were then expressed as units/mg total protein.

Results:

i) EC-SOD Transgenic Mice

Figure 1:
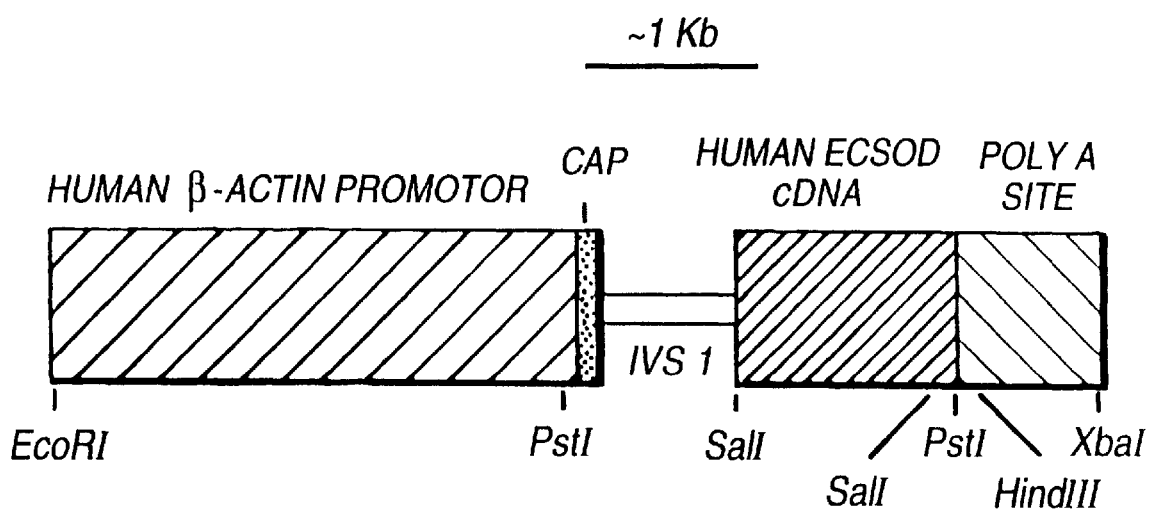
FIG. 1 shows the EC-SOD expression vector used to construct transgenic mice. Transgenic mice were generated with the Eco-RI-Xbal fragment. IVS1: Intervening sequence 1 from the human β-actin promoter.
Figure 2:
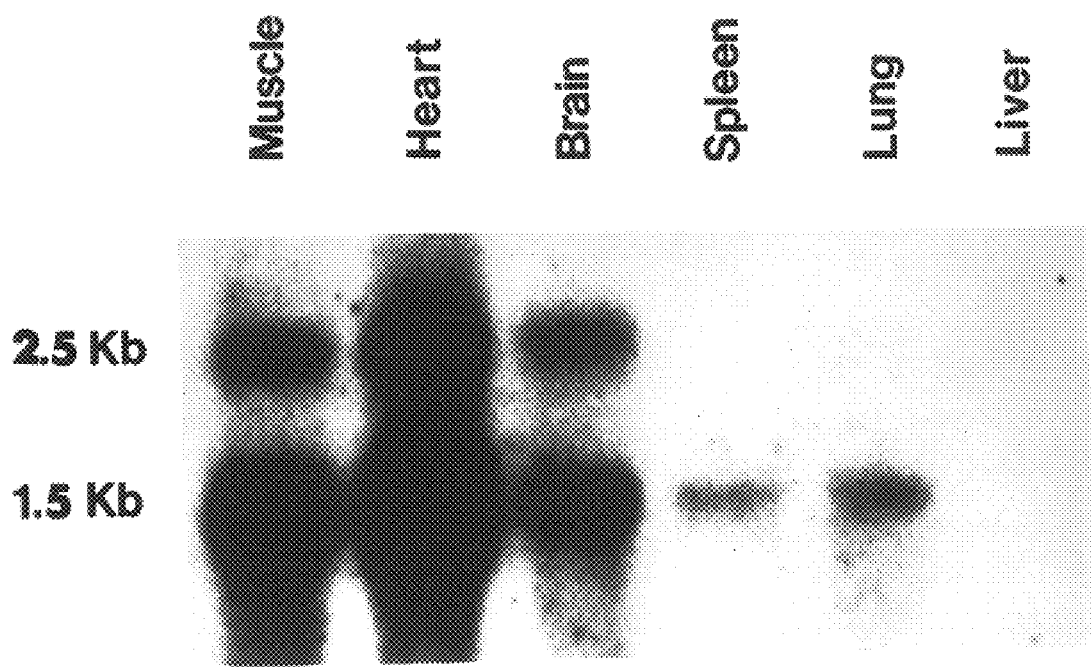
FIG. 2 shows the Northern analysis of tissues from transgenic-mice. Twenty μg of total RNA from the tissues of transgenic mice were denatured with glyoxal and electrophoresed through a 1.2% agarose gel and blotted onto nitrocellulose. The filter was probed with the entire human EC-SOD cDNA. The 2.5 Kb band corresponds to mRNA of the human EC-SOD transgene containing the 1 Kb intervening sequence (see FIG. 1). The 1.5 Kb band corresponds to the fully processed mRNA of the human EC-SOD transgene.

Characterization of transgenic mice: Mice carrying the human EC-SOD transgene were detected by Southern blot analysis. Northern analysis of various tissues from the F1 of one mouse found to carry the transgene is shown in FIG. 2. High levels of message for human EC-SOD were detected in the heart, skeletal muscle, and brain of transgenic mice, with little or no message observed in the lung, liver, and spleen. No message was detectable in nontransgenic littermates.

Homozygous mice were generated by breeding two heterozygous F1 mice. Homozygous mice were detected by differential band intensities found using Southern blot analysis of equal amounts of PstI digested DNA from the offspring. EC-SOD activity in the mice was found to increase in response to the total copies of the EC-SOD transgene (Table I).

TABLE I

EC-SOD activity in tissues of nontransgenic, heterozygous transgenic, and homozygous transgenic mice. Tissues from 3 mice were combined for each measurement. Activity is expressed as Units/g tissue wet weight.

| Tissue | Nontransgenic | Heterozygous | Homozygous |
| --- | --- | --- | --- |
| Brain | 18 | 38 | 50 |
| Heart | 35 | 69 | 102 |

EXAMPLE II

Central Nervous System Oxygen Toxicity

Protocols:

Oxygen exposures: 7–8 week old mice were exposed to hyperbaric oxygen five at a time in a small-animal chamber (Bethlehem, Pa.). After flushing the chamber with pure oxygen, compression to 50 meters (6 ATA) was performed within 5 minutes. The oxygen concentration in the chamber was monitored continuously with a Servomex oxygen analyzer (model 572, Sybron, Norwood, Mass.) and maintained at ≧99%. The carbon dioxide concentration was analyzed from intermittent samples of chamber gas with an IR detector (IR Industries, Santa Barbara, Calif.) and was not allowed to rise above 0.1%. The chamber temperature was maintained at 25–26° C., but the compression of oxygen in the chamber raised the temperature to 30–32° C. transiently, but an environmental control system restored the normal chamber temperature within 3 minutes. The exposures lasted 25 to 75 minutes and were followed by decompression for 5 minutes. The mice were observed continuously for signs of oxygen toxicity from the beginning of the exposure until 4 hours after removal from the chamber. The time to the first generalized convulsion (seizure latency) and the time to death were recorded. These exposure conditions are designed to cause CNS oxygen toxicity without appreciable evidence of pulmonary oxygen toxicity.

Treatment with diethyldithiocarbamate: One hour prior to exposure to 6 ATA oxygen, mice were given either i.p. injections of either 0.008 cc/g saline or 400 mg/kg diethyldithiocarbamate dissolved in normal saline (0.008 cc/g). The mice were then exposed to 6 ATA oxygen for 25 mintues as described above.

To determine the extent of EC-SOD and CuZn SOD inhibition by diethyldithiocarbamate, mice were given diethyldithiocarbamate and sacrificed one hour later. The brains were removed and assayed for EC-SOD and CuZn SOD activity as described above.

Treatment with β-mercaptoethanol: One hour prior to exposure to 6 ATA oxygen, mice were given either i.p. injections of 0.008 cc/g saline or 180 mg/kg β-mercaptoethanol (0.008 cc/g). This dose of β-mercaptoethanol was selected because it contains an equal number of reducing thiols as the dose of diethyldithiocarbamate. The mice were then exposed to 6 ATA oxygen for 30 minutes as described above.

Treatment with N-ω-nitro-L-arginine, an inhibitor of nitric oxide synthase: Ten minutes prior to beginning compression, 0.008 cc/g saline or 20 mg/kg (0.008 cc/g) N-ω-nitro-L-arginine dissolved in sterile water was given i.p to the transgenic and nontransgenic mice. Mice were then exposed at 6 ATA oxygen for 25 or 75 minutes as described above.

Statistical analysis: A paired Student's t-test was used to compare enzyme activities in transgenic and nontransgenic mice. A $X^2$ test with Bonferroni correction was used to assess significance in survival differences to hyperbaric exposures. Analysis of variance with a Scheffe F-test was used to compare differences in seizure latency in the different groups of mice.

Figure 3:
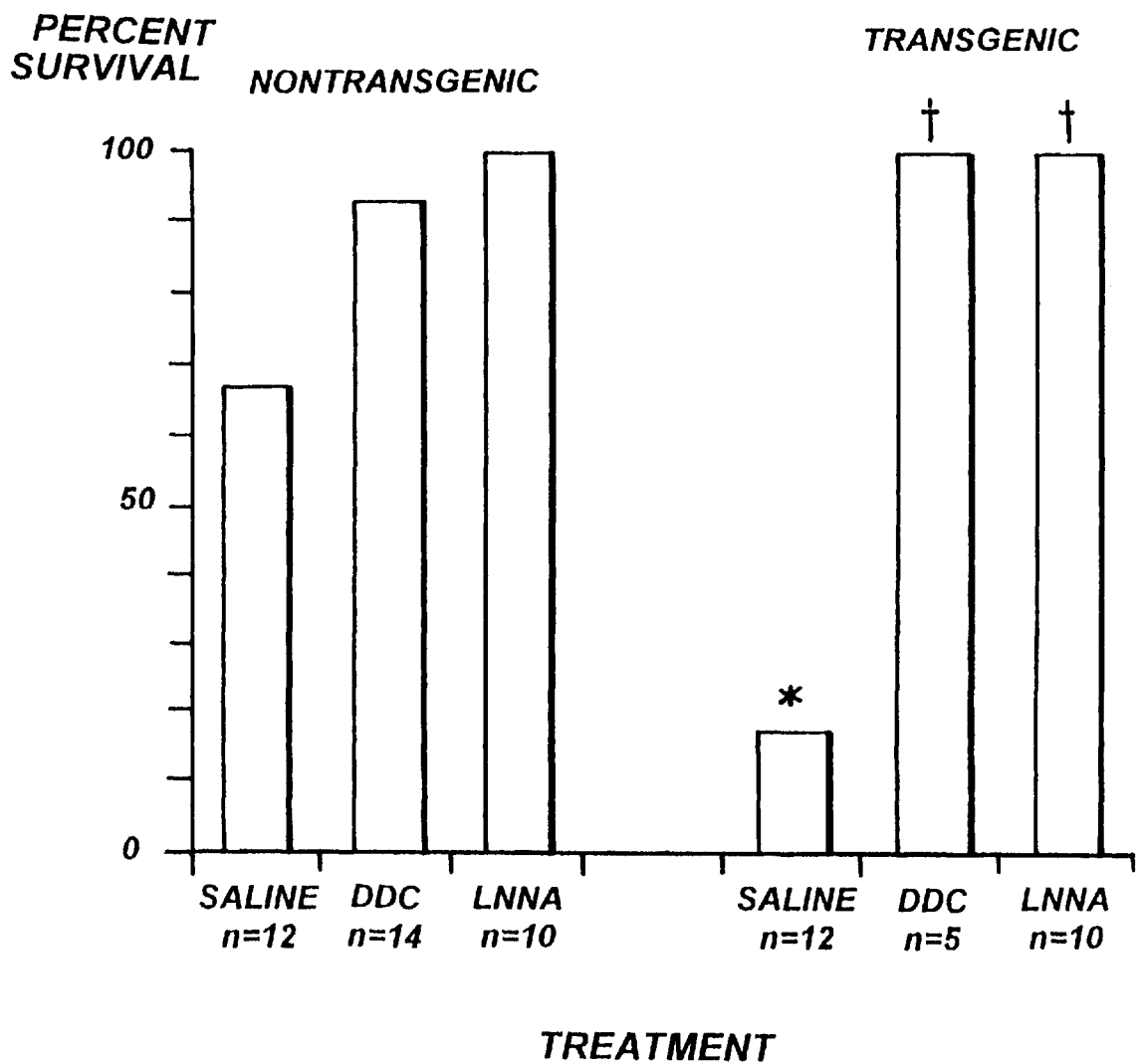
FIG. 3 shows the percent survival of transgenic and nontransgenic mice exposed to 6 ATA oxygen for 25 minutes. Mice were injected with saline or given 20 mg/kg N-ω-nitro-L-arginine (LNNA) i.p. 10 minutes before compression. 400 mg/kg of diethyldithiocarbamate (DDC) in saline was injected i.p. 55 min before compression. *$p<0.017$ tested by $X^2$ with Bonferroni correction, compared to transgenic saline treated mice.

Results:

Hyperbaric oxygen exposures: To test the effects of increased brain EC-SOD levels on CNS oxygen toxicity, both transgenic and nontransgenic mice (see Example I) were exposed to 6 ATA oxygen for 25 minutes. Transgenic mice were more susceptible (83% mortality) to CNS oxygen toxicity than nontransgenic mice (33% mortality) (FIG. 3).

Transgenic and nontransgenic mice were subsequently treated with an inhibitor of CuZn SOD, diethyldithiocarbamate, to confirm that the increased sensitivity of transgenic mice to CNS oxygen toxicity was the result of increased SOD activity. In both transgenic and nontransgenic mice, treatment with 400 mg/kg diethyldithiocarbamate resulted in 80% inhibition of EC-SOD and 60% inhibition of CuZn SOD in the brain. This is consistent with previous findings (Frank et al, Biochem.

Figure 4:
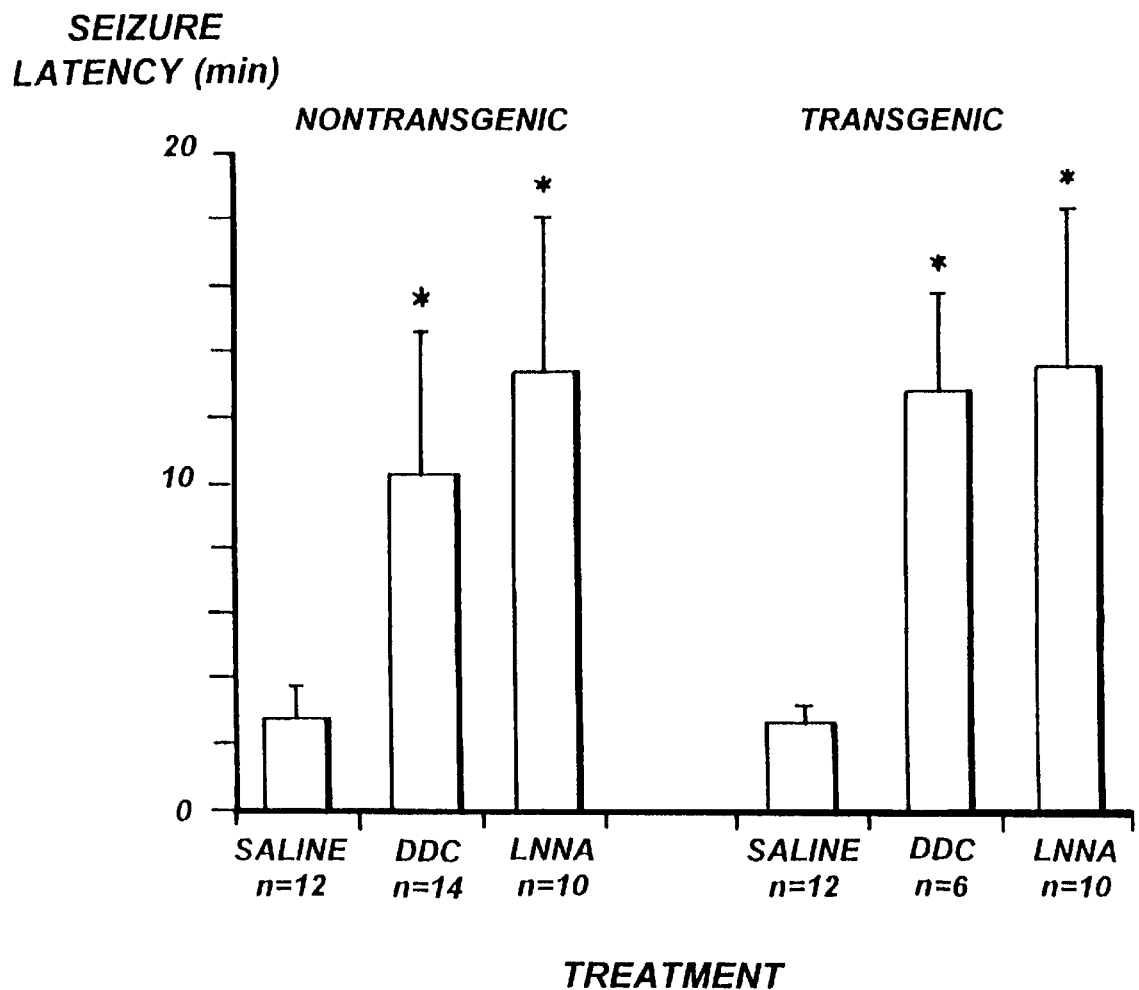
FIG. 4 shows time to onset of first seizure in transgenic and nontransgenic mice exposed to 6 ATA oxygen. Mice were injected with saline or given 20 mg/kg N-ω-nitro-L-arginine (LNNA) i.p. 10 minutes before beginning compression. 400 mg/kg diethyldithiocarbamate (DDC) was injected i.p. 55 minutes prior to compression. Results are expressed as mean±S.D. of time to first seizure with zero time taken once chamber reached 6 ATA. *$p<0.05$ tested by analysis of variance with the Scheffe F-test compared to nontransgenic saline treated mice.

Pharmacol. 27:251 (1978); Heikkila et al, J. Biol. Chem. 251:2182 (1976)). Treatment with diethyldithiocarbamate conferred increased resistance to CNS oxygen toxicity for both transgenic and nontransgenic mice. Survival increased to 100% in transgenic mice and 93% in nontransgenic mice (FIG. 3). The onset of seizures was also delayed four-fold in mice treated with diethyldithiocarbamate (FIG. 4).

Figure 5:
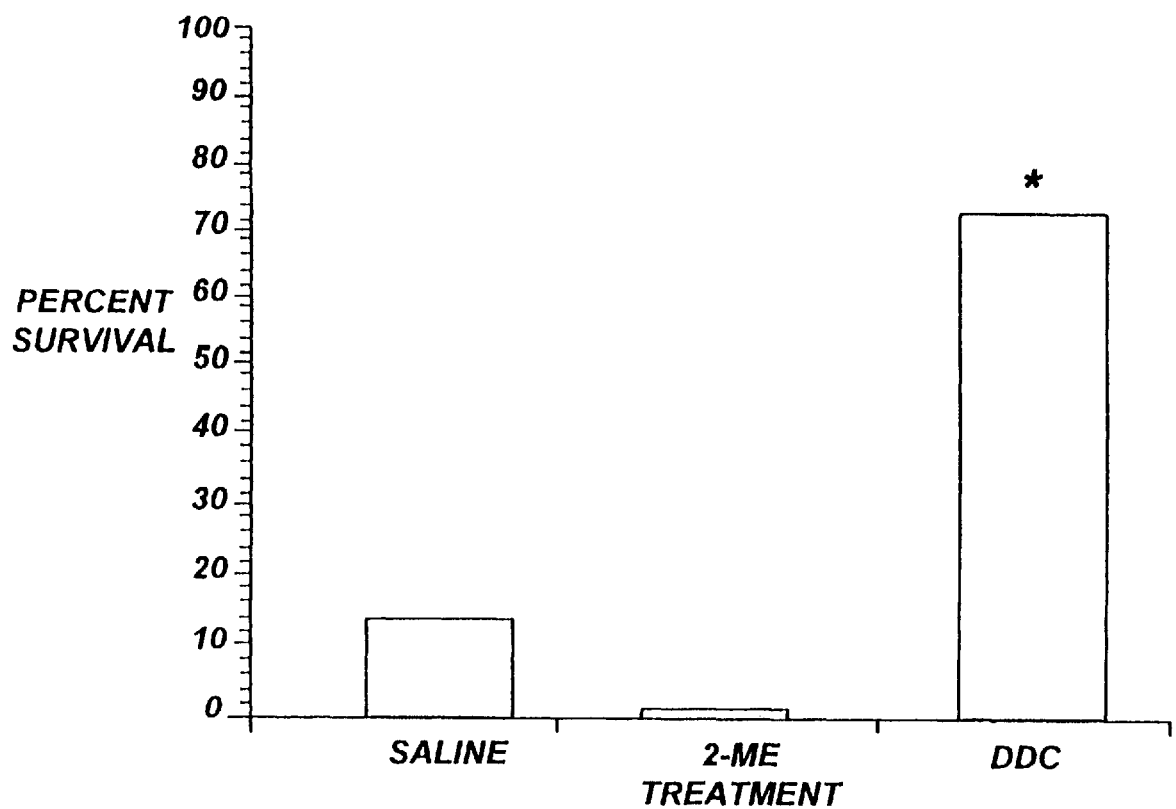
FIG. 5 shows the effect of diethyldithiocarbamate and β-mercaptoethanol on survival in 6 ATA oxygen for 30 minutes. (C57BL/6×C3H)F1 mice were injected i.p. with saline, 180 mg/kg β-mercaptoethanol (2-ME), or 400 mg/kg diethyldithiocarbamate (DDC) in saline 55 min. before compression. *$p<0.025$ tested by $X^2$ with Bonferroni correction compared to saline treated mice.

To evaluate whether or not diethyldithiocarbamate protects against CNS oxygen toxicity by acting as a reducing agent rather than as an inhibitor of SOD activity, mice were treated with an equimolar amount of reducing thiols in the form of β-mercaptoethanol and exposed to hyperbaric oxygen. FIG. 5 shows that β-mercaptoethanol did not protect against CNS oxygen toxicity.

Figure 6:
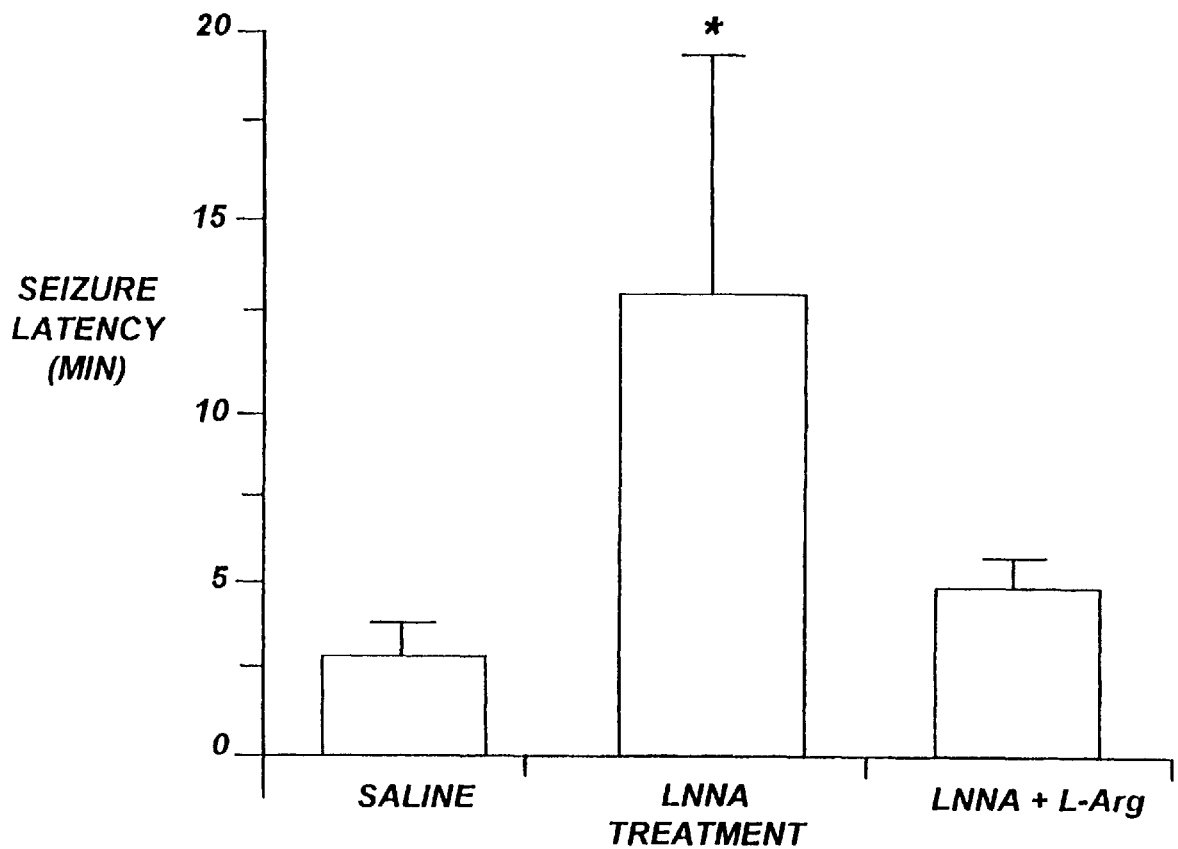
FIG. 6 shows the seizure latency in wild-type mice exposed to 6 ATA oxygen after being treated with saline or 20 mg/kg N-ω-nitro-L-arginine (LNNA) or 20 mg/kg N-ω-nitro-L-arginine plus 50 mg/kg L-arginine (LNNA+L-Arg). *$p<0.05$ tested by analysis of variance with a paired Student's t-test compared to saline treated mice.
Figure 7:
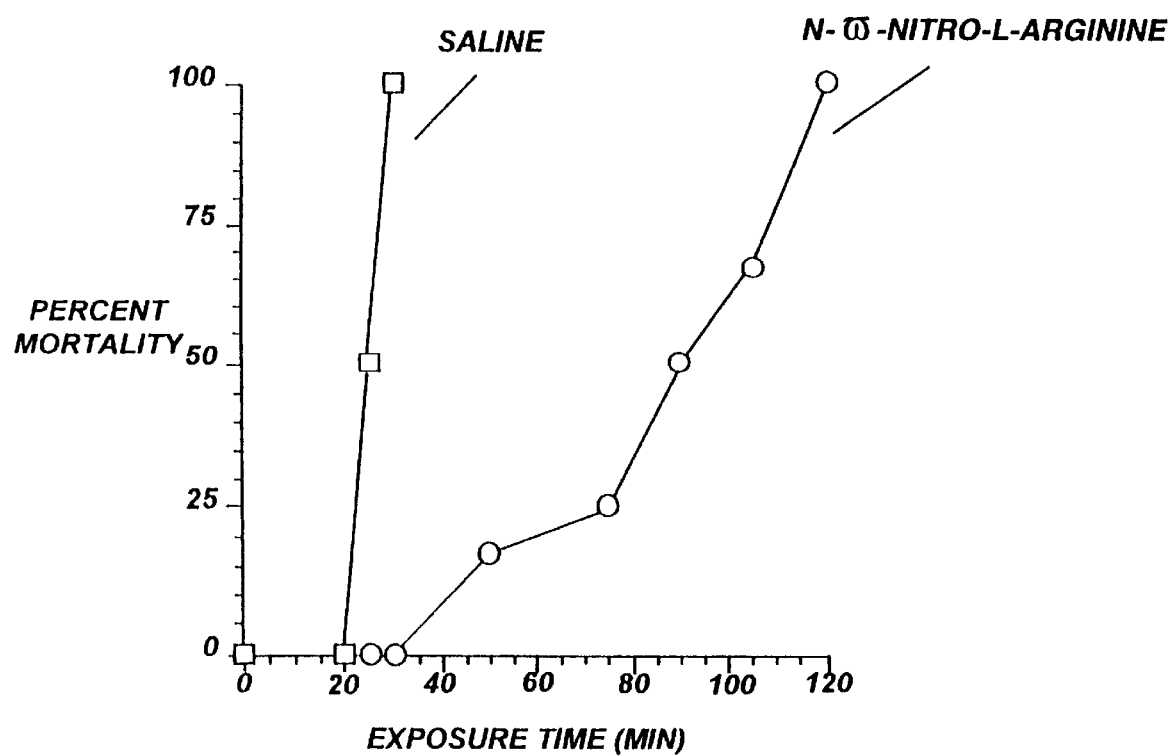
FIG. 7 shows the percent survival in wild-type mice exposed to 6 ATA oxygen. Mice were given an i.p. injection of normal saline (0.008 cc/g) or 20 mg/kg N-ω-nitro-L-arginine (LNNA) (0.008 cc/g) 15 minutes prior to compression. The mice were exposed to 6 ATA of oxygen for 20 minutes (n=10, saline only), 25 minutes (n=10, both groups), 30 minutes (n=10, saline only), 50 minutes (n=6, LNNA only), 75 minutes (n=12, LNNA only), 90 minutes (n=14, LNNA only), 105 minutes (n=6 LNNA only) and 120 minutes (n=6, LNNA only) and percent survival was measured for each group.
Figure 8:
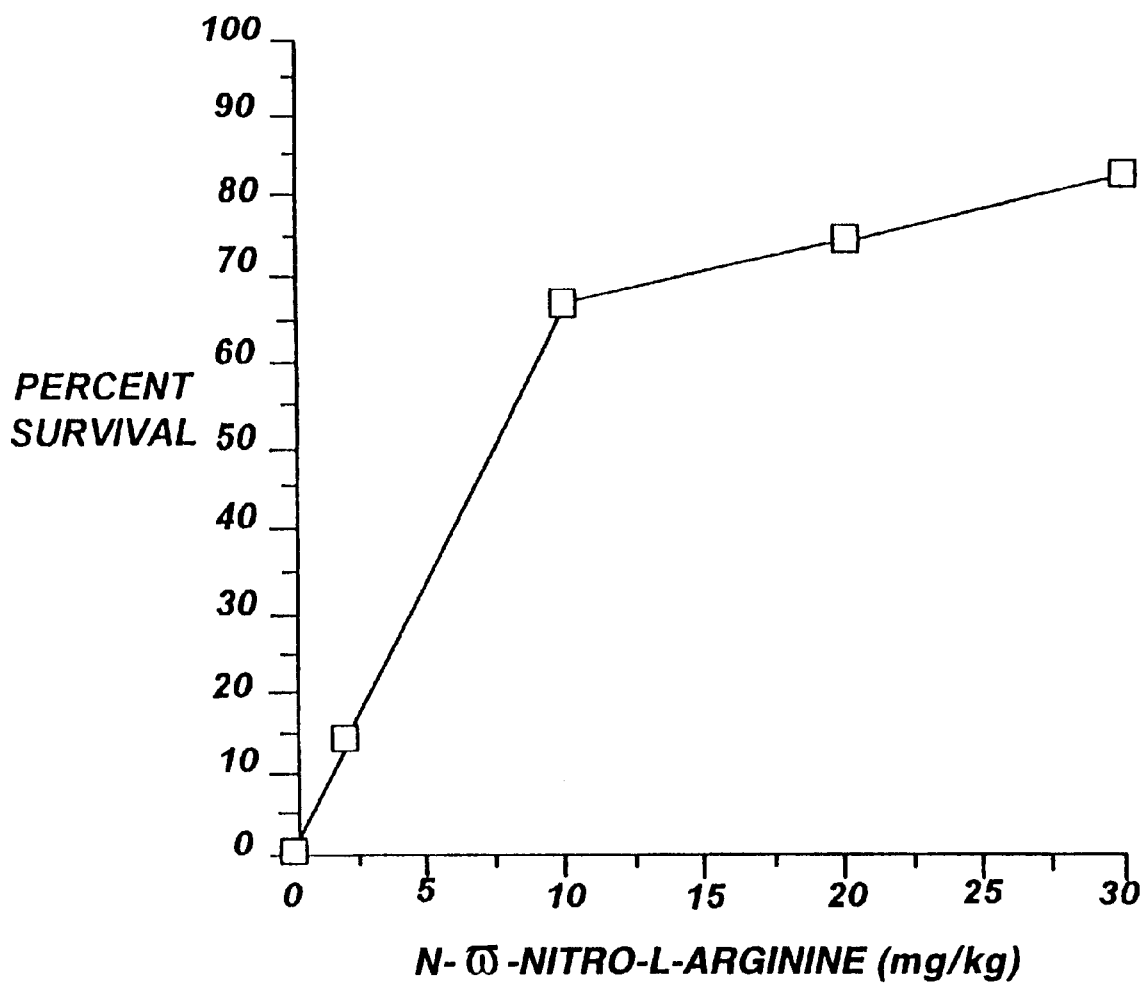
FIG. 8 shows the survival dose response curve for N-ω-nitro-L-arginine (LNNA). Wild-type mice were given an i.p. injection of normal saline (0.008 cc/g) or 0, 2, 10, 20, or 30 mg/kg LNNA (0.008 cc/g) 15 minutes prior to compression and then exposed to 75 minutes at 6 ATA oxygen. Percent survival was calculated for each treatment group.
Figure 9:
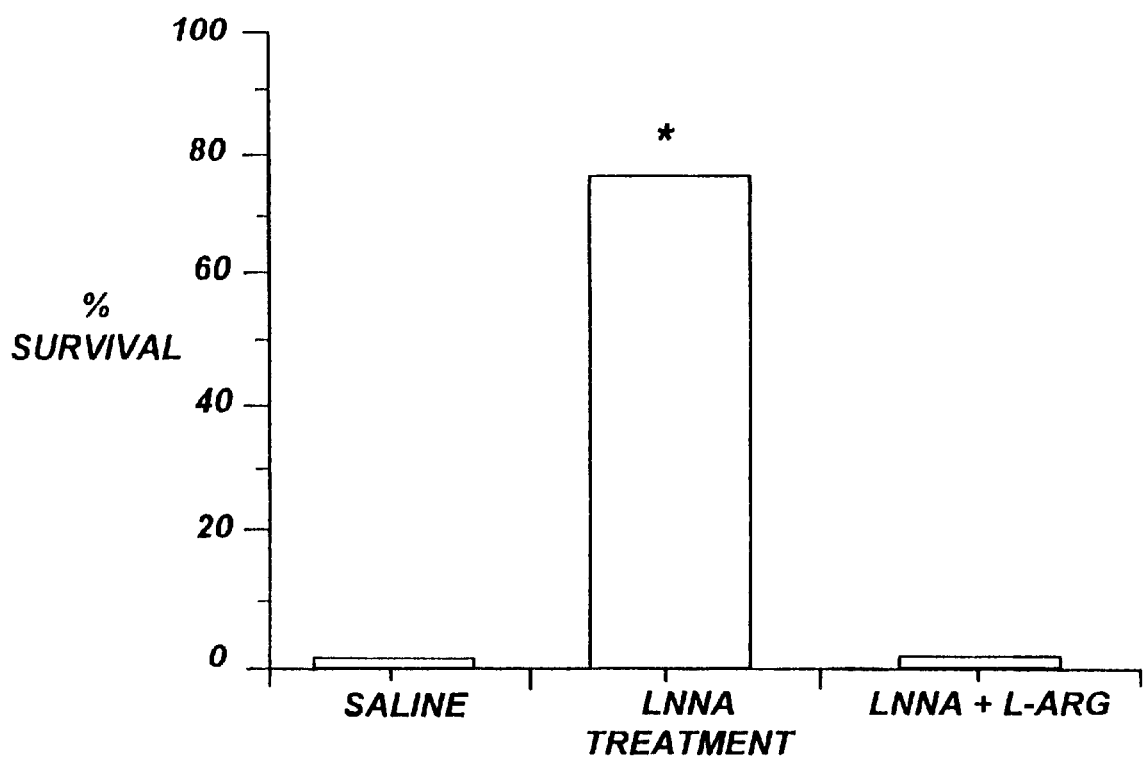
FIG. 9 shows the percent survival in wild-type mice pretreated with saline, 20 mg/kg N-ω-nitro-L-arginine (LNNA), or 20 mg/kg N-ω-nitro-L-arginine plus 50 mg/kg L-arginine (LNNA+L-Arg) and then exposed to 75 minutes of 6 ATA oxygen. *$p<0.05$ tested with a X-square test with Bonferroni correction.

One possibility that might explain why EC-SOD exacerbates CNS oxygen toxicity would be that nitric oxide is a mediator of CNS oxygen toxicity and EC-SOD is protecting nitric oxide from superoxide mediated inactivation. To test the hypothesis that nitric oxide contributes to CNS oxygen toxicity, wild-type (C57BL/6 X C3H)F1 mice were treated with an inhibitor of nitric oxide synthase, N-ω-nitro-L-arginine. FIG. 6 shows the effects of N-ω-nitro-L-arginine on seizure latency in mice. Pretreatment with N-ω-nitro-L-arginine resulted in a significant increase in seizure latency (13.50±5.6 min) when compared to saline treated mice (2.75±1 min). FIG. 7 shows that nitric oxide synthase inhibition also significantly increased survival after exposure to hyperbaric oxygen. Mice given the inhibitor of nitric oxide synthase displayed 50% mortality after exposure to 90 minutes of 6 ATA oxygen and 100% mortality was not obtained until after 2 hours of this exposure. Saline treated mice, however, had a 50% mortality after only 25 minutes of exposure, with 100% mortality after only 30 minutes at 6 ATA of oxygen. FIG. 8 shows that the percent survival in hyperbaric oxygen was dependent on the dose of the inhibitor given. The protection offered by this competitive inhibitor of nitric oxide synthase could be reversed when an excess of L-arginine was given (FIG. 6 and FIG. 9).

Figure 10:
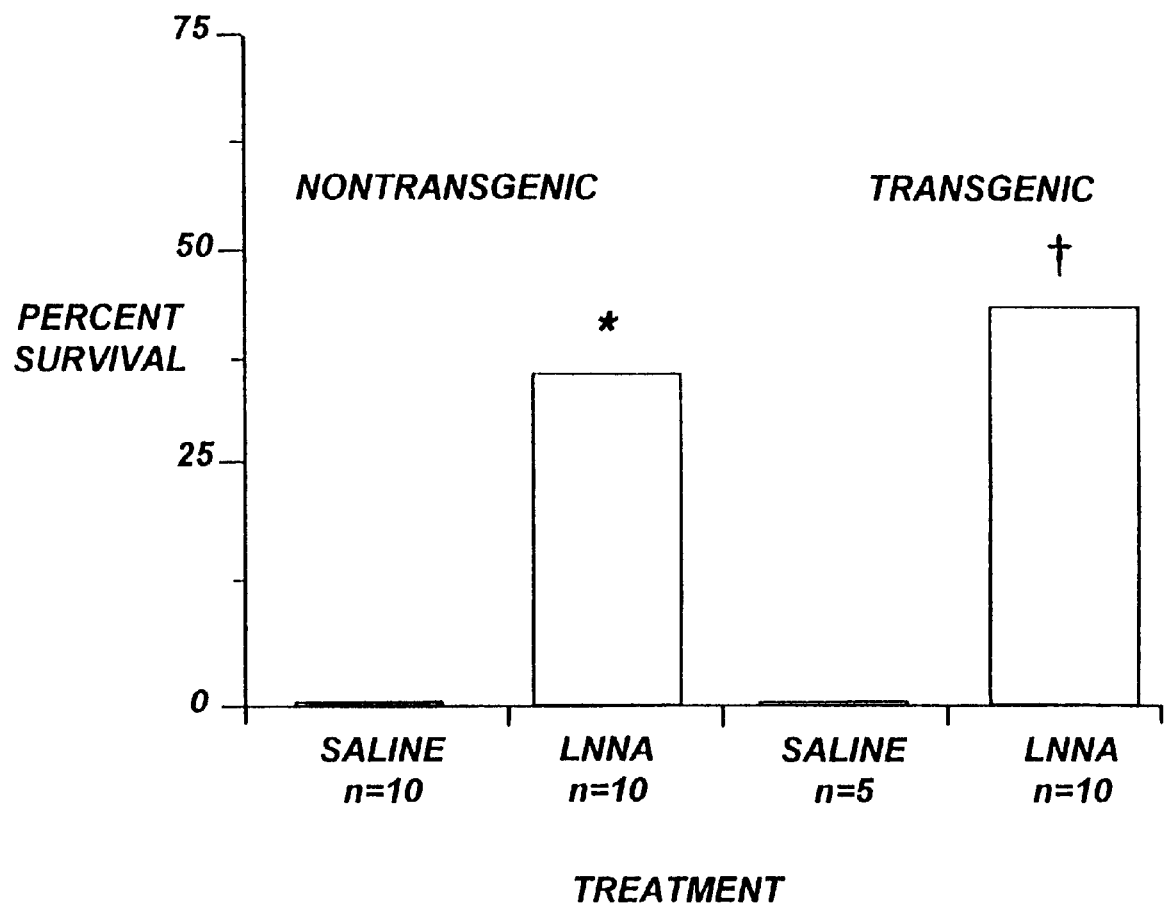
FIG. 10 shows the percent survival in transgenic and nontransgenic mice exposed to 6 ATA oxygen for 75 minutes. Mice were injected with saline or given 20 mg/kg N-ω-nitro-L-arginine (LNNA) i.p. 10 minutes before compression. *$p<0.05$ tested by $X^2$ compared to nontransgenic saline treated mice. †$p<0.05$ tested by $X^2$ compared to transgenic saline treated mice.

The effects of the nitric oxide synthase inhibitor, N-ω-nitro-L-arginine, upon CNS oxygen toxicity was then studied in the transgenic mice. This treatment dramatically reduced CNS oxygen toxicity in both transgenic and nontransgenic mice. Survival after a 25 minute exposure to 6 ATA oxygen increased to 100% in both groups (FIG. 3). Seizure latency was also significantly delayed (FIG. 4). The exposure time was then increased to 75 minutes to investigate whether transgenic mice were still more sensitive than nontransgenic mice to hyperbaric oxygen. The results in FIG. 10 indicate that treatment with N-ω-nitro-L-arginine abolished the difference in sensitivity that was observed between untreated transgenic and nontransgenic mice during the 25 minute exposure shown in FIG. 3.

EXAMPLE III

Cold-Induced Brain Edema

Protocols:

Injury model: Young (6–7 week) mice (see Example I) were anesthetized with 60 mg/kg pentobarbital (Nembutal, Abbott Laboratories, Chicago, Ill.). An incision was then made in the scalp and a steel rod 20 cm long, 3 mm in diameter, equilibrated in liquid nitrogen with an 8 cm bath of liquid nitrogen 4 cm from the end of the rod, was placed on the skull over the right cerebral hemisphere for 30 seconds. The skin incision was then sutured.

Two hours after the injury the mouse was given an additional dose of pentobarbital. The chest cavity was opened, the lungs were excised, and the mouse was then perfused with 20 ml saline through the left ventricle of the heart. The brain was then removed and the cerebellum was excised. The right (R) and left (L) cerebral hemispheres were separated and immediately weighed (wet weight, W). Each hemisphere was then dried at 70° C. for 2–3 days in a hot air oven until a constant weight was achieved (dry weight, D). An index of edema (I) was then calculated as shown in equation 13.

$$I=(W/D\ R-W/D\ L)/(W/D\ L)\times 100 \qquad [13]$$

This calculation allowed the left hemisphere to serve as an internal control for the injured right hemisphere in each mouse.

Chemical treatments: Six groups of experiments were conducted to investigate the importance of extracellular superoxide, iron, and nitric oxide in cold-induced brain edema. In all groups, drugs were dissolved in saline and injected at 0.008 cc/g 15 minutes prior to cold injury. In Group 1, edema formation of EC-SOD transgenic mice was compared with that of nontransgenic littermates. Group 2 compared edema formation between wild-type (C57BL/6 X C3H)F1 mice treated with saline and (C57BL/6 X C3H)F1 mice treated with 0.33 mg/g deferoxamine (0.51 µmoles/g). Group 3 compared (C57BL/6 X C3H)F1 mice treated with saline to (C57BL/6 X C3H)F1 mice treated with 0.51 µmoles/g $Fe^{3+}$-saturated deferoxamine. Group 4 consisted of (C57BL/6 X C3H)F1 mice treated with saline and (C57BL/6 X C3H)F1 mice treated with 0.02 mg/g N-ω-nitro-L-arginine methyl ester. Group 5 consisted of (C57BL/6 X C3H)F1 mice treated with saline and (C57EL/6 X C3H)F1 mice treated with 0.02 mg/g N-ω-nitro-L-arginine methyl ester plus 0.05 mg/g L-arginine. Group 6 compared edema formation between nontransgenic mice, EC-SOD transgenic mice treated with saline, and EC-SOD transgenic mice treated with 0.02 mg/g N-ω-nitro-L-arginine methyl ester.

Iron saturated deferoxamine was made by dissolving equimolar amounts of deferoxamine and then ferric chloride in saline. Saturation of deferoxamine with ferric iron was determined spectrophotometrically be measuring the absorbance at 425 nm ($\epsilon$=2500 $M^{-1}\ cm^{-1}$ for $Fe^{3+}$-deferoxamine) (Monzyk and Crumbliss, J. Amer. Chem. Soc. 104:4921 (1982)).

Evan's blue treatment: One hour and 50 minutes after cold injury, 5 ml/kg of 1% Evan's Blue in saline was injected into the femoral artery of transgenic and nontransgenic mice. The mice were sacrificed 10 minutes later. The lungs were then excised and the mice were then perfused with normal saline through the left ventricle until there was no more blue color in the effluent. The brains were then removed and photographed.

Statistical analysis: A paired Student's t-test was used to compare significance of edema development compared to nontransgenic mice or saline treated mice for each of the groups examined. Analysis of variance with a Fisher PLSD test was used to compare significance in Group 6. P-value less than 0.05 were considered to be significant.

Figure 11:
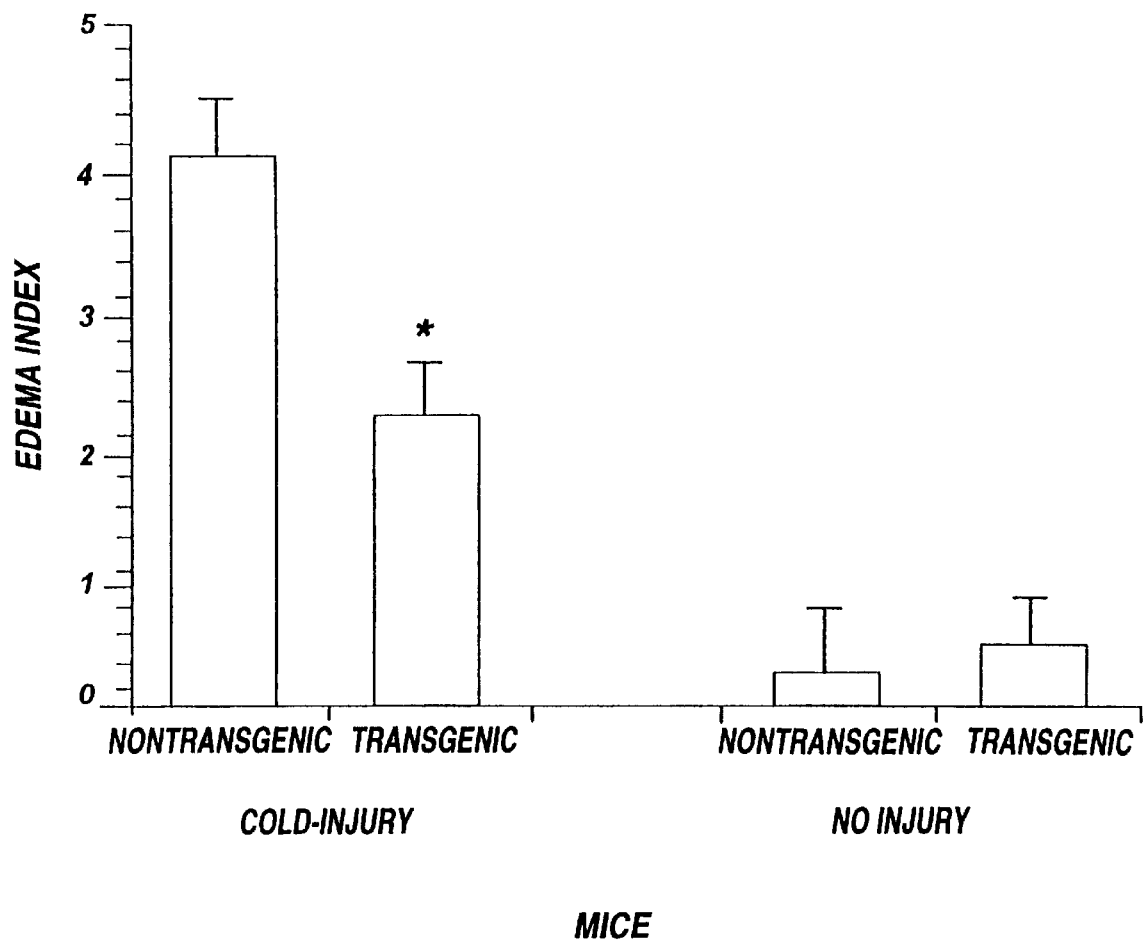
FIG. 11 shows the comparison of edema formation in EC-SOD transgenic mice to edema formation in nontransgenic littermates after cold-induced injury to the right cerebral hemisphere as well as in non-injured mice. Values are presented as mean±standard error. *$p<0.05$ compared to Edema Index of respective nontransgenic controls using a paired Student's t-test.
Figure 12:
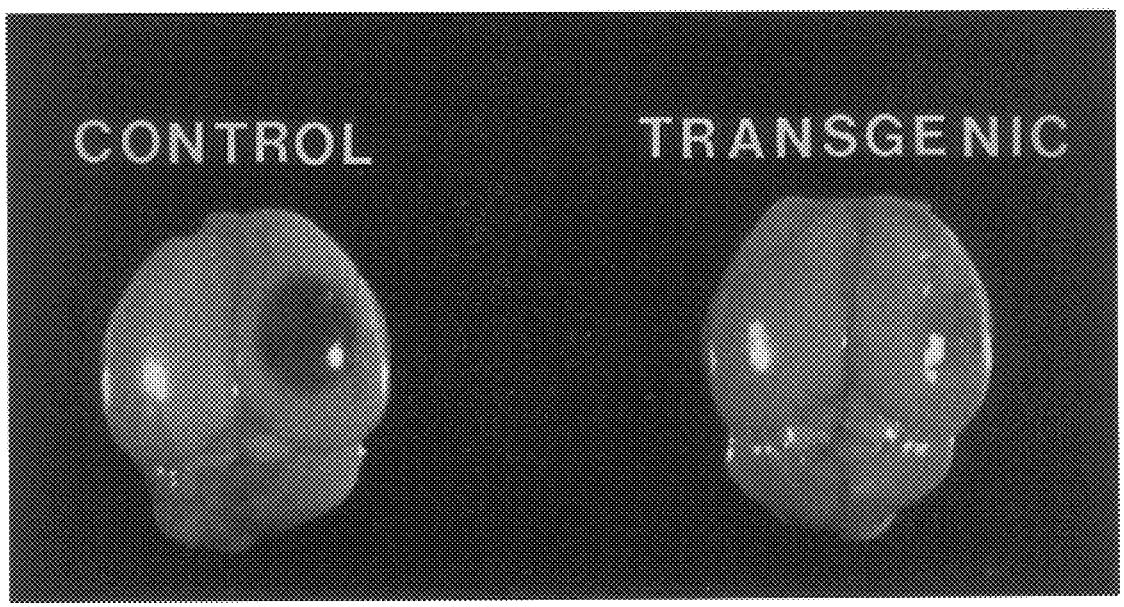
FIG. 12 shows the effect of augmented levels of EC-SOD on vascular permeability changes after cold-induced brain injury. Vascular permeability is demonstrated as Evan's blue leakage in the injured right cerebral hemispheres of nontransgenic (control) and EC-SOD transgenic mice.

Results:

Cold-induced Brain Edema: When transgenic mice and nontransgenic littermates were subjected to cold-induced injury to the right cerebral hemisphere it was found that the transgenic mice were significantly protected against edema formation compared to nontransgenic littermates (FIG. 11). Percent edema was 44% less in transgenic mice then in nontransgenic littermates and Evan's blue dye extravasation was visibly less in transgenic mice compared to nontransgenic littermates (FIG. 12).

To test the contribution of iron to edema formation in this model, mice were pretreated with i.p. injections of deferoxamine or saline prior to cold-induced injury. Table II shows that pretreatment with deferoxamine resulted in 43% less edema formation compared to mice only given saline. Mice were then pretreated with i.p. injections of iron-saturated deferoxamine or saline before cold-induced injury to see if the iron chelating properties of this compound were truly necessary for protection against edema formation. Table IV shows that, even when deferoxamine was saturated with iron, it was still capable of protecting against edema formation and resulted in 32–48% less edema than that found in saline treated controls. The absolute values for the edema index were found to quite variable, however, repeated experiments consistently show the same signficant trends in protection against edema formation in the various treatments examined.

TABLE II

Evaluation of the effect of the ferric iron chelator deferoxamine on edema formation after cold-induced brain injury. Wild-type (C57BL/6 × C3H)F1 mice were treated with deferoxamine to determine what effect the iron chelating properties of this compound had on edema formation. Values are presented as mean ± standard error.

| | Treatment | n | Edema Index |
|---|---|---|---|
| Run 1: | Saline | 7 | 5.92 ± 0.62 |
| | Deferoxamine | 7 | 3.41 ± 0.49* |
| Run 2: | Saline | 6 | 8.24 ± 0.53 |
| | Fe-Deferoxamine | 6 | 5.63 ± 0.63* |
| | Saline | 5 | 7.65 ± 1.30 |
| | Fe-Deferoxamine | 5 | 3.97 ± 0.59* |

*$p < 0.05$ compared to Edema Index of respective saline treated controls using a paired Student's t-test.

These results indicate that deferoxamine is capable of protecting against edema formation by a mechanism independent of its ability to scavenge iron. Because deferoxamine is capable of scavenging both the peroxynitrite anion (Radi et al, Arch. Biochem. Biophys. 288(2):481 (1991)) as well as the hydroxyl radical (Hoe et al, Chemico-Biological Interactions 41:75 (1982)), it was hypothesized that it is these properties of deferoxamine that enable it to protect against vasogenic edema.

To test this hypothesis, the synthesis of nitric oxide was inhibited with N-ω-nitro-L-arginine methyl ester, a competitive inhibitor of the enzyme nitric oxide synthase, to determine if this would result in protection against edema formation after a cold-induced injury. Table III shows that treatment with N-ω-nitro-L-arginine methyl ester significantly protected mice against edema formation resulting in 37% less edema formation than that occurring in saline treated controls. This protection by N-ω-nitro-L-arginine methyl ester was reversed by simultaneous administration of an excess of L-arginine to the mice (Table III).

TABLE III

The effect of inhibition of nitric oxide synthesis on edema formation after cold-induced brain injury. Wild-type (C57BL/6 × C3H)F1 mice were treated with the competitive inhibitor of nitric oxide synthase, N-ω-nitro-L-arginine methyl ester (LNAME) to determine what effect nitric oxide had on vasogenic edema. Mice were also given N-ω-nitro-L-arginine methyl ester plus an excess of L-arginine (LNAME + L-Arg) to see if the effects seen with LNAME alone could be reversed. Values are presented as mean ± standard error.

| Treatment | n | Edema Index |
|---|---|---|
| Saline | 6 | 5.77 ± 0.29 |
| LNAME | 6 | 3.65 ± 0.51* |
| Saline | 6 | 6.56 ± 0.21 |
| LNAME + L-Arg | 6 | 6.03 ± 0.71 |

*$p < 0.05$ compared to Edema Index of respective saline treated controls using a paired Student's t-test.

In the final experiments, EC-SOD transgenic mice were treated with either saline or N-ω-nitro-L-arginine methyl ester to determine if there was an additive effect in preventing edema formation in mice which have both increased levels of EC-SOD as well as the inhibitor of nitric oxide synthase. Table IV shows that when EC-SOD transgenic mice were given the inhibitor of nitric oxide synthase, no added protection against edema formation was detected relative to transgenic mice protected only by increased levels of EC-SOD in the brain.

TABLE IV

Evaluation of the effect of inhibition of nitric oxide synthesis on edema formation in transgenic mice. Comparison of edema formation in nontransgenic mice to edema formation in transgenic mice with elevated levels of brain EC-SOD activity, and to edema formation in transgenic mice treated with an inhibitor of nitric oxide synthesis (20 mg/kg N-ω-nitro-L-arginine; Transgenic + LNAME) 15 minutes prior to cold-induced injury. Values are presented as mean ± standard error and were compared using analysis of variance with a Fisher PLSD test. No significant difference was seen between transgenic and transgenic ± LNAME mice.

| Treatment | n | Edema Index |
|---|---|---|
| Nontransgenic | 6 | 7.91 ± 0.67 |
| Transgenic | 6 | 4.91 ± 0.78* |
| Transgenic + LNAME | 6 | 4.30 ± 0.96* |

*$p < 0.05$ compared to Edema Index of nontransgenic mice.

EXAMPLE IV

Immunolocalization of EC-SOD

Protocols:

Human lung: Five human lung samples were obtained to evaluate the distribution of EC-SOD in human lung tissue. One sample was obtained from a surgical pathology specimen of a right upper lobe resected from a 43 year old white female with a 50 pack year smoking history (equivalent to one pack per day for one year) and a solitary nodule found on chest X-ray. The patient was diagnosed with squamous cell carcinoma. Tissue from a region not involved in the carcinoma from this lobe was used in the studies presented here. A second lung was obtained from a right upper lobe surgical pathology specimen resected from a 51 year old white male with a 60 pack year smoking history found to have an isolated nodule on X-ray. The patient had no other illness and was diagnosed with squamous cell carcinoma.

Lung tissue not involved in the carcinoma from this specimen was used for the localization of EC-SOD. A third lung was obtained from a rapid autopsy (tissue obtained 6 hours after death) of a 66 year old white male with dementia, but no history of smoking or lung disease. The fourth lung examined was obtained from excess lung tissue of a lung too large for the recipient of a lung transplant. The lung was donated from a 45 year old white female with no history of smoking or lung disease. The fifth lung examined in these studies was also from excess lung tissue used for lung transplantation from a 39 year old white male with no history of smoking or lung disease. Notably, no differences in labeling patterns were seen between the surgical pathology specimens, the autopsy tissues from donors for lung transplantation.

The tissues were fixed in 2% paraformaldehyde/0.2% gluteraldehyde in 0.01 M phosphate buffered saline (PBS; 1.2 g $NaH_2PO_4$, 8 g NaCl, 0.2 g KCl, in 1 liter pH 7.3) for 1 hour followed by overnight fixation in 4% paraformaldehyde at 4° C. and then in O.C.T. compound. The tissues were frozen in liquid nitrogen chilled hexane and stored at −70° C. until they were sectioned for light microscopic studies.

For electron microscopic studies, lung tissues were processed as in the light microscopic studies up to the equilibration in sucrose. After equilibration in sucrose, the lung tissues were infiltrated with 10% gelatin at 37° C. for 10 minutes. The tissue slices, in gelatin, were then solidified on ice, cut into 2 mm/side cubes, and then cryoprotected in 4% polyvinyl alcohol containing 2 M sucrose overnight. These samples were then mounted onto stubs, flash frozen in liquid nitrogen, and then stored in liquid nitrogen until they were sectioned for electron microscopic studies.

Characterization of antibody to human recombinant EC-SOD: Human recombinant EC-SOD (furnished by S. L. Marklund, UmeÅ, Sweden; Tibell et al Proc. Natl. Acad. Sci. USA 84:6634 (1987)) and the 20,000×g supernatant of a human lung homogenate were denatured in the presence of β-mercaptoethanol and sodium dodecyl sulfate by boiling for 5 minutes and then electrophoresed through 12% polyacrylamide gel in the presence of sodium dodecyl sulfate. The protein was then electrophoretically transferred to nitrocellulose. The blot was then incubated with 4.3 μg/ml of an IgG purified fraction of rabbit anti-rh-EC-SOD (furnished by S. M. Marklund, UmeÅ University Hospital, UmeÅ, Sweden) affinity purified with rh-EC-SOD followed by incubation with $^{125}$I-protein A and autoradiography.

Absorption of anti-EC-SOD IgG: CNBr activated sepharose was swollen in PBS. Swollen gel was mixed with PBS so that the settled gel occupied 50% of the volume. The gel was suspended and 100 μl was mixed with 100 μg pure rh-EC-SOD for 2 hours at room temperature while gently agitating. The gel was then washed 4 times with PBS+1% bovine serum albumin (BSA) and made up 100 μl with PBS+1% BSA. 100 μl of rabbit anti-rh-EC-SOD at two times the concentration used for immunolabeling was then added and mixed for 2 hours with gentle agitation at room temperature. Non-immune rabbit IgG was then added to the supernatant in a concentration equivalent to the predicted concentration of anti-rh-EC-SOD IgG removed by the procedure. This supernatant was then used for subsequent immunolabeling.

Light microscopic immunohistochemistry: 4 μm serial sections of O.C.T. embedded tissue were cut on a cryostat at −20° C. and put on poly-L-lysine-coated slides (3 sections/slide). Sections were stored at −70° C. until labeling was done. Sections were then labeled for EC-SOD using an indirect immunoperoxidase method (Milde et al, J. Histochem. Cytochem. 37:1609 (1989); Randell et al, Am. J. Respir. Cell. Mol. Biol. 4:544 (1991)) with a biotinylated goat anti-rabbit IgG and streptavidin-horseradish peroxidase (Jackson, ImmunoResearch Laboratoreis (West Grove, Pa.)) (Table V). To reduce background staining, the sections were incubated in 1% $H_2O_2$ in methanol to inactivate endogenous peroxidases, 10 mM borohydride to block aldehydes, and nonspecific binding was blocked by incubation with 5% normal goat serum (NGS), 5% milk, and 1% BSA in PBS. The optimal primary and secondary antibody dilutions were determined empirically and made in PBS with 1% milk plus 1% BSA (milk was not included in the streptavidin solution). The slides were developed using diaminobenzidine (10 mg diaminobenzidine, 50 ml 0.05 M Tris.Cl, pH 7.6, 100 μl 3% $H_2O_2$) and counterstained with 1% methyl green. As a control, serial sections were separately labeled with either rabbit anti-rh-EC-SOD (EC-SOD), non-immune rabbit IgG, or rabbit anti-rh-EC-SOD from which EC-SOD binding IgG had been absorbed out (EC-SOD absorbed; see above).

TABLE V

Staining procedures for light microscopic immmunohistochemistry. All incubations were performed in a humidified chamber at room temperature.

| | Incubation Time | |
|---|---|---|
| Step 1 | 1% $H_2O_2$ in methanol | 30 minutes |
| Step 2 | 10 mM borohydride in PBS (gluteraldehyde fixed tissue only) | 30 minutes |
| Step 3 | 5% NGS, 5% milk, 1% BSA/PBS 30 minutes | |
| Step 4 | Primary antibody 1% milk, 1% BSA/PBS 1 hour (various dilutions) | |
| Step 5 | Biotin-labeled goat anti-rabbit IgG (1:6000 in 1% milk, 1% BSA/PBS) | 1 hour |
| Step 6 | Streptavidin-Horse radish peroxidase (1:2000 in 1% BSA/PBS) | 1 hour |
| Step 7 | Diaminobenzidine | 15 minutes |
| Step 8 | 1% Methyl Green in water | 15 minutes |

Electron microscopic immunocytochemistry: Ultrathin cryo sections (70 nm) of human lung tissue were immunolabeled with rabbit anti rh-EC-SOD and 10-nm protein A-gold as prevsiously described (Crapo et al, Proc. Natl. Acad. Sci. USA 89:10405 (1992)) (Table VI). Briefly, sections were first incubated three times for five minutes at room temperature in 0.15% glycine in PBS to block aldehyde groups. Nonspecific binding was further blocked by incubation in 1% BSA in PBS for 10 minutes. Primary and secondary antibody dilutions were determined empirically and made in PBS containing 1% BSA. Sections were stained with uranyl oxalate and uranyl acetate in methyl cellulose as previously described (Crapo et al, Proc. Natl. Acad. Sci. USA 89:10405 (1992)). Control groups were as described for light microscopy above.

TABLE VI

Staining procedures for electron microscopic immunohistochemistry. All incubations were performed at room temperature.

| | Incubation Time | |
|---|---|---|
| Step 1 | PBS + 0.15% glycine | 3 × 5 minutes |
| Step 2 | 1% BSA/PBS | 5 minutes |

TABLE VI-continued

Staining procedures for electron microscopic immunohistochemistry. All incubations were performed at room temperature.

| | | Incubation Time |
|---|---|---|
| Step 3 | Primary antibody in 1% BSA/PBS | 45 minutes |
| Step 4 | Protein -A gold | 30 minutes |
| Step 5 | Uranyl oxalate | 5 minutes |
| Step 6 | Uranyl acetate/methyl cellulose | 10 minutes |

Figure 13:
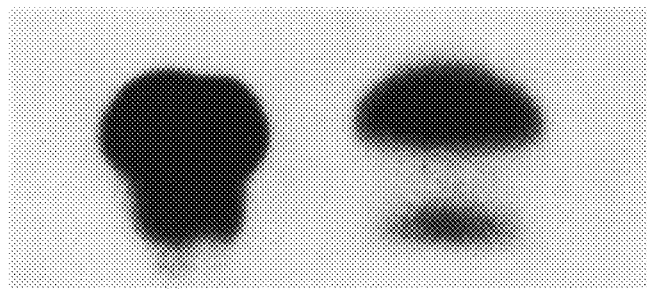
FIG. 13 shows a Western blot analysis of rh-EC-SOD and a human lung homogenate to demonstrate antibody specificity. Proteins were separated on a 10% 0.75 mm SDS-polyacrylamide gel and transferred to nitrocellulose. Proteins were hybridized with the antibody to recombinant human EC-SOD (4.3 µg/ml) and the antibody was detected by hybridization with $^{125}$I-Protein-A followed by autoradiography. The EC-SOD lane contained 0.05 µg of pure recombinant human type C EC-SOD lane protein. The lung lane contained 10 µg of a 20,000×g supernatant of a human lung homogenate.

Results:

Characteristic of EC-SOD antibody: The antibody to rh-EC-SOD was characterized by Western blot analysis of rh-EC-SOD and a human lung homogenate. FIG. 13 shows that the antibody reacted with both the EC-SOD type C (top band) and the type A (bottom band) subunits (Sandstrom et al, Biochem. J. 267:18205 (1992) in a human lung homogenate. The type A subunit does not exist in the interstium of tissues in vivo (Sandström et al, Biochem. J. 290:623 (1993)). The antibody reacted with three bands in the lane containing purified type C rh-EC-SOD. The two lowest molecular weight species in FIG. 13 are due to partial insufficient glycosylation of the rh-ECSOD in the heavily overproducing CHO-cells.

Figure 14A:
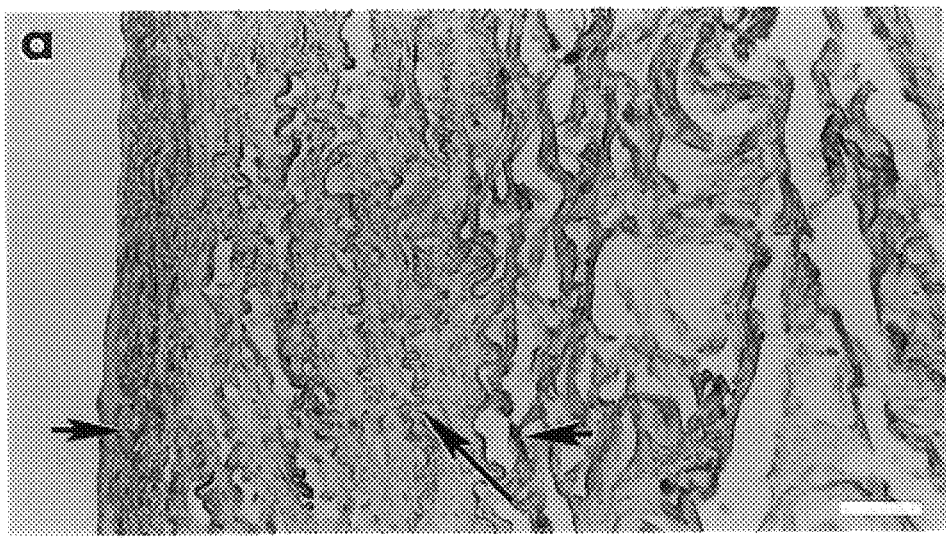
FIGS. 14A–14C show the light microscopic immunohistochemical localization of EC-SOD in human lung. Tissues were labeled using the antibody to recombinant human EC-SOD (5.4 mg/ml; anti-EC-SOD) or the same antibody in which the anti-EC-SOD IgG was absorbed out using purified recombinant EC-SOD attached to CNBr-sepharose (EC-SOD absorbed). Antibody was detected using a biotin/streptavidin-hoseradish peroxidase labeling technique. A, Large elastic pulmonary artery labeled with anti-EC-SOD. Note labeling around smooth muscle cells beneath the endothelium and beneath the elastic layer of the vessel (short arrow), and the lack of labeling for EC-SOC on the surface of endothelial cells (open arrow) and on elastin (long arrow). B, Muscular pulmonary artery labeled with anti-EC-SOD. Note high amount of labeling in the connective tissue matrix surrounding the vessel and lymphatics (long arrow), in the matrix surrounding smooth muscle cells (short arrow), and the lack of labeling on the surface of endothelial cells (open arrow). C, Muscular pulmonary artery labeled with EC-SOD absorbed antisera. The absorption of anti-EC-SOD IgG abolished all labeling in the muscular vessel. (Bars=50 µm).
Figure 14B:
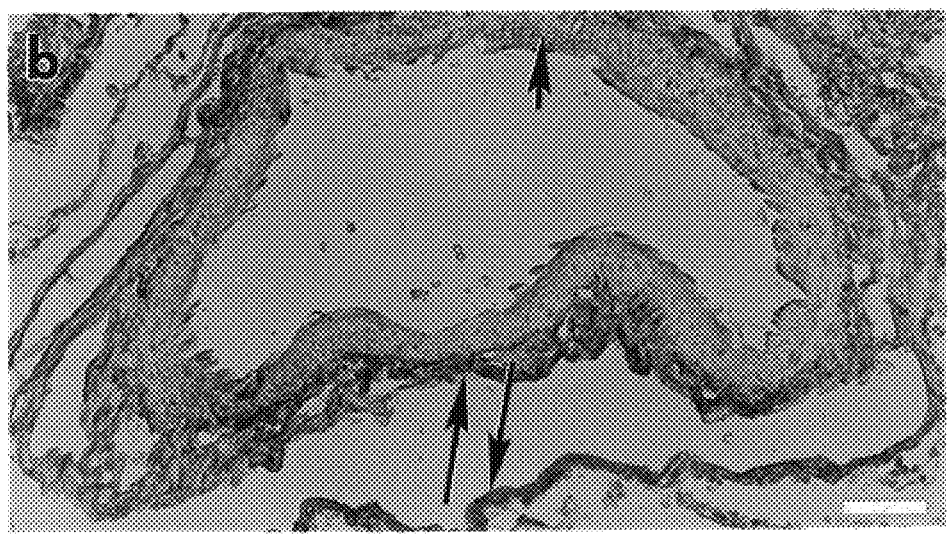
Figure 15A:
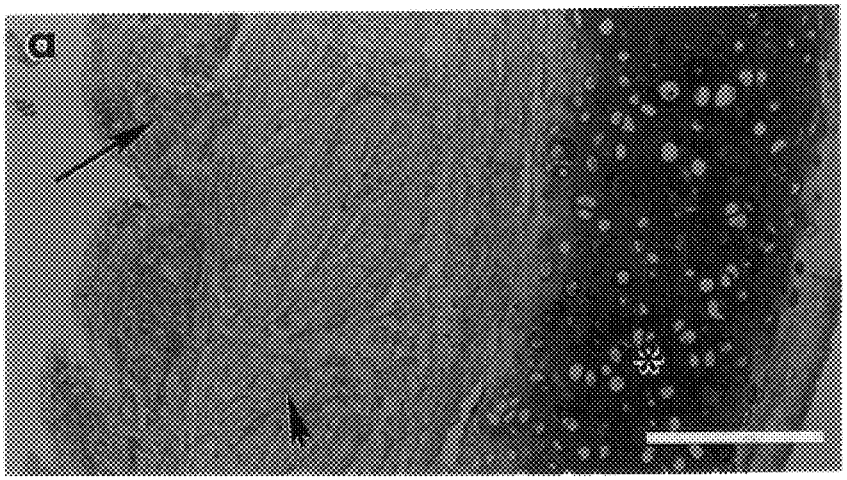
FIGS. 15A–15C show the immunohistochemical localization of EC-SOD in human lung. Tissues were labeled using the antibody to recombinant human EC-SOD (5.4 mg/ml; anti-EC-SOD). Antibody was detected using a biotin/streptavidin-horseradish peroxidase labeling technique. A, Large cartilaginous airway labeled with anti-EC-SOD. Note the intense labeling for EC-SOD in the matrix around smooth muscle cells (short arrow), between the epithelial cells (long arrow), and the lack of labeling on the surface of the epithelial cells (open arrows), and in the matrix of cartilage (asterisk). B, Noncartilaginous airway labeled with anti-EC-SOD. Note the intense labeling for EC-SOD throughout the entire matrix beneath the epithelium (short arrow), and the lack of labeling on the surface of the epithelium (open arrow). C, Lung parenchyma labeled with anti-EC-SOD. EC-SOD labeling is primarily at alveolar septal tips (short arrow), and in the matrix surrounding small vessels (long arrow). No labeling for EC-SOD was seen on the surface of alveolar epithelial cells (open arrow). (Bars=50 µm).
Figure 15B:
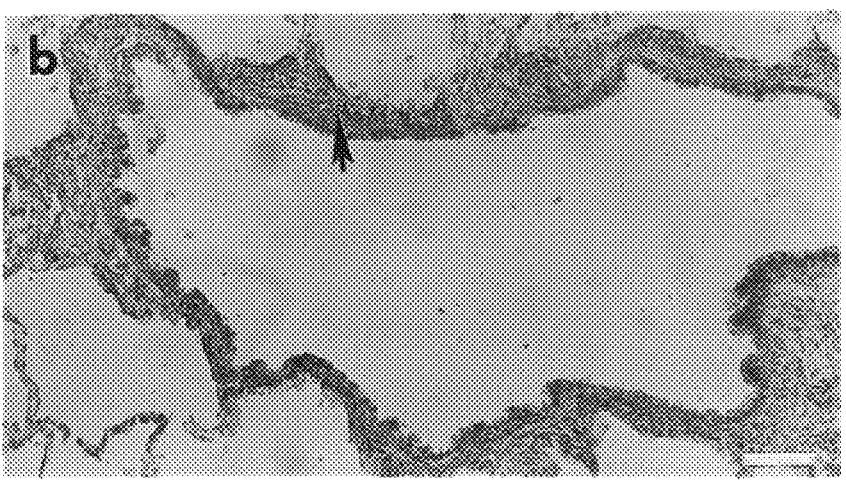
Figure 15C:
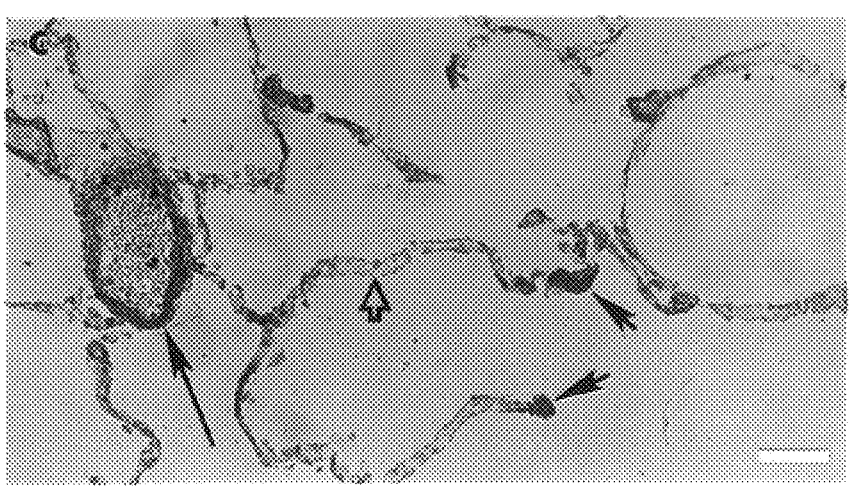

Light microscopic immunohistochemistry: Using an antibody to rh-EC-SOD, this protein was immunolocalized in human lungs. Light microscopic immunohistochemistry revealed with EC-SOD is mainly associated with the connective tissue matrix around vessels and airways in the lung (FIG. 14a and b, FIG. 15a, b, and c). EC-SOD was found in close proximity to vascular and airway smooth muscle (FIG. 14a and b, and FIG. 15a). EC-SOD was also seen in connective tissue of alveolar septal tips (FIG. 15c) suggesting an affinity of EC-SOD for connective tissue matrix. No labeling was seen in association with vascular endothelial cells in large elastic arteries, medium-sized vessels, or capillaries, (FIG. 14a and b). EC-SOD was notably absent from the epithelial cell surfaces of airways (FIG. 15a and b) and was also not present in cartilage (FIG. 15a).

Figure 14C:
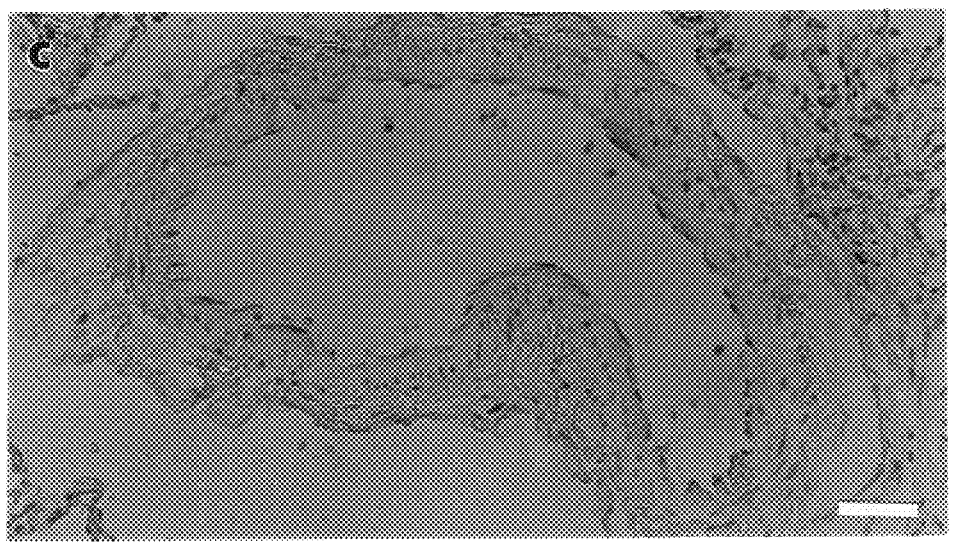

The antibody to EC-SOD was an IgG polyclonal rabbit antibody which was affinity purified using rh-EC-SOD. To test the specificity of the labeling for EC-SOD, IgG specific for EC-SOD was absorbed out of the antisera using pure rh-EC-SOD bound to cyanogen bromide sepharose. Nonimmune rabbit IgG was then added to this absorbed antibody in a sufficient amount to replace the absorbed IgG. Labeling lung tissues with this preabsorbed antibody preparation resulted in the absence of labeling in all areas of the lung including the pulmonary vasculature (FIG. 14c). Labeling lung tissue with nonimmune IgG alone also resulted in the absence of labeling in all areas of the lung. The controls indicate that the labeling observed with the primary antibody is specific for EC-SOD in the lung.

Figure 16A:
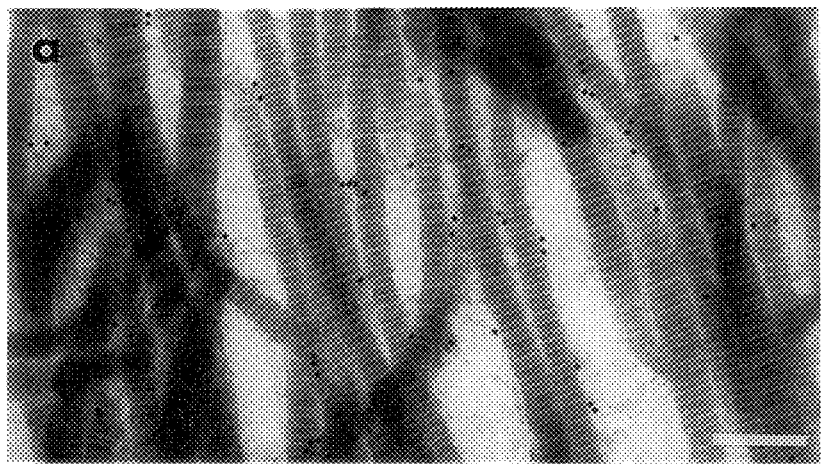
FIGS. 16A–16C show the electron microscopic immunolocalization of EC-SOD in vascular connective tissue. Tissues were labeled using the antibody to recombinant human EC-SOD (40 µg/ml; anti-EC-SOD) or the same antibody after the anti-EC-SOD IgG was absorbed out using purified recombinant EC-SOD attached to CNBr-sepharose (EC-SOD absorbed). Antibody was detected using 10 nm protein-A gold. A, Vascular collagen labeled with anti-EC-SOD, B, Vascular elastin labeled with anti-EC-SOD. C, Vascular collagen labeled with EC-SOD absorbed antisera.
Figure 16B:
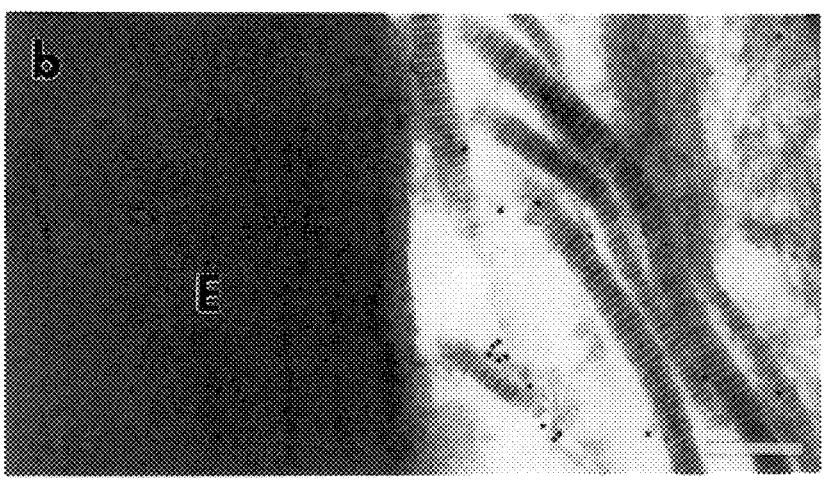

Electron microscopic immunocytochemistry: A summary of the labeling for EC-SOD in the lung found using electron microscopic immunocytochemistry is summarized in Table VII. EC-SOD was mainly associated with extracellular matrix proteins in all regions of the lung. In particular, a high degree of labeling was seen in areas rich in type I collagen (FIG. 16) and in association with other unidentified proteoglycans in extracellular matrix (FIG. 17). Notably, no labeling for EC-SOD was seen in elastin-rich areas (FIG. 16). A high degree of labeling was observed near the surface of smooth muscle cells and in the connective tissue matrix surrounding smooth muscle cells in vessels (FIG. 17) and airways. Labeling was notably absent from the surface of endothelial cells on small, medium and large vessels (FIGS. 18a and b). The lack of endothelial cell labeling found with the light microscopic immunohistochemistry support the electron microscopic findings. Labeling of EC-SOD was also seen in plasma within the lumen of blood vessels (FIG. 18a). The localization of EC-SOD in plasma is expected as this protein was first discovered in plasma (Marklund, Acta Physiol. Scand., 5492:19 (1980)). Labeling for EC-SOD was observed in the intercellular junctions between bronchial epithelial cells (FIG. 19), but was absent from the apical surface of these cells. Finally, EC-SOD labeling was absent from the surface of type I and type II cells. A moderate, but consistent amount of intracellular EC-SOD was found in type II epithelial cells and in bronchial epithelial cells (FIG. 19).

TABLE VII

Distribution of EC-SOD in human lung. (+) indicates presence of labeling for EC-SOD and (−) indicates no labeling for EC-SOD. (±) represents areas where low low amounts of labeling for EC-SOD were inconsistently observed.

| Location | EC-SOD |
|---|---|
| Cell Surfaces | |
| Endothelial | − |
| Type I cell | − |
| Type II cell | − |
| Smooth muscle cell | + |
| Fibroblast | ± |
| Extracellular Matrix | |
| Type I collagen | + |
| Elastin | − |
| Cartilage | − |
| Unidentified matrix elements | + |
| Intracellular | |
| Endothelial cell | ± |
| Type I cell | − |
| Type II cell | + |
| Bronchial epithelial cell | + |
| Smooth muscle cell | − |
| Fibroblast | ± |
| Blood | |
| Plasma | + |
| Red Blood Cell | − |

Figure 16C:
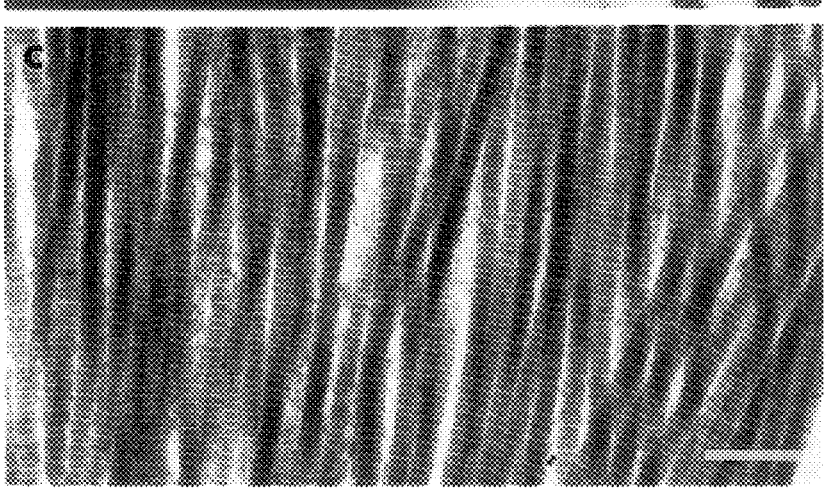

Controls done by absorbing EC-SOD specific antibody out of the primary antibody and replacing this absorbed antibody with nonimmune rabbit IgG resulted in the absence of labeling in all areas of the lung including areas rich in type I collagen as seen in FIG. 16c. In addition, use of nonimmune rabbit IgG instead of the primary antisera also resulted in the absence of labeling in all areas of the lung. The lack of labeling with these controls indicates that the labeling observed with the primary antisera is specific for EC-SOD in the lung.

The localization of EC-SOD on the surface of smooth muscle cells and in the extracellular matrix around these cells in both blood vessels and airways indicates that EC-SOD may have an important function in this location. Superoxide is known to rapidly react with nitric oxide and inactivate its properties as a smooth muscle relaxant. Therefore, the presence of EC-SOD along the diffusion path of nitric oxide to smooth muscle cells should increase the half life of this short lived intercellular messenger in this particular region and thus increase its potency as a vasodilator. The high labeling for EC-SOD seen around vascular and airway smooth muscle cells indicates a function for EC-SOD as a mediator of nitric oxide activity in the maintenance of low pulmonary vascular pressures and airway resistance.

In addition to the labeling of EC-SOD in association with smooth muscle cells, EC-SOD also appears to strongly colocalize with type I collagen. Collagen has previously been demonstrated to be susceptible to attack by reactive oxygen species such as the superoxide anion. In addition, the superoxide anion may be capable of activating latent collagenases from polymorphonuclear leukocytes (PMN) which can lead to further collagen degradation. Because collagen fragments have been shown to chemoattract and activate PMN's, any increased produced of superoxide that results in collagen degradation may accelerate inflammatory reactions and tissue destruction through PMN recruitment and activation. Consequently, the association of EC-SOD with collagen may be important in preventing superoxide mediated degradation of collagen and therefore, represent a means of controlling inflammatory responses.

EXAMPLE V

Human EC-SOD Gene

Protocols:

Materials and radiochemicals:

$[\alpha\text{-}^{35}S]dATP$ (~1400 Ci/mmol), $[\gamma\text{-}^{32}P]ATP$ (3000 Ci/mmol), and $[\alpha\text{-}^{35}P]CTP$ (800 Ci/mmol), were purchased from New England Nuclear. Human genomic DNA, $T_7$, $T_3$, and SP6 RNA polymerase, RNasin, and the pGEM3Zf(+) plasmid were obtained from Promega Biotec. Sequenase sequencing kit (V 2.0) was from United States Biochemicals Corporation. Human poly A+ RNA was acquired from Clontech. SeaPlaque GTG agarose was from FMC BioProducts. Restriction enzymes were from New England Biolabs. All other reagents used were molecular biology grade. Oligonucleotides were synthesized using an Applied Biosystems 380B or 392 by the Duke University, Department of Botany DNA synthesis facility. Charged nylon membranes (GeneScreen Plus) were from DuPont.

Human Northern blot or analysis :

Two µg poly A+RNA were purified from eight different human tissues. These mRNAs were electrophoresed on a denaturing formaldehyde 1.2% agarose gel and transferred to a charge-modified nylon membrane followed by UV irradiation fixation. The membrane was prehybridized in 50% formamide, 0.25 M $NaPO_4$ (pH 7.2), 0.25 M NaCl, 1 mM EDTA, 7% SDS, and 5% polyethylene glycol (molecular weight 8000). The blot was hybridized in the same buffer overnight at 60° C. with $1\times10^6$ cpm/ml of $[^{32}P]$-labeled human EC-SOD RNA generated by transcription of the full-length cDNA using $T_3$ RNA polymerase in the presence of $[\alpha\text{-}^{32}P]CTP$. The blot was washed in 0.25 M $NaPO_4$ (pH 7.2), 1% SDS, and 1 mM EDTA at 75° C. followed by a second wash using 0.04 M $NaPO_4$ (pH 7.2), 1% SDS, and 1 mM EDTA at 75° C. for 30 minutes. This was followed by exposure to XAR-5 film using a Lightening Plus intensifier screen at –70° C. The autoradiogram was scanned using an LKB Ultrascan XL laser densitomer, and the peaks were quantitated by integration using the internal digital integrator of the densitometer or by cutting out the peak from a printer tracing and weighing.

5' Rapid amplification of cDNA ends:

0.5 µg of poly A+ mRNA from human heart was reversed transcribed using 2 pmoles of EC7, a 5' EC-SOD gene specific anti-sense oligonucleotide (5'-ATGACCTCCTGCCAGATCTCC-3'), following a protocol by GIBCO BRL (5' RACE System). The RNA template was degraded by the addition of RNase H at 55° C. for 10 minutes. The resulting cDNA was isolated using a Glass-MAX DNA (GIBCO BRL) isolation spin cartridge. The purified cDNA was dc-tailed using terminal deoxynucleotidyl transferase (TdT, 0.5 units/ul). 200 µM dCTP, 10 mM Tris-HCl (pH 8.4), 25 mM KCl, 1.25 mM $MgCl_2$ and 50 µg/ml bovine serum albumin for 10 minutes at 37° C. The TdT was heat inactivated for 10 minutes at 70° C.

Products of this reaction were next PCR amplified using the "anchor" primer (GIBCO BRL), which hybridizes to the homopolymeric tail, and EC4 (a nested internal 5' EC-SOD gene specific anti-sense oligonucleotide, 51'-AGGCAGGAACACAGTAGC-3'). Alternatively, the dc-tailed products were PCR amplified using EC7 and HEC1 (a sense-strand EC-SOD gene specific primer, 5'-TGGGTGCAGCTCTCTTTTCAGG-3'). The final composition of the reaction included 20 mM Tris-HCl (pH 8.4), 50 mM KCl, 2.5 mM $MgCl_2$, 100 µg/ml bovine serum albumin, 400 nM Anchor primer, 200 nM gene-specific primer, and 200 µM each of dATP, dCTP, dGTP, dTTP. After incubating the PCR reaction for 5 minutes at 94° C., amplitaq (Perkin Elmer Cetus) was added at a final concentration of 0.04 units/µl. PCR cycling was performed on a Perkin Elmer 9600 for 35 cycles with melting at 94° C. for 45 seconds and annealing at 53° C. for 15 seconds and extension at 72° C. for 90 seconds. The full-length EC-SOD cDNA (6 ng) was used as a positive control in the PCR reaction. The PCR products were electrophoresed in a 2% SeaPlaque GTG agarose gel, transferred to charged nylon membranes by the method of Southern (Southern, J. Mol. Biol. 98:503 (1975)) using the alkaline transfer protocol (Reed et al, Nuc. Acids Res. 13:7207 (1985)). The DNA was fixed to the membrane by baking at 80° C. in a vacuum oven for 2 hours. The subsequent blot was hybridized to [32p] end-labeled HEC2 (an internal, nested EC-SOD specific primer, 5'-TCCAGCTCCTCCAAGAGAGC-3') overnight at 37° C. The blot was washed at increasing stringencies until background hybridization was removed. This was followed by exposure to XAR-5 film using a Lightening Plus intensifier screen at –70° C.

Human genomic Southern blot analysis:

Ten µg human genomic DNA were digested BamH I, EcoR I, Kpn I, and Pst I restriction endonuclease enzymes until completion. The DNA was then electrophoresed on 1% agarose gel and transferred to a charged nylon membrane by the Southern technique (Southern, J. Mol. Biol. 98:503 (1975)), after alkaline denaturation (Reed et al, Nuc. Acids Res. 13:7207 (1985)). The DNA was fixed to the membrane by heating to 80° C. in a vacuum oven for 2 hours. $[^{32}P]CTP$-labeled human EC-SOD antisense strand cRNA was synthesized using the EC-SOD cDNA which had been linearized with Stu I. The blot was hybridized ($500\times10^3$ cpm/ml) in 50% formamide, 0.25 M $NaPO_4$ (pH 7.2), 0.25 M NaCl, 1 mM EDTA, 7% SDS, and 5% polyethylene glycol (molecular weight 8000), at 50° C. Following overnight hybridization, they were washed in 0.25 M $NaPO_4$ (pH 7.2), 2% SDS, and 1 mM EDTA followed by 0.04 M $NaPO_4$ (pH 7.2), 1% SDS, and 1 mM EDTA at increasing stringencies until background hybridization was minimized. The blot was exposed to XAR-5 film using a Lightening Plus intensifier screen at –70° C.

Isolation of the Human gene for EC-SOD:

A human adult female leukocyte genomic library constructed in the EMBL-3 vector was obtained from Clontech. Approximately $1\times10^6$ pfu were screened at a density of ~50,000 pfu/plate using [$^{32}$P]CTP-labeled human EC-SOD cRNA ($1\times10^6$ dpm/ml). The primary through tertiary screens identified approximately 7 unique putative positive plaques. Individual plaques were isolated and lambda DNA purified using LambdaSorb phage adsorbent (Promega Biotec). The size of the insert DNA from each clone was assessed by Sal I restriction endonuclease digestion followed by electrophoresis in 0.7% agarose. Selected clones underwent extensive restriction endonuclease mapping. Based on the restriction mapping results and asymmetric hybridization using 5' and 3' annealing EC-SOD oligonucleotides, Clone #7 was selected for all subsequent DNA sequence analysis. Clone #7 contains an approximate 18–20 kb fragment.

DNA sequencing of the human EC-SOD gene:

The overall strategy used for sequencing clone #7 is illustrated in FIG. 20. Various size restriction endonuclease DNA fragments from clone #7 were subcloned into the pGEM3Zf(+) vector DNA. The dideoxy sequencing method using double-stranded DNA (Ausubel et al, Current Protocols in Molecular Biology, Green Publishing Assoc. and Wiley Interscience, New York (1992)) as template and Sequenase enzyme (United States Biochemicals) were employed (Sanger et al, Proc. Natl. Acad. Sci. USA 74:5463 (1977)). Both the Universal and −40 M13 sequencing primers were used to initiate DNA sequencing for each subcloned fragment. Oligonucleotides derived from this initial sequencing data were synthesized approximately every 250 base pairs until the complete nucleotide sequence was obtained. Sequencing data were obtained from both strands as shown in FIG. 20B except at the 3' portion of the gene where DNA sequence was obtained on one strand only.

Computer-assisted sequence analysis and transcriptional database search:

The IntelliGenetics Geneworks program (Version 2.2) was used for organizing the DNA sequence data. Homology searching was performed at the NCBI using the BLAST (Altschul et al, J. Mol. Biol. 215:403 (1990)) network service and the non-redundant nucleotide sequence database (GenBank(77.0)+EMBL(35.0)+EMBLUpdate+GBUdate). Transcriptional factor database searching was performed using both the SIGNAL SCAN 3.0 algorithm (Prestridge et al, CABIOS 9:113 (1993)) as well as the FINDPATTERNS program of the GCG Package (V 7.2) using Release 6.3 of the Transcription Factor Database (Gosh, Nuc. Acids Res. 18:1749 (1990)). For a prediction of the site of signal peptide cleavage, the programs SIGSEQ1 (Folz et al, J. Biol. Chem. 261:14752 (1986)) and SIGSEQ2 were employed (Folz et al, Biochem. Biophys. Res. Commun. 146:870 (1987)).

Results:

Tissue specific expression of human EC-SOD:

To investigate the expression of human EC-SOD, poly A(+) mRNA from eight different human tissues was fractionated on a denaturing agarose gel and transferred to a charged nylon membrane. Because a previous paper reported long exposures times in order to identify EC-SOD specific bands during genomic Southern analysis (Hendrickson et al, Genomics 8:736 (1990)), a radiolabeled antisense cRNA probe derived from full-length human EC-SOD cDNA was used (Oury et al, Proc. Nat. Acad. Sci. USA 89:9715 (1992)). A discrete band of approximately 1.4 kb can be seen in all eight human tissues analyzed (FIG. 21A). In addition, skeletal muscle contains an approximate 4.2 kb message, not detected in the other tissues. By densitometric scanning of the 4.2 and 1.4 kb bands, it can be calculated that larger message to make up about 32% of the total skeletal muscle EC-SOD message. In brain, a very faint band of 2.2 kb can be seen. This band was too weak for quantitation by laser densitometer. Quantitation of these bands was performed by laser densitometry and integration of peaks of autoradiograms obtained in the linear range of exposure (FIG. 21B). After normalizing to the brain, the heart showed the most expression with 10.1 times brain. This was followed by the placenta, pancreas, and lung which gave 13.6, 10.2, and 7.5, respectively. Expression in skeletal muscle was 4.7 for the 1.4 kb band or 6.9 for both 1.4 kb and 4.2 kb message, while the kidney and liver gave 6.3 and 4.1 time expression over brain. These patterns of expression have been reproduced based on probing an additional independent multiple tissue Northern blot. The bands are specific based on the relatively high stringencies of washing and from data using a sense strand EC-SOD cRNA as a probe which showed no hybridization under the conditions given.

Mapping the site transcription initiation:

Initially, mapping of the site of transcription initiation was attempted using the primer extension method. Using several different end-labeled 5' oligonucleotides and both human lung and human heart poly A+ mRNA as well as total RNA isolated from human foreskin fibroblasts, a positive signal was not obtained even after long exposure times. This did not seem to be due to technique since it was not possible to get positive signals using RNA generated by in vitro transcription of the EC-SOD cDNA. Whether lack of success using this technique was due to very low abundance of mRNA encoding EC-SOD or some other problem(s) is unclear. Working under the assumption of low abundance mRNA, the technique of rapid amplification of cDNA ends in order to PCR amplify this signal was attempted. The EC-SOD gene specific primer EC7 was used for hybridization and reverse transcription of human heart poly A+ mRNA as shown in FIG. 22. Half of this reaction was 3' dC tailed using terminal deoxynucleotidyl transferase and the remaining half was not. These templates were then subjected to PCR amplification using the gene specific primers HEC1+ EC7 as well as the anchor primer +EC4. The products of these reactions were fractioned by agarose electrophoresis, transfered to nylon membranes, and probed with the interal nested gene specific primer HEC2. An autoradiogram of this experiment is shown in FIG. 22A. Using EC-SOD cDNA as a control template and HEC1+EC7, a band of 217 bp is expected (lane 3 of FIG. 22A). Since the primers HEC1 and EC7 are expected to amplify independant of dC tailing, bands of equal intensity in lanes 4 and 5, which are also of the same size as the EC-SOD control, are seen. Using the anchor primer (which hybridizes to the dC tail) and EC4, only one band of ~190 bp was seen (lane 1). Since the template was not poly C tailed, lane 2 shows no signal as expected. By subtracting 48 bp (the size of the anchor primer), the size of the reverse transcribed DNA would correspond to ~136 bp 5' of the EC4 primer. This analysis would predict that there is approximately 6 base pairs of additional 5' sequence on the cDNA clone and that transcription initiation starts about 6 bp upstream of the first intron (indicated by a dashed box). Although eukaryotic transcription initiation usually begins at an adenosine residue, it is expected that it will begin at a G (Breathnach et al, Ann. Rev. Biochem. 50:349 (1981)).

Genomic Southern blot analysis:

To begin to charcterize the human EC-SOD gene, 10 μg of the total human genomic DNA was restriction digested and the reaction products electrophoresed on an agarose gel followed by transfer to a nylon membrane. The blot was probed with a [$^{32}$p]-labeled partial EC-SOD cRNA. An autoradiogram of this blot is shown in FIG. 23. As can be seen for each lane, there are unique bands associated with each restriction digest. No shadow bands which might suggest pseudogenes were seen. When a full-length cRNA probe was used for Kpn I digested DNA, an additional band of ~4000 bp was seen which corresponds to the 3' end of the gene. In addition, the Kpn I lane shows a 0.5 kb band which was better seen on other blots. This banding pattern was similar to a restriction map of the human EC-SOD clone #7 (see FIG. 20A).

Isolation and characterization of the human EC-SOD by DNA sequencing:

Multiple independent positive clones were identified from a human adult leukocyte genomic library constructed in EMBL-3. These clones underwent extensive restriction endonuclease mapping and were probed with EC-SOD specific 5' and 3' oligonucleotides in order to determine the relative orientation of the inserts. Based on these results, clone #7 was picked for further analysis. Clone #7 is about 18 to 20 kb and contains at least 5000 bp of 5' flanking DNA and at least 4000 bp of 3' flanking DNA. Restriction mapping of clone #7 is shown in FIG. 20A. This map is similar to the results obtained with genomic Southern blot analysis data indicating that clone #7 contains the EC-SOD gene. The strategy for sublconing and sequencing clone #7 is shown in FIG. 20B. Various size continguous and overlapping restriction fragments were subcloned into the plasmid vector pGEM32f(+) (FIG. 20B). The DNA inserts were sequenced on both strands using a combination of primer walking and vector specific, universal sequencing primers. The 3' half of 7K36 insert was sequenced on one strand only. Published sequence data for the human EC-SOD cDNA (Hjalmarsson et al, Proc. Natl. Acad. Sci. USA 84:6340 (1987)) as well as DNA sequence information obtained from an independant cDNA clone which contained additional 5' untranslated data (Hendrickson et al, Genomics 8:736 (1990)) were used to determine the genomic intron/exon structure. Based on a comparison of these data with the genomic sequence information, the human EC-SOD gene was determined to contain three exons and two introns (FIG. 20C). Exon 1 contains at least 5 base pairs and is probably larger (by about 6 base paris), since the exact start of transcription initiation was not determined (note below). Exon 2 contains 84 bp and is separated from exon 1 by a 572 bp intervening sequence marked as intron 1. Exon 3 is separated from exon 2 by intron 2, a 3849 bp segment. Exon 3 contains a total of 1336 bp and at 17 bp into this exon starts the beginning of the complete coding sequence for preEC-SOD (FIG. 20D). This includes an 18 amino acid signal peptide that precedes the 222 amino acid mature protein sequence. There are no introns separating the various structural domains of EC-SOD. These domains are shown schematically in FIG. 20D and include amino acids 1–95 which contain a glycosylated Asn-89 and show no sequence homology with other proteins. Resides 96–193 show strong homology with CuZn-SOD protein sequences with preservation of critical amino acids important in enzyme catalysis and structure. Amino acids 194–222 contain multiple charged resides which have been shown to be important in binding to sulfated proteoglycans. 558 bp of the 5'-flanking region containing putative regulatory elements and 3675 bp of the 3'-flanking region were also sequenced. The exonic DNA sequence data are in agreement with the published cDNA sequence (Hjalmarsson et al, Proc. Natl. Acad. Sci. USA 84:6340 (1987)). The intron-exon boundries are shown in Table VIII and conform to the eukaryotic consensus splice sequence (Senapathy et al, Methods Enzymol. 183:252 (1990)). Both introns split sequences in the $5^1$-nontranslated region of the EC-SOD gene.

TABLE VIII

Sequences at intron/exon splice junctions
The size of the introns and exons are shown in base pairs (bp). The uppercase letters indicate exon sequence while the lowercase letters indicate intron sequence. The splice junctions shown conform to previously published concensus sequences for splice junctions (Senapathy et al, Methods Enzymol. 183:252 (1990)).

| Donor | | Intron size (bp) | Acceptor | | Exon |
|---|---|---|---|---|---|
| TGCGGG | gt ggac | 572 | gccc ag | GCTCCA | 84 |
| GGAAAG | gt gggt | 3849 | ccgc ag | GTGCCC | 1336 |

FIG. 24 shows the entire sequence for the human EC-SOD gene. Exonic sequences are shown in boxed uppercase letters while intronic, 5'- and 3'-flanking sequence are shown in lowercase. Exon 3 contains the entire uninterrupted coding region for EC-SOD and the protein sequence is shown using the single letter amino acid code. The 18 amino acid signal peptide and 222 amino acid mature protein sequence are highlighted. The identification of the signal peptide cleavage site is consistent with computer algorithms which predict the site of eukaryotic signal peptide cleavage (Folz et al, Biochem. Biophys. Res. Comm. 146:870 (1987)); Von Heijne, Eur. J. Biochem. 133:17 (1983)).

Transcriptional factor database searching was used to putatively identify transcriptional regulatory elements. Although almost all eukaryotic promoters utilize a TATA box element to fix the position of transcription initiation, an obvious TATA box cannot be discerned for the EC-SOD gene. Two CAAT box elements were identified. One is in the reverse orientation and located about 20 bp upstream of the first exon, while the second can be found about 335 bp upstream. The putative signal for polyadenylation is shown and the site of poly A adenylation is indicated. Transcriptional factor database searching of the 5'-nontranslated region and first intron identified several potential regulatory elements. A c$\mu$MP responsive element (CREB) (TGACGT) which is similar to the adenovirus transcription virus (ATF) element can be found starting at 121 bp (Fink et al, Proc. Natl. Acad. Sci. USA 85:6662 (1988); Sassone-Corsi Proc. Natl. Acad. Sci. USA 85:7192 (1988)). A half site for the glucocorticoid response element (GRE) (TGTCCT) is located at 370 bp (Karin et al, Nature 308:513 (1984)). A skeletal muscle specific trans-activating factor response element (M-CAT) (CATTCCT) is found in the reverse orientation beginning at position 238 (Mar et al, Mol. Cell. Biol. 10:4271 (1990)). A xenobiotic responsive element (XRE) (CACGCW) is found within the first intron at position 1085 bp (Rushmore et al, J. Biol. Chem. 265:14648 (1990)). A metal regulatory element (MRE) (TGCRCYC) is found at position 89 (Culotta et al, Mol. Cell. Biol. 9:1376 (1989)). Two putative antioxidant response elements (ARE) (RGTGACNNNGC) are found at position 650 and 5022 (Rushmore et al, J. Biol. Chem. 266:11632 (1991)). A sis responsive element (SIF) (CCCGTC) important in the induction of the c-fos proto-oncogene is found in the reverse orientation at position 251 (Wagner et al, EMBO J. 9:4477 (1990)). There is an AP1 binding site or TPA responsive element (TRE) (TGACTCA) found at position 162 (Risse et al, EMBO J. 8:3825 (1989)). The SV40 enhancer region AP4 (CAGCTGTGG) can be found at position 171 (Jones et al, Genes Dev. 2:267 (1988)).

EXAMPLE VI

Screening Patients for Gene Defects in EC-SOD

Preparation of leukocyte derived genomic DNA from patients: Normal healthy control patients and patients with asthma, primary pulmonary hypertension, and secondary pulmonary hypertension will be identified. Genomic DNA will be purified utilizing a Qiagen Blood PCR Kit. One ml of blood containing ~$10^7$ leukocytes/ml will be collected in sodium citrate from each patient or control subject. The blood is placed into a QIAGEN-spin column and the leukocytes are entrapped in the resin by brief centrifugation, while erythrocytes and hemoglobin are washed through. The leukocytes are lysed by the addition of 0.7 ml of lysis buffer and incubated at room temperature for 30 minutes. DNA that is released, binds to the resin in the tube. Remaining cellular debris is washed away by multiple wash/spin cycles. The DNA is eluted by the addition of 1.2 M KCl, 50 mM MOPS, 15% ethanol, pH 8.3. This typically yields ~10 μg of genomic DNA (Reihsaus et al, Am. J. Respir. Cell. Mol. Biol. 8:334 (1993)).

Primer design and PCR amplification of EC-SOD exonic sequences: Sense and antisense oligonucleotide primers (or use primers already obtained from sequencing the genomic DNA) will be designed containing a 3'GC clamp (Sheffeld et al, Proc. Natl., Acad. Sci. USA 86:232 (1989)). These primers will encode the intronless coding region of the EC-SOD gene. A 172 bp region in the 3' untranslated region has been amplified using DNA sequencing primers and human genomic DNA. PCR conditions are as described (Reihause et al, Am. J. Respir. Cell. Mol. Biol. 8:334 (1993); Innis et al (eds) Academic Press San Diego pp. 1–12 (1990)) using Taq polymerase, with temperature cycling as follows: initial denaturation at 95° C. for 5 min followed by 35 cycles of 94° C. denaturing for 20 sec, 57° C. annealing for 15 sec, and 72° C. elongation for 45 sec. Because of the GC composition and actual primer sequence, it will be necessary to experimentally optimize conditions for PCR amplification using each set of primers. Three sets of primers will be used to encompass the entire coding region.

Identification of mutations with single-strand conformational polymorphism (SSCP) analysis: SSCP analysis has been used to detect single base pair mismatch (Orita et al, Genomics 5:874 (1989)). Temperature-gradient gel electrophoresis (TGGE) will be used to detect differences in mobility (Wartell et al, Nuc. Acids Res. 18:2699 (1990)). Samples for TGGE will be prepared by heat denaturing the PCR product at 98° C. for 5 min, then renaturing at 50° C. for 15 min with the corresponding wild-type DNA derived from PCR of the cloned gene. Electrophoresis will be carried out on a 5 acrylamide, 8 M urea gel over a temperature gradient. The temperature gradient will be optimized for each of the EC-SOD DNA segments. Typical gradients for the detection of $\beta_2$-adrenergic receptor mutations were between 35° C. to 60° C., and required 4 to 6 hours of run time (Rosen, Nature 262:59 (1993)).

All PCR samples found to be positive for mutations by TGGE will be sequenced directly using the dideoxy technique (Sanger et al, Proc. Natl. Acad. Sci. USA 74:5463 (1977)).

EXAMPLE VII

Inhibition of Xanthine Oxidase

In a first study, assays were performed in a 1 ml quartz cuvette containing 50 mM carbonate buffer, pH 10, 0.1 mM EDTA, 1 nM xanthine oxidase (Boehringer Mannheim) at 25° C. Xanthine oxidase activity was measured spectrophotometrically by following the loss of xanthine over time at 295 nm. Four concentrations of xanthine (25, 50, 250, 500 μM) and 2 concentrations of MnTBAP (5, 10 μM) were used. Two inhibition constants were then derived from the curve's intercepts (Kii=5.5 μM) and slopes (Kis=15 μM). The results presented in FIG. 25 show that MnTBAP inhibits xanthine oxidase in a non-competitive manner.

In a second study, calf pulmonary artery endothelial cell cultures (CPA-47 (Tissue and Cell 10:535 (1978)) were grown to confluence in Ham's F-12K medium with 10% fetal bovine serum at pH 7.4 and 37° C. Cells were then trypsinized and seeded at equal densities in 24 well plates and grown to 90% confluence. Cells were washed and pre-incubated for 1 hour with 50 μM of MnTBAP in minimum essential medium (MEM) or MEM only. Varing amounts of xanthine oxidase (XO) plus 200 μM xanthine (X) were added and allowed to incubate for 24 hours. Cell injury was quantitiated by measuring the release of cellular lactate dehydrogenase (LDH) into the medium. The efficacy of MnTBAP is shown in FIG. 26 by the decrease in XO/X-induced LDH release.

EXAMPLE VIII

SOD Mimetic Affords Cellular Protection From Paraquat-Induced Injury

Rat pulmonary epithelial cell cultures (L2 (Kaighn and Douglas J. Cell Biol. 59:160a (1973)) were grown to confluence in Ham's F-12K medium with 10% fetal bovine serum at pH 7.4 and 37° C. Cells were then trypsinized and seeded at equal densities in 24 well plates and grown to 90% confluence. Cells were washed and pre-incubated for 1 hour with 100 μM of MnTBAP or MnTMPyP in MEM or MEM only. Paraquat (2.5 mM) was added and allowed to incubate for 48 hours. Cell injury was quantitiated by-measuring the release of cellular lactate dehydrogenase (LDH) into the medium. FIG. 27 shows that MnTPyP (hatched bars) and MnTBAP (grey bars) decrease paraquat-induced LDH release.

In a further study, calf pulmonary artery endothelial cell cultures (CPA-47 (Tissue and Cell 10:535 (1987)) were grown to confluence in Ham's F-12K medium with 10% fetal bovine serum at pH 7.4 and 37° C. Cells were then trypsinized and seeded at equal densities in 24 well plates and grown to 90% confluence. Cells were washed and pre-incubated for 1 hour with varing concentrations of MnTBAP in MEM or MEM only. Paraquat (2 mM) was added and allowed to incubate for 24 hours. Cell injury was quantitiated by measuring the release of cellular lactate dehydrogenase (LDH) into the medium. MnTBAP decreases paraquat-induced LDH release in a dose-dependent manner (see FIG. 28).

In contrast to MnTBAP, ZnTBAP does not protect against paraquat-induced injury. Calf pulmonary artery endothelial cell cultures (CPA-47) were grown to confluence in Ham's F-12K medium with 10% fetal bovine serum at pH 7.4 and 37° C. Cells were then trypsinized and seeded at equal densities in 24 well plates and grown to 90% confluence. Cells were washed and pre-incubated for 1 hour with varing concentrations of ZnTBAP in MEM or MEM only. Paraquat (2 mM) was added and allowed to incubate for 24 hours. Cell injury was quantitiated by-measuring the release of cellular lactate dehydrogenase (LDH) into the medium. The results presented in FIG. 29 demonstrate that ZnTBAP does not possess SOD-like activity. ZnTBAP can be used as a negative control to show that the redox metal is important in the protection against paraquat toxicity.

EXAMPLE IX

Protection by MnTBAP Against Paraquat-Induced Lung Injury

Mice were treated with either paraquat (PQ, 45 mg/kg, ip) or saline (10 ml/kg, ip) and exposed to MnTBAP (2.5 mg/ml, nebulized into a 2 L chamber at 2 L/min for 30 minutes twice daily for 2 days) or room air. Mice were killed 48 hours after start of treatment and lung injury was assessed by analysis of bronchoalveolar lavage fluid (BALF). BALF damage markers used were lactate dehydrogenase (LDH, as units/L), protein concentration (as mg/dl), and percent of polymorphonuclear leukocytes (PMN). MnTBAP treatment provided partial protection against paraquat-induced lung injury (see FIG. 30).

EXAMPLE X

Catalase activity was measured by means of a Clark oxygen electrode using a modified assay previously described by Del Rio et al, Anal. Biochem. 80:409 (1977). Briefly, reactions were performed in a nitrogen degassed phosphate buffer (50 mM, pH 7.8) containing 0.1 mM EDTA at 25° C. Three concentrations of hydrogen peroxide (1–4 mM) and four metalloporphyrin concentrations (0.5–50 $\mu$M) were used to determine second order rate constants. The rate of oxygen evolution was followed for 2 minutes. The results are shown in FIG. 31.

Calf pulmonary endothelial cell (CPA-47) line was grown to near confluence in 12-well plates with F-12K medium containing 10% fetal calf serum. CPA-47 cells were loaded with $Cr^{51}$ as previously described by Simon et al J. Clin. Invest. 78:1375 (1986) in high glucose minimum essential medium (DMEM). Cells were pretreated with MnTBAP (100 $\mu$M) for 1 hour and then exposed to various concentrations of hydrogen peroxide generator, glucose oxidase, for 4 hours. Cell injury was then quantitated as the specific CrsI release from CPA-47 cells which has been adjusted for spontaneous $Cr_{51}$ release. The results are shown in FIG. 32.

Calf pulmonary endothelial cell (CPA-47) line was grown to near confluence in 12-well plates with F-12K medium containing 10% fetal calf serum. CPA-47 cells were loaded with $Cr^{51}$ as previously described by Simon et al (J. Clin. Invest. 78:1375 (1986)) in high glucose minimum essential medium (DMEM). Cells were pretreated with various concentrations of either: (A) MnTBAP; (B) MnTMPyP; (C) ZnTBAP; or (D) CuZnSOD for 1 hour and then exposed to the hydrogen peroxide generator, glucose oxidase (100 Mu/ml), for 4 hours. Cell injury was then quantitated as the specific $Crs^{51}$ release from CPA-47 cells which has been adjusted for spontaneous $Cr^{51}$ release. The results are shown in FIGS. 33A–33D.

EXAMPLE XI

Mimetics as Protectants Against Excitotoxic Cell Death

Experimental Procedures

Tissue culture: Mixed neuronal and glial cultures were prepared from embryonic day-18 rat cerebral cortices (Sprague-Dawley, Zivic Miller). Briefly, the cerebral cortices were dissected and enzymatically dissociated by incubation in $Ca^{++}$-, $Mg^{++}$-free Hank's balanced salt solution (HESS) supplemented with 10 mM HEPES and 0.25% trypsin for 20 min. at 37° C. The tissue was rinsed and dispersed into single cell suspension by gentle passage through a fire polished Pasteur pipette. The cell suspension was centrifuged and resuspended in Minimum Essential Media (MEM), containing Earle's salts supplemented with 3 g/L glucose, 5% horse serum and 5% fetal bovine serum (growth media). The cells were plated in poly-D-lysine-coated multi-well plates: 12-well plates for aconitase measurement, and 24 well plates for toxicity experiments. Cells were maintained at 37° C. in a humidified incubator with 5% $CO_2$/95% air in growth media. Media was not replaced so as to reduce glial overgrowth and neuronal loss. Mature cells (14–17 days in vitro) were used for all experiments.

Cell treatment: The growth media was replaced with MEM supplemented with 25 mM glucose (MEM-g). For both neurotoxicity studies and aconitase measurement, cells were incubated in the designated treatment for the indicated length of time at 37° C. Unless otherwise specified, antagonists or SOD-mimetics were added 15 min. prior to agonists. For measurement of neurotoxicity, cells were incubated with treatments for 18 hr at 37° C. in MEM-g. To assess the ability of antagonists to inhibit acute NMDA toxicity or rescue cells from an ongoing NMDA insult, an alternate paradigm of NMDA treatment was used in addition to the one described above. In this paradigm, growth media was replaced with $HBSS^+$ ($Ca^{++}$-, $Mg^{++}$-free Hank's Balanced Salt Solution supplemented with 2 mM $CaCl_2$, 1 mM $NaHCO_3$, 10 mM HEPES and 5 $\mu$M glycine), cells were treated with vehicle or 100 $\mu$M NMDA for 15 min. after which $HBSS^+$ was replaced with MEM-g and cells were returned to the incubator for 18 additional hrs. Antagonists or SOD-mimetics were added to the cells 15 min. before NMDA exposure or 15, 30 or 60 min. following final media replacement. For determination of $Ca^{++}$-dependence, cells were incubated in HBSS+with no added $Ca^{++}$. When kainate (KA) was used as an agonist, 100 $\mu$M D-APV was routinely included to block secondary NMDA receptor activation. Catalase (100 U/ml) was always included when xanthine plus xanthine oxidase (X+XO) was used as a treatment to rule out the contribution of hydrogen peroxide.

Neurotoxicity studies: Neurotoxicity was determined by the measurement of LDH released in the supernatant media as previously described (Patel et al, Toxicol. Appl. Pharmacol. 115:124 (1991) and Neurotoxicology 14:35 (1992)). LDH was measured by the method of Vassault, Lactate dehydrogenase. In: Methods of Enzymatic Analysis, Bergmeyer HU (ed), Verlag Chemie, Weinheim, pp. 118–126 (1983). Additionally, cell death was confirmed with ethidium-1 homodimer (EthD-1). Briefly, the cells were washed with HBSS, loaded with 20 $\mu$M EthD-1 for 30 min., rinsed and viewed through fluorescence optics. The number of dead cells labeled with EthD-1 were counted in 4–6 randomly selected fields, the numbers averaged to give an estimate of cell death and the experiment was repeated 3 times.

Aconitase measurement: For the measurement of aconitase, following treatment with agents, media was removed and cells lysed in ice-cold 50 mM Tris/HCl, pH 7.4 containing 0.6 mM $MnCl_2$, 1 mM L-cysteine, 1 mM citrate and 0.5% Triton-X 100. The aconitase activity of cell lysates was measured spectrophotometrically by monitoring the formation of cis-aconitate from isocitrate at 240 nm in 50 mM Tris/HCl, pH 7.4, containing 0.6 mM $MnCl_2$ and 20 mM isocitrate at 25° C. (Kreb and Holzach, Biochem. J. 52:527 (1952); Gardner and Fridovich, J. Biol. Chem.

267:8757 (1992)). Inactive aconitase was reactivated by a 30 min. incubation of cortical cell lysates (90 μl) with 0.5 M DTT (10 μl), 20 mM Na$_2$S (1 μl) and 20 mM ferrous ammonium sulfate (1 μl) in 50 mM Tris/HCl, pH 8.0. at 37° C. Aconitase activity in cortical cell lysates was inhibited by 0.1 mM potassium ferricyanide or by boiling of sample.

Statistical analyses: One-way analysis of variance (ANOVA) was used to compare three or more treatments and Dunnet's test for comparing multiple treatment groups with a control group. Tukey-Kramer multiple comparisons test was used to detect differences between treatments. Student's t-test was used for comparison of two treatments. Results Validation of aconitase activity as a marker of $O_2^-$ radical formation in cortical cell culture: With the use of agents that are known to generate $O_2^-$ (X+XO and PQ$^{++}$), aconitase activity was established as a valid marker of $O_2^-$. The $O_2^-$ generators selectively and reversibly inactivated aconitase and did so in a SOD-preventable manner.

Aconitase inactivation produced by PQ$^{++}$, NMDA and KA correlate with cell death: Cortical cells were treated with varying concentrations of KA, NMDA, and PQ$^{++}$ for 18 hr. and the media analyzed for LDH activity. Sister cultures were treated with varying concentrations of KA, NMDA, or PQ$^{++}$ for 6, 1 or 3 hr., respectively, and cell lysates analyzed for aconitase activity; a shorter time of incubation was assessed for aconitase activity because death of neurons leads to irreversible inactivation of aconitase activity, presumably due to protein degradation. Therefore, an earlier time point was selected for measuring aconitase activity based upon the time of approximating the steady state of reversible inactivation (FIGS. 34A and B for 50 μM NMDA and 300 μM KA, respectively).

KA treatment produced proportionate decreases in aconitase activity and cell death as monitored by LDH release (FIG. 35A). Likewise, PQ$^{++}$ treatment produced a proportionate decrease of aconitase activity and the amount of LDH release (FIG. 35B). At higher concentrations (30–1000 μM), NMDA produced proportionate decrease in aconitase activity and also cell death. However, low concentrations (3 and 10 μM) of NMDA produced cell death (LDH release) but no detectable aconitase inactivation (FIG. 35C).

MNTBAP prevents aconitase inactivation and cell death produced by PQ, NMDA and KA: To determine whether MnTBAP can prevent aconitase inactivation and cell death produced by NMDA, PQ$^{++}$ and KA, cortical cells were incubated with PQ$^{++}$, NMDA and KA in the absence and presence of 200 μM MnTBAP. PQ$^{++}$, NMDA, and KA produced a 70%, 40% and 42% decrease in aconitase activity after 3, 1 and 6 hrs., respectively; 200 μM MnTBAP markedly inhibited the PQ$^{++}$-, NMDA- and KA-mediated decreases of aconitase activity (FIG. 36A). Parallel effects were evident on cell death as measured by LDH release. MnTBAP (200 μM) markedly inhibited PQ$^{++}$-, NMDA- and KA-mediated cell death (FIG. 36B). The effects of MnTBAP on cell death were concentration dependent (FIG. 36B). MnTBAP (200 μM) produced a right-ward and down-ward shift in the concentration-response curve for NMDA, providing complete protection at low concentrations of NMDA (FIG. 37).

The possibility that MnTBAP simply prevented activation of NMDA or μMPA receptors was examined and eliminated.

To strengthen the possibility that MnTBAP decreased aconitase inactivation and prevented cell death by its SOD-mimetic action, the effects of the structurally related congener, ZnTBAP, with diminished SOD activity (ie 10-fold less) were examined. EthD-1 was used to quantitate cell death in these experiments because preliminary studies showed that ZnTBAP interfered with the measurement of LDH (MnTBAP was found to have no effect on LDH measurement). Concentration-response curves for NMDA and KA demonstrated a strong correlation between cell death measured using LDH release and dead cells quantitated by EthD-1. Concentration-response curves disclosed that MnTBAP exhibited markedly increased neuroprotective effects in comparison to ZnTBAP against PQ$^{++}$, NMDA and KA toxicities (FIG. 38).

To determine whether addition of MnTBAP after initiation of the excitotoxic insult exerted neuroprotective effects, 100 μM NMDA was included for 15 min. in HBSS+(Ca$^{++}$-, Mg++-free HBSS containing 5.6 mM glucose and supplemented with 2 mM CaCl$_2$, 1 mM NaHCO$_3$, 10 mM HEPES and 5 μM glycine). This acute exposure paradigm induced delayed neuronal death (measured 18 hr. later) and allowed determination of the temporal relationship between MnTBAP exposure and neuroprotection. The neuroprotective effects of MnTBAP were assessed when it was: 1) present 15 min. prior to and during a 15 min. NMDA application (but not for the 18 hr. period after media change) (condition "pre"); 2) present 15 min. prior to and during a 15 min. NMDA application and for the ensuing 18 hr. (condition "pre+post"); 3) added 15, 30 or 60 min. following a 15 min. incubation with 100 μM NMDA and left in the media for the ensuing 18 hr. Condition "pre" resulted in a 25% reduction of LDH release measured 18 hr. later; using an identical time course of application of 100 μM D-APV in condition "pre", a complete blockade of LDH release was observed. In contrast, MnTBAP incubated as in condition "pre+post" resulted in a 51% reduction of LDH release. Addition of 200 μM MnTBAP 15, 30 or 60 min. following a 15 min. exposure to 100 μM NMDA resulted in a 38%, 30% and 25% reduction of LDH release respectively. In contrast, addition of 10 μM MK801 15 min. after NMDA treatment had a modest protective effect (17%) when added 15 min. after the NMDA insult. In order to investigate the possibility that NMDA-induced aconitase inactivation resulted from peroxynitrite formation, the effects of nitric oxide synthase (NOS) inhibitors on NMDA-induced aconitase inactivation and cell death were examined. NMDA-induced aconitase inactivation and LDH release were unchanged by the presence of 1 mM of either N$^G$-nitro-L-arginine methyl ester, N$^G$-nitro-L-arginine or N$^G$-monomethyl-L-arginine. NOS, however, was expressed in the cortical neuronal preparation used. Thus, peroxynitrite would not appear to play an etiological role in NMDA-induced aconitase inactivation or cell death under the conditions used.

EXAMPLE XII

Learning Impairment in EC-SOD Knocked-Out Mice

EC-SOD knocked-out mice were obtained from Dr. Lena Carlsson and Dr. Stephan Marklund, Umeå, Sweden. Learning was assessed in knock-out mice and control mice (controls were derived from (+/+) litter mates bearing normal levels of EC-SOD) using an eight arm radical maze in which food was placed in a well at the end of each arm. Food was withheld from the mice for a period of eight hours and then the mice were placed into the maze. A count was made of the number of arms the mice went down to recover food before they went down any arm for a second time. Naive animals randomly went down between four and five different arms of the maze before beginning to repeat.

The results presented in FIG. 39 demonstrate that when the experiment is done on 24 successive days, control mice learn the pattern and are able to increase the number of arms that they go down to find food without error. The EC-SOD knock-out animals failed to show any significant learning over the entire 24 sessions.

EXAMPLE XIII

Scavenging of Peroxynitrite by Mimetics

Experimental Protocols

Cell culture: J774 macrophages were cultured in DMEM medium, supplemented with L-glutamine (3.5 mmol/L) and 10% fetal calf serum. Cells were cultured in 96-well plates (200 μl medium/well) until confluence. To induce the inducible isoform of nitric oxide synthase (iNOS), fresh culture medium containing E. coli LPS (011:B4; 10 μg/ml) alone or in combination with murine γ-interferon (γ-IFN, 10 U/ml) was added in the presence or absence of the NOS inhibitor, the SOD mimetic of the combination of the two compounds for 24 h. Moreover, cells were exposed to the NO donor compounds S-nitroso-N-acetyl-DL-penicillamine (SNAP) (3 mM) and diethylamine:NO NONOate (DNO) (3 mM) for 24 h or to authentic peroxynitrite (1 mM) for 1 h. Nitrite/nitrate concentration in the medium and mitochondrial respiration were then measured as described below.

Measurement of nitrite/nitrate production: Nitrite/nitrate production, an indicator of NO synthesis, was measured in the supernatant. First, nitrate in the culture medium was reduced to nitrite by incubation with nitrate reductase (670 mU/ml) and NADPH (160 μM) at room temperature for 2 h. After 2 h, nitrite concentration in the samples was measured by the Griess reaction, by adding 100 μl of Griess reagent (1% sulfanilamide and 0.1% naphthylethylenediamide in 5% phosphoric acid) to 100 μl samples of conditioned medium. The optical density at 550 nm ($OD_{550}$) was measured using a Spectramax 250 microplate reader (Molecular Devices, Sunnyvale, Calif.). Nitrate concentrations were calculated by comparison with $OD_{550}$ of standard solutions of sodium nitrate prepared in culture medium. All measurements were corrected for the interference of MnTBAP at this wavelength. MnTBAP (up to 300 μM) did not scavenge nitrite or nitrate and did not interfere with the activity of nitrate reductase.

Measurement of mitochondrial respiration: Cell respiration was assessed by the mitochondrial-dependent reduction of 3-(4,5-dimethylthiazol-2-yl)-2,5-diphenyltetrazolium bromide (MTT) to formazan. Cells in 96-well plates were incubated at 37° C. with MTT (0.2 mg/ml) for 1 hour. Culture medium was removed by aspiration and the cells were solubilized in DMSO (100 μl). The extent of reduction of MTT to formazan within cells was quantitated by the measurement of $OD_{550}$. All measurements were corrected for the interference of MnTBAP at this wavelength.

Measurement of peroxynitrite-induced oxidation of dihydrorhodamine 123: The peroxynitrite-dependent oxidation of dihydrorhodamine 123 to rhodamine 123, was measured based on the principles of the method described by Kooy et al, Free Radical Biol. Med. 16:149 (1994). Briefly, peroxynitrite at 5 μM was added into phosphate-buffered saline containing 10 μM dihydrorhodamine 123, in the absence or presence of MnTBAP (3–100 μM). After a 10 min incubation at 22° C., the fluorescence of rhodamine 123 was measured using a Perkin-Elmer fluorimeter (Model LS50B; Perkin-Elmer, Norwalk, Conn.) at an excitation wavelength of 500 mn, emission wavelength of 536 nm (slit widths 2.5 and 3.0 nm, respectively).

Measurement of NO· induced vascular relaxations: New Zealand white rabbits weighing 3–4 kg were anesthetized with pentobarbital (30 mg/kg). The descending thoracic aorta was isolated, removed, cleaned and placed in Krebs buffer (pH 7.5). Vessels were cut into 5 mm rings and hung on stirrups connected to force transducers. Rings were suspended in 20 ml jacketed baths which were kept at 37° C. and bubbled with 95% $O_2$ and 5% $CO_2$. Rings were equilibrated with 2 g resting tension for 1 h before use and contracted with phenylephrine. Saturated NO solution was prepared by bubbling compressed NO gas through a NaOH trap and then into anaerobic deionized water. Aliquots of the nitric oxide solutions (final concentration: 75–300 nM) were added to the rings (in the presence or absence of 100 μM MnTBAP) and relaxant responses were recorded.

Data analysis: All values are expressed as mean±standard error of the mean of n observations, where n represents the number of wells studied (12 wells from 2-3 independent experiments). Data sets were examined by analysis of variance and individual group means were then compared with Student's unpaired t-test. A p-value less than 0.05 was considered significant.

Results

MnTBAP is not a scavenger of nitric oxide: MnTBAP did not inhibit the relaxations in vascular rings in response to authentic NO· Moreover, MnTBAP, at 300 μM, did not inhibit nitrite/nitrate accumulation in the culture medium in response to the NO donor compound SNAP and caused a slight inhibition in response to DNO. These data, and the finding that NO does not affect the spectral changes of MnTBAP soret band, indicate that NO does not complex with the manganese in MnTBAP.

MnTBAP inhibits peroxynitrite-mediated oxidation: Peroxynitrite induced significant oxidation of dihydrorhodamine 123 to rhodamine 123, which was dose-dependently inhibited by MnTBAP with 50% inhibition at 30 μM (FIG. 40). This suggests that MnTBAP, like cysteine, urate, ascorbate and alpha-tocopherol, inhibits the oxidations caused by peroxynitrite.

MnTBAP inhibits the suppression of mitochondrial respiration by authentic peroxynitrite in J774 cells. Mitochondrial respiration was profoundly inhibited by exposure to 1 mM peroxynitrite at lh (FIG. 41A). This effect was partially and dose dependently prevented by MnTBAP.

MnTBAP inhibits the suppression of mitochondrial respiration by NO donors in J774 cells: Mitochondrial respiration was also inhibited by exposure to the NO donor compound SNAP (FIG. 41B) and DNO for 24 h (FIG. 41C). This effect was partially and dose dependently prevented by MnTBAP.

Effects of MnTBAP on NO production and suppression of mitochondrial respiration in immunostimulated J774 macrophages: Immunostimulation of the cells by lipopolysaccharide (LPS; 10 μg/ml) alone, and, more pronouncedly, in the presence of gamma interferon (IFN; 10 U/ml), resulted in nitrite/nitrate formation and a pronounced inhibition of the mitochondrial respiration. Administration of IFN alone did not induce detectable nitrite/nitrate production and only caused a mild (<15%) suppression of respiration (n=12).

MnTBAP caused a dose-dependent inhibition of nitrite/nitrate production in cells stimulated with LPS. However, in cells immunostimulated with the combination of LPS and IFN, MnTBAP caused a less pronounced inhibition of nitrite, nitrate accumulation (300 μM). For instance, at 100 μM and 300 μM, MnTBAP caused a significant, 63 and 86% inhibition, of the LPS-induced nitrite/nitrate accumulation. When given in the combined presence of LPS and IFN, 100 μM MnTBAP only caused a 25% inhibition of nitrite/nitrate accumulation and pronounced inhibition (61%) was only observed at the highest concentration of MnTBAP tested (300 μM). L-NMA (N^G-methyl-L-arginine) caused a near-complete inhibition of the production of NO in cells stimulated with LPS or LPS and IFN; and MnTBAP had no additional effect on nitrite/nitrate formation in the presence of L-NMA. The inhibition of nitrite/nitrate accumulation by MnTBAP in LPS-stimulated macrophages diminished by more than 50% when the agent was applied 6 h after LPS, whereas in the case of the inhibition seen with L-NMA, the extent of inhibition seen was similar when the compound was given together with LPS or at 6 h thereafter (n=6).

MnTBAP caused a dose-dependent, partial restoration of the immunostimulation-induced suppression of the mitochondrial respiration in both LPS-treated and (less potently) LPS and IFN-treated cells. Inhibition of NOS with L-NMA caused a restoration of the respiration to an extent comparable with that of 300 μM MnTBAP. The combined administration of 300 μM MnTBAP and 3 mM L-NMA caused an additional restoration of the mitochondrial respiration. In the presence of L-NMA and MnTBAP, respiration was restored to initial levels in the LPS-stimulated cells, but remained below normal in cells stimulated with LPS and IFN.

EXAMPLE XIV

Synthetic Reaction Schemes

Figure 42A:
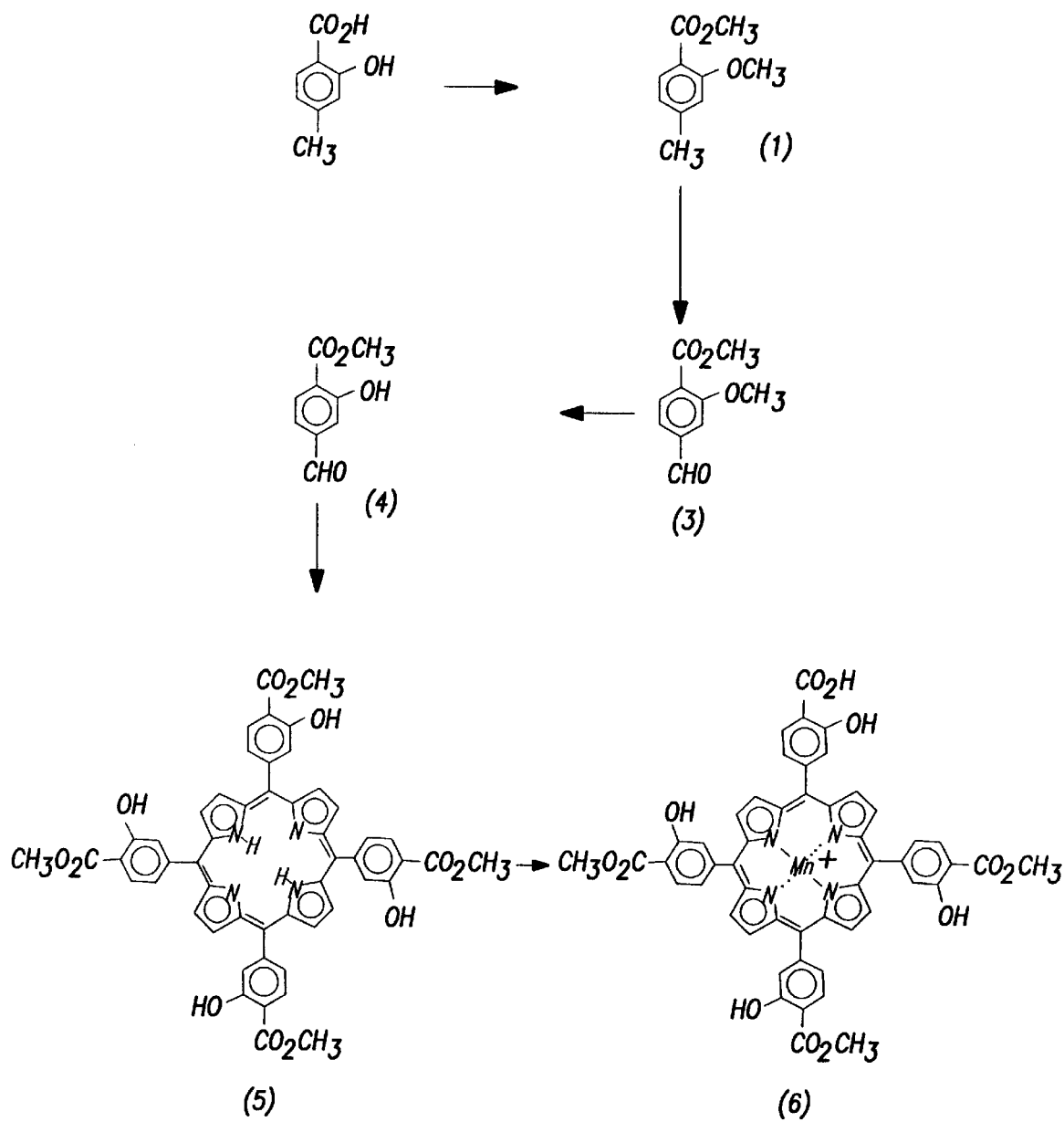

Synthesis of 10303 (FIG. 42A)

1. Methyl 2-methoxy-3-methyl benzoate (1)

To a magnetically stirred solution of 2-hydroxy-3-methyl benzoic acid (2.22 g, 14.6 mmol), finely ground anhydrous $K_2CO_3$ (8.06 g, 58.3 mmol) and acetone (150 mL) was added $(CH_3O)_2SO_2$ (2.9 mL, 30.6 mmol). The solution was stirred at room temperature for 18 hours then heated at reflux until analysis by TLC indicated the reaction was complete (1–2 hours). The reaction mixture was cooled to room temperature, filtered and the excess $K_2CO_3$ cake was thoroughly washed with acetone. The filtrate was evaporated and the residue was redissolved in EtOAc (100–125 mL) and triethylamine (~5–9 mL) was added. The reaction mixture was stirred at room temperature for 30 minutes, transferred to a separatory funnel and washed successively with $H_2O$ (100 mL), 2N HCl (until slightly acidic), $H_2O$ (100 mL) and brine (100 mL), then dried ($Na_2SO_4$) filtered and evaporated under reduced pressure. Chromatography of the residue on silica gel (ht of silica: 15 cm, diameter: 3 cm, eluent: 1:1 hexanes/$Et_2O$) provided 2.50 g (95w) of pure (1).

2. Methyl 2-methoxy-4-(α,α-dibromomethyl) benzoate (2)

A magnetically stirred solution of 1 (24.43 g, 135.6 mmol), NBS (54.41 g, 305.7 mmol) and $CCl_4$ (1 L) was exposed to a 100 watt lamp for 6 hours. Analysis by TLC indicated that the reaction mixture was composed of the mono, di and tribrominated benzoates, wherein the dibromide was the major product. The reaction mixture was quenched with $H_2O$ (200 mL) then saturated $Na_2S_2O_3$ (500 mL) was added to destroy $Br_2$. The mixture was transferred to a separatory funnel, vigorously shaken then separated. The organic layer was dried ($Na_2SO_4$), filtered and evaporated under reduced pressure. The crude $^1H$ NMR spectrum indicated that methyl-2-methoxy-4-(α,α-dibromo-methyl) benzoate was the major product, and was used without further purification.

3. Methyl 4-formyl-2-methoxy-benzoate (3).

The crude product 2 was dissolved in acetone/$H_2O$ (200 mL, 83:17) then $AgNO_3$ (47.25 g, 278.2 mmole) was added. The flask was covered with foil to avoid decomposition of the $AgNO_3$ by light. The reaction mixture was stirred at room temperature for 2–3 hours, then the AgBr salts were filtered off from the solution. The filtrate was diluted with EtOAc (400 mL), transferred to a separatory funnel, then washed with saturated $NaHCO_3$ (300 mL) to extract acid away from the aldehyde. The organic layer was washed successively with $H_2O$ (300 mL) and brine (300 mL), dried ($Na_2SO_4$), filtered and evaporated under reduced pressure. Chromatography of the residue on silica gel (ht of silica: 15 cm, diameter: 5 cm, eluent: 1:1 hexanes/$Et_2O$) provided 11.92 g (42%) of pure aldehyde (3).

4. Methyl 4-formyl-2-hydroxy benzoate (4)

To a magnetically stirred solution of methyl 4-formyl-2-methoxy benzoate (3) (1.82 g, 9.37 mmol) in $CH_2Cl_2$ (35 mL) at 0° C. and under $N_2$ was added dropwise, 1M $BCl_3$ (18.7 mL, 18.7 mmole). The reaction mixture was stirred at 0° C. for 10–30 minutes then quenched with $H_2O$ (50 mL). Ether (100 mL) was added to the mixture then transferred to a separatory funnel and layered. The aqueous layer was extracted with ether (35 mL). The combined organic extracts were washed with brine (100 mL), dried ($Na_2SO_4$), filtered, and evaporated under reduced pressure. Chromatography on silica gel (ht of silica: 12.5 cm, diameter: 5 cm, eluent: 1:1 hexanes/$Et_2O$ provided 1.60 g (95%) of pure methyl 4-formyl-2-hydroxy benzoate as an oil.

5. Tetramethyl 2,2',2'',2'''-tetrahydroxy-4,4', 4'', 4'''-(21H, 23H-porphine-5,10,15,20-tetrayl)tetrabenzoate (5).

In a foil-covered, 1 L 3 neck round-bottomed flask equipped with a reflux condenser, magnetic stirrer and a $N_2$ inlet was added methyl 4-formyl-2-hydroxy benzoate (1.01 g, 5.6 mmole), pyrrole (397 μL, 5.6 mmole) and dry $CH_2Cl_2$ (560 mL). The reaction mixture was stirred at room temperature for 10–30 minutes then $BF_3.OEt_2$ (69 μL, 0.56 mmole) was added. The extent of reaction was followed by uv-vis spectrophotometry. After 1.5 hours at room temperature tetrachloro-1,4-benzoquinone (1.03 g, 4.2 mmole) was added and the reaction mixture was heated at reflux for 3.5 hours. The reaction mixture was allowed to cool to room temperature then the solvent was evaporated under reduced pressure. After 2 chromatographic purifications on silica gel, 0.38 g (30%) of (5) was obtained as a violet solid. General procedure for chromatographic purification of 5.

On a 1 g scale of aldehyde, the crude product was usually combined with 2–3 g silica gel to make a mixture which was then divided into 2 batches for 2 separate chromatographic purifications on silica gel (ht of silica: 12–15 cm, diameter 5 cm). The first eluent used was ether 1:1 hexanes/$Et_2O$ or 4:1 hexanes/EtOAc (depending on how porphyrin behaves on TLC) to remove hydroquinone by-products and other non-polar impurities. After all non-polar impurities were removed, the eluent was changed to either $CH_2Cl_2$ or $CHCl_3$ to elute the porphyrin.

6. Trimethyl 2,2',2'',2'''-tetrahydroxy-4-benzoic acid-4', 4'',4''' (porphine -5,10,15,20-tetrayl)-tribenzoate manganese (III) chloride (6).

A solution of 5 (0.38 g, 0.42 mmole) and $MnCl_2$ (0.26 g, 2.1 mmole) in DMF (25 mL) was heated at reflux for 1.5 hours, then air was bubbled for 1.5 hrs as the solution was being cooled to room temperature. The DMF was evaporated under reduced pressure, then the residue was combined with silica gel (1 g) and $CH_2Cl_2$ (10 mL) to make a slurry. The $CH_2Cl_2$ was evaporated leaving a solid mixture which was loaded dry into a column packed with silica gel (ht of column: 12.5 cm, diameter: 5 cm, eluent: 3% MeOH/$CH_2Cl_2$). The preceeding purification yielded 124 mg (32%) of pure 6 as a dark green solid. (mp >300° C.; UV-VIS $\lambda_{max}$ 467 nm (131,000); FAB-MS calculated for $C_{51}H_{34}MnN_4O_{12}$ 949, found 949)

Figure 42B:
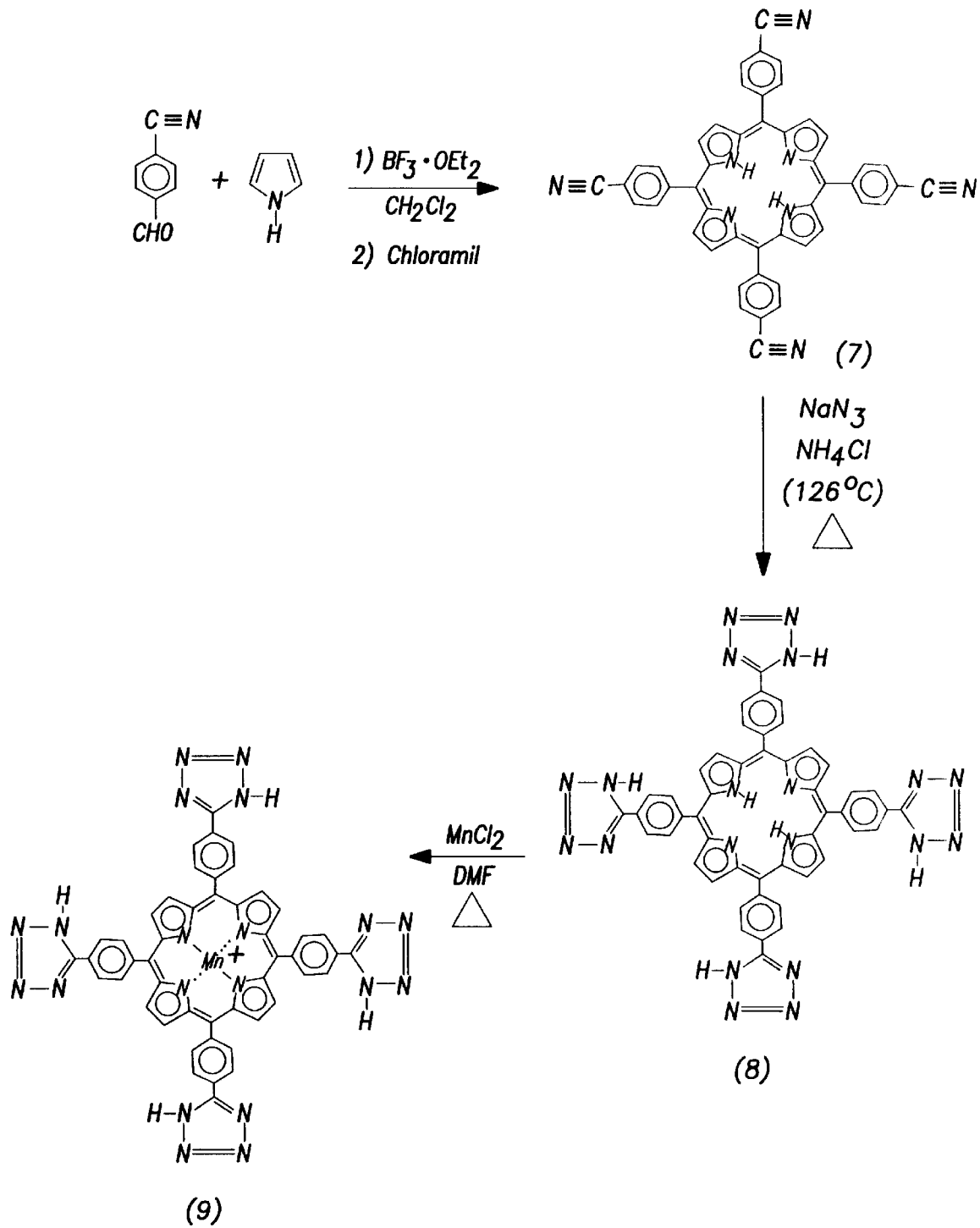

Synthesis of 10204 (FIG. 42B)

7. 4,4',4'',4'''-(21H,23H-porphine-5,10,15,20-tetrayl)-tetrakis(benzonitrile) (7).

In a foil-covered 2 L 3-neck round-bottomed flask equipped with a reflux condenser, magnetic stirrer and a $N_2$ inlet was added 4-formyl benzonitrile (1.13 g, 8.6 mmole), pyrrole (0.6 ml, 8.6 mmole) and $CH_2Cl_2$ (850 ml). The reaction mixture was stirred for 15 minutes at RT then $BF_3.OEt_2$ (105 µl, 0.85 mmole) was added. The extent of reaction was followed by uv-vis spectrophotometry. After 2 hours, tetrachloro-1,4-benzoquinone (1.56 g, 6.34 mmole) was added and the reaction mixture was heated at reflux for 2 hours. The reaction mixture was evaporated to a volume of 50–100 ml, then added to 2.8 g of silica gel. The rest of the solvent was evaporated under reduced pressure to provide a solid mixture for chromatographic purifications. After 3 separate purifications, 700 mg (46w) of pure 7 was obtained as a powdery violet solid.

8. 1,1',1'',1'''-Tetra-(1H-tetrazol-5-yl)-4,4',4'',4'''-(21H, 23H-porphine-5,10,15,20-tetrayl)-tetrakisbenzene (8).

A solution of 7 (0.30 g, 0.42 mmole), $NaN_3$ (0.24 g, 3.69 mmole), $NH_4Cl$ (0.18 g, 3.37 mmole) and DMF (25 ml) was heated at 120° C. for 3 days. Additional $NaN_3$ (0.17 g, 2.59 mmole) and $NH_4Cl$ (0.11 g, 2.05 mmole) were added in portions during day 2 to drive the reaction to completion. The DMF was evaporated under reduced pressure then cold $H_2O$ (10 ml) was added. The resulting solution was acidified with 6N HCl then $CH_2Cl_2$ (10 ml) was added. The resulting precipitate was collected and dried under vacuum to provide 0.37 g (99%) of 8 as a greenish solid which was used without further purification.

9. 1,1',1'',1'''-Tetra-(1H-tetrazol-5-yl)-4,4',4'',4'''-(porphine-5,10,15,20-tetrayl)-tetrakisbenzene manganese (III) chloride (9).

A solution of 8 (0.35 g, 0.4 mmole) and $MnCl_2$ (0.25 g, 2 mmole) in DMF (20 mL) was heated at reflux for 4–5 hours. The reaction mixture was allowed to cool to room temperature then DMF was evaporated under reduced pressure. The crude product was adsorbed onto 1.5 g of silica gel with 10–15 mL $CH_2Cl_2$. The $CH_2Cl_2$ was evaporated leaving a solid which was loaded dry into a column packed with silica gel slurry (ht of silica: 12.5 cm, diameter: 5 cm, eluent: 6 $CHCl_3$/3 MeOH/1 $NH_4OH$). Chromatographic purification provided 0.19 g (50%) of pure 9 as a dark green solid. (mp >320° C.; UV-VIS $\lambda_{max}$ 468 nm (42,000); FAB-MS calculated for $C_{48}H_{28}MnN_{20}$ 939, found 939)

Figure 42C:
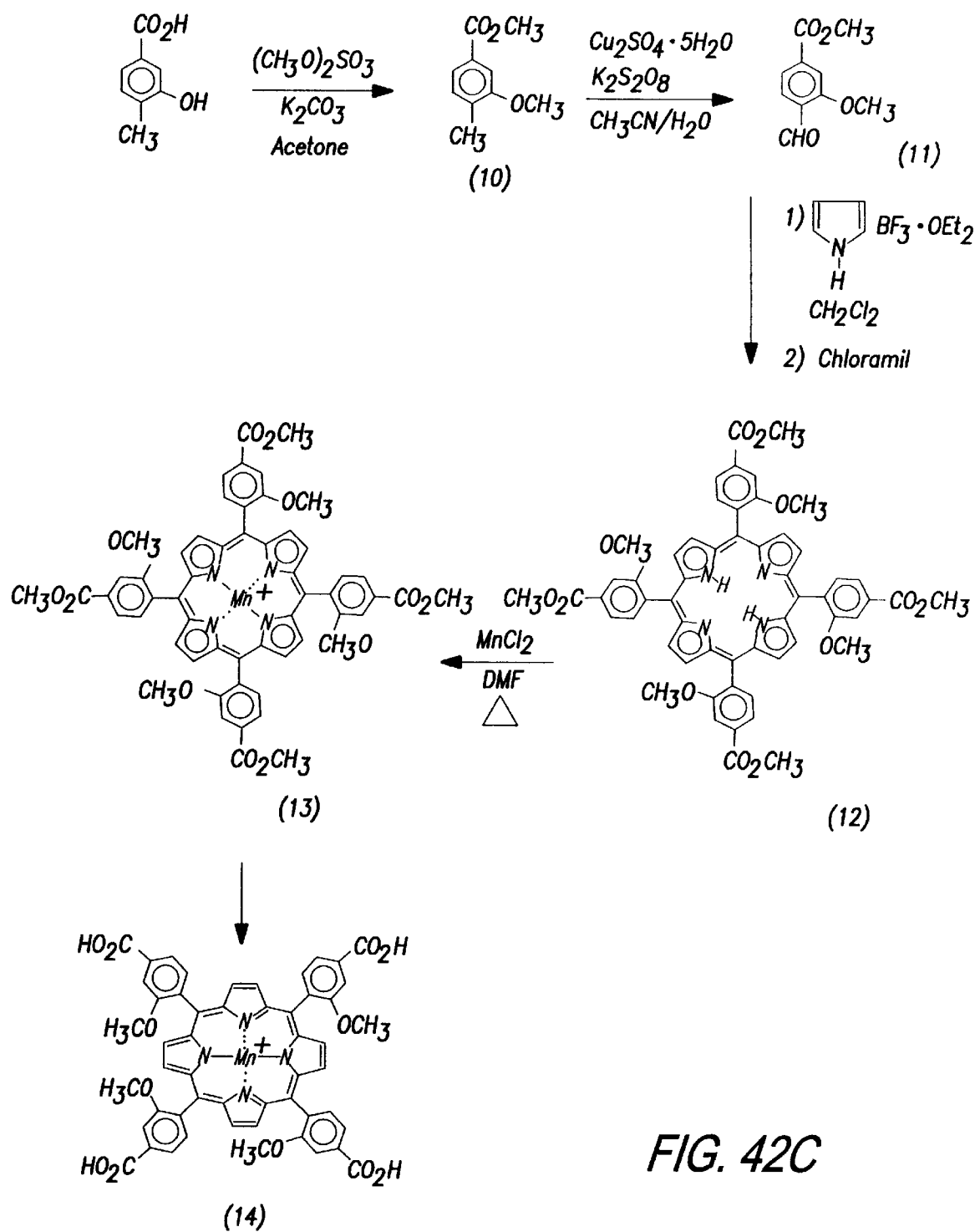

Synthesis of 10305 (FIG. 42C)

10. Methyl 3-methoxy-4-methyl benzoate (10).

To a magnetically stirred solution of 3-hydroxy-4-methyl benzoic acid (15.1 g, 99.2 mmole), finely ground anhydrous $K_2CO_3$ (43.7 g, 317 mmole) and acetone (250 mL) was added $(MeO)_2SO_2$ (21 mL, 222 mmole). The reaction mixture was stirred at room temperature for 24 hours then excess $K_2CO_3$ was filtered off. The acetone was removed by evaporation and the residue was redissolved in EtOAc (250 mL) then $Et_3N$ (15 mL) was added. The solution was stirred at room temperature for 30 minutes, transferred to a separatory funnel and washed successively with $H_2O$ (100 mL), 1N HCl (until slightly acidic), $NaHCO_3$ (100 mL), $H_2O$ (100 mL) and brine (100 mL), dried ($Na_2SO_4$), filtered and evaporated under reduced pressure. Chromatography of the residue on silica gel (ht of silica gel: 25 cm, diameter: 4 cm, eluent: 1:1 $CH_2Cl_2$/hexanes) provided 16.84 g (94%) of pure 10.

11. Methyl 4-formyl-3-methoxy benzoate (11).

To a magnetically stirred solution of 10 (5.87 g, 32.6 mmol) in 1:1 $CH_3CN/H_2O$ (250 mL) was added consecutively $CuSO_4 \cdot 5H_2O$ (8.13 g, 32.6 mmol) and $K_2S_2O_8$ (26.4 g, 97.7 mmole). The reaction mixture was heated at reflux for 50 minutes then transferred to a separatory funnel and extracted with EtOAc (2×100 mL). The combined organic extracts were dried over $Na_2SO_4$, filtered and evaporated. Purification on silica gel by gravity chromatography (ht of silica gel: 33 cm, diameter: 4 cm, eluent: 5:1 hexanes/EtOAc then 4:1 hexanes/EtOAc) provided 1.47 g (23%) of pure 11.

12. Tetramethyl 3,3',3'',3'''-tetramethoxy-4,4',4'',4'''-(21H, 23H-porphine-5,10,15,20-tetrayl)tetrabenzoate (12).

In a foil-covered 2 L 3 neck round-bottomed flask equipped with a reflux condenser, magnetic stirrer and a $N_2$ inlet was added methyl 4-formyl-3-methoxy benzoate (11) (1.23 g, 6.3 mmole), pyrrole (448 µl, 6.3 mmole) and dry $CH_2Cl_2$ (630 mL). The reaction mixture was stirred for 15 minutes then $BF_3.OEt$ (78 µL, 0.63 mmole) was added. The reaction was monitored by uv-vis spectrophotometry. After 3 hours, tetrachloro-1,4-benzoquinone (1.17 g, 4.7 mmole) was added and the reaction mixture was heated at reflux for 2.5 hours. The reaction mixture was allowed to cool to room temperature then the solvent was evaporated in vacuo. The crude product was added onto 2.6 g silica gel with 10–15 mL, $CH_2Cl_2$. The $CH_2Cl_2$ was evaporated and the resulting mixture was divided into 3 equal portions for three separate chromotographic purifications. Each portion was separately loaded dry into a column packed with silica gel (ht of silica gel: 15 cm, diameter: 5 cm, eluent: 1:1 hexanes/$Et_2O$ then $CH_2Cl_2$). The combined product 0.461 g (30%) of pure 12 was obtained as a mixture of rotational isomers.

13. Tetramethyl 3,3',3'',3'''-tetramethoxy-4,4'',4''',4'''-(porphine-5,10,15,20-tetrayl)-tetrabenzoate manganese (III) chloride (13)

A solution of 12 (0.32 g, 0.33 mmole) and $MnCl_2$ (0.20 g, 1.56 mmole) in DMF (32 mL) was heated at reflux for 6.5 hours. Air was then bubbled into the solution for 1.25 hours as the reaction mixture cooled to room temperature. The DMF was evaporated off and the crude mixture was adsorbed onto 1.5 g silica gel with 10–15 mL $CH_2Cl_2$. The $CH_2Cl_2$ was evaporated and the resulting solid mixture was loaded dry into a column packed with silica gel (ht of silica: 12.5 cm, diameter: 5 cm, eluent: 5% MeOH in $CH_2Cl_2$). Chromatographic purification provided 294 mg (84%) of pure 13 as a green-black solid. (mp >300° C.; UV-VIS $\lambda_{max}$ 467 nm (145,000); FAB-MS calculated for $C_{56}H_{44}MnN_4O_{12}$ 1019, found 1019).

14. 3,3',3'',3'''-Tetramethoxy-4,4',4'',4'''-(porphine-5,10,15,20-tetrayl)tetrakis(benzoic acid) (14).

A magnetically stirred solution of manganated tetrabenzoate 13 in 10 mL Claisen's case ($KOH/MeOH/H_2O$) was heated at reflux for 40–60 minutes. The reaction was cooled to room temperature then to 0° C. The cold solution was then acidified with 6N HCl then MeOH was evaporated under reduced pressure. The solids were filtered away from the acidic solution and was washed thoroughly with cold water. The solids were collected and dried under vacuum at 80° C. overnight provide 96 mg (87%) of pure 14 as a dark green solid (mp >300° C.; uv-vis; $\lambda_{max}$ 467 nm (150,000); FAB-MS calculated for $C_{52}H_{36}MnN_4O_{12}$ 963, found 963).

Synthesis of 10109 (FIG. 42D)

15. 4,4',4'',4'''-(Porphine-5,10,15,20-tetrayl)-tetrakis (benzoylchloride) manganese (III) chloride (15)

Mn TBAP (500 mg, 0.57 mmole) was suspended in dry benzene (125 ml) in a 3-neck round bottom flask equipped with a reflux condenser and a $N_2$ inlet. Thionylchloride (45 ml; 617 mmol) was added to the mixture and the reaction mixture was heated at reflux for 22 hours. The benzene and the unreacted $SOCl_2$ was removed by distillation. The residue was washed with dry benzene (50 ml) and evaporated on rotary evaporator to dryness. This washing and evaporating was repeated twice. The dark green residue was dried under high vacuum to yield 0.54 g (100%).

16. Tetra(N,N-dimethyl) 4,4',4'',4'''-(porphine-5,10,15,20-tetrayl)-tetrakis(benzamide) manganese (III) chloride (16).

To compound 15 (340 mg, 0.36 mmole) in THF (20 mL) was added dimethylamine in THF solution (10 ml, 2M solution). The reaction mixture was refluxed for 6 hours. TLC analysis (eluent:1 methanol:3 chloroform) showed complete conversion of the acid-chloride to the product. After cooling to room temperature, deionized water (100 ml) was added to the reaction mixture and the solid was filtered off. The crude solid was purified by column chromatography on silica gel (methylene chloride:methanol=4:1 eluent). The combined fractions (Rf=0.75 in $CH_2Cl_2$:MeOH=4:1) were evaporated, and dried under high vacuum, to provide the product as a green solid 0.11 g (31%). (UV-VIS $\lambda_{max}$ 467 nm (56,100); FAB-MS calculated for $C_{56}H_{49}MnN_8O_4$ 952, found 952.)

Synthesis of 10402, 10602, 11001, 11002, 11003 and 11103

Insofar as compounds 10402, 10602, 11001, 11002, 11003, and 11103 are concerned, synthesis can be carried out essentially, as described in Example XIV sections 5 and 6; the following starting material substitutions are required: 4-hydroxybenzaldehyde for methyl 4-formyl-2-hydroxy benzoate in the case of 10402, 4-hydroxy-3-nitrobenzaldehyde for methyl 4-formyl-2-hydroxy benzoate in the case of 10602, indole-3-carboxaldehyde for methyl 4-formyl-2-hydroxy benzoate in the case of 11001, 4-quinolinecarboxaldehyde for methyl 4-formyl-2-hydroxy benzoate in the case of 11002, 3-quinolinecarboxaldehyde for methyl 4-formyl-2-hydroxy benzoate in the case of 11003; and 3-fluoro-4-methoxybenzaldehyde for methyl 4-formyl-2-hydroxy benzoate in the case of 11103.

Synthesis of 10207 and 10208

Acetonitrile is reacted with hydroxylamine to prepare the amide oxime. An excess of the amide oxime is allowed to react with the product described in Example XIV, section 15, to provide a mixture of 10207 and 10208. Chromatographic purification of the reaction mixture provides pure 10207 and 10208.

Synthesis of 10209

Commercially available 4-methylbenzoic acid is transformed into its acid chloride by reaction with oxalyl chloride or thionyl chloride. The resulting acid chloride is heated in the presence of cuprous cyanide to provide the α-ketonitrile derivative. The α-ketonitrile is hydrolyzed with anhydrous methanol saturated with anhydrous hydrogen chloride gas to give the α-ketonitrile ester derivative. The aromatic methyl group is efficiently oxidized to the aldehyde oxidation state by first reaction with N-bromosuccinimide and subsequent hydrolysis with silver nitrate. Synthesis of 10209 can be carried out essentially as described in Example XIV, sections 5 and 6; the substitution of is starting material of methyl 4-formyl-2-hydroxy benzoate with the aldehyde described hereinabove being required.

All documents cited above are hereby incorporated in their entirety by reference.

One skilled in the art will appreciate from a reading of this disclosure that various changes in form and detail can be made without departing from the true scope of the invention. In addition to the compounds described herein, compounds disclosed in the following references can also be used as oxidant scavengers consistent with the invention: U.S. Pat. No. 5,227,405; Nagele et al, Biochem. Pharmacol. (UK) 47:555–562 (1994); Baudry et al, Biochem. Biophys. Res. Comm. 192:964–968 (1993); Duran et al, Cancer Lett (IRE) 69:167–172 (1993); Itami et al, Biochem. Biophys. Res. Comm. 197:536–541 (1993); Kitajima et al, Inorg. Chem. 32:1879–1880 (1993); Riley et al, Free Radical Biol. & Med. 15:514 (1993); Weiss et al, J. Biol Chem. (US) 268:23049–23054 (1993); Foye, Ann. Pharmacother. 26:1144–1147 (1992); Haseloff et al, J. Biolumin. Chemilumin. (UK) 7:171–175 (1992); Pelletier, J., Biochem. Pharmacol. 43:1061–1066 (1992); Yaping et al, J. Free Radic. BiolMed 13:533–541 (1992); Schechinger et al, Biol. Met. 1:112 (1988); Linss et al, Inorg. Chim. Acta 125:117 (1986); and Weser et al, Adv. Exp. Med. Biol. 264:51 (1990).

TABLE IX

ACTIVITY OF COMPOUNDS

| compound (metal complex) | Porphyrin Carbon number(s) | R1 (or $R_1'$) (or $P_1$) | R2 (or $R_2'$) | R3 (or $R_3'$) | side group class | Biochemistry SOD[2] μg/USOD | Biochemistry Catalase[3] min$^{-1}$ | in vitro Null SOD[4] E. coli bioassay | in vitro $H_2O_2$ HUVEC[5] |
|---|---|---|---|---|---|---|---|---|---|
| (Mn) 10101 | 5,10,15,20 | —C₆H₄—C(O)—NH— | —$(CH_2)_2$— | —$NH_2$ | cationic | 213 | 3.74 | + | + |
| (Mn) 10104 | 5,10,15,20 | —C₆H₄—C(O)—NH— | —$(CH_2)_2$— | —$N^+(CH_3)_3$ | cationic | 349 | N.D. | N.D. | N.D. |
| 10105 (Mn) | 5,10,15 | —C₆H₄—C(O)—NH— | —$(CH_2)_2$— | —$N^+(CH_3)_3$ | cationic | 445 | 1.11 | – | – |
|  | 20 | —C₆H₄— |  | BOND | —COOH |  |  |  |  |

TABLE IX-continued

ACTIVITY OF COMPOUNDS

| compound (metal complex) | Porphyrin Carbon number(s) | R1 (or R₁') (or P₁) | R2 (or R₂') | R3 (or R₃') | side group class | Biochemistry SOD[2] μg/USOD | Catalase[3] min⁻¹ | in vitro Null SOD[4] E. coli bioassay | $H_2O_2$ HUVEC[5] |
|---|---|---|---|---|---|---|---|---|---|
| 10106 (Mn) | 5,20 | –C₆H₄– | BOND | —COOH | cationic | 140 | 0.53 | + | – |
|  | 10,15 | –C₆H₄–C(O)–NH– | —(CH₂)₂— | —N⁺(CH₃)₃ |  |  |  |  |  |
| 10107 (Mn) | 5,15 | –C₆H₄–C(O)–NH– | —(CH₂)₂— | —N⁺(CH₃)₃ | cationic | 172 | 1.69 | – | + |
|  | 10,20 | –C₆H₄– | BOND | —COOH |  |  |  |  |  |
| 10108 (Mn) | 5 | –C₆H₄–C(O)–NH– | —(CH₂)₂— | —N⁺(CH₃)₃ | cationic | 375 | 0.88 | + | – |
|  | 10,15,20 | –C₆H₄– | BOND | —COOH |  |  |  |  |  |
| (Mn) 10109 | 5,10,15,20 | –C₆H₄–C(O)– | BOND | —N(CH₃)₂ | cationic | 470 | 0.59 | – | + |
| (Mn) 10201 | 5,10,15,20 | –C₆H₄– | BOND | —COOH | anionic | 33 | 0.8 | + | + |
| (Mn) 10202 | 5,10,15,20 | –C₆H₄–CO₂CH₃ | BOND | —H | anionic | 15 | 1.5 | – | + |
| (Mn) 10203 | 5,10,15,20 | –C₆H₄– | BOND | —SO₃H | anionic | inactive | 0.9 | + | + |
| (Mn) 10204 | 5,10,15,20 | –C₆H₄– | BOND | tetrazolyl (NH) | anionic | 1.3 | 0.33 | – | – |
| (Mn) 10205 | 5,10,15,20 | –C₆H₄– | BOND | 1,3,4-oxadiazol-2-yl (5-CH₃) | anionic | 28 | 1.8 | – | – |
| (Mn) 10206 | 5,10,15,20 | –C₆H₄– | BOND | 1,2,4-oxadiazol-5-yl (3-CH₃) | anionic | 447 | 1.9 | – | – |
| 10207 (Mn) | 5,10,20 | –C₆H₄– | BOND | 1,2,4-oxadiazol-5-yl (3-CH₃) | anionic | inactive | inactive | – | – |
|  | 15 | –C₆H₄– | BOND | —COOH |  |  |  |  |  |

TABLE IX-continued

ACTIVITY OF COMPOUNDS

| compound (metal complex) | Porphyrin Carbon number(s) | R1 (or R$_1$') (or P$_1$) | R2 (or R$_2$') | R3 (or R$_3$') | side group class | Biochemistry SOD[2] μg/USOD | Catalase[3] min$^{-1}$ | in vitro Null SOD[4] E. coli bioassay | $H_2O_2$ HUVEC[5] |
|---|---|---|---|---|---|---|---|---|---|
| 10208 (Mn) | 5,15 | —⟨phenyl⟩— | BOND | —COOH | anionic | 201 | inactive | N.D. | — |
|  | 10,20 | —⟨phenyl⟩— | BOND | 3-methyl-1,2,4-oxadiazole |  |  |  |  |  |
| (Mn) 10209 | 5,10,15,20 | —⟨phenyl⟩—C(O)—C(O)— | BOND | —OCH$_3$ | anionic | inactive | 0.1 | – | – |
| (Mn) 10301 | 5,10,15,20 | —⟨phenyl with CH$_3$, CO$_2$CH$_3$⟩ | BOND | —OH | chelator | 314 | 0.85 | + | – |
| (Mn) 10302 | 5,10,15,20 | —⟨phenyl with CH$_3$, CO$_2$CH$_3$⟩ | BOND | —OCH$_3$ | chelator | 37 | 2.9 | – | – |
| 10303 (Mn) | 5 | —⟨phenyl with CO$_2$H, CH$_3$⟩ | BOND | —OH | chelator | 78 | 1.4 | + | + |
|  | 10,15,20 | —⟨phenyl with CO$_2$CH$_3$, CH$_3$⟩ | BOND | —OH |  |  |  |  |  |
| (Mn) 10304 | 5,10,15,20 | —⟨phenyl with CO$_2$CH$_3$, CH$_3$⟩ | BOND | —OH | chelator | ppt | ppt | – | – |
| (Mn) 10305 | 5,10,15,20 | —⟨phenyl with CO$_2$H, CH$_3$⟩ | BOND | —OCH$_3$ | chelator | inactive | 2.2 | + | + |
| (Mn) 10306 | 5,10,15,20 | —⟨phenyl with CO$_2$CH$_3$, CH$_3$⟩ | BOND | —OCH$_3$ | chelator | 50 | 9.9 | + | – |
| (Mn) 10401 | 5,10,15,20 | —⟨phenyl with C(CH$_3$)$_3$, C(CH$_3$)$_3$⟩ | BOND | —OH | antioxidant | insol | insol | N.D. | N.D. |
| (Mn) 10402 | 5,10,15,20 | —⟨phenyl⟩— | BOND | —OH | antioxidant | 268 | inactive | – | – |
| (Mn) 10601 | 5,10,15,20 | —⟨phenyl with CH$_3$⟩ | BOND | —NO$_2$ | nitro | 18 | 0.5 | + | – |

TABLE IX-continued

ACTIVITY OF COMPOUNDS

| compound (metal complex) | Porphyrin Carbon number(s) | R1 (or R₁') (or P₁) | R2 (or R₂') | R3 (or R₃') | side group class | Biochemistry SOD[2] μg/USOD | Catalase[3] min⁻¹ | in vitro Null SOD[4] E. coli bioassay | $H_2O_2$ HUVEC[5] |
|---|---|---|---|---|---|---|---|---|---|
| (Mn) 10602 | 5,10,15,20 | —C₆H₃(CH₃)—OH | BOND | —NO₂ | nitro | 74 | 0.1 | + | + |
| (Mn) 10701 | 5,10,15,20 | —C₆H₄— | BOND | —H | un-substit | 96 | 2.1 | − | − |
| (Mn) 10901 | 5,10,15,20 | —C₆H₄— | BOND | —CN | cyano | 169 | 3.2 | − | − |
| (Mn) 11001 | 5,10,15,20 | BOND | BOND | 3-indolyl (NH) | heterocyclic | 404 | 0.9 | N.D. | − |
| (Mn) 11002 | 5,10,15,20 | BOND | BOND | 4-quinolinyl | heterocyclic | 22 | 3.3 | N.D. | − |
| (Mn) 11003 | 5,10,15,20 | BOND | BOND | 3-quinolinyl | heterocyclic | 106 | 1.02 | N.D. | + |
| 11101 (Cu) | 5,10,15,20 | —C₅H₄N⁺— | BOND | —CH₃ | halogenated | inactive | inactive | N.D. | N.D. |
|  | 2,3,7,8,12,13,17,18 | —Br |  |  |  |  |  |  |  |
| 11102 (Mn) | 5,10,15,20 | —C₅H₄N⁺— | BOND | —CH₃ | halogenated | 0.6 | 4.6 | N.D. | N.D. |
|  | 2,3,7,8,12,13,17,18 | —Br |  |  |  |  |  |  |  |
| (Mn) 11103 | 5,10,15,20 | —C₆H₃(CH₃)—OCH₃ | BOND | —F | halogenated | N.D. | 2.4 | N.D. | ppt |

Footnote to Table IX

[1]Porphine carbon numbers refer to the methine bridge carbons (5, 10, 15, 20) at which each R group is attached, or to the pyrrole carbon (2, 4, 7, 8, 12, 13, 17 or 18), at which P is attached. P is hydrogen unless otherwise defined.
[2]SOD activity determined as described by McCord and Fridovich, J. Biol. Chem. 244:6049 (1969).
[3]Catalase activity determined as described by Del Rio et al, Anal. Biochem. 80:409 (1977). Metalloporphyrins were assayed at various concentrations in the presence of 1 mM hydrogen peroxide for catalase-like activity. A Clark electrode was used to measure the formation of oxygen from the breakdown of hydrogen peroxide over a period of 2 minutes.
[4]Rates of growth of cultures of null SOD E. coli (JI132 strain) were followed turbidimetrically at 700 nm to minimize interferences from the absorbance of test compounds. Growth medium contained 0.2% glucose, 0.2% casamino acids, 30 mg/L thiamine, 30 mg/L pantothenic acid, and M9 salts in water, pH adjusted to 7.0. Test compounds were filter-sterilized before adding to media. (Faulkner et al, J. Biol. Chem. 269:23471 (1994)).
[5]Human umbilicord vein endothelial cells (HUVEC) (ATCC #CRL-1730) (Moldow et al, Methods in Enzymology 105:378–385 (1984)) were grown in Ham's F-12K medium supplemented with 10% fetal bovine serum, 0.1 mg heparin and 0.03 mg/ml endothelial cell growth factor in T-75 culture flasks in a humidified atmosphere containing 5% carbon dioxide and 95% air. Cells were plated at ~3.5×10⁴ cells/well in 24-well plates. Experiments were performed 48 hours later. Medium was changed to EMEM without serum supplement but including heparin and endothelial cell growth factor at the start of each study. Stock solutions of D-aminoacid oxidase and metalloporphyrins were diluted into (EMEM) and passed through a 0.2 cc filter before use. HUVEC cells were labelled with $Cr^{51}$ by incubating them with EMEM containing radiolabeled sodium chromate for 4 hrs at an isotope concentration of 20 $\mu Ci/10^6$ cells. Unincorporated $Cr^{51}$ was removed by repeated washes in EMEM. Injury was initiated by incubation of endothelial cells for 5 hours with a hydrogen peroxide generating system consisting of D-alanine (1 mM) and 40 mU/ml of D-aminoacid oxidase in EMEM. D-amino acid oxidase is found in PMNs (polymorphonuclear leucocytes) and is thought to be part of the oxidative burst which is a key part of the PMN mediated inflammatory response (Robinson et al, J. Cell Biology, 77:59 (1978); Cline et al, Microbiology 62:756 (1969); De Chatelet J. Reticul. Soc. 24:73 (1978)). Supernatant from each well was collected at the end of the incubation period, cells were washed with PBS and then lysed with 0.4 N sodium hydroxide. Radioactivity in both supernatants and cell lysates were measured separately in a gamma counter. A set of wells in each plate were used to measure basal release of $Cr^{51}$ from HUVEC incubated in EMEM alone. $Cr^{51}$ release was expressed as a percent of radioactivity in supernatant to total radioactivity [($Cr^{51}$ in supernatant+$CR^{51}$ in lysate)×100].

What is claimed is:

1. An oxidant scavenger of the formula:

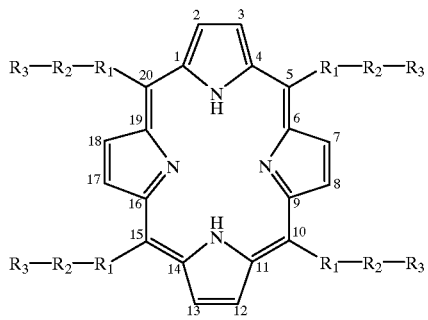

or a pharmaceutically acceptable salt thereof, wherein:

$R_1$ is a bond,

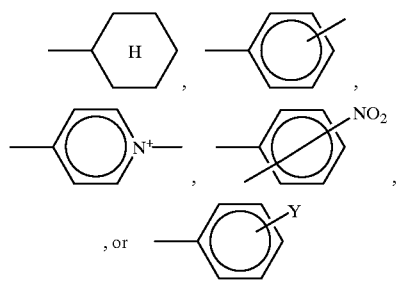

wherein and Y is an alkyl group and wherein

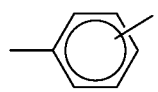

indicates bonding to $R_2$ at any position and

indicates bonding to $R_2$ and the substituent at any position; and $R_2$ is a bond, $-(CY'_2)_n{}^-$, $-(CY'_2-CY'=CY')_n{}^-$, $-(CY'_2-CY'_2CH=CH)_n{}^-$, $-(CY'=CY')_n{}^-$,

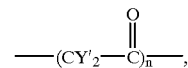

wherein Y' is hydrogen or an alkyl group and wherein n is 1 to 8; and $R_3$ is $-Y''$, $-N^+(Y'')_3$, $-COOH$, $-COO^-$, $-CH_2-PO_3H_2$ or $-CH_2-PO_3H^-$, wherein Y'' is an alkyl group, wherein, when $R_1$ is

and $R_2$ is a bond, $R_3$ is not Y'', and wherein, $-R_1-R_2-R_3$ is not

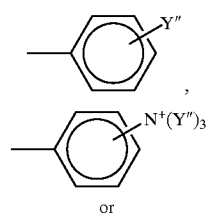

or

2. An oxidant scavenger of the formula:

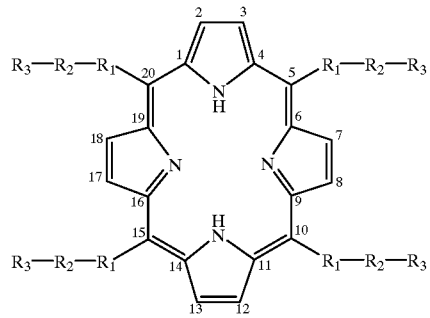

or a pharmaceutically acceptable salt thereof, wherein:

71

$R_1$ is a bond,

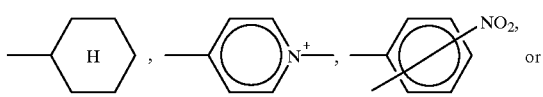

wherein and Y is an alkyl group and wherein

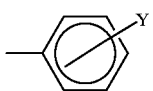

indicates bonding to $R_2$ at any position and

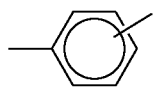

indicates bonding to $R_2$ and the substituent at any position; and $R_2$ is a bond, $-(CY'_2)_n^-$, $-(CY'_2-CY'=CY')_n^-$, $-(CY'_2-CY'_2-CH=CH)_n^-$, $-(CY'=CY')_n^-$, or

wherein Y' is hydrogen or an alkyl group and wherein n is 1 to 8; and $R_3$ is $-Y''$, $-OH$, $-NH_2$, $-N^+(Y'')_3$, $-COOH$, $-COO^-$, $-CH_2-PO_3H_2$ or $-CH_2-PO_3H^-$, wherein Y'' is an alkyl group, wherein, when $R_1$ is

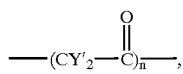

and $R_2$ is a bond, $R_3$ is not Y'', and wherein $R_1-R_2-R_3$ is not

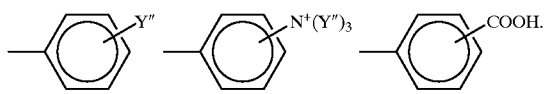

72

3. An oxidant scavenger of the formula:

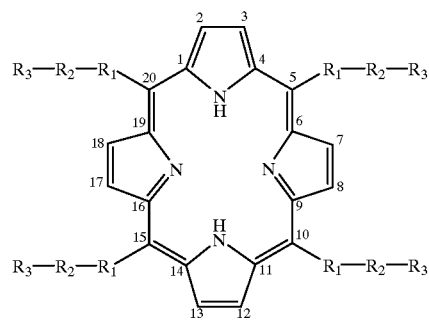

or a pharmaceutically acceptable salt thereof, or metal complex thereof wherein said metal is selected from the group consisting of manganese, copper and iron, each $R_1'$ is independetly a bond,

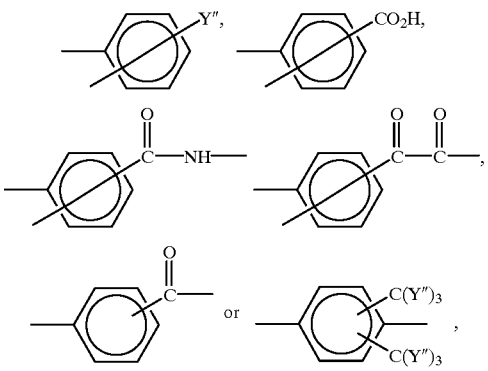

wherein Y'' is an alkyl group, and wherein

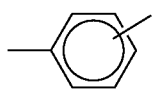

indicates bonding to $R_2'$ at any position and

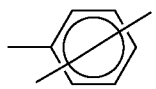

indicates bonding to $R_2'$ and the $R_1'$ phenyl substituent at any position;

each $R_2'$ is independently a bond, or $-(CH_2)_n-$ wherein n is 1–4, each $R_3'$ is independently $-Y'''$, $-COY''$, or a heterocyclic group, wherein Y'' is as defined above and Y''' is a primary, secondary, tertiary or quaternary amine, wherein when $R_1'$ is

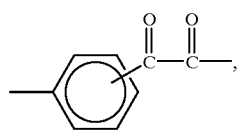

$R_3'$ is not COY",
wherein when $R_1'$ is

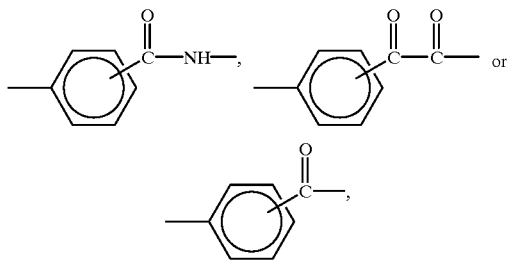

$R_3'$ is not —$NO_2$, and
wherein —$R_1'$—$R_2'$—$R_3'$, collectively, are not

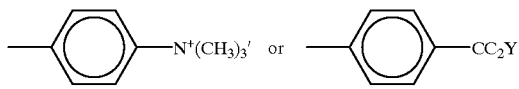

4. A method of protecting cells from oxidant-induced toxicity comprising contacting said cells with an amount of a scavenger of the formula,

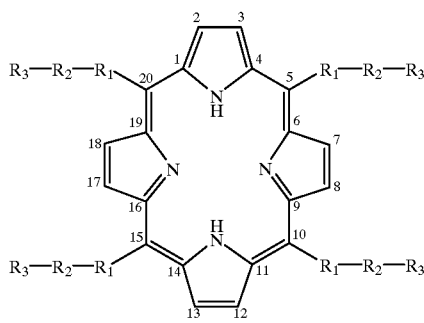

or a pharmaceutically acceptable salt thereof, sufficient to effect said protection, wherein:
$R_1$ is a bond,

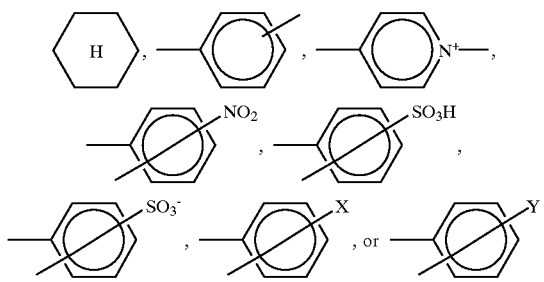

wherein X is a halogen and Y is an alkyl group and wherein

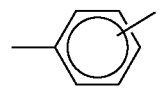

indicates bonding to $R_2$ at any position and

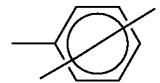

indicates bonding to $R_2$ and the substituent at any position; and
$R_2$ is a bond, —$(CY'_2)_n$—, —$(CY'_2$—$CY'$=$CY')_n$—, —$(CY'_2$—$CY'_2$—$CH$=$CH)_n$—, —$(CY'$=$CY')_n$—, or

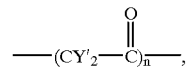

wherein Y' is hydrogen or an alkyl group and wherein n is 1 to 8; and
$R_3$ is —Y", —OH, —$NH_2$, —$N^+(Y")_3$, —COOH, —COO$^-$, —$SO_3H$, —$SO_3^-$, —$CH_2$—$PO_3H_2$ or —$CH_2$—$PO_3H^-$, wherein Y" is an alkyl group, optionally complexed with a metal selected from the group consisting of manganese, copper and iron, sufficient to effect said protection.

5. The method according to claim 4 wherein said scavenger is complexed with a metal selected from the group consisting of manganese, copper or iron.

6. The method according to claim 4 wherein said cells are mammalian cells or plant cells.

7. A method of inhibiting damage due to oxidation of a substance comprising contacting said substance with an amount of a scavenger of the formula,

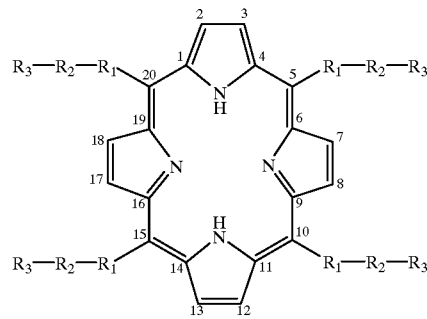

or a pharmaceutically acceptable salt thereof, sufficient to effect said inhibition, wherein:
$R_1$ is a bond,

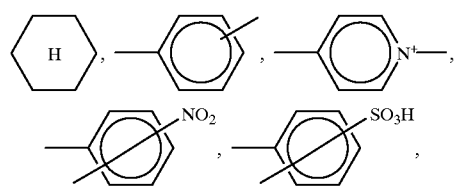

-continued

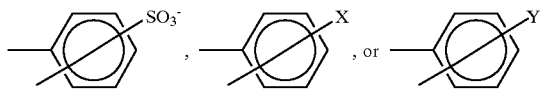

wherein X is a halogen and Y is an alkyl group and wherein

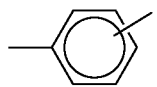

indicates bonding to $R_2$ at any position and

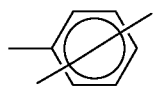

indicates bonding to $R_2$ and the substituent at any position; and $R_2$ is a bond, $-(CY'_2)_n^-$, $-(CY'_2-CY'=CY')_n^-$, $-(CY'_2-CY'_2-CH=CH)_n^-$, $-(CY'=CY')_n^-$, or

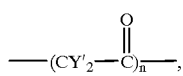

wherein $Y'$ is hydrogen or an alkyl group and wherein n is 1 to 8; and $R_3$ is $-Y''$, $-OH$, $-NH_2$, $-N^+(Y'')_3$, $-COOH$, $-COO^-$, $-SO_3H$, $-SO_3^-$, $-CH_2-PO_3H_2$ or $-CH_2-PO_3H^-$, wherein $Y''$ is an alkyl group, optionally complexed with a metal selected from the group consisting of manganese, copper and iron, sufficient to effect said inhibition.

8. The method according to claim 7 wherein said mimetic is completed with a metal selected from the group consisting of manganese, copper or iron.

9. A pharmaceutical composition comprising the scavenger according to claim 1 or 2 and a pharmaceutically acceptable carrier.

10. A kit comprising the scavenger according to claim 1 or 2 disposed within a container means.

11. An oxidant scavenger of the formula:

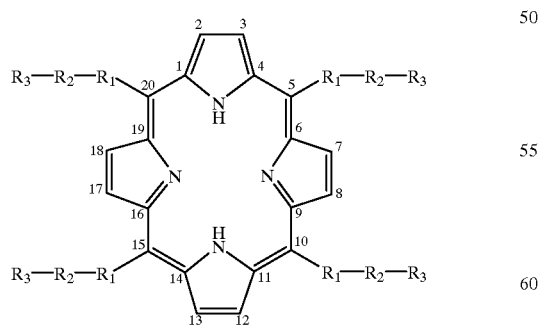

or a pharmaceutically acceptable salt thereof, or metal complex thereof wherein said metal is selected from the group consisting of manganese, copper and iron, wherein:

each $R_1'$ is independently

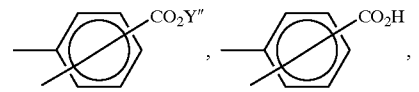

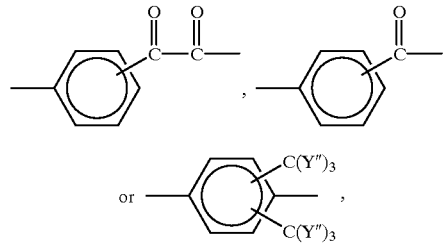

wherein $Y''$ is an alkyl group, and wherein

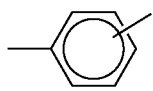

indicates bonding to $R_2'$ at any position and

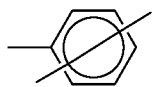

indicates bonding to $R_2'$ and the $R_1'$ phenyl substituent at any position;

each $R_2'$ is independently a bond, or $-(CH_2)_n-$ wherein n is 1–4, each $R_3'$ is independently $-Y''$, $-Y'''$, $-H$, $-OH$, $-OY''$, $-NO_2$, $-CN$, $-NH_2$, $-COOH$, $-COY''$, $-COO^-$, or a heterocyclic group, wherein $Y-$ is as defined above and $Y'''$ is a primary, secondary, tertiary or quaternary amine, wherein when $R_1'$ is

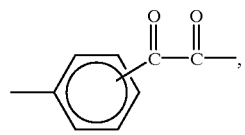

$R_3'$ is not COOH, $COY''$ or $COO^-$, wherein when $R_1'$ is

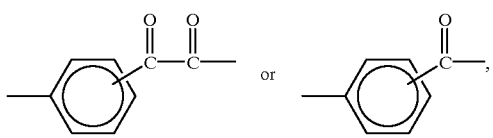

$R_3'$ is not —$NO_2$, and wherein —$R_1'$—$R_2'$—$R_3'$, collectively, are not

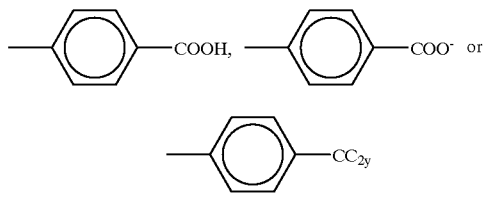

12. The scavenger according to claim 3 or 11 wherein Y'" is a secondary, tertiary or quaternary amine and each hydrogen replacement group on the amine nitrogen is a $C_1$–$C_4$ alkyl group.

13. A compound having the structure

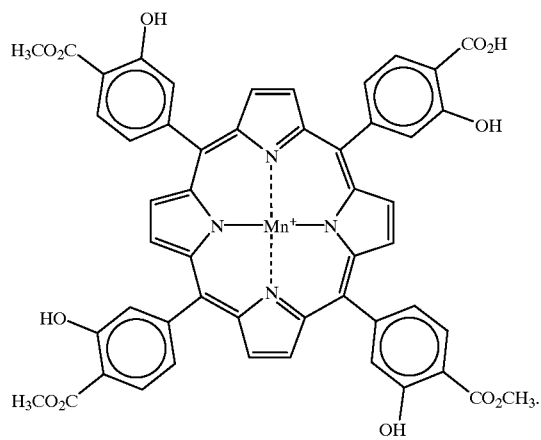

14. A compound having the structure

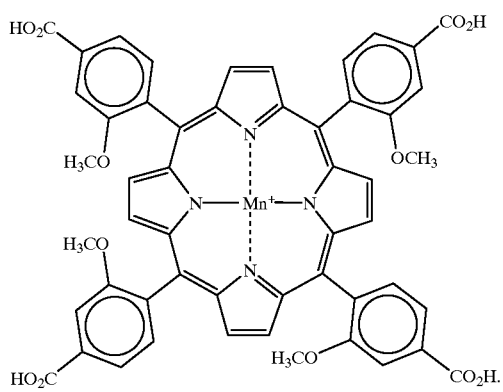

15. A compound having the structure

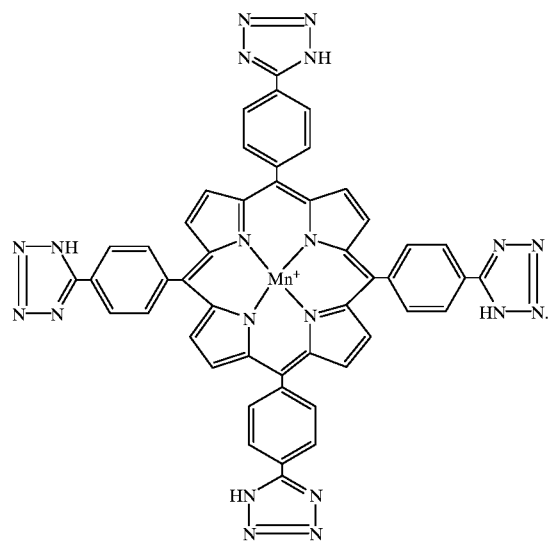

16. A compound having the structure

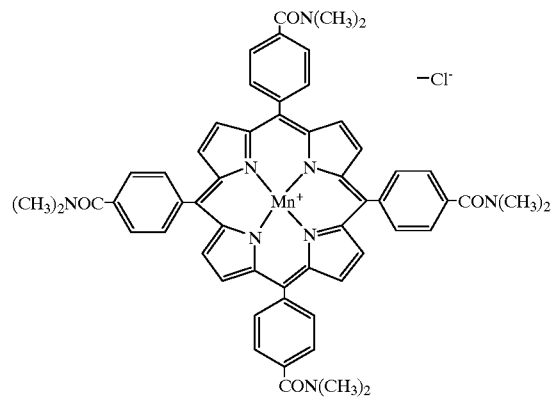

17. An oxidant scavenger of the formula:

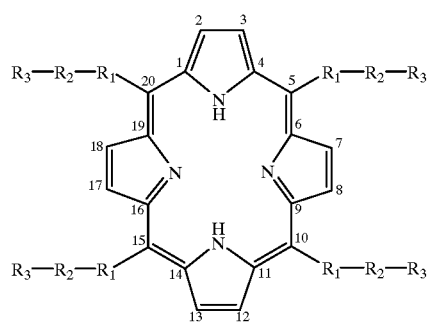

or a pharmaceutically acceptable salt thereof, wherein:

$R_1$ is a bond,

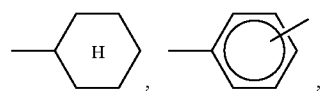

-continued

[chemical structures: pyridinium, nitrobenzene, and phenyl-Y]

wherein and Y is an alkyl group and wherein

[phenyl structure]

indicates bonding to R₂ at any position and

[disubstituted phenyl structure]

indicates bonding to R₂ and the substituent at any position; and $R_2$ is a bond, $-(CY'_2)_n^-$, $-(CY'_2-CY'=CY')_n^-$, $-(CY'_2-CY'_2-CH=CH)_n^-$, $-(CY'=CY')_n^-$, or $$-(CY'_2-\overset{O}{\underset{\|}{C}})_{\overline{n}}-,$$

wherein Y' is hydrogen or an alkyl group and wherein n is 1 to 8; and $R_3$ is $-Y''$, $-N^+(Y'')_3$, $-COOH$, $-COO^-$, $-CH_2-PO_3H_2$ or $-CH_2-PO_3H^-$, wherein Y'' is an alkyl group, wherein, when $R_1$ is

[pyridinium structure]

and $R_2$ is a bond, $R_3$ is not $-CH_3$, and wherein, $R_1-R_2-R_3$ is not

[structures: -C₆H₄-CH₃, -C₆H₄-N⁺(CH₃)₃, or -C₆H₄-COOH]

18. An oxidant scavenger of the formula:

[porphyrin structure with R₃—R₂—R₁ substituents and P substituents]

or a pharmaceutically acceptable salt thereof, wherein:
each $R_1$ is independently, a bond,

[structures: cyclohexyl-H, phenyl, pyridinium-N⁺, nitrophenyl-NO₂, phenyl-SO₃H, phenyl-SO₃⁻, phenyl-X, or phenyl-Y]

wherein X is a halogen and Y is an alkyl group and wherein

[phenyl structure]

indicates bonding to R₂ at any position and

[disubstituted phenyl structure]

indicates bonding to R₂ and the substituent at any position; and each $R_2$ is independently, a bond, $-(CY'_2)_n^-$, $-(CY'_2-CY'=CY')_n^{31}$, $-(CY'_2-CY'_2-CH=CH)_n^-$, $-(CY'=CY')_n^-$, or $$-(CY'_2-\overset{O}{\underset{\|}{C}})_{\overline{n}}-,$$

wherein Y' is hydrogen or an alkyl group and wherein n is 1 to 8; and each $R_3$ is, independently $-Y''$, $-OH$, $-NH_2$, $-N^+(Y'')_3$, $-C-PO_3H_2$ or $-C-PO_3H^-$, wherein Y'' is an alkyl group, each P is, independently, an electron withdrawing group or hydrogen wherein at least one P is not hydrogen wherein said oxidant scavenger is a metal complex wherein said metal is selected from the group consisting of manganese, copper or iron, wherein when said metal is copper and all P's are Br, and when R₁ is

and R₂ is a bond, R₃ is not —CH₃.

19. A manganese, copper or iron complex of
octobromo—TBAP (tetrakis (4-benzoic acid)porphyrin)
octochloro—TBAP
octofluro—TBAP
octonitro—TBAP
octobromo—TMPyP (tetrakis (1-methyl-4-pyridyl) porphyrin)
octochloro—TMPyP
octofluro—TMPyP
octonitro —TMPyP
octobromo—tetrakis 4-phenyl sulfonate porphyrin
octochloro—tetrakis 4-phenyl sulfonate porphyrin
octofluro—tetrakis 4-phenyl sulfonate porphyrin or
octonitro—tetrakis 4-phenyl sulfonate porphyrin.

20. A method of protecting a biological substance from oxidative stress or a method of maintaining biological function of NO·, or active forms thereof, in an intracellular or extracellular space of a tissue or organ comprising contacting said substance or said tissue or organ with an amount of said scavenger according to claim 18 sufficient to effect said protection or said maintenance.

21. The scavenger according to claim 1 wherein at least one of said R₁'s, R₂'s, or R₃'s is different than the other of said R₁'s, R₂'s, or R₃'s, respectively.

22. The scavenger according to claim 21 wherein at least one of said R₁'s, R₂'s, or R₃'s is different than the other of said R₁'s, R₂'s, or R₃'s, respectively.

23. The scavenger according to claim 3 wherein said scavenger is complexed with manganese.

24. The method according to claim 5 wherein said scavenger is complexed with manganese.

25. The method according to claim 8 wherein said mimetic is complexed with manganese.

26. The scavenger according to claim 1 or claim 2 wherein said scavenger is complexed with a metal selected from the group consisting of manganese, copper and iron.

27. The scavenger according to claim 3 or 11 wherein said scavenger is a manganese complex.

28. A pharmaceutical composition comprising the scavenger according to claim 3 or 11 and a pharmaceutically acceptable carrier.

29. A kit comprising the scavenger according to claim 3 or 11 disposed within a container means.

30. An oxidant scavenger of the formula:

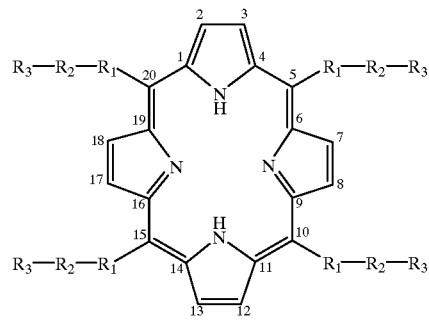

or a pharmaceutically acceptable salt thereof, wherein:

R₁ is a bond,

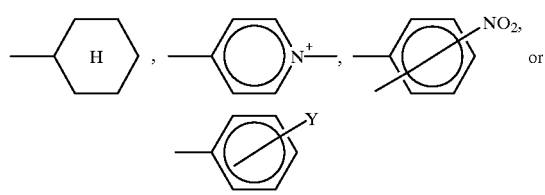

wherein and Y is an alkyl group and wherein

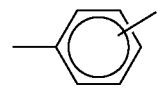

indicates bonding to R₂ at any position and

indicates bonding to R₂ and the substituent at any position; and

R₂ is a bond, —(CY'₂)ₙ⁻, —(CY'₂—CY'=CY')ₙ⁻, —(CY'₂—CY'₂—CH=CH)ₙ⁻, —(CY'=CY')ₙ⁻, or

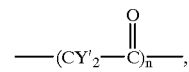

wherein Y' is hydrogen or an alkyl group and wherein n is 1 to 8; and

R₃ is —Y", —OH, —NH₂, —N⁺(Y")₃, —COOH, —COO⁻, —CH₂—PO₃H₂ or —CH₂—PO₃H⁻, wherein Y" is an alkyl group, wherein, when R₁ is

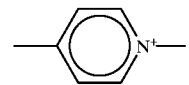

and R₂ is a bond, R₃ is not —CH₃, and wherein, when R₁—R₂—R₃ is not

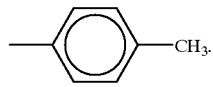

31. A pharmaceutical composition comprising the scavenger according to claim 18 and a pharmaceutically acceptable carrier.

32. A kit comprising the scavenger according to claim 18 disposed within a container means.

33. An oxidant scavenger of the formula:

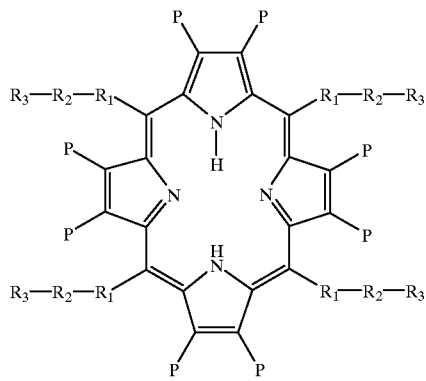

or a pharmaceutically acceptable salt thereof, wherein each $R_1'$ is independently a bond,

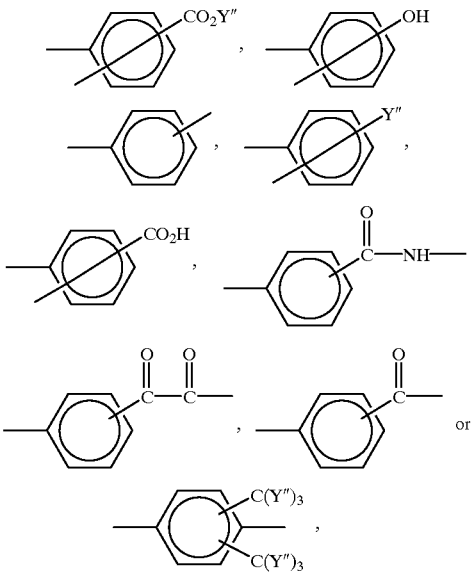

wherein Y″ is an alkyl group, and wherein

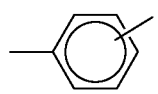

indicates bonding to $R_2'$ at any position and

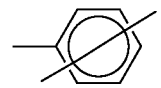

indicates bonding to $R_2'$ and the $R_1'$ phenyl substituent at any position;

each $R_2'$ is independently a bond, or —(CH₂)$_n$— wherein n is 1–4, each $R_3'$ is independently —Y″, —Y‴, —OY″, —NO₂, —CN, —NH₂, —COY″, or a heterocyclic group, wherein Y″ is as defined above and Y‴ is a primary, secondary, tertiary or quaternary amine, each P is, independently, an electron withdrawing group or hydrogen wherein at least one P is not hydrogen;

wherein said oxidant scavenger is a metal complex wherein said metal is selected from the group consisting of manganese, copper or iron.

34. A pharmaceutical composition comprising the scavenger according to claim 33 and a pharmaceutically acceptable carrier.

35. A kit comprising the scavenger according to claim 33 disposed within a container means.

36. The complex according to claim 19 wherein said complex is a manganese complex.

37. A method of protecting a biological substance from oxidative stress or a method of maintaining biological function of NO·, or active forms thereof, in an intracellular or extracellular space of a tissue or organ comprising contacting said substance or said tissue or organ with an amount of said scavenger according to claim 33 sufficient to effect said protection or said maintenance.

38. The scavenger according to claim 1 wherein $R_1$ is a bond,

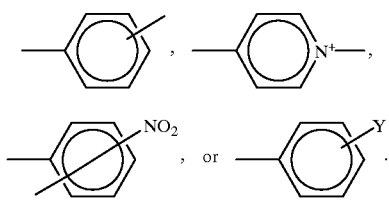

39. The scavenger according to claim 33 wherein $R_1$ is

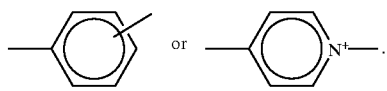

40. The scavenger according to claim 21 wherein R$_1$ is a bond,

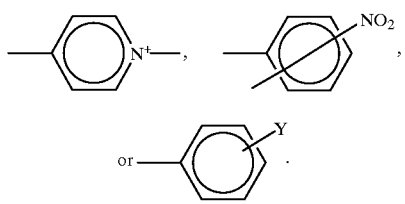

41. The scavenger according to claim 40 wherein R$_1$ is

42. The scavenger according to claim 1 or 2 wherein R$_2$ is a bond or —(CY'$_2$)$_n$—.

43. The scavenger according to claim 1 wherein R$_3$ is —Y", —N$^+$(Y")$_3$, —COOH, or —COO$^-$.

44. The scavenger according to claim 43 wherein R$_3$ is —N$^+$(Y")$_3$, —COOH, or —COO$^-$.

45. The scavenger according to claim 2 wherein R$_3$ is —Y", —OH, —NH$_2$, —N$^+$(Y")$_3$, —COOH, or —COO$^-$.

46. The scavenger according to claim 45 wherein R$_3$ is —N$^+$(Y")$_3$, —COOH, or —COO$^-$.

47. The scavenger according to claim 11 wherein R$_1$' is

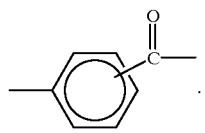

48. The scavenger according to claim 26 wherein R$_1$' is a bond,

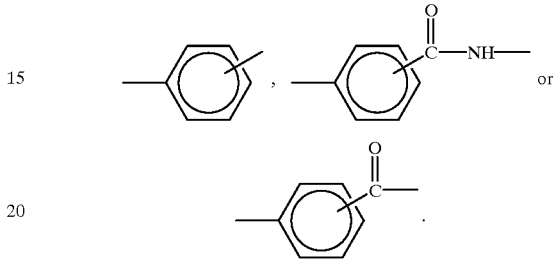

49. The scavenger according to claim 28 wherein R$_3$' is —NO$_2$, —NH$_2$, —COOH, —COY" or —COO$^-$.

50. The scavenger according to claim 26 wherein R$_3$' is COY".

51. The method according to claim 4 or 7 wherein R$_1$ is

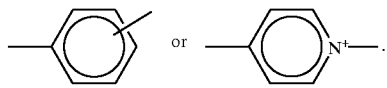

52. The method according to claim 4 or 7 wherein R$_2$ is a bond or —(CY'$_2$)$_n$.

53. The method according to claim 4 or 7 wherein R$_3$ is —N$^+$(Y")$_3$, —COOH, —COO$^-$, —SO$_3$H or —SO$_2^-$.

* * * * *

UNITED STATES PATENT AND TRADEMARK OFFICE
CERTIFICATE OF CORRECTION

PATENT NO. : 6,127,356
DATED : October 3, 2000
INVENTOR(S) : Crapo et al.

It is certified that error appears in the above-identified patent and that said Letters Patent is hereby corrected as shown below:

<u>Title page,</u>
Change Item "[73] Assignee: Duke University, Durham, N.C." to
-- [73] Assignee: Duke University, Durham, NC;
University of Alabama at Birmingham Research Foundation, Birmingham, AL; and
Aeolus Pharmaceuticals, Inc., Research Triangle Park, NC --

Signed and Sealed this

Twenty-eighth Day of September, 2004

JON W. DUDAS
*Director of the United States Patent and Trademark Office*